(12) United States Patent
Benner

(10) Patent No.: US 6,377,893 B1
(45) Date of Patent: Apr. 23, 2002

(54) APPLICATION OF PROTEIN STRUCTURE PREDICTIONS

(76) Inventor: Steven Albert Benner, 1501 NW. 68th Ter., Gainesvillle, FL (US) 32605

( * ) Notice: Subject to any disclaimer, the term of this patent is extended or adjusted under 35 U.S.C. 154(b) by 0 days.

(21) Appl. No.: 08/914,375

(22) Filed: Aug. 19, 1997

Related U.S. Application Data

(63) Continuation-in-part of application No. 07/857,224, filed on Mar. 25, 1992.

(51) Int. Cl.[7] .............................. G06G 7/48; G06F 7/08
(52) U.S. Cl. ............................. 702/20; 702/27; 702/31; 436/86; 436/89
(58) Field of Search .............................. 435/6; 935/77; 530/350; 702/19, 20, 27, 22, 31; 436/86, 89

(56) References Cited

U.S. PATENT DOCUMENTS

| | | | |
|---|---|---|---|
| 4,923,808 A | * | 5/1990 | Matteucci .................. 435/69.8 |
| 5,878,373 A | * | 3/1999 | Cohen et al. .................. 702/22 |

OTHER PUBLICATIONS

Benner, Steven A., Ian Badcoe, Mark A. Cohen and Dietlind L. Gerloff, "Bona Fide Prediction of Aspects of Protein Conformation: Assigning Interior and Surface Residues from Patterns of Variation and Conservation in Homologous Protein Sequences," Journal o, Jan. 21, 1994.*

Jenny, Thomas F., Dietling L. Gerloff and Mark A. Choen and Steven A. Benner, "Predicted Secondary and Supersecondary Structure for the Serine–Threonine–Specific Protein Phosphatase Family," Proteins: Structure, Function and Genetics, vol. 21, pp 1–10 (Zu, Jan. 1995.*

* cited by examiner

*Primary Examiner*—Kamini Shah

(57) ABSTRACT

A method for making a model for the folded structure of a set of proteins from an evolutionary analysis of a set of aligned homologous protein sequences was claimed in Ser. No. 07/857,224. The instant application concerns methods for using these models. The first method is used to confirm or deny a hypothesis that two proteins are homologous, and is comprised of comparing a predicted structure model for one family of proteins with a predicted structure model for a second family of proteins, or an experimental structure for the second family, and deducing the presence or absence of homology based on the presence or absence of structural similarity flanking key residue motifs in the polypeptide sequence. The second method identifies mutations during the divergent evolution of a protein sequence that are potentially adaptive by identifying episodes during the divergent evolution of a family of proteins where there is a high absolute rate of amino acid substitution, or a high ratio of non-silent substitutions to non-silent substitutions. Amino acids that are changing during this episode are likely to be adaptive. The third is a method for identifying specific in vitro properties of the protein that are likely to play a physiological role in vivo in an organism. This methods involves synthesizing in the laboratory proteins having the reconstructed amino acid sequences of a protein before and after a period of rapid sequence evolution that characterizes adaptive substitution, measuring the in vitro properties of the protein before the episode of rapid sequence evolution, and then measuring the in vivo properties of the protein after the episode of rapid sequence evolution. The in vitro behaviors that remained unchanged through this episode are not likely to have adaptive significance physiologically. The in vitro behaviors that changed through this episode are likely to have adaptive significance physiologically. The fourth concerns method for organizing genome sized sequence databases.

23 Claims, 2 Drawing Sheets

DRAWING 1
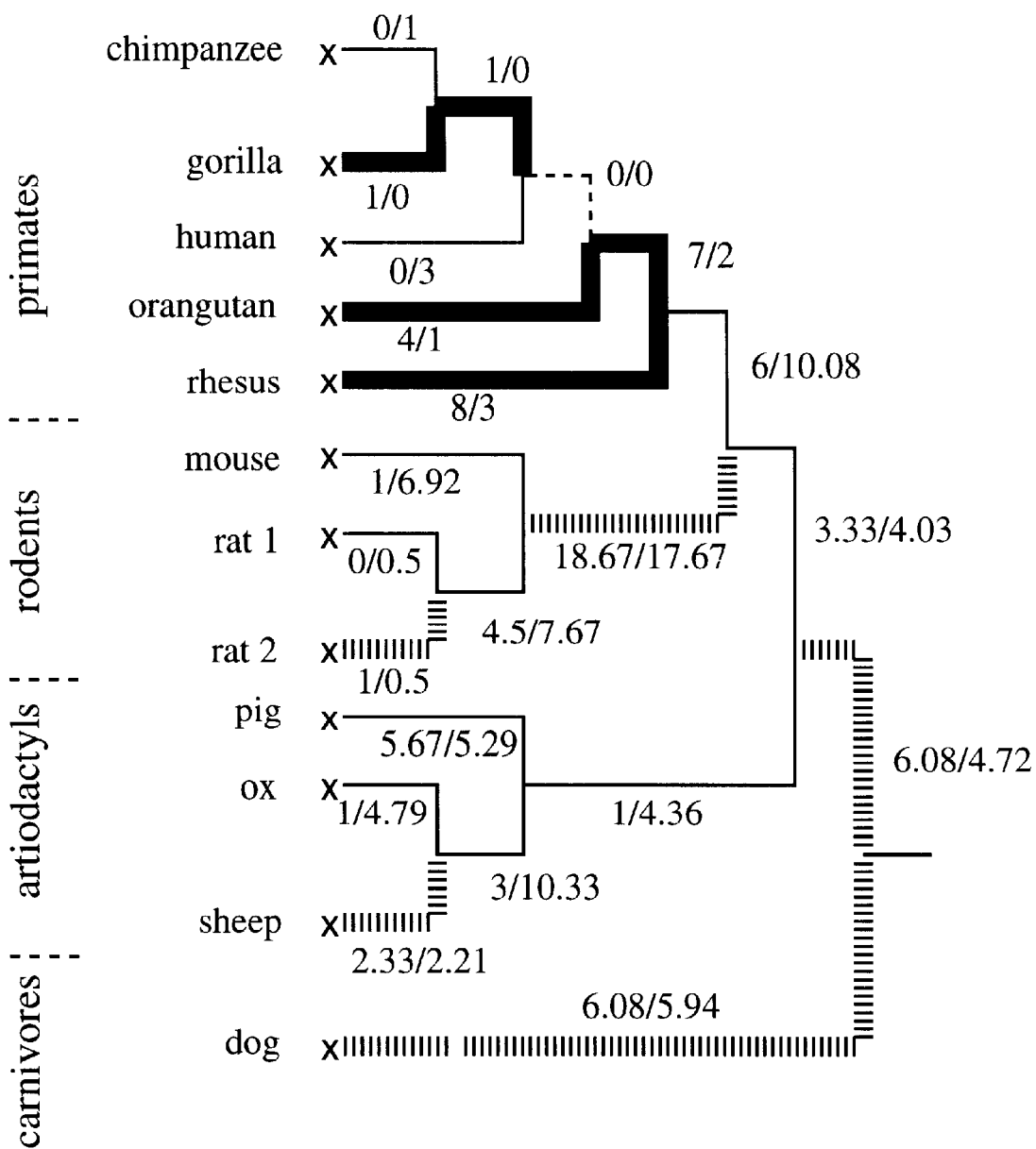

DRAWING 2
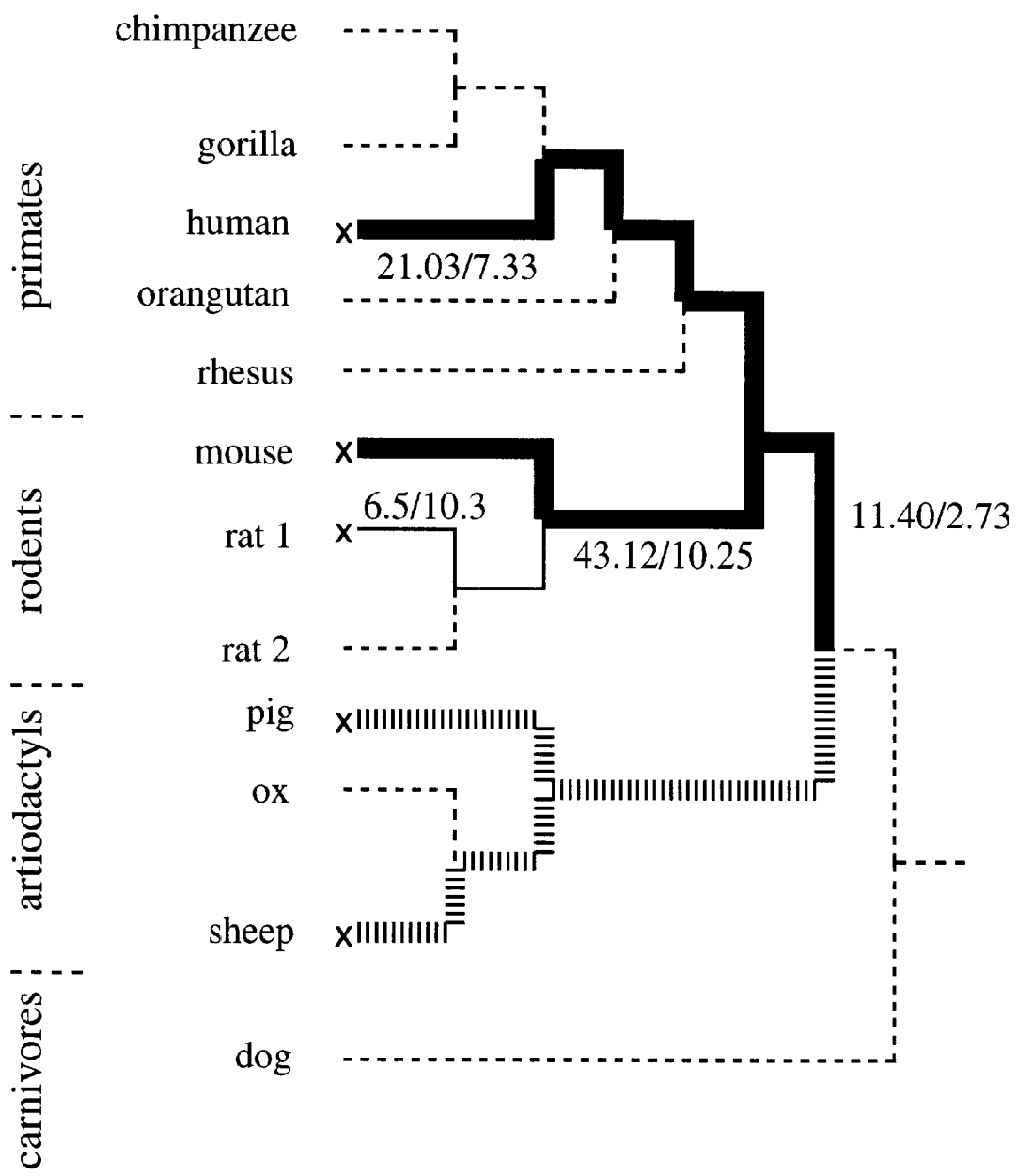

APPLICATION OF PROTEIN STRUCTURE PREDICTIONS

CROSS REFERENCE TO RELATED APPLICATIONS

This application is a continuation-in-part of copending application Ser. No. 07/857,224, filed Mar. 25, 1992, the disclosure of which is herein incorporated by reference.

INTRODUCTION

1. Field of the Invention

This invention relates to the area of bioinformatics, more specifically to methods for analyzing the sequences of evolutionarily related proteins, and most specifically for identifying evolutionary and functional relationships between proteins and the genes that encode them.

2. Background

Proteins are linear polypeptide chains composed of 20 different amino acid building blocks. Determining the sequence of amino acids in a protein is now experimentally routine, both by direct chemical analysis of the proteins themselves, and by translation of genes that encode proteins. The size of protein sequence databases will grow explosively over the next decade as genome sequencing projects are completed.

The polypeptide chain in a protein folds to give secondary structural units (most commonly alpha helices and beta strands) which then fold to give supersecondary structures (for example, a beta sheet or a strand-turn-helix) and a tertiary structure. These are collectively termed "conformation" or, more colloquially, the "fold". Most behaviors of a protein are determined by the fold, including those that are important for allowing the protein to function in a living system. The folded structure must be known before pharmaceuticals can be rationally designed to bind to the protein, for example.

In principle, the linear polypeptide sequence, by providing the constitution of the protein, also determines all of its other properties, including secondary and tertiary structure, stability, interaction with other molecules, and through these and other properties, biological activity. The connection between amino acid sequence and these other properties is not transparent, however. For example, some 30 years have been spent developing tools that allow the biochemist to predict secondary structure of proteins starting from sequence data. Many of the classical approaches attempting to predict secondary structure from sequence, of example, were summarized in the disclosure of Ser. No. 07/857,224, filed Mar. 25, 1992, which is herein incorporated by reference.

In the mid 1970's, a relationship between evolutionary ancestry and protein conformation was established. Rossman noted that lactate, glyceraldehyde-3-phosphate, and alcohol dehydrogenases acting on quite different substrates all have a domain that folds to give a parallel sheet flanked by helices (a "Rossman fold"). [Rossman, M. G., & Argos, P. (1976). Exploring structural homology of proteins. 105, 75–95].

It is now widely appreciated that homologous proteins can have diverged so much that no significant sequence similarity remains between them, even though their overall folds might be the same. Since 1976, many have attempted to exploit the fact that homologous proteins have the same fold as a tool for predicting fold. For cases where the target protein was sufficiently similar in sequence to a protein with a known conformation to establish homology with reasonable statistical similarity, "homology modelling" was used. Homology modeling is best defined strictly as a process for building a model of the conformation of a target protein that begins by identifying a protein with known conformation that is a homolog of a target, and uses the homolog as a starting point to model the conformation of the target.(May, & Blundell, 1995; Sali, 1995) [May, A. C. W., & Blundell, T. L. (1995). Automated comparative modelling of protein structures. 5, 355–360. Sali, A. (1995). Modeling mutations and homologous proteins. 6, 437–51.]

As is well known to those skilled in the art, sequence analysis becomes ineffective as a tool to establish homology after sequence identity between two homologous proteins drops below approximately 25% for a protein of typical length. At this point (the "twilight zone"), non-homologous sequences share the same level of sequence similarity with a target protein as homologous sequences, making it impossible to determine from sequence data alone whether two proteins are homologous or not. Thus, while a high similarity score (corresponding to a high sequence identity in an alignment with few gaps) is generally a strong indicator of homology, a low score is generally not a reliable indicator of non-homology. Much of the sequence analysis tools presently being developed attempt to extract evidence of homology from sequence data for proteins that have statistically marginal or sub-significant similarities, and to use this to predict conformation.

One approach for identifying long distance homologs when alignment scores are statistically marginal is to do a "profile analysis" [Gribskov, M., McLachlan, A. D., Eisenberg, D. Profile analysis: Detection of distantly related proteins. *Proc. Nat. Acad. Sci.* 84, 4355–4358 (1987)]. In this approach, a set of sequences of members of a protein family is examined. The sequence similarities in this set of proteins must be sufficient to establish that the proteins in the set are homologous and adopt the same fold. A multiple alignment of the sequences is constructed. Then, for each position in the multiple alignment, a position-specific scoring matrix is constructed using as input the amino acids at that position for each protein in the multiple alignment. A "profile" of the protein is the collection of each of these matrices for each position for the entire protein sequence alignment. The sequence of a protein that is a possible homolog of family (but whose sequence is too dissimilar from that of any individual member of the family to give a score that is statistically adequate) is then matched against the profile and scored. If the score is high, the hypothesis that the protein is a possible homolog of the family is strengthened.

In practice, profile analyses identify many proteins in a database that are possible homologs, where the correct "hits" are buried in a large number of false positives. For this reason, profile analysis is virtually useless as a tool for excluding the possibility that two proteins are homologous, or contain the same core fold.

Another approach for identifying long distance homologs when alignment scores are statistically marginal is to search for sequence "templates" or "motifs", short segments of polypeptide chain that might be conserved over long distances [Taylor, W. R. *J. Mol. Biol.* 188, 233–258 (1986); Taylor, W. R., Thornton, J. M. *Mol. Biol.* 173, 487–514 (1984); Wierenga, R. K., Terpstra, P., Hol, W. G. J., *J. Mol. Biol.* 187, 101–107 (1986)]. Here, the presence of analogous motifs in two protein sequences can be used to infer long distance homology between a target protein and a protein with known conformation, and from this inference, a model of the target protein can be modelled on the structure of the other. As with profile modelling, the presence of a template is not a reliable indicator of long distance homology and similar fold. For example, in the first example presented in Ser. No. 07/857,224 (for protein kinase), several groups had noted that the protein has a sequence motif Gly-Xxx-Gly-Xxx-Xxx-Gly (where Xxx is any amino acid) [Sternberg, M. J. E., Taylor, W. R. Modeling the ATP binding site of oncogene products, the epidermal growth-factor receptor and related proteins FEBS Lett. 1984, 175, 387–392.]. Further it was noted that a similar motif was found in adenylate kinase, where a crystal structure was known. Therefore, it was proposed that the two structures are homologous. From this proposal, it was deduced in the literature that protein kinase would adopt the same fold as adenylate kinase. This proposal was proposed in Ser. No. 07/857,224 to be incorrect, and later shown to be incorrect experimentally [Knighton, D. R., Zheng, J., Ten Eyck, L., Ashford, F. V. A., Xuong, N. H. Taylor, S. S., Sowadski, J. M. (1991) Crystal structure of the catalytic subunit of cyclic adenosine-monophosphate dependent protein-kinase. *Science* 253, 407–414.].

Further, motif analysis has not (prior to Ser. No. 07/857,224) been used as part of any tool to infer the absence of homology. The statistics of motif analysis are such that they could not be without supporting analysis.

The majority of effort to exploit the relationship between evolutionary history and conformation implicit in Rossman's observation has been applied to attempting to establish homology based on sequence similarity, and then to infer conformation. Very few investigators have pursued the inverse problem, developing tools to use the similarity of two folds as an indicator of distant homology.

Some efforts had been made to use predicted structures (as opposed to experimental structures) to detect long distance homology. For example, Pearl and Taylor [Pearl, L. H., & Taylor, W. R. (1987). A structural model for the retroviral proteases. 329, 351–4] and Bazan and Fletterick [Bazan, J. F., & Fletterick, R. J. (1988). Viral cysteine proteases are homologous to the trypsin-like family of serine proteases: structural and functional implications. 85, 7872–7876] were able to interpret a secondary structure prediction made by consensus GOR prediction for viral proteases with unknown structure to confirm the speculation that these proteases are homologs of aspartic proteases with known experimental structures. Sheridan et al. [Sheridan, R. P., Dixon, J. S., Venkataraghavan, R. Generating plausible protein folds by secondary structure similarity. *Int. J. Pept. Prot. Res.* 25, 132–143 (1985)] were perhaps the first to suggest than an array of predicted secondary structural elements might be used as a query to search proteins of known conformation to detect possible distant homologs. In none of these studies, however, was it recognized that core secondary structural elements must be weighted strongly in this comparison.

Prior to Ser. No. 07/857,224, no art had concerned itself with the question of how to use predicted structures to show that two proteins were not homologous. While secondary structure predictions, coupled with experimental data, could on occasion detect similar folds (primarily all helical folds), they were clearly insufficiently reliable to permit the exclusion of homologous folds in proteins that had a potential for distant relationship. Both threading and profile analyses methods usually generate long lists of potential targets, without clearly excluding any as homologs.

Tools able to rule out homology will become more important as genome projects begin to produce large numbers of data. As is well appreciated by those of ordinary skill in the art, genome sequencing projects frequently identify the sequence of a protein for which little or nothing is known about its physiological function. Under these circumstances, the most reliable approach for assigning physiological function to a protein is to identify a homologous protein with known function. It is frequently the case that no homolog with known function is known with a sequence similarity that allows a statistically significant case to be made for homology. In these cases, tools that rule out long distance homology are as useful as tools that establish it, as they limit the number possible long distance homologs.

SUMMARY OF THE INVENTION

A method for making a model for the folded structure of a set of proteins from an evolutionary analysis of a set of aligned homologous protein sequences was claimed in Ser. No. 07/857,224. The instant application concerns methods for using these models. The first method is used to confirm or deny a hypothesis that two proteins are homologous, and is comprised of comparing a predicted structure model for one family of proteins with a predicted structure model for a second family of proteins, or an experimental structure for the second family, and deducing the presence or absence of homology based on the presence or absence of structural similarity flanking key residues in the polypeptide sequence. The second method identifies mutations during the divergent evolution of a protein sequence that are potentially adaptive by identifying episodes during the divergent evolution of a family of proteins where there is a high absolute rate of amino acid substitution, or a high ratio of non-silent substitutions to non-silent substitutions. Amino acids that are changing during this episode are likely to be adaptive. The third is a method for identifying specific in vitro properties of the protein that are likely to play a physiological role in vivo in an organism. This methods involves synthesizing in the laboratory proteins having the reconstructed amino acid sequences of a protein before and after a period of rapid sequence evolution that characterizes adaptive substitution, measuring the in vitro properties of the protein before the episode of rapid sequence evolution, and then measuring the in vivo properties of the protein after the episode of rapid sequence evolution. The in vitro behaviors that remained unchanged through this episode are not likely to have adaptive significance physiologically. The in vitro behaviors that changed through this episode are likely to have adaptive significance physiologically. The fourth concerns method for organizing genome sized sequence databases.

BRIEF DESCRIPTION OF THE DRAWINGS

Drawing 1. Evolutionary tree showing the evolutionary history of the leptins. Heavy lines show branches with expressed/silent ratios higher than 2. Hatched lines show branches with expressed/silent ratios from 1 to 2. Dotted lines show branches with expressed/silent ratios less than 1, or indeterminate. Numbers on the lines indicate the ratio of expressed/silent changes for that branch. An "x" at the end of a branch signifies that a sequence for the protein is available in the database.

Drawing 2. Evolutionary tree showing the evolutionary history of the leptin receptors. Heavy lines show branches with expressed/silent ratios higher than 2. Hatched lines show branches with expressed/silent ratios from 1 to 2. Dotted lines show branches with expressed/silent ratios less than 1, or indeterminate. Numbers on the lines indicate the ratio of expressed/silent changes for that branch. An "x" at

DETAILED DESCRIPTION OF THE INVENTION

In Ser. No. 07/857,224, a method was disclosed for predicting the secondary structure for a protein family starting from a set of aligned homologous protein sequences. The structural model so produced is a "consensus model", describing conformation in those regions of a protein where all of its homologs have the same conformation. The method is characterized by several operational features, each of which is essential for the method to be effective:

(i) The method examines aligned sequences of a set of homologous proteins, rather than a single sequence of a single protein.

(ii) The method extracts information concerning the three dimensional structure of the protein family from patterns of conservation and variation within a set of homologous sequences, not by a simple averaging of a property of the sequences taken individually.

(iii) The method combines algorithms that assign positions in the alignment to the surface of the folded structure, to the interior of the folded structure, and to the active site, as a first step for predicting secondary structural elements.

(iv) The method identifies separate secondary structural elements in the alignment using parsing algorithms that identify gaps in the alignment and specific parsing sequence strings.

(v) The algorithms used by the method are applied to subgroups of proteins with clearly identified evolutionary relationships, in particular, a clearly specified sequence identity and evolutionary distance.

(vi) The algorithms are designed to reflect how natural selection and neutral drift, two evolutionary processes, influence the divergent evolution of protein sequences.

Structure models constructing using the method disclosed in Ser. No. 07/857,224 are useful in their own right. In addition, however, the value of the models can be amplified by assembling the secondary structural elements to form supersecondary and tertiary structural models by orienting these elements using disulfide bridges, active site assignments, and covariation analysis. More importantly, the value of the structural models predicted using the method disclosed in Ser. No. 07/857,224 can be amplified by setting the predicted model within an evolutionary context. As disclosed in examples in Ser. No. 07/857,224, and further below, the predicted models of conformation can be used to address questions of physiological function in proteins.

Ser. No. 07/857,224 also disclosed a method showing how structure predictions can be used to make a clear statement about the evolutionary relatedness of protein families, in particular, that two proteins are not homologous and do not have similar folds. In the method disclosed in Ser. No. 07/857,224, a consensus model for the secondary structure of a protein family is predicted. This predicted model is then compared with the consensus secondary structure (experimental or predicted) of the putatively homologous family. If the two secondary structural models are congruent (meaning that they share core secondary structural elements), in particular in segments flanking one or more sequence motifs that are suspected to be indicators of long distance homology, then the hypothesis that the two proteins are homologs is supported. If, however, the secondary structural models are not congruent, in particular in segments flanking a sequence motif that is suspected to be an indicator of long distance homology, then the hypothesis that the two proteins are homologs is denied.

The latter was the case in Example 1 of Ser. No. 07/857, 224, for protein kinase. The protein kinase family has the sequence motif Gly-Xxx-Gly-Xxx-Xxx-Gly (where Xxx is any amino acid). A similar motif is present in adenylate kinase, where an experimental structure was known. In adenylate kinase, the strand and helix flanking the motif were both core elements, conserved in divergent members of the adenylate kinase family. Further, the strand flanking the Gly-Xxx-Gly-Xxx-Xxx-Gly motif was internal to the beta sheet; it formed backbone hydrogen bonding interactions to two other strands of both of its edges. Thus, it is difficult to conceive how it could be removed without disrupting the fold; it is therefore a core strand. In contrast, the predicted model for adenylate kinase found two strands flanking the motif. This suggested that adenylate kinase and protein kinase could not be homologs, as no model of divergent evolution explains how a core strand can be replaced by a core helix through a process of continuous evolution under functional constraints. This suggestion was later shown to be correct. This is, to the inventor's knowledge, the first example in the art of the use of a secondary structure prediction to deny the assertion that two proteins are homologous. The example disclosed in Ser. No. 07/857,224 also shows both the inadequacy of a simple motif analysis as a tool to exclude homology between weakly similar sequences Ser. No. 07/857,224 also introduced value of distinguishing core and non-core secondary structural elements when using secondary structure predictions. It introduced several definitions of "core" and "non-core" elements, and these are amplified here.

When an experimental structure is known for a protein (for example, by crystallography or n.m.r.), core elements are conveniently defined geometrically; a core element is one where a substantial fraction is buried. Thus, a core strand is one that forms strand-strand interactions is one that is central to a beta sheet, a strand that forms backbone hydrogen bonding interactions with two other strands on both of its edges. By this definition, a core strand is distinct from an edge strand, which forms backbone hydrogen bonds to only one other strand on only one if its edges.

The geometric definition of a core secondary structural element has two principal deficiencies. Most obviously, it cannot be applied when no experimental structure is known. Further, definition of a core secondary structural unit by inspection of a single crystal structure in a single protein from a large family of proteins cannot identify a residue that is conserved across large evolution distances. It is the conservation of an element that makes it useful for identifying long distance homologs. Very often, buried secondary structural elements are in fact conserved over long distances.

A more general definition of a core secondary structural unit focuses on the evolutionary stability of the secondary structural unit. For the purpose of detecting long distance homologs, a secondary structural element, predicted or otherwise, is one that cannot be lost during divergent evolution without damaging the integrity of the protein fold. This is based on notions of continuity in protein evolution, most fundamentally on the assumption that a protein that has one "topology" of protein fold (e.g., an eight fold alpha-beta barrel) cannot by continuous evolutionary processes be converted into a protein with another (e.g., an immunoglobulin fold). It is clear that divergence of biological function can add or subtract peripheral secondary structural elements to create or remove contact elements, expand or eliminate binding sites, or to modify the performance of the protein in other fashions.

Thus, one recognizes noncore segments of a protein family when one has a set of sequences, preferably between 100 and 150 PAM units divergent for the most divergent pairs, as regions that are deleted. If a segment (including a segment containing a helix or a strand) is deleted in a protein family built from members all sharing significant sequence similarity, it cannot be essential for the integrity of the fold in the family. In applying this tool, one must be concerned about database mistakes; a part of sequence that is "deleted" because the scientist providing the entry into the database neglected to collect it, or neglected to enter it, is not a deletion from the purpose of detecting non-core segments.

A second method for identifying a core segment of a protein sequence is applicable to any set of sequences containing three sequences or more. In the tool, a pairwise alignment is constructed for each pair of sequences in the set using a dynamic programming tool. Consider for example a set of sequences with three proteins, A, B and C. A core segment of the multiple alignment is defined as those regions where the alignment of A with B and the alignment of B with C is consistent with the alignment of A with C.

A third method is for identifying a core segment in a multiple alignment seeks segments where the overall sequence divergence is greater than the average within the set of proteins in the alignment.

A final method relates to the reconstructed ancestral sequence of the protein. It has long been appreciated [Pauling, L., Zuckerkandl, E. (1963) Acta Chem. Scand. 17 (Suppl. 1), S9–S16] that when the sequences of two or more homologous proteins are available, it is possible to construct a probabilistic model for the sequence of the ancestral protein. The part of the ancestral sequence that is reconstructed with high probability is the "core" of the protein. These reconstructions are done by maximum likelihood tools well known in the art (for example, as implemented on the web server at the address cbrg@inf.ethz.ch, see also [Gonnet, G. H., Benner, S. A. Computational Biochemistry Research at ETH. *Technical Report* 154, *Departement Informatik,* March (1991)]). Here, probabilities are given for each of the 20 amino acids being present position in the multiple alignment, with the sum of the propbabilities totalling to unity. A core is defined from the ancestral sequences as a segment of the multiple alignment where the average probability of the most frequent amino acid at that positions is greater than one standard deviation above the average probability of all of the reconstructed positions in the multiple alignment. The core defined in this way is a tree-weighted measure of the divergence in the family as a whole, and correlates with core regions defined in the other ways, as the region of the ancestral sequence that is reconstructed with high probability is also the one that has not suffered insertions and deletions, and the one that has seen relatively little sequence divergence. These segments also correlate with core segments defined geometrically.

Given these definitions of a core, the process of determining congruency begins by identifying motifs in the two protein sequences that are common and conserved in both families. There may be none or of one of these, but preferably there are two or more. The first secondary structural elements flanking these motifs on each side are then aligned in the two protein families. Around each motif, the model can have one of four forms: helix-motif-helix, helix-motif-strand, strand-motif-helix, and strand-motif-strand. The secondary structural alignments are said to be congruent if and only if the forms flanking all motifs correspond between the two proteins, and that the secondary structural elements on each side of the motif are core as assigned by one or more of the methods above. Homology is not denied if and only if the secondary structures are congruent. This method is preferably applied when each family contains proteins that are at least 120 PAM units divergent, more preferably at least 140 PAM units divergent.

If no sequence motifs can be found in common for the two protein families, then the core motifs of each protein family are aligned sequentially. In this process, the secondary structural motifs are considered to be congruent when every core element from one family finds a core element in the other of the same type (helix or strand), in the same order, where gaps matched against non-core elements (where a non-core element in one family is not aligned against any element in the other) are allowed in any number, and a core element in one protein may be missing in the other, but may not be aligned with a core element in the other of a different type (i.e., helix against strand). Homology is not denied if n core secondary structural elements from one segment are aligned out of n+1 secondary structural elements, where n is at least 5, and preferably 7 or more. This method is preferably applied when each family contains proteins that are at least 120 PAM units divergent, more preferably at least 140 PAM units divergent.

As disclosed in Ser. No. 07/857,224, a model for the conformation of a protein predicted from a set of homologous proteins sequences is a consensus model. The consensus model corresponds approximately to the structure of the most recent common ancestor of the family of proteins in the set, minus elements that are deleted from one or more functional descendants of the family. It has long been appreciated [Pauling, L., Zuckerkandl, E. (1963) Acta Chem. Scand. 17 (Suppl. 1), S9–S 16] that when the sequences of two or more homologous proteins are available, it is possible to construct a probabilistic model for the sequence of the ancestral protein. This sequence again defines a "core" of the protein, that part of the sequence that is deleted in neither descendent protein. The sequence of the core can be reconstructed using "maximum parsimony" or "maximum likelihood" methods, all well known in the art [Huelsenbeck, J., Rannala, B. Phylogenetic methods come of age: Testing hypotheses in an evolutionary context. *Science* 276, 227–232 (1997)][W. P. Maddison, D. R. Maddison, *MacClade. Analysis of Phylogeny and Character Evolution.* Sinauer Associates, Sunderland Mass. (1992)].

While detecting distant homology is usually sufficient to establish that two protein families have the same core fold, it is not sufficient to establish that two proteins have the same function. Much of the variation in sequence between two protein families is "neutral", having no impact on behavior important to function, arising through "random drift". Nevertheless, genes and their encoded proteins performing one function in an ancestor can be recruited to perform another. While some behavior is frequently conserved through this recruitment, many of the features most obvious in in vitro experiments (substrate specificity, catalytic properties, stability, for example) are lost, and the functional analogy two homologous proteins following a recruitment event can often be quite abstract. For example, aspartate, fumarase, and argininosuccinate lyase are homologous proteins and share an analogous behavior: the ability to add H—X to a double bond (where X is an oxygen or a nitrogen). But the analogy is rooted in the mechanistic fundamentals of the reaction; the physiological and metabolic roles of these three proteins are quite different.

For these reasons, sophisticated bioinformatics tools must be used to extract the structural and functional information that the gene databases contain, where careful attention is paid to whether substitutions are adaptive or neutral. Tools that incorporate this into a structure prediction tool were disclosed in Ser. No. 07/857,224.

As discussed in Ser. No. 07/857,224, during the divergent evolution of two proteins from a common ancestor, mutations of two types accumulate. The first have no impact on the ability of the host organism to survive, select a mate, and reproduce; these are called "neutral" mutations. The second influence the behavior of the protein in a way that influences the ability of the organism to survive, select a mate, and reproduce. These are termed "adaptive mutations." When evolving a new function, proteins undergo an episode of rapid sequence evolution that corresponds to adaptive "positive selection", as is well known in the art [Kreitman, M., Akashi, H. Ann. Rev. Ecol. Syst. 26, 403–422 (1995)].

As disclosed in Ser. No. 07/857,224, to be useful to predict secondary structure, heuristics that extract structural information from a set of aligned homologous protein sequences must consider the presence of both adaptive and neutral mutations. Methods to identify which mutations are adaptive, which are neutral, and what properties of the protein measured in vitro are likely to play a physiological role in vivo would be useful.

With the emergence of massive amounts of sequence information as a result of genome projects, the ability to construct detailed evolutionary histories of protein families will increase. This will make the inventions disclosed herein of still greater value, as is appreciated by one of ordinary skill in the art.

In a biological system, the physiological function of a biomolecule is ultimately determined by the contribution that the biomolecule makes to the efforts of the host organism to survive, select a mate (in higher organisms), and reproduce. Determining the physiological function of a protein is not trivial, as discussed at length by Benner and Ellington [Benner, S. A., Ellington, A. D. Interpreting the behavior of enzymes. Purpose or pedigree? *CRC Crit. Rev. Biochem.* 23, 369–426 (1988)]. Still more difficult is identifying which behaviors of a protein as measured in vitro are relevant for physiological function in vivo. Nevertheless, the identification is important. In vitro behaviors that have relevance to physiological function in vivo are those that are interesting to study for biotechnological, biomedical, or other applications. There is at present in the art no general method for determining what in vitro properties are relevant to in vivo function.

To understand how the models of the method disclosed in Ser. No. 07/857,224 can be used, the concept of "homology" from evolutionary biology must be discussed. "Homology" means "relationship by common ancestry". Two proteins, genes, or other biomolecular structures are homologous when they share a common ancestor, that is, when they arose from a common ancestor by a process known in the art as "divergent evolution." Thus, the statement that two proteins (for example) are homologous is a statement about events in the past. The accuracy of such a statement is, of course, difficult to determine by direct experiment. Rather, statements about the historical past must generally be inferred from information gathered from contemporary objects.

Homology is an important concept in extracting information from sequence databases because conclusions can be drawn about the chemical behavior and biological function when two proteins are homologous that cannot be drawn when they are not. For example, if two proteins are homologous, then it is likely that they fold similarly, even if they share no evident sequence similarity. If two proteins are homologous, they are likely to have some chemical and biological behaviors that are in some sense analogous. Thus, much of the effort in bioinformatics is devoted to determining whether two proteins are homologous.

One way to deduce whether two proteins are homologous is to compare their amino acid sequences. Procedures are well established in the art for comparing two protein sequences, scoring their similarities, and using this score to assess the likelihood that the similarities arose by reason of common ancestry rather than arising by random chance [Gonnet, G. H., Cohen, M. A., Benner, S. A. Exhaustive matching of the entire protein sequence database. *Science* 256, 1443–1445 (1992)]. An alignment typically receives a similarity score, which is the logarithm of the probability that the sequences arose by common ancestry divided by the probability that they arose by random chance. This score presumes rules stating the probability that individual amino acids have undergone substitution with other amino acids.

The claims in Ser. No. 07/857,224 cover a method for making structural models for a protein family, in particular, predicting secondary structure models from a set of aligned homologous protein sequences. The claims in this continuation-in-part relate to methods for using these models. These methods are of several types.

In the first, the predicted structural models and their corresponding models of ancestral sequences are used to organize the protein sequence database to provide rapid search and retrieval of sequence databases.

In the second, the predicted model of secondary structure for a protein family is compared with either a predicted or an experimental secondary structure for another family of proteins. Congruence of the two, especially in core secondary structural elements, indicates that the two protein families are homologous. Lack of congruence of the two, especially in core secondary structural elements, indicates that the two protein families are not homologous.

In the third, the predicted model of secondary structure is coupled with the sequences of proteins and their encoding genes that are intermediates in the evolution of the protein family to which the predicted structure applies. Patterns of variation in the reconstructed ancestral proteins and genes are interpreted in terms of neutral and adaptive evolution, and coupled with experiments to assign in vitro behaviors that correlate with evolution of new function in the protein family.

In each case, to apply the models of secondary structure predicted using the methods disclosed in Ser. No. 07/857,224, the predicted models must be set within the evolutionary history of the protein family. The evolutionary history is defined by a multiple alignment of the sequences of members of the protein family, an evolutionary tree connecting these members, and ancestral sequences reconstructed in probabilistic form throughout the tree.

(a) A multiple alignment, an evolutionary tree, and ancestral sequences at nodes in the tree are constructed by methods well known in the art for a set of homologous proteins. These three elements of the description are interlocking, as is well known in the art. The presently preferred methods of constructing ancestral sequences for a given tree is the maximum parsimony methods, as implemented (for example) in the commercially available program MacClade [W. P. Maddison, D. R. Maddison, *MacClade. Analysis of Phylogeny and Character Evolution.* Sinauer Associates, Sunderland Mass. (1992)]. Trees are compared based on their scores using either maximum parsimony or maximum likelihood criteria, and selected based on considerations of score and correspondence to known facts. Step (a) is part of the process used to generate the predictions of secondary structure using the method disclosed in Ser. No. 07/857,224.

A corresponding multiple alignment is constructed by methods well known in the art for the DNA sequences that encode the proteins in the protein family. The multiple alignment is constructed in parallel with the protein alignment. In regions of gaps or ambiguities, the amino acid sequence alignment can be adjusted to give the alignment with the most parsimonious DNA tree. The presently preferred method of constructing ancestral DNA sequences for a given tree is the maximum parsimony method. The DNA and protein trees and multiple alignments must be congruent, meaning that when amino acids are aligned in the protein alignment, the corresponding codons are aligned in the DNA alignment. Likewise, the connectivity of the two evolutionary trees must show the same evolutionary relationships. In regions where the connectivity of the amino acid tree is not uniquely defined by the amino acid sequences, the tree that gives the most parsimonious DNA tree is used to decide between two trees or reconstructions of equal value. Finally, the ancestral amino acids reconstructed at nodes in the tree must correspond to the reconstructed codons at those nodes. When the ancestral sequences are ambiguous, and where the DNA sequences cannot resolve the ambiguity, the reconstructed DNA sequences must be ambiguous in parallel. Approximate reconstructions are valuable even when exact reconstructions are not possible from available data, and the tree is preferably constrained to correspond to evolutionary relationships between proteins inferred from biological data (e.g., cladistics).

(c) Mutations in the DNA sequences are then assigned to each branch of the DNA evolutionary tree. These may be fractional mutations to reflect ambiguities in the sequences at the nodes of the tree. When ambiguities are encountered, alternatives are weighted equally. Mutations along each branch are then assigned as being "silent", meaning that they do not have an impact on the encoded protein sequence, and "expressed", meaning that they do have an impact on the encoded protein sequence. Fractional assignments are made in the case of ambiguities in the reconstructed sequences at nodes in a tree.

(d) Intermediates in the evolutionary tree are then prepared in the laboratory using protein engineering and biotechnology methods well known in the art [Jermann, T. M., Opitz, J. G., Stackhouse, J., Benner, S. A. Reconstructing the evolutionary history of the artiodactyl ribonuclease superfamily. *Nature* 374, 57–59 (1995).]

(e) The invention disclosed in Ser. No. 07/857,224 is then applied to each protein family. For each protein family, a secondary structure is predicted for the family, and this predicted secondary structure is aligned with the ancestral sequence at the root of the tree. If the root of the tree is unassigned, the predicted secondary structure is aligned with the ancestral sequence calculated for an arbitrary point near the center of gravity of the tree.

As the quality of a multiple alignment and the precision of the reconstructed ancestral sequences decreases if proteins are included in the family with sequences diverging by over 150 PAM units, where a PAM unit is the number of point accepted mutations per 100 amino acids, while the quality of the secondary structure prediction determined by the methods disclosed in Ser. No. 07/857,224 becomes worse if the family does not contain at least some protein sequence pairs 40 PAM units or more divergent, families used in this invention preferably contain at least some protein sequence pairs more than 40 PAM units divergent, but contain no protein pairs more than 150 PAM units divergent. Most preferably, a majority of protein pairs are 40 or more PAM units divergent and no protein pair is more than 120 PAM units divergent. The sequences in a protein family are, however, generally determined by the availability of sequences in the database. As genome projects are completed, the number of sequences in the database will grow, and the method of the instant invention will be applicable to all families of proteins. It is estimated that there will be on the order of 10,000 families of proteins as defined by steps (a) through (e) after all the genomes are sequenced for all of the organisms on earth.

Once the models for secondary structure predicted by the methods disclosed in Ser. No. 07/857,224 are placed into their evolutionary context as described above, the context can be used in the following ways:

1. Rapidly searchable database

Steps (a) through (e) provide a method to organize the protein sequence database in a rapidly searchable form. The ancestral sequences and the predicted secondary structures associated with the families defined by steps (a) through (e) are surrogates for the sequences and structures of the individual proteins that are members of the family. The reconstructed ancestral sequence represents in a single sequence all of the sequences of the descendent proteins. The predicted secondary structure associated with the ancestral sequence represents in a single structural model all of the core secondary structural elements of the descendent proteins. Thus, the ancestral sequences can replace the descendent sequences, and the corresponding core secondary structural models can replace the secondary structures of the descendent proteins.

This makes it possible to define two surrogate databases, one for the sequences, the other for secondary structures. The first surrogate database is the database that collects from each of the families of proteins in the databases a single ancestral sequence, at the point in the tree that most accurately approximates the root of the tree. If the root cannot be determined, the ancestral sequence chosen for the surrogate sequence database is near the center of mass of the tree. The second surrogate database is a database of the corresponding secondary structural elements. The surrogate databases are much smaller than the complete databases that contain the actual sequences or actual structures for each protein in the family, as each ancestral sequence represents many descendent proteins. Further, because there is a limited number of protein families on the planet, there is a limit to the size of the surrogate databases. Based on our work with partial sequence databases [Gonnet et al., op. cit. 1992], we expect there to be fewer than 10,000 families as defined by steps (a) through (e).

Searching the surrogate databases of the instant invention for homologs of a probe sequence thus proceeds in two steps. In the first, the probe sequence (or structure) is matched against the database of surrogate sequences (or structures). As there will be on the order of 10000 families of proteins as defined by steps (a) through (e) after all the genomes are sequenced for all of the organisms on earth, there will be only on the order of 10000 surrogate sequences to search. Thus, this search will be far more rapid than with the complete databases. A probe protein sequence (or DNA sequence in translated form) can be exhaustively matched [Gonnet et al., op. cit. 1992] against this surrogate database (that is, every subsequence of the probe sequence will be matched against every subsequence in the ancestral proteins) more rapidly than it could be matched against the complete database.

Should the search yield a significant match, the probe sequence is identified as a member of one of the families already defined. The probe sequence is then matched with the members of this family to determine where it fits within the evolutionary tree defined by the family. The multiple alignment, evolutionary tree, predicted secondary structure and reconstructed ancestral sequences may be different once the new probe sequence is incorporated into the family. If so, the different multiple alignment, evolutionary tree, and predicted secondary structure are recorded, and the modified reconstructed ancestral sequence and structure are incorporated into their respective surrogate databases for future use.

The advantage of this data structure over those presently used is apparent. As presently organized, sequence and structure databases treat each entry as a distinct sequence. Each new sequence that is determined increases the size of the database that must be searched. The database will grow roughly linearly with the number of organismal genomes whose sequences are completed, and become increasingly more expensive to search.

The surrogate database will not grow linearly. Most of the sequence families are already represented in the existing database. Addition of more sequences will therefore, in most cases, simply refine the ancestral sequences and associated structures. In any case, the total number of sequences and structures in their respective databases will not grow past ca. 10000, the estimate for the total number of sequence families that will be identifiable after the genomes of all organisms on earth are sequenced. If a dramatically new class of organism is identified, this estimate may grow, but not exponentially (as is the growth of the present database).

Further, alignment of ancestral sequences with ancestral sequences has an advantage in detecting longer distance homology, as the ancestral sequences contain information about what amino acid residues are conserved within the nuclear family, and therefore are more likely to be conserved between diverging nuclear families.

2. Detection of long distance homologs, and excluding the possibility that a sequence in question is a member of a protein family While approximately 10,000 families of proteins as defined by steps (a) through (e) will be present when all genomes on the planet are sequenced, this number is larger than the number of families of homologous proteins. Sequences of homologous proteins can diverge more than 150 PAM units, the presently preferred upper limit on sequence divergence used when constructing protein sequence families as described above. Under the procedures presently most preferred, sequences pairs that have diverged by 150 PAM or farther will be placed in different families following the procedure of steps (a) through (e).

Still more distantly homologous proteins will not show statistically significant sequence similarity at all. Even so, they have the same fold and some analogy in their biological function. Thus, it is useful to detect these long distance homologs between families, even though they do not have significantly similar sequences. Conversely, while a certain level of identity between two sequences is sufficient to establish homology, no level of dissimilarity is sufficient to disprove homology. This means that a method for excluding homology of two sequences is applied in the method of the instant invention as a key tool in organizing the database.

Secondary structure predictions aligned with the ancestral sequences of protein families can be used to detect distantly homologous protein families, those where no statistically significant sequence similarity, and exclude homology under conditions when sub-statistical sequence similarity exists. One method of the instant invention is applied when sequence motifs suggest that long distance homology might exist. As noted as background, sequence motifs are not by themselves statistically reliable indicators of homology. The issue then becomes whether the motifs are true indicators of homology, or whether they arose by convergent evolution. To address this question, the secondary structural elements flanking the motifs in the two protein families are compared. The model can have one of four forms: helix-motif-helix, helix-motif-strand, strand-motif-helix, and strand-motif-strand. If the motif truly indicates distant homology, it should be embedded within the same core secondary structural elements in both protein families. If it does not, this fact essentially rules out the possibility that the motif is an indicator of distant homology.

Alternatively, the number and sequence of the core secondary structural elements can be compared overall. Here, the ancestral sequences are important, as it helps distinguish core secondary structural elements (the segments that are better defined in the ancestral sequence) from non-core elements (segments that are more poorly defined in the ancestral sequence). It is well known [Jenny, T. F., Benner, S. A. Evaluating predictions of secondary structure in proteins. *Biochem. Biophys. Res. Comm.* 200, 149–155 (1994)] that the former are more likely to be conserved between long distance homologs, the latter less likely. In practice, such comparison begins by confirming extended families, and examining the output by hand.

We will use in this disclosure the phrase "significant sequence similarity". By this, we mean similarity adequate to give a score using a standard dynamic programming heuristic (such as the one implemented in DARWIN, available at the Web site cbrg@inf.ethz.ch, see also reference [Gonnet, G. H., Benner, S. A. Computational Biochemistry Research at ETH. *Technical Report* 154, *Departement Informatik,* March (1991)] that meets a statistical test.

The efficacy of the method of the present invention was demonstrated by the prediction of a secondary structure for protein kinase in advance of any information regarding the crystal structure. The prediction was recorded by Benner and Gerloff [(1991) op. cit.] on Sep. 21, 1990, before the crystal structure of any member of the protein family was solved by Sowadski, Taylor and their colleagues. The results of the crystal structure were published in July, 1991 [D. R. Knighton, J. Zheng, L. F. Ten Eyck, V. A. Ashford, N. H. Xuong, S. S. Taylor, J. M. Sowadski: "Crystal Structure of the Catalytic Subunit of Cyclic Adenosine Monophosphate-dependent Protein Kinase", *Science,* 253, 407–414 (1991)]. The crystal structure showed that the prediction was remarkably accurate. Knighton et al. [(1991) op. cit.] wrote:

"Although most of the predictions of secondary structure in the C subunit have been quite inaccurate and do not correlate well with the actual structure, the recent prediction by Benner and Gerloff is an exception. Their prediction of the secondary structure . . . is remarkably accurate, particularly for the small lobe."

Another indication of the inefficacy of the prior art and the efficacy of the method of the present invention comes from the paper of Thornton et al. [J. M. Thornton, T. P. Flores, D. T. Jones, M. B. Swindells: "Prediction of Progress at Last", *Nature,* 354, 105–106 (1991)]. Thornton et al. noted that:

"Benner and Gerloff tackled secondary-structure prediction; this was essentially a case study of the catalytic domain of the protein kinases, the structure of which was then unknown. The cause for excitement is that the structure has since been solved by X-ray crystallography, and Benner and Gerloff's prediction of the core secondary structures was much better than that achieved by standard methods."

Another indication of the efficacy of the method of the present invention comes from Table 1, which summarizes the prediction for the catalytic domain of protein kinases.

It is worth noting at this point that several groups had attempted to predict the folded structure of the catalytic domain of protein kinases using classical approaches, and that all of these predictions were far from the mark. For example, a prediction by Shoji et al. [S. Shoji, D. C. Parmelee, R. D. Wade, S. Kumar, L. H. Ericsson, K. A. Walsh, H. Neurath, H. L. Long, J. G. Demaille, E. H. Fischer, K. Titani, "Complete amino acid sequence of the catalytic subunit of bovine cardiac muscle cyclic AMP-dependent protein kinase", *Proc. Nat. Acad. Sci.* 78, 848–851 (1981)] using a Chou-Fasman algorithm found three regions of the catalytic domain with different secondary structures, the first (positions 1–98 in the alignment discussed here) being highly (79%) helical, the second consisting of 3 "subdomains" (positions 99–146, 147–188, and 189–251) each consisting of a beta strand followed by two alpha helices and separated by two beta turns, and the third (252-end) being highly aperiodic (only 18% alpha helix and 20% beta strand). Other predictive work mentioned above [Sternberg et al., 1984, op cit.] focused on the fact that the amino terminal portion of the domain has the sequence GXGXXG, a sequence that is conserved in most members of the family. Such a sequence is also found in the "Rossman fold", an $\alpha$-$\beta$-$\alpha$ a supersecondary structural unit that is present in several proteins that bind nucleotides and dinucleotides. Thus, several authors have suggested that this supersecondary structural unit is formed by the catalytic domains of protein kinases.

3. Identification of residues, secondary structural elements, and evolutionary episodes that are involved in functional adaptation The genetic code is degenerate. More than one triplet codon encodes the same amino acid. Therefore, a mutation in a gene can be either silent (not changing the encoded amino acid) or expressed (changing the encoded amino acid). Especially in multicellular organisms, and most particularly in multicellular animals (metazoa), silent changes are not under selective pressure. In contrast, expressed changes at the DNA level, by changing the structure of the protein that the gene encodes, change the property of the protein.

When examining a protein from higher organisms during a period of evolutionary history where, at the outset of the period, the behavior of a protein is optimized for a specific biological function, and where that function remains constant for the protein throughout the period being examined, changes in the DNA sequence that lead to a change in the sequence of the encoded protein (expressed changes) will diminish the survival value of the protein [Benner, S. A., Ellington, A. D. Interpreting the behavior of enzymes. Purpose or pedigree? *CRC Crit. Rev. Biochem.* 23, 369–426 (1988)] and therefore will be removed by natural selection. During the same period, silent changes will not be removed by natural selection, but will accumulate at an approximately clock-like rate, as silent changes are approximately neutral, especially in higher organisms. Thus, the ratio of expressed to silent changes will be low during a period of evolution of a protein family where the ancestor and its descendants share a common function.

In contrast, in genes for proteins that are neutrally drifting without functional constraints, the expressed/silent ratio will reflect random introduction of point mutations. Given the genetic code and a typical distribution of amino acid codons within the gene, a ratio of expressed to silent changes will be approximately 2.5 during the period of evolution of a protein family where the ancestor and its descendants have no function.

A third situation concerns a period of evolution where a protein is acquiring a new derived function. The amino acid sequence of the protein at the beginning of this episode will be optimized for the ancestral function, rather than the derived function. Thus, changes in the gene that are expressed in changes in the sequence of the encoded protein that improve the behavior of the protein as is required for the new biological function will be selected for. In proteins in such an evolutionary episode seeking new function, natural selection seeks expressed changes, and the ratio of expressed to silent substitutions at the DNA level will be high during the period of evolution of a protein family where the function of the ancestor has changed with a new function emerging in its descendants. Ratios as high as 4:1 or more are known.

In a family of proteins defined by steps (a) through (e) above, individual periods of evolution are defined by lines between nodes on an evolutionary tree. In step (c), silent and expressed point mutations are assigned to individual periods of evolution. Periods of evolution with high ratios of expressed to silent mutations are episodes where physiological function is rapidly changing. Periods of evolution with low ratios of expressed to silent mutations are episodes where physiological function is slowly changing.

Further, during episodes of rapid sequence evolution, amino acid substitutions will be concentrated in secondary structural elements defined by the method claimed in Ser. No. 07/857,224. These are secondary structural elements that are important in the acquisition of new function. A general method for identifying secondary structural elements that contribute to the origin of new biological function is comprised of identifying an element in the predicted secondary structure model where the corresponding section of the gene has a high ratio of expressed to silent changes.

4. Identification of in vitro behaviors that contribute to physiological function.

In vitro experiments in biological chemistry extract data on proteins and nucleic acids (for example) that are removed from their native environment, often in pure or purified states. While isolation and purification of molecules and molecular aggregates from biological systems is an essential part of contemporary biological research, the fact that the data are obtained in a non-native environment raises questions concerning their physiological relevance. Properties of biological systems determined in vitro need not correspond to those in vivo, and properties determined in vitro need have no biological relevance in vivo.

To date, there has been no simple way to say whether or not biological behaviors are important physiologically to a host organism. Even in those cases where a relatively strong case can be made for physiological relevance (for example, for enzymes that catalyze steps in primary metabolism), it has proven to be difficult to decide whether individual properties of that enzymes ($k_{cat}$, $K_m$, kinetic order, stereospecificity, etc.) have physiological relevance. Especially difficult, however, is to ascertain which behaviors measures in vitro play roles in "higher" function in metazoa, including development, regulation, reproduction, digestion.

A general method to determine whether a behavior measured in vitro is important to the evolution of new physiological function is comprised of the following steps:

(a) Prepare in the laboratory proteins that have the reconstructed sequences corresponding to the ancestral proteins before, during, and after the evolution of new biological function, as revealed by an episode of high expressed to silent ratio of substitution in a protein. This high ratio compels the conclusion that the protein itself serves a physiological role.

(b) Measure in the laboratory the behavior in question in ancestral proteins before, during, and after the evolution of new biological function, as revealed by an episode of high expressed to silent ratio of substitution. Those behaviors that increase during this episode are deduced to be important for physiological function. Those that do not are not.

EXAMPLES

Example 1

Using predicted models of secondary structure to deny long distance homology

Example 1 of Ser. No. 07/857,224 described the prediction of Benner & Gerloff (1991) for the secondary structure of protein kinase. This prediction was made by analysis of the patterns of variation and conservation of a set of aligned homologous sequences for protein kinase, using methods disclosed in Ser. No. 07/857,224. Protein kinases contain a conserved motif Gly-Xxx-Gly-Xxx-Xxx-Gly. This motif is also found in adenylate kinase, a protein whose structure was determined by crystallography in the 1970's [G. E. Schulz, C. D. Barry, J. Friedman, P. Y. Chou, G. D. Fasman, A. V. Finkelstein, V. I. Lim, O. B. Ptitsyn, E. A. Kabat, T. T. Wu, M. Levitt, B. Robson, K. Nagano, Comparison of experimentally determined secondary structure of adenylate kinase, *Nature* 250, 140–142 (1974)]. Based on these motifs, it was speculated that protein kinases and adenylate kinases were homologous, as discussed above.

To deny this speculation, the method of the instant invention was implemented via the following steps:

(a) The secondary structural elements predicted to precede and follow the Gly-Xxx-Gly-Xxx-Xxx-Gly motif in protein kinase were noted. These were a strand and a strand, respectively [Benner & Gerloff, op. cit., 1991].

(b) The core nature of these strands was evaluated. The pairwise alignment of the sequence preceding and following the motif was observed to be consistent within each functional class of proteins. A core segment is defined by the sequences to be regions where pairwise alignments constructed by dynamic programming methods of proteins within a functional class are consistent, that is, that the alignment of sequence 1 with sequence 2, and the alignment of sequence 2 with sequence 3, is consistent with the independent alignment using dynamic programming methods of sequence 1 with sequence 3. In protein kinase, these two predicted strands were assigned as core strand.

(c) The secondary structural elements observed to precede and follow the Gly-Xxx-Gly-Xxx-Xxx-Gly motif in adenylate kinase were noted. These were a strand and a helix, respectively.

(d) The crystal structure and clearly homologous protein sequences were examined to determine whether this strand and helix were core structure. Again, a core segment is defined by the sequences to be regions where pairwise alignments constructed by dynamic programming methods of proteins within a functional class are consistent, that is, that the alignment of sequence 1 with sequence 2, and the alignment of sequence 2 with sequence 3, is consistent with the independent alignment using dynamic programming methods of sequence 1 with sequence 3. An independent assessment of core was based on the crystal structure, where core strands are defined as those where the average side chain accessibility of the residues in the strand is less than 50%, while the helix directly joins two core strands.

(e) From the discrepancy, it was concluded that the conformation of protein kinases in this family is not similar to that of adenylate kinase, and the protein kinase family is not homologous to the adenylate kinase family.

Example 2

Assigning a catalytic function to the heat shock protein 90 (HSP 90) family as a gyrase using predicted secondary structures A multiple alignment (Table 1) for the heat shock protein HSP90 family was built from sequences extracted from SwissProt [Bairoch, A., Boeckmann, B. The SWISS-PROT protein sequence data bank. *Nucleic Acids Res.* 20, 2019–2022 (1992)] (Version 33) and GenBank (National Center for Biotechnology Information, URI www.ncbi.nlm.nih.gov) using the DARWIN system [Gonnet, G. H, Benner, S. A. Computational Biochemistry Research at ETH. Technical Report 154, Departement Informatik, March, 1991][Gonnet, G. H., Cohen, M. A., Benner, S. A. Exhaustive matching of the entire protein sequence database. *Science* 256, 1443–1445 (1992)]. Gaps in the alignment were shifted using a procedure that identifies misaligned gaps of identical length in nearby regions of the multiple alignment, and shift residues to align the gaps. This improves the placement of gaps, but does not guarantee that the globally optimum multiple alignment is found. The improvement in the multiple alignment was followed using the multiple alignment scoring tool of Korostensky and Gonnet [Korostensky, C., Gonnet, G. H. Evaluation measures of multiple sequence alignments. Symposium on Discrete Algorithms, submitted 1997].

Surface and interior residues were assigned by automated procedures similar to those described in Ser. No. 07/857,224, and elsewhere [Benner, S. A, Gerloff, D. Patterns of divergence in homologous proteins as indicators of secondary and tertiary structure. The catalytic domain of protein kinases. *Adv. Enz. Reg.* 31, 121–181 (1991); Benner, S. A., Badcoe, I., Cohen, M. A, Gerloff, D. L. Bona fide prediction of aspects of protein conformation. Assigning interior and surface residues from patterns of variation and conservation in homologous protein sequences. *J. Mol. Biol.* 235, 926–958 (1994)], incorporated by reference. The multiple alignment was parsed into units forming independent secondary structures automatically, and elements of secondary structure were predicted within the parsed segments from patterns of interior and surface assignments, as described in Ser. No. 07/857,224. Many of the automated routines used in this prediction are available to the public on a server accessible via email at the address cbrg@inf.ethz.ch.

"Parsing strings", consecutive positions that contain Pro, Gly, Ser, Asn, or Asp, were also used to assign breaks in secondary structure. Separately, secondary structure predictions were assigned manually following rules outlined in Ser. No. 07/857,224.

Table 1 reports the multiple alignment, surface and interior assignments, parsing assignments, active site assignments, and two secondary structure assignments, the first made fully automatically (Auto), the second made by the experts manually, before and after refinement in light of "low resolution" tertiary structure model building.

One use for predicted secondary structural models is to detect long distance homology between protein families where divergence has been so great that no statistically significant sequence similarities remain, even though the overall fold is similar. The predicted secondary structural elements were matched against the secondary structural elements of proteins whose crystal structures were known. The core elements in Table 1 were weighted preferentially (excluding, for example, segment 126–130 as a non-core unit). The active site residues predicted for HSP90 were then used as "motifs" to compare with other active site residues in other proteins. A match was found between the predicted structure of HSP90 and the structure of the experimentally determined N-terminal fragment of DNA gyrase B (ATPase fragment) [Wigley, D. B., Davies, G. J., Dodson, E. J., Maxwell, A., Dodson, G. Crystal structure of an N-terminal fragment of the DNA gyrase B protein. *Nature* 351, 624–629 (1991)]. Table 2 proposes a correlation between the predicted secondary structural elements of the HSP90 family and the experimental elements in gyrase.

The gyrase domain adopts a unique fold with a central eight-stranded beta-sheet which can be subdivided into two antiparallel sheets with six and two strands joined by a parallel strand-pairing. The ATPase active site is located in the middle of the sheet surface near a long helical segment, which provides residues that bind to the nucleotide, and is covered by a "lid" segment ca. 34 residues long containing both short helical and coil segments. The lid is connected to the core at two short glycine-rich hinge sites. Movement of the lid is likely to account for conformational changes observed upon the binding of ATP to the protein.

In fitting the proposed secondary structure prediction for HS90 to the known structure of DNA gyrase B, several suggestions arose as to how the multiple alignment might be adjusted from this "knowledge-based" perspective. For example, the two structures (predicted for HSP90 and experimental for gyrase) fit somewhat better if the gap placed at positions 126–127 were moved further down in the alignment (see below). Further application of the optimization heuristic found multiple alignments with improved scores if the gap was shifted in this direction.

Likewise, the four residue insertion at positions 178–181, interpreted in the prediction as reflecting introduction of a single turn of a helix, might be shifted down as well. As placed in the automated tool, this gap prevents the tool from identifying a helix found by the "expert". Further application of the optimization heuristic (not shown in FIG. 1) shifted this gap and improved the score of the resulting multiple alignment. These results illustrate that the gap shifting heuristic is, of course, not an algorithm. It is not guaranteed to find the optimal alignment. However, the combination of the scoring algorithm and the gap shifting heuristic apparently re-evaluate the multiple alignment much as it is done by eye, given enough computation time.

The fitting also assisted in assigning secondary structure near the active site, where patterns of variation and conservation that normally might otherwise indicate particular types of secondary structure are obscured by patterns that reflect catalytic or binding function, and suggested that some of the predicted secondary structural elements should be re-evaluated. For example, a strand is predicted in a region (positions 204–207) that aligns against a short internal helix in gyrase. Internal helices are well known for being difficult to predict using the transparent methods applied here [Jenny, T. F., Benner, S. A. Evaluating predictions of secondary structure in proteins. Biochem. Biophys. Res. Comm. 200:149–155, 1994]. The automated program notices that a helix might be assigned to positions 207–212, but rejects it in favor of two strand assignments at positions 204–207 and 210–214. Most "experts" would prefer the two beta strands as well. Inspection of the gyrase multiple alignment (data not shown) suggests that both the manual and automated procedures would probably have misassigned this segment of conserved hydrophobic positions in gyrase as well. Thus, in a "knowledge-based" environment, one might find support in this analysis for distant homology even if this particular secondary structure unit were predicted incorrectly.

The first strand in the predicted HSP90 model forms an extended coil at the N-terminus of the gyrase structure; the strand prediction is weakened by the comparison, as this segment is presumably non-core. A region at the putative active site between positions 98 and 110 is predicted to be a long helix contributing amino acid side chains that serve as ligands to divalent magnesium. To accommodate the predicted insertion in the HS90 proteins over positions 123–145, an additional short strand segment is predicted to pair with the strong amphiphilic pattern at 134–139 (see below). The remainder of the secondary structure prediction (excluding positions 158–194, discussed below) fits well with the experimentally determined secondary structural elements in gyrase up to the final 8 residues (positions 297–304). In the gyrase structure, this final segment forms an exposed edge strand leading into the following domain, and this may also be the case with HSP90.

This analysis was published before an experimental structure of HSP90 was known [Gerloff, D. L., Cohen, Fred E., Korostensky, C., Turcotte, M., Gonnet, G. H., Benner, S. A. A predicted consensus structure for the N-terminal fragment of the heat shock protein HSP90 family. *Proteins: Struct. Funct. Genet.* 27, 450–458 (1997)]. If the proposed fitting between HSP90 and gyrase were correct, there would be three regions where the folds of the heat shock protein 90 and the N-terminal domain of gyrase B might differ. Most important, the model proposes an additional antiparallel hairpin structure between strands 1 and 2 in the gyrase structure. The apparently strong exposure to solvent of the weakly predicted strand at 126–130 (in the rearranged alignment) suggests that this segment would form the edge of a beta-sheet. Hence, while the exact location of the inserted hairpin remains speculative, it is not likely to be part of the main sheet in the domain.

Next, the sequence of the "lid" segment of DNA gyrase B (not shown, residues 36–113 in the gyrase from *E. coli*) is not sufficiently similar to any segment in the corresponding region of HSP90 to permit a speculative alignment in this region. While the segment is still predicted to contain helical and coil segments and to form a "lid" anchored at the glycine-rich sequence motifs DXGXG (alignment positions 151–155) and GXXGXG (195–200), the tertiary structure must be remodelled ab initio to obtain a more precise definition of conformation. As a biochemical clue for the modelling, the conserved serine at position 171 was proposed to be the site of the autophosphorylation events observed by Csermely et al. [Csermely P., Kahn C. R. The 90-kDa heat shock protein (HSP-90) possesses an ATP binding site and autophosphorylating activity. J. Biol. Chem. 266, 4943–4950 (1991)]. As an alternative explanation for the poor correspondence in the "lid" segment, ATP might not be bound in the exact same conformation by the two proteins. Finally, the N-terminal 25 residues (corresponding to alignment positions 71–95 for the heat shock proteins) are not part of the core in our template. Thus, the relative orientation of the predicted helix at positions 85–95 and the extended N-terminus could be slightly different.

Example 3
Identifying mutations and in vitro properties of seminal ribonuclease that contribute to selected function.

Bovine seminal ribonuclease (RNase) diverged from bovine pancreatic RNase approximately 35 million years ago. Seminal RNase represents approximately 2% of the total protein in bovine seminal plasma. It displays antispermatogenic activity [Dostal, J., Matousek, J. (1973) Isolation and some chemical properties of aspermatogenic substance from bull seminal vesicle fluid. *J. Reprod. Fertil.* 33, 263–274], immunosuppressive activity [Soucek, J., Matousek, J. (1981) Inhibitory effect of bovine seminal ribonuclease on activated lymphocytes and lymphoblastoid cell lines in vitro. *Folia Biol. Praha* 27, 334–345. Soucek, J., Hrubá, A., Paluska, E., Chudomel, V., Dostál, J., Matousek, J. (1983) Immunosuppressive effects of bovine seminal fluid fractions with ribonuclease activity. *Folia biologica* (Praha) 29, 250–261. Soucek, J., Chudomel, V., Potmesilova, I., Novak, J. T. (1986) Effect of ribonucleases on cell, mediated lympholysis reaction and on GM, CFC colonies in bone marrow culture. *Nat. Immun. Cell Growth Regul.* 5, 250–258], and cytostatic activity against many transformed cell lines [Matousek, J. (1973) The effect of bovine seminal ribonuclease on cells of Crocker tumor in mice. *Experientia* 29, 858. Vescia, S., Tramontano, D., Augusti-Tocco, G., D'Alessio, G. (1980) In vitro studies on selective inhibition of tumor cell growth by seminal ribonuclease. *Cancer Res.* 40, 3740 ] Each of these biological activities is essentially absent from pancreatic RNase. Further, seminal RNase binds to anionic glycolipids, binds and melts duplex DNA, hydrolyzes duplex RNA, has a dimeric quaternary structure, and binds to spermatozoa.

Each of these behaviors is measured in vitro and is well known in the art. In the absence of the method of the instant invention, the behaviors are difficult to interpret. Some, any, or all of the behaviors might serve an adaptive role. It is possible that none of these behaviors serve adaptive roles. Indeed, it is conceivable that the protein has no adaptive role at all. This makes it difficult to make even the simplest research decisions, as the only in vitro properties of a protein that are interesting to study are those that have a physiological function.

To resolve these issues, genes for seminal and pancreatic RNases were obtained from a variety of organisms closely related to *Bos taurus*, using cloning procedures well known in the art. These were then sequenced, and a maximum parsimony tree was constructed using MacClade. From this tree were calculated the sequences of RNases that were intermediates in the evolution of the seminal RNase, using the maximum parsimony method well known in the art.

Next, the ratio of expressed to silent substitutions was calculated along each branch of the evolutionary tree. A very high ratio of expressed to silent substitutions was observed in the evolutionary period following the divergence of kudu [Trabesinger-Rüf, N., Jermann, T. M., Zankel, T. R., Durrant, B., Frank, C., Benner. S. A. Pseudogenes in ribonuclease evolution. A source of new biomacromolecular function? *FEBS Lett.* 382, 319–322 (1996)] from the lineage leading to ox, until the divergence of water buffalo and ox. This is indicative of an episode of adaptive evolution, where the protein acquires a new physiological function. Further work indicated that the seminal RNase gene was not expressed in the period of evolution since the divergence of the seminal RNase family and the divergence of kudu.

Last, protein engineering methods were used to prepare the seminal RNase that was at the beginning of the episode of rapid sequence evolution. It properties were then examined experimentally. It was discovered that the ability of the protein to bind to anionic glycolipids was roughly the same before and after this episode of rapid evolution. So too was its sensitivity to inhibition by placental RNase inhibitor. Thus, both of these properties are not likely to be under selective pressure.

In contrast, the immunosuppressivity of the ancestral RNase ($IC_{50}$ ca. 8 micrograms/mL) was greater than that of pancreatic RNase ($IC_{50}$ ca. 100 micrograms/mL). But following the period of rapid sequence evolution characteristic of a protein evolving to serve a new physiological function, the immunosuppressivity became still greater ($IC_{50}$ ca. 2 micrograms/mL). Thus, one concludes that immunosuppressivity as measured in vitro is a selected trait of the protein, or is closely structurally coupled to a trait that is selected.

Likewise, the ability of the seminal RNase protein to bind and melt duplex DNA, and to hydrolyze duplex RNA, also underwent rapid increase between the time of divergence of kudu from modern ox. Thus, it too is either a selected trait of the protein, or is closely structurally coupled to a trait that is selected.

Example 4
Assignment of episodes of adaptive evolution in the protein leptin, and placing these in predicted secondary structural elements.

From the GenBank database, DNA and protein sequences were retrieved for the genes encoding leptins and the corresponding proteins, also known as the obesity gene product. A multiple alignment for the protein sequences was constructed for the DNA sequences and the protein sequences. These were converted to a file suitable for MacClade to use. For both the DNA and protein sequences, a tree using MacClade was built based on the known relationship between the organisms from which these sequences were derived; this proved to be the most parsimonious tree as well. MacClade was also used to built a tree for the protein sequences based on the known relationship between organisms; this proved not to be the most parsimonious tree (by 1 change). The DNA tree was taken to be definitive because of its consistency with the biological (cladistic) data showing that the primates form a lade.

A secondary structure prediction was made for the protein family using the tools disclosed in Ser. No. 07/857,224. The evolutionary divergence of the sequences available for the leptin family is small; only 21 PAM units (point accepted mutations per 100 amino acids), predictions were biased to favor surface assignments [Benner, S. A., Badcoe, I., Cohen, M. A., Gerloff, D. L. Bonafide prediction of aspects of protein conformation. Assigning interior and surface residues from patterns of variation and conservation in homologous protein sequences. *J. Mol. Biol.* 235, 926–958 (1994)]. Thus, positions holding conserved KREND were assigned as surface residues, conserved H and Q were assigned to the surface as well, while positions holding conserved CST were assigned as uncertain suface and interior assignments are summarized in Table 3.

A secondary structure was then predicted for the leptins using the methods disclosed in Ser. No. 07/857,224. The multiple alignment is shown in Table 3. Five separate secondary structural elements were identified results are summarized in Table 3. A disulfide bond is presumed to connect positions 96 and 146. These secondary structural elements can be accommodated by only a small number of overall folds. Interestingly, the pattern of secondary structure in this prediction is consistent with an overall fold that resembles that seen in cytokines such as colony stimulating factor [Hill, C., P., Osslund, T. D., Eisenberg, D. (1993) *Proc. Nat. Acad. Sci.* 90, 5176–5181] and human growth hormone [de Vos, A. M., Ultsch, M. & Kossiakoff, A. A. (1992). *Science* 255, 306–312].

To decide whether evolutionary function may have changed under selective pressure during the divergent evolution of the protein family, a multiple alignment of the protein sequences and a multiple alignment for the corresponding DNA sequences were constructed. A MacClade-generated maximum parsimony tree was printed for each position in the protein sequence where there was a change, and for each position in the DNA sequence where there was a change. Each mutation on each tree was examined by hand, and silent and expressed mutations occurred were assigned to individual branches on the evolutionary tree. For each branch of the tree, the sum of the number of silent and expressed changes were tabulated, and the ratio of expressed to silent changes calculated. These are shown in Drawing 1. Tables 4 and 5 contain the data used in this example.

The branches on the evolutionary tree leading to the primate leptins from their ancestors at the time that rodents and primates diverged had an extremely high ratio of expressed to silent changes. From this analysis, it was concluded that the biological function of leptins has changed significantly in the primates rlative to the function of the leptin in the common ancestor of primates and rodents.

Example 5

Core and non-core regions of phospho-beta-galactosidase.

To illustrate the application of tools for defining core secondary structural elements, the phospho-beta-galactosidase superfamily was examined. This was recorded in [Gerloff, D. L., S. A. Benner. A consensus prediction of the secondary structure for the 6-phospho-beta-D-galactosidase superfamily. *Proteins. Struct. Funct. Genet.* 21, 273–281 (1995)], and analyzed in [Benner, S. A., Gerloff, D. L, Chelvanayagam, G. The phospho-β-galactosidase and synaptotagmin predictions. *Proteins. Struct. Funct. Genet.* 23, 446–453 (1995)]. This is an excellent target for placing the method to a test. The protein is large; the target sequence has 468 amino acids. The protein family appears to adopt quaternary structure, at least in some cases. Both the thioglucosidase from *Brassica napus* (rape) and the thioglucosidase from *Sinapis alba* (white mustard) are reported to be homodimers, while the beta-galactosidase from *Sulfolobus solfataricus* (not shown in the alignment) is a homotetramer. This implies that quaternary contacts might bury some residues that are on the surface of subunits, complicating the secondary structure prediction. Further, there has been substantial divergence in biological function within the protein family, as measured by a wide divergence in substrate specificity in the member proteins.

A multiple alignment for the protein family was built from sequences extracted from SwissProt 29 using the DARWIN system. Surface and interior residues were assigned by procedures disclosed in Ser. No. 07/857,224, the multiple alignment was parsed into units forming independent secondary structures, and elements of secondary structure were predicted within the parsed segments from patterns of conservation and variation, as described in Serial No. 07/857,224. Many of the automated routines used in this prediction are available to the public on a server accessible via electronic mail at the address cbrg@inf.ethz.ch, or using the World Wide Web (WWW) with URL http://cbrg.inf.ethz.ch/.

The secondary structure prediction is presented residue-by residue in Table 7, and summarized in Table 6. A summary of the secondary structure prediction follows:

Strand A (a009–a011;b049–051) is a short internal segment confirmed in both subfamilies.

Strand B (a014–020;b053–060) is separated from strand A by a GG dipeptide in a well anchored region of the alignment. It is largely internal. This region is interesting from a methodological point of view, as a strong assignment would not have been possible if only one of the two subfamilies were available. In both subfamilies considered alone, an internal helix would be possible. Together, however, a GG dipeptide parse at (a012–103) and a GG dipeptide parse at positions (b062–063), together with strong alignment anchoring excludes an internal helix in this region.

Parse region (a048–059;b071–081) is problematic. Subfamily b could contain a beta strand in this region (b073–078). However, it is matched with a parsing string (PGDSG; a050–054) in sequence e of subfamily a, and a strand was not assigned.

Helix 1 (a072–084;b095–107) is reliably assigned in both subfamilies, is well anchored, and displays good amphiphilicity.

Strand C (a089–093; b111–115) is problematic in subfamily a, in part because of the small number of sequences available in this subfamily. In subfamily b, the surface and interior assignments display alternating periodicity, which confirms the strand assignment.

Active site a (a095–102;b117–125) contains conserved Arg, Ser, Trp and Arg. It is strongly assigned.

Helix 2 (a116–130; b138–153) is reliably assigned in both subfamilies, is well anchored, and displays good amphiphilicity.

Strand D (a136–140;b159–163) is well parsed in subfamily 2, is confirmed in both subfamilies, and is largely internal.

Active site b (a141;b164–166) contains conserved Thr (part of the preceding strand) and His.

Helix 3 (a158–177;b181–198) is reliably assigned in both subfamilies, is well anchored, and displays good amphiphilicity.

Strand E (a182–185;b205–208) is assigned to a region that is near the active site, where conservation associated with active site function often obscures patterns of variation and conservation that might be used to assign secondary structure.

Active site c (a184–187;b205–209) is relatively weak, be based ultimately on a single conserved Asn. A conserved Thr two residues before supports this conclusion. Interesting, a Trp two residues earlier is almost completely conserved in the superfamily as well, as is a Glu immediately following the conserved Asn.

A region (b212–215) following this active site segment might be assigned as a beta strand in subfamily b. It is not paired with a reliable assignment in subfamily a, which contains repeated parsing elements that almost certainly exclude a standard secondary structural element in this area. A similar beta strand might be assigned in subfamily b (b219–221); this again has no corresponding element in subfamily a, and might form a beta hairpin with the preceding strand. The alignment is poorly anchored in this region, and considerable sequence divergence between the two subfamilies is evident.

Helix 4 (a212–226;b248–268) is cleanly amphiphilic up to position a227, when an interior assignment appears on the surface arc of the amphiphilic helix. The following segment also forms a short (8 residues) amphiphilic helical pattern. In subfamily b, the helix is largely internal. Nevertheless, to the extent that amphiphilicity is detected, it extends past the position where the amphiphilic pattern is broken. This indicates that the contacts made in subfamily a are different from those made in subfamily b. Interestingly, this helix contains a conserved His (a218;b255) and a nearly conserved His (a224;b261).

Strand x (a242–245) is cleanly parsed in subfamily a, and is canonically assigned as a short beta strand. The segment is disrupted by parsing elements in subfamily b, which appears to be well anchored. It is possible to identify a plausible beta segment in this subfamily. Our experience, however, has been that the experimental assignments made for such regions depends strongly on the experimental secondary structure assignment tool.

Helix x (a259–273) is not cleanly amphiphilic (position a269), but is assigned nevertheless when considering subfamily a alone. A gap is placed in its middle in subfamily b (positions b311–312). If the multiple alignment of subfamily b2 is rearranged, a helix can be detected from positions (b303–317; total length 13 positions). If the multiple alignment of subfamily b1 is adjusted, and the sequence with the deletion discarded, a weak helix can also be found. The ambiguous alignment makes all of these assignments insecure, however, and there is significant possibility that the conformations of different members of the superfamily are quite different.

Strand y (a275–280) is assigned in subfamily a only. It corresponds to a parsed region in subfamily b. Two interior residues (b323–324) might form a corresponding structure, however, in subfamily b.

The amphiphilicity of helix 5 (a286–293;b332–342) is difficult to detect when examining the alignment overall. Examining subalignments, especially of subfamily b1 and subfamily b2, makes the amphiphilicity clearer.

The region (a314) might be assigned as a short helix (7–10 residues) if the left side of subfamily a is examined alone. There is no confirmation of this helix elsewhere, however, as this region of the alignment has undergone massive sequence divergence.

Strand F (a323–327;b381–388) is badly parsed in subfamily a. The segment is conceivably a continuation of a putative helix that may follow. In subfamily b, the strand is more reliably assigned. An excellent set of anchors align the subalignments, and we have chosen on these grounds to make the assignment definitive in the consensus secondary structure model.

Helix y (a329–339) is short, and contains a problematic residue at position (a336). There is no confirmation for a helix assignment in subalignment b. The ambiguous alignment makes this assignment further insecure, and there is significant possibility that the conformations of different members of the superfamily are quite different.

Strand z (a375–382) is assigned in a region of the multiple alignment that has undergone massive sequence divergence, and where DARWIN had extreme difficulties achieving a plausible matching. It has plausible amphiphilicity in subfamily a. Therefore, the multiple alignment in subfamily b was collapsed in an effort to obtain regions that might also form beta strands. For subfamily b1, segment (b446–452) displayed an alternating pattern. For subfamily b2, this was not possible, although it cannot be excluded that further rearrangement of the multiple alignment upon refinement could find an analogous region. As time was inadequate to do a complete search of different possible multiple alignments, no strand was assigned in this region in the consensus model.

Helix 6 (a385–398;b456–469) is well parsed, well anchored, amphiphilic, and confirmed in both subfamilies. It might, however, be missing one turn in some proteins in subfamily b.

Strand G (a404–407;b476–479) is well parsed, internal, and confirmed in both subfamilies.

Active site d (a408–410;b480–482), containing conserved Glu, Asn, and Gly, is not strongly assigned by analysis of the sequences themselves. It is, however, supported by biochemical work [Wacker, H., Keller, P., Falchetto, R., Legler, G., Semenza, G. Location of the two catalytic sies in intestinal lactase-phlorizin hydrolase. J. Biol. Chem. 267:18744–18752 (1992)].

Helix 7 (a431–448;b497–517) is well parsed, well anchored, amphiphilic, and confirmed in both subfamilies.

Residues (a451–a482;b522–554) form a remarkable segment. In subfamily b, the segment is not parsed for 35 residues, has a large number of interior residues, and apparently contains more than one secondary structural element. The first task is to parse this section. To this end, four additional columns were added to the multiple alignment by recognizing that lactase phlorizin hydrolase has multiple internal repeats. Interestingly, in two of these repeats, a parsing string PG appears. However, the repeats that contain this parsing string are cleaved proteolytically during the post-translational modification. These repeats are also missing Glu (b480), presumed to be part of an active site. Thus, there is no guarantee that these repeats have divergently evolved under functional constraints. This example makes an important point regarding the analysis of homologous sequences in the prediction of a protein structure.

In this region, an internal helix must be considered. Assignment of internal helices (as opposed to internal strands) relies on accurate parsing. The two subalignments were first carefully anchored. A reliable parse at (a471) was matched with a weak parse at (b541). A dipeptide GP parse in subfamily a (a460–462) was used to divide the first part of this segment. The conserved Asp was assumed to also indicate a break in secondary structure (as opposed to being an indicator of an active site position). This led to the assignment of four secondary structural elements in this region as follows:

Strand H (a450–454;b521–525) is amphiphilic and confirmed in both subfamilies.

Strand I (a456–459;b527–530) is interior and confirmed in both subfamilies. It may be longer by two residues in subfamily b.

Strand J (a464–467;b535–539) is interior and confirmed in both subfamilies.

Strand K (a478–482;b548–554) is interior, well anchored, and confirmed in both subfamilies.

Finally, helix 8 (a496–509;b563–576) is amphiphilic, well anchored, and confirmed in both subfamilies.

In examining the consensus secondary structural model reported in Table 1, it is difficult not to notice the secondary structural pattern characteristic of an eight-fold alpha-beta barrel protein. This tertiary structural hypothesis does not rest solely on pattern recognition. The model is, in fact, enforced to a large degree by the active site assignments designated in the Table. Here, beta strands C, D, E, and G all must terminate near the active site of the protein, as in an eight fold alpha beta barrel. While other topologies could also bring these residues together, this was our preferred tertiary structural model in a bonafide prediction setting

[Gerloff, D. L., S. A. Benner. A consensus prediction of the secondary structure for the 6-phospho-beta-D-galactosidase superfamily. *Proteins. Struct. Funct. Genet.* 21, 273–281 (1995)]. This assignment of topology was subsequently shown to be correct [Benner, S. A., Gerloff, D. L, Chelvanayagam, G. The phospho-β-galactosidase and synaptotagmin predictions. *Proteins. Struct. Funct. Genet.* 23, 446–453 (1995)].

TABLE 1

Residue-by-residue consensus secondary structure prediction for the heat shock protein HSP90 family. The SIA column records assignments of positions to the surface (S, s), interior (I, i) or near the "active site" (A, a) using the method disclosed in Serial No. 07/857,224. Automated assignments are given, with the output generated by DARWIN. Services of DARWIN are available by server to the user on the Web (URL http://cbrg.inf.ethz.ch/). Secondary structure is indicated by E (strong strand assignment), e (weak strand assignment), H (strong helix assignment), and h (weak helix assignment). Sequences, designated using single letters, are from the SwissProt database and Genbank, as summarized below. Sequence "a" is the target sequence. The column marked "Auto" contains output from the fully automated secondary structure prediction tool. The column marked "Manual" contains assignments from semi-manual analysis of the same data. The column marked "3D refined" contains secondary structure assignments made after comparison with the experimentally-determined structure of the N-terminal domain of DNA gyrase B, where a * indicates where a shift in the alignment is required. The sequences key:

| | | |
|---|---|---|
| a -- | (P02829) | HS82_YEAST HEAT SHOCK PROTEIN HSP90. Saccharomyces cerevisiae SEQ.ID.NO.:1 |
| b -- | (P15108) | HS83_YEAST HEAT SHOCK COGNATE PROTEIN HSC82. Saccharomyces cerevisiae SEQ.ID.NO:2 |
| c -- | (P46598) | HS90_CANAL HEAT SHOCK PROTEIN 90 HOMOLOG. Candida albicans SEQ.ID.NO:3 |
| d -- | (P41887) | HS90_SCHPO HEAT SHOCK PROTEIN 90 HOMOLOG. Schizosaccharomyces pombe SEQ.ID.NO:4 |
| e -- | (P33125) | HS82_AJECA HEAT SHOCK PROTEIN 82. Ajellomyces capsulata (histoplasma capsulatum). SEQ.ID.NO:5 |
| f -- | (Q04619) | HS9B_CHICK HEAT SHOCK COGNATE PROTEIN HSP 90-BETA. Gallus gallus SEQ.ID.NO:6 |
| g -- | (P33126) | HS82_PRYSA HEAT SHOCK PROTEIN 82. Pryza sativa SEQ.ID.NO:7 |
| h -- | (Q03930) | HS81_ARATH HEAT SHOCK PROTEIN 81 (HSP81-1). Arabidopsis thaliana SEQ.ID.NO:8 |
| i -- | (P36181) | HS80_LYCES HEAT SHOCK COGNATE PROTEIN 80. Lycopersicon esculentum SEQ.ID.NO:9 |
| j -- | (Q08277) | HS82_MAIZE HEAT SHOCK PROTEIN 82. Zea mayz SEQ.ID.NO:10) |
| k -- | (P04809) | HS83_DROPS HEAT SHOCK PROTEIN 83 (HSP 82) (FRAGMENT). Drosophila pseudoobscura SEQ.ID.NO:11 |
| l -- | (P46633) | HS9A_CRIGR HEAT SHOCK PROTEIN HSP 90-ALPHA (HSP 86). Cricetulus griseus SEQ.ID.NO:12 |
| m -- | (P07900) | HS9A_HUMAN HEAT SHOCK PROTEIN HSP 90-ALPHA (HSP 86). Homo sapiens SEQ.ID.NO:13 |
| n -- | (P-2828) | HS83_DROME HEAT SHOCK PROTEIN 83 (HSP 82). Drosophila melanogester SEQ.ID.NO:14 |
| o -- | (P08238) | HS9B_HUMAN HEAT SHOCK PROTEIN HSP 90-BETA (HSP 84) (HSP 90). Homo sapiens SEQ.ID.NO:15 |
| p -- | (P11501) | HS9A_CHICK HEAT SHOCK PROTEIN HSP 90-ALPHA. Gallus gallus. SEQ.ID.NO:16 |
| q -- | (P06660) | HS85_TRYCR HEAT SHOCK LIKE 85 KD PROTEIN. Trypanosoma cruzi. SEQ.ID.NO:17 |
| r -- | (P24724) | HS90_THEPA HEAT SHOCK PROTEIN 90 (HSP90). Theileria parva. SEQ.ID.NO:18 |
| s -- | (P27741) | HS83_LEIAM HEAT SHOCK PROTEIN 83 (HSP 83). Leishmania amazonensis, SEQ.ID.NO:19 |
| t -- | (P12861) | HS83_TRYBB HEAT SHOCK PROTEIN 83. Trypanosoma brucei brucei. SEQ.ID.NO:20 |
| u -- | (P36183) | EMPL_HORVU ENDOPLASMIN HOMOLOG PRECURSOR (GRP94 HOMOLOG). Hordeum vulgare (barley). SEQ.ID.NO:21 |
| v -- | (P35016) | ENPL_CATRO ENDOPLASMIN HOMOLOG PRECURSOR (GRP94 HOMOLOG). Catharanthus roseus SEQ.ID.NO:22 |
| w -- | (P08110) | ENPL_CHICK ENDOPLASMIN PRECURSOR (TRANSFERRIN-BINDING PROTEIN). Gallus gallus SEQ.ID.NO:23 |
| x -- | (P41148) | ENPL_CANFA ENDOPLASMIN PRECURSOR (94 KD GLUCOSE-REGULATED PROTEIN) (GRP94). Canis familiaris SEQ.ID.NO:24 |
| y -- | (P14625) | ENPL_HUMAN ENDOPLASMIN PRECURSOR (94 KD GLUCOSE-REGULATED PROTEIN) (GRP94). Homo sapiens SEQ.ID.NO:25 |
| z -- | (P08113; P11427) | ENPL_MOUSE ENDOPLASMIN PRECURSOR (94 KD GLUCOSE-REGULATED PROTEIN) (GRP94). Mus musculus SEQ.ID.NO:26 |

TABLE 1-continued

Residue-by-residue consensus secondary structure prediction for the heat shock protein HSP90 family. The SIA column records assignments of positions to the surface
(S, s), interior (I, i) or near the "active site" (A, a) using the method disclosed in Serial No.
07/857,224. Automated assignments are given, with the output generated by DARWIN. Services of DARWIN are available by server to the user on the Web (URL http://cbrg.inf.ethz.ch/). Secondary structure is indicated by E (strong strand assignment), e
(weak strand assignment), H (strong helix assignment), and h (weak helix assignment). Sequences, designated using single letters, are from the SwissProt database and Genbank, as
summarized below. Sequence "a" is the target sequence. The column marked "Auto" contains output from the fully automated secondary structure prediction tool. The column marked "Manual" contains assignments from semi-manual analysis of the same data. The column marked "3D refined" contains secondary structure assignments made after comparison with the
experimentally-determined structure of the N-terminal domain of DNA gyrase B, where a *
indicates where a shift in the alignment is required. The sequences key:

```
A -- (P44516)          HTPG_HAEIN HEAT SHOCK PROTEIN HTPG. SEQ.ID.NO:27
                       Haemophilus influenzae.
B -- (P10413)          HTPG_ECOLI HEAT SHOCK PROTEIN HTPG. SEQ.ID.NO:28
                       Escherichia coli.
C -- (P46208)          HTPG_BACSU HEAT SHOCK PROTEIN HTPG HOMOLOG. SEQ.ID.NO:29
                       Bacillus subtilis.
D -- (Gb_ro:S45392/    HEAT SHOCK PROTEIN 90. Rattus sp. brain SEQ.ID.NO:30
      PID:g256089)
E -- (Gb_              HEAT SHOCK PROTEIN 83 (HSP83) GENE.
pl:Phnhsp83a/
PID:g169296)           Pharbitis nil (strain violet). SEQ.ID.NO:31
```

```
 95|T|SS|SSSSS S SSS SSSSS SSSSSSSS|KKKK SS|   s H H H
 96|Q|NN|NNNNN N NNN NNNNN NNNNNNNN|NNNN NN|   s   H
 97|K|KK|KKKKK K KKK KKKKK KKKKKKKK|KKKK KK|   s A a h
 98|E|EE|EEEEE E EEE EEEEE EEEEEEEE|EEEE DD|   s   a H
 99|I|II|IIIII I III IIIII IIIIIIII|IIII II|   i A a H
100|F|FF|FFFFF F FFF FFFFF FFFFFFFF|FFFF FF|   i A a H
101|L|LL|LLLLL L LLL LLLLL LLLLLLLL|LLLL LL|   i A a H
102|R|RR|RRRRR R RRR RRRRR RRRRRRRR|RRRR RR|   s A a H
103|E|EE|EEEEE E EED EEEEE EEEEEEEE|EEEE EE|   s   a H
104|L|LL|LLLLL L LLV LLLLL LLLLLLLL|LLLL LL|   I A a H
105|I|II|IIIII I III IIIII IIIIIIII|IIII II|   i A a H
106|S|SS|SSSSS S SSS SSSSS SSSSSSSS|SSSS SS|P  A a H
107|N|NN|NNNNN N NNN NNNNN NNNNNNNN|NNNN NN|P s a H
108|S|AA|AFAAA A SSA AASSS AASSSAAA|AAAA AA|P i A a H
109|S|SS|"SSSSS S SSS SSSSS SSSSSSSS|SSSS SS|P . A a H
110|D|DD|DDDDD D DDD DDDDD DDDDDDDD|DDDD DD|P s A a H
111|A|AA|AAAAA A AAA AAAAA AAAAAAAA|AAAA AA|   i   a h
112|I|AA|LLLLL L CCC LLLLL LLLLLLLL|LLLL LL|   I   a h
113|D|DD|DDDDD E DDD DDDDD DDDDDDDD|DDDD DD|   s A a
114|K|KK|KKKKK K KKK KKKKK KKKKKKKK|KKKK KK|   s   e
115|I|LL|IIIII I III IIIII IIIIIIII|IIII II|   I E E e
116|Y|RR|RRRRR R RRR RRRRR RRRRRRRR|RRRR RR|   s E E E
117|Y|FF|YYYYY Y YYY FFFFF YYYYYYYY|LLLL FF|   I E E E
118|K|KR|QKQQK E QQQ EEEEE EEEEEEEE|IIII LL|   S E E E
119|A|AA|SAAAS A SSS SSSSS SSSTSSSS|SSSS AA|   s E E E
120|L|LL|LLLLL I LLL LLLLL LLLLLLLL|LLLL LL|   I E E E
121|T|SS|SSSSS K TTT TTTTT TTTTTTTT|TTTT TT|P  .   e
122|D|NN|DDDDD D NND DDDDD DDDDDDDD|DDDD DD|P s
123|D|PP|PPPPP P QQP KKKKK PPPPPPPP|EEEE KK|P S
124|A|AD|HSSKK K SAS SSSSS SSSSSSSS|NNNN EE|P S
125|L|LL|AKQQQ Q VVV NKKKK KKKKKKKK|AAAA VI|  S
126|_|__|_____ _ ___ ___PLUS CODE 123 IS NOT DEFINED ___ _____|____
 ML|P . |        e*
127|_|__|_____ _ ___ ___PLUS CODE 123 IS NOT DEFINED ___ _____|____
 GG|P i |        e*
128|T|YY|LLLLL I LLL VLLLL LLLLLLLL|LLLL EE|   i        e*
129|F|EE|DEEEE E GGG NDDDD DDDDDDDD|AASA GG|P S        e*
130|D|GG|ASSTT D DDD AAGGA SSSSSSST|GGGG DD|P S        e*
131|K|DD|EDEEE Q EEA QQQQQ GGGGGGGG|NNNN TT|P S
132|D|GG|KKPPP P PST PPPPP KKKKKKKK|EEEE AA|P S
133|S|DE|DDEDD D HHR EEEEE EEDEEEED|EEEE KK|P S   E
134|Y|LL|LLLLL Y LLL LLLLL LLLLLLLL|LLLL LL|   I E E E
135|Y|RR|FRFFF Y RRC FFFFF YYKHHKKK|TTTT EE|   S E E E
136|I|VV|IIIII I IIV IIIII IIIIIIII|VVVV II|   I E E E
137|K|RR|RDRRR R RRR RRRHH KKNNNDDD|KKKK QQ|   S E E E
138|V|VV|IIIII L VVV LLLII LLLLIIII|IIII II|   I E E E
139|A|SS|TTITT Y IVV VVVIV IIIIIIIV|KKKK KK|   i E E E
```

TABLE 1-continued

Residue-by-residue consensus secondary structure prediction for the heat shock protein HSP90 family. The SIA column records assignments of positions to the surface (S, s), interior (I, i) or near the "active site" (A, a) using the method disclosed in Serial No. 07/857,224. Automated assignments are given, with the output generated by DARWIN. Services of DARWIN are available by server to the user on the Web (URL http://cbrg.inf.ethz.ch/). Secondary structure is indicated by E (strong strand assignment), e (weak strand assignment), H (strong helix assignment), and h (weak helix assignment). Sequences, designated using single letters, are from the SwissProt database and Genbank, as summarized below. Sequence "a" is the target sequence. The column marked "Auto" contains output from the fully automated secondary structure prediction tool. The column marked "Manual" contains assignments from semi-manual analysis of the same data. The column marked "3D refined" contains secondary structure assignments made after comparison with the experimentally-determined structure of the N-terminal domain of DNA gyrase B, where a * indicates where a shift in the alignment is required. The sequences key:

```
140|A|FF|PPPPP A PPP PPPPP PPPPPPPP|CCCC LL|P i    e
141|D|DD|DDQKK D DDD DDDDD NNNNNNNN|DDDD DD|P s
142|K|AK|KKKPP K RKK KKKKK KKKKKPPP|KKKK KK|P S
143|D|DD|EEDEE N VAE ATSAA TTHQQQQR|EEEE EE|P S
144|A|KK|NNQEQ|N NNN SNNNS AADDDEED|KKKK NK|P S
145|R|GR|KKKKK N KKK KKKNN GGRRRARP|NNNN KK|P S
146|T|TT|ITVVV T TTT TTTTT TTTTTTTT|MLLL II|  I E E E
147|L|IL|LLLLL L LLL LLLLL LLLLLLLL|LLLL LL|  I E E E
148|T|TT|TTEEE T TTT SSSTS TTTTTTTT|HHHH SS|  s E E E
149|I|II|IIIII I VVV IIIII IIIIILLL|VVVV II|  I E E E
150|S|SS|RRRRR E EEE IIIII IIVVVVVL|TTTT RR|  S E E E
151|D|DD|DDDDD D DDD DDDDD DDDDDDDD|DDDD DD|P S A E E
152|T|NN|TTSSS S STN SSSSS TTTTTTTT|TTTT RR|P s   E e
153|G|GG|GGGGG G GGG GGGGG GGGGGGGG|GGGG GG|P i
154|I|IV|IIIII I III VVIII IIIIIIII|IVVV VI|P I    e
155|G|GG|GGGGG G GGG GGGGG GGGGGGGG|GGGG GG|P i   e
156|M|MM|MMMMM M MMM MMMMM MMMMMMMM|MMMM MM|  I    e
157|T|TT|TTTTT T TTT TATTT TTTTTTTT|TTTT TT|  I    e
158|K|RR|KKKKK K KKK KKKKK KKKKKKKK|KRRR KK|  s
159|D|ED|NAAAA A AAA SAAAS SSAAAAAA|EEEE EE|  s H h H
160|E|QE|DDDEE D DED DDDDD DDDDDDDD|EEEE DD|  S H h H
161|L|VV|LLLLL L LLL LLLLL LLLLLLLL|LLLL LL|  I H h H
162|E|II|IVVII V VVV VVVVV VVVIIIIV|IVVV II|  i H h H
163|Q|DD|NNNNN N NNN NNNNN NNNNNNNN|KKKK KK|  s H h H
164|H|HH|NNNNN N NNN NNNNN NNNNNNNN|NNNN NN|  s H h H
165|L|LL|LLLLL L LLL LLLLL LLLLLLLL|LLLL LL|  i H h h
166|G|GG|GGGGG G GGG GGGGG GGGGGGGG|GGGG GG|  i H h
167|T|TT|VTTTT T TTT TTTTT TTTTTTTT|TTTT TT|  I
168|I|II|IIIII I III IIIII IIIIIIII|IIII II|  i
169|A|AA|AAAAA A AAA AAAAA AAAAAAAA|AAAA AA|  i
170|K|KK|KRKKK K RRR RRRRR KKKKKKKK|KKKK KK|  s
171|S|SS|SSSSS S SSS SSSSS SSSSSSSS|SSSS SS|  . A
172|G|GG|GGGGG G GGG GGGGG GGGGGGGG|GGGG GG|  i A
173|S|TT|TTTTT T TTT TTTTT TTTTTTTT|TTTT TT|  i   H h
174|L|KK|KKKKK R KKK KKKKK KKKKKKKK|SSSS SS|  s   H H
175|A|ES|QQSAA A SAA EEEE AAAAAAAA|EEEE AA|  S   H H
176|F|FF|FFFFF F FFF FFFFF FFFFFFFF|FFFF FF|  i   H H
177|K|LL|MMMMM M MMM MMMMM MMMMMMMM|LLLL VV|  i   H H
178|K|TE|____ _ ___ _____ _____|NNNN __|P S h
179|_|_|____ _ ___ _____ _____|KKKK __|P s    h
180|_|_|____ _ ___ _____ _____|MMMM __|P i    h
181|_|_|____ _ ___ _____ _____|TTTT __|P      h
182|E|AS|EEEEE E EEE EEEEE EEEEEEEE|EEEE EE|  s   H H
183|N|LL|AAAAA A AAA AAAAA AAAAAAAA|MAAA KK|  .   H H
184|E⊕GG|ALLLL L LLL LLLLL LLLLLLLL|QQQQ MM|  i   H H
185|L|QS|ATSSS Q EEE AQQAA QQQQQQQQ|DEEE QQ|  s   h h
186|K|DD|SAAAA A AAA AAAAA AAAAAAAA|DDDD TT|  s
187|D|QQ|GGGGG G GGG GGGGG GGGGGGGG|SGGG GS|  s
188|G|AA|AAAAA S GGA AAAAA AAAAAAAA|QQQQ GG|  s
189|_|KK|____ _ ___ T___ _____|SSSS __|P s
190|_|ND|DDDDD D DDD DDDDD DDDDDDDD|TTTT DD|  s
191|H|SS|IIVVV M MMM VVVVV IIIIIIII|SSSS LL|  i
192|D|QQ|SSSSS S SSS SSSSS SSSSSSSS|EEEE NN|  s
193|I|LL|MMMMM M MMM MMMMM MMMMMMMM|LLLL LL|  I
194|I|II|IIIII I III IIIII IIIIIIII|IIII II|  i   a
195|G|GG|GGGGG G GGG GGGGG GGGGGGGG|GGGG GG|  i   a
196|Q|QQ|QQQQQ Q QQQ QQQQQ QQQQQQQQ|QQQQ QQ|  .   a
197|F|FF|FFFFF F FFF FFFFF FFFFFFFF|FFFF FF|  i   a
```

TABLE 1-continued

Residue-by-residue consensus secondary structure prediction for the heat shock protein HSP90 family. The SIA column records assignments of positions to the surface (S, s), interior (I, i) or near the "active site" (A, a) using the method disclosed in Serial No. 07/857,224. Automated assignments are given, with the output generated by DARWIN. Services of DARWIN are available by server to the user on the Web (URL http://cbrg.inf.ethz.ch/). Secondary structure is indicated by E (strong strand assignment), e (weak strand assignment), H (strong helix assignment), and h (weak helix assignment). Sequences, designated using single letters, are from the SwissProt database and Genbank, as summarized below. Sequence "a" is the target sequence. The column marked "Auto" contains output from the fully automated secondary structure prediction tool. The column marked "Manual" contains assignments from semi-manual analysis of the same data. The column marked "3D refined" contains secondary structure assignments made after comparison with the experimentally-determined structure of the N-terminal domain of DNA gyrase B, where a * indicates where a shift in the alignment is required. The sequences key:

```
198|G|GG|GGGGG G GGG GGGGG GGGGGGGG|GGGG GG|P i    a
199|V|VV|VVVVV V VVV VVVVV VVVVVVVV|VVVV VV|P i    a
200|G|GG|GGGGG G GGG GGGGG GGGGGGGG|GGGG GG|P i    a H
201|F|FF|FFFFF F FFF FFFFF FFSFFFFF|FFFF FF|  i    a H
202|Y|YY|YYYYY Y YYY YYYYY YYYYYYYY|YYYY YY|  i    a H
203|A|SS|SSSSS S SSS SSSSS SSSSTSSS|SSSS SS|  s    e H
204|A|AA|AALLL A AAA AAAAA AAAAAAAA|AAAA VV|  I E  e H
205|F|FF|YYFFF Y YYY YYYYY YYYYYYYY|FFFF YY|  I E  e H
206|M|II|LLLLL L LLL LLLLL LLLLLLLL|LLLL LL|  I E  e h
207|V|VV|VVVVV V VVV VVVVV VIVVVVVV|VVVV VV|  I E  e h
208|A|AA|AAAAA A AAA AAAAA AAAAAAAA|AAAA AP|P i    e
209|D|DD|DDDDD D DDD DEEEE DDEEEEEE|DDDD DD|P s
210|V|KK|KKHRR K RRR RKKKR KRKKKKKK|RKLKK YY|    S E E E
211|V|VV|VVVVV V VVV VVVVV VVVVVVVV|VVV VV|   i E E E
212|T|TT|QTQQQ T TTT MIVVV TTTTTVVV|IIII EE|  s E E E
213|V|VV|VVVVV V VVV VVVVV VVVVVVVV|VVVV VV|  i E E E
214|I|KR|VIIII V VVT TTTTT TTIIIIII|TTTT VI|  s E E E
215|S|TT|SSSSS S SSS TTTTT SSTTTTRT|SSSS SS|  s   e E
216|K|RR|KKKKK K KKK KKKKK KKKKKKKK|KKKK KK|  s
217|A|AA|____ _ ___ ____ _____|____ __|P i
218|L|AA|____ _ ___ ____ _____|____ __|P i
219|G|GG|____ _ ___ ____ _____|____ __|P i
220|_|EE|HSHNS N NNN HHHHH NNHHHHHH|HHHH HH|  s
221|_|EK|NNNNN N NNN NNNNN NNNNNNNN|NNNN DD|P
222|S|AP|DDDED A EDS DDDDD DDDDDDDD|NNNN DD|P s
223|E|DE|DDDDD D DDD DDDDD DDDDDDDD|DDDD DD|P s
224|E|KN|EEEEE D DEE EEEEE EEEEEEEE|TTTT KK|  S       e
225|A|AG|QQQQQ Q AAV QQQQQ QQQQQQQQ|QQQQ QQ|  .     e E
226|Y|VV|YYYYY Y YYY YYYYY YYYYYYYY|HHHH YY|  I     e E
227|K|LF|IIVII V TTV VIVVV VVAAAAAA|IIII VI|  i     e E
228|W|WW|WWWWW W WWW WWWWW WWWWWWWW|WWWW WW|  i     e E
229|E|EE|EEEEE E EEE EEEEE EEEEEEEE|EEEE EE|  s A A E
230|S|SS|SSSSS S SSS SSSSS SSSSSSSS|SSSS SS|  . A A
231|A|AA|SNNNN T SSS QQQQQ SSSSSSSS|DDDD KK|  S
232|G|GG|AAAAA A AAA AAAAA AAAAAAAA|SSSS AA|  i
233|A|EE|GGGGG S GGG GGGGG GGGGGGGG|____ GG|P s
235|G|EE|STKSS H TTT SSSSS SSSSSSSS|EEEE SA|P      e
236|Y|YY|FFFFF F FFF FFFFF FFFFFFFF|FFFF FF|  I E E E
237|T|ST|TKTTT T TTT TTTTT TTTTTTTT|SSSS AA|  s E E E
238|I|VV|VVVVV V VVI VVVVV VVVVVVVV|VVVV II|  I E E E
239|E|AA|TTTTT K TTT TTTTT _____|IIII SS|P s   E E
239|P|DD|LQLLL K SPS HRRRR RKRRRRRR|DAAA EE|P S   E E
241|C|II|DDDDD D TTA DDDDD AALTTAAT|DDDD DD|P s   e E
242|E|ET|TDEEE D PPP TVVTT DDDDDDDD|PPPP TV|P S
243|K|KK|DDTVV S DDE TDDSS NNNTTHHH|RRRR WW|P S
244|D|KE|GGNNN H CCS GGGGG SSGGGGGG|GGGG NN|P S
245|S|SD|PREEE E DDD EEEEE EEEEEEEE|NNNN EE|P S
246|V|RR|RARRR P ___ QQPNQ PPPPPPPP|TTTT PP|P S
247|_|__|LILII L LLM LLLLL LLLMMIII|LLLL LL|P i
248|_|__|LGGGG K KKK GGGGG GGGGGGGG|GGGG GG|P s
249|_|__|RRRRR R RRL RRRRR RRRRRRMR|RRRR RR|P s
250|G|GG|GGGGG G GGP GGGGG GGGGGGGG|GGGG GG|P .   e E
251|T|TT|TTTTT T TTA TTTTT TTTTTTTT|TTTT TT|  I E E E
252|D|DE|EKMVI R RRR KKKKK KKKKKKKK|TTTT EE|  S E E E
253|I|VI|IMLLL L III IIIMI IIVVVVVV|IIII II|  I E E E
254|I|IT|RIRRR I VVT TTTVT VVIIIIII|TTTT KR|  s E E E
255|L|LL|LLLLL L LLL LLLLL LLLLLLLL|LLLL LL|  i E E E
256|K|HH|FHFFF H HHH FFFYY YYHHHHHY|VVVV HH|  s E E E
```

TABLE 1-continued

Residue-by-residue consensus secondary structure prediction for the heat shock protein HSP90 family. The SIA column records assignments of positions to the surface (S, s), interior (I, i) or near the "active site" (A, a) using the method disclosed in Serial No. 07/857,224. Automated assignments are given, with the output generated by DARWIN. Services of DARWIN are available by server to the user on the Web (URL http://cbrg.inf.ethz.ch/). Secondary structure is indicated by E (strong strand assignment), e (weak strand assignment), H (strong helix assignment), and h (weak helix assignment). Sequences, designated using single letters, are from the SwissProt database and Genbank, as summarized below. Sequence "a" is the target sequence. The column marked "Auto" contains output from the fully automated secondary structure prediction tool. The column marked "Manual" contains assignments from semi-manual analysis of the same data. The column marked "3D refined" contains secondary structure assignments made after comparison with the experimentally-determined structure of the N-terminal domain of DNA gyrase B, where a * indicates where a shift in the alignment is required. The sequences key:

```
257|I|LL|MLLLL L LLL LLLLL IILLLLLL|LLLL LL|   I E E e
258|K|RR|KKKKK K KKK KKKK KKKKKKKK|KKKK RR|   s E e
259|E|EE|EDEDD E EEE DEDED EEEEEEEE|EEEE DD|  S E
260|N|DG|DEDDD D DDD DDDDD DDDDDDDD|EEEE EE|   s
261|T|EE|QQQQQ Q QQQ QQQQQ QQQQQQQQ|AAAA AA|   i
262|E|KD|LTLLL T QQL LLLLL TTTTTTTT|SSSS KQ|   s
263|D|EE|QEEEE E EEE EEEEE DDEEEEEE|DDDD EE|   S
264|D|__|____ _ ___ ____ _____|____ __|P s
265|S|__|____ _ ___ ____ _____|____ __|P .
266|Y|__|____ _ ___ ____ _____|____ __|P i
267|D|__|____ _ ___ ____ _____|____ __|P s
268|E|__|____ _ ___ ____ _____|____ __|P s
269|F|FF|YYYYY Y YYY YYYYY YYYYYYYY|YYYY YY|   I   e h
270|L|LL|LLLLL L LLL LLLLL LLLLMLLL|LLLL LL|   I   e h
271|E|ND|ENEEE E EEE EEEEE EEEEEEEE|EEEE ED|   S     h
272|E|ED|EEEEE E EEA EEEEE EEEEEEEE|LLLL EE|   S H   h
273|Y|WW|KSKKK R RRR RRRRR SSRRRRRR|DDDD GF|   S H h H
274|R|RR|TKRRR R RRR RRRRR KKRRRRRR|TTTT KK|   S H H H
275|L|LV|IIIII L LLL LILLL IIIIIVVV|VIII LL|   I H H H
276|K|RR|KKKKK K KKK KKKKK KKKKKKKK|KKKK KK|   s H H H
277|A|ES|DEEEE E DDE DDDDD EEEEEEEE|NNNN DE|   S H H H
278|I|II|TVVVV L LLL LLLLL IIIIIVVV|LLLL LL|   I H H H
279|I|II|VVVII V III VVVII VVVVVVVV|VVVV VV|   I H H H
280|K|GS|KKKKK K KKK KKKKK NNKKKKKK|KRKK KK|   s H H H
281|K|KK|KKKRR K KKK KKKKK KKKKKKKK|KKKK KR|   s H H H
282|Y|YY|HQHHH H HHH HHHHH HHHHHHHH|YYYY YY|   I H H H
283|S|SS|SSSSS S SSS SSSSS SSSSSSSS|SSSS SS|   . H H H
284|D|DD|EEEEE E EEE EEEEE QQQQQQQQ|QQQQ EE|   s H H H
285|F|HH|FFFFF F FFF FFFFF FFFFFFFF|FFFF FF|   I H H H
286|I|II|IIVVV I III IIIII IIIIIIII|IIII II|   I H H H
287|R|GA|SFAAA S GGG SSSSS GGGGGGGG|NNNN NN|P s   h
288|Y|LL|YYYYY F YYY YYYYY YYYYYYYY|FFFF FF|P I
289|P|PP|PPPPP P DDD PPPPP PPPPPPPP|PPPP PP|   s   e
290|I|VV|IIIII I III IIIII IIIIIIII|IIII II|   I E E E
291|K|EE|QYQQQ S EEE YYYSS KKRTTTTT|YYYY YY|   S E E E
292|M|MI|LLLLL L LLL LLLLL LLLLLLLL|VVVV LL|   I E E E
293|D|LE|VHVLV S MMM WWWWW LLFFFYY WWWW WW|   s E E E
294|T|TK|VVVVV V VVV YYIVT VVVVVLLV|SSSS AA|   .     e
295|T|KR|TLTTT E EEE EEEEE EEEEEEEE|SSSS TS|   s     e
296|I|EE|RKKKK K NKK KKKKK KKKKKKKK|KKKK KK|   S
297|N|YE|EEEEE T TAT TTTTT EEEEEEEE|TTTT EE|   S
298|K|DK|VNVVV Q TTT TTTIT RRRRRRRR|EEEE VV|   S
299|P|D_|EEEEE E EEE EEEEE EEDDDEEE|TTTT DE|   S   e
300|K|E_|KKKKK T KKK KKKKK KKKKKKKK|VVVV VV|   .   e
301|E|__|EEEEE E EEE EEEEE EEEEEEEE|EEEE EE|   s   e
302|G|__|VVVVV V VVV IIIII VVVVVIIV|EEEE VV|   .   e
303|S|__|PPPPP T TTT SSSSS SSSSSSSS|PPPP OO|P s
304|E|__|EDEII D DDD DDDDD DDDDDDDD|VLMM AA|P s
```

TABLE 2

Refined secondary structure assignments for the heat-shock protein 90 family

| Unit | Alignment Positions | Comments | approximately corresponding region in E. coli DNA gyrase B |
|---|---|---|---|
| strand 0 | 76–82 | prediction weakened by model; non-core, | coil/strand (9–14) |
| parse | 83 | weak parse | |
| helix A | 84–95 | relatively buried | helix(17–24) |
| parse | 96–97 | surface parse | |
| helix B | 98–112 | possibly 3/10 at C-end | helix(35–55) |
| parse | 113–114 | active site | |
| strand 1 | 115–121 | amphiphilic | strand(59–65) |
| parse | 122–125 | DPS parse, exposed | |
| strand I1 | 126–130 | rearranged alignment, weak edge strand? | — |
| parse | 131–133 | DGD, PD dipeptide parses, exposed | |
| strand I2 | 134–139 | amphiphilic | — |
| parse | 140–145 | PDP parse, exposed | |
| strand 2 | 146–152 | amphiphilic | strand(69–74) |
| parse | 153–158 | DxGxG (151–155) near active site | DxGxG(73–77) |
| helix C | 159–165 | short, active site | .[insufficient] |
| active site | 166–172 | conserved S at 171 | [correspondence] |
| helix D | 173–185 | 10 residues in target; break in the middle | [to match region] |
| parse | 186–190 | GGD tripeptide and gap | |
| coil/parse | 191–199 | note possible strand in seq a–t, E, D (191–194); GxxGxG (195–200) hinge | GxxGxG(114–119) |
| helix E | 200–207 | conserved hydrophobic segment | helix(119–126) |
| parse | 208–209 | weak parse | |
| strand 3 | 210–215 | amphiphilic, weakly | strand(131–136) |
| parse | 216–223 | NNDD parse and gaps | |
| strand 4 | 224–229 | oriented towards separate active site? | strand(140–146) |
| parse | 230–235 | SNAGGS parse and gap | |
| strand 5 | 236–241 | amphiphilic/exposed | strand(154–160) |
| parse | 242–249 | polypeptide parses, | |
| strand 6 | 250–257 | amphiphilic | strand(164–170) |
| parse | 258–268 | surface parse and insert in sequence C | |
| helix F | 269–286 | amphiphilic; N-term overrides weak strand prediction; possible parse (271–274) | helix(184–200) |
| parse | 287–289 | GxP parse | |
| strand 7 | 290–295 | amphiphilic, but weakly | strand(202–207) |
| parse | 296–298 | surface parse | |
| strand 8/co | 299–302 | possibly coil, predicted from model | strand(215–219) |

TABLE 3

Predicted surface, interior, and secondary structure assignments for leptin, S and s, I and i indicate strong and weak surface and interior assignments respectively. P and p indicate strong and weak parses respectively. A "?" indicates that no assignment is made. A "c" indicates that the position is involved in a disulfide bond. Secondary structure was assigned using the method of Serial No. 07/857,224, where positions denoted "?" were permitted to fall in either the surface or interior arc of the helix. Underlined residues are part of parsing strings.

```
          010       020       030       040       050              SEQ. NO. 44
           .   |     .   |     .   |     .   |     .   |
VPIQKVQDDTKTLIKTIVTRINDISHTQSVSSKQKVTGLDFIPGLHPILT            human
VPIQKVQDDTKTLIKTIVTRINDISHTQSVSSKQKVTGLDFIPGLHPILT            chimp
VPIQKVQDDTKTLIKTIVTRINDISHTQSVSSKQKVTGLDFIPGLHPILT            gorilla
VPIQKVQDDTKTLIKTVITRINDISHTQSVSSKQKVTGLDFIPGLHPILT            orang
VPIQKVQSDTKTLIKTIVTRINDISHTQSVSSKQRVTGLDFIPGLHPVLT            rhesus VPIHKVQDDTKTLIKTIVTRINDISHTQSVSARQRVTGLDFIPGLHPILS            rat
VPIHKVQDDTKTLIKTIVTRINDISHTQSVSARQRVTGLDFIPGLHPILS            ratnor
VPIQKVQDDTKTLIKTIVTRINDISHTQSVSARQRVTGLDFIPGLHPILS            mouse VPIWRVQDDTKTLIKTIVTRISDISHMQSVSSKQRVTGLDFIPGLHPVLS            pig
VPIRKVQDDTKTLIKTIVTRINDISHTQSVSSKQRVTGLDFIPGLHPLLS            sheep
VPIRKVQDDTKTLIKTIVTRINDISHTQSVSSKQRVTGLDFIPGLHPLLS            ox VPIRKVQDDTKTLIKTIVARINDISHTQSVSSKQRVAGLDFIPGLQPVLS            dog
ipiSSisss?s?iis?Ii?siSsissispppssSii?isiiPPispiis             surf/int
 |-------- helix --------►| weak parse  strong parse          predict
 |-------- helix 1 -------►|        coil                      expt
MLRFEVQLGSFVLLALMISLFLLDGSSMKDIMMNWDDAGCAFVPPAFTFLC           bact
    **

060       070       080       090       100
           .   |     .   |     .   |     .   |     .   |
LSKMDQTLAVYQQILTSMPSRNVIQISNDLENLRDLLHVLAFSKSCHLPW            human
LSKMDQTLAVYQQILTSMPSRNMIQISNDLENLRDLLHVLAFSKSCHLPW            chimp
LSKMDQTLAVYQQILTSMPSRNMIQISNDLENLRDLLHVLAFSKSCHLPW            gorilla
LSKMDQTLAVYQQILTSMPSRNVIQISNDLENLRDLLHVLAFSKSCHLPW            orang
LSQMDQTLAIYQQILINLPSRNVIQISNDLENLRDLLHLLAFSKSCHLPL            rhesus LSKMDQTLAVYQQILTSLPSQNVLQIAHDLENLRDLLHLLAFSKSCSLPQ            rat
LSKMDQTLAVYQQILTSLPSQNVLQIAHDLENLRDLLHLLAFSKSCSLPQ            ratnor
LSKMDQTLAVYQQVLTSLPSQNVLQIANDLENLRDLLHLLAFSKSCSLPQ            mouse LSKMDQTLAIYQQILTSLPSRNVIQISNDLENLRDLLHLLASSKSCPLPQ            pig
LSKMDQTLAIYQQILASLPSRNVIQISNDLENLRDLLHLLAASKSCPLPQ            sheep
LSKMDQTLAIYQQILTSLPSRNVVQISNDLENLRDLLHLLAASKSCPLPQ            ox LSRMDQTLAIYQQILNSLHSRNVVQISNDLENLRDLLHLLASSKSCPLPR            dog
i?Siss?i?iissiiSSiPPSsIIsiiSsississiisii?i?s?cPPPS            surf/int
 |---helix---►|     |<helx>| |<helix>|                        predict
◄----helix 2 ----►|      |◄---helix 3 ---►|                   expt
```

TABLE 3-continued

Predicted surface, interior, and secondary structure assignments for leptin, S and s, I and i indicate strong and weak surface and interior assignments respectively. P and p indicate strong and weak parses respectively. A "?" indicates that no assignment is made. A "c" indicates that the position is involved in a disulfide bond. Secondary structure was assigned using the method of Serial No. 07/857,224, where positions denoted "?" were permitted to fall in either the surface or interior arc of the helix. Underlined residues are part of parsing strings.

```
          110       120       130       140
           .    |    .    |    .    |    .
ASGLETLDSLGGVLEASGYSTEVVALSRLQGSLQDMLWQLDLSPGC          human
ASGLETLDSLGGVLEASGYSTEVVALSRLQGSLQDMLWQLDLSPGC          chimp
ASGLETLDSLGGVLEASGYSTEVVALSRLQGSLQDMLWQLDLSPGC          gorilla
ASGLETLDRLGGVLEASGYSTEVVALSRLQRSLQDMLWQLDLSPGC          orang
ASGLETLESLGDVLEASLYSTEVVALSRLQGSLQDMLWQLDLSPGC          rhesus TRGLQKPESLDGVLEASLYSTEVVALSRLQGSLQDILQQLDLSPEC          rat
TRGLQKPESLDGVLEASLYSTEVVALSRLQGSLQDILQQLDVSPEC          ratnor
TSGLQKPESLDGVLEASLYSTEVVALSRLQGSLQDILQQLDVSPEC          mouse ARALETLESLGGVLEASLYSTEVVALSRLQGALQDMLRQLDLSPGC          pig
VRALESLESLGVVLEASLYSTEVVALSRLQGSLQDMLRQLDLSPGC          sheep
VRALETLESLGGVLEASLYSTEVVALSRLQGALQDMLRQLDLSPGC          ox ARGLETFESLGGVLEASLYSTEVVALSRLQAALQDMLRRLDLSPGC          dog
iSiiSSiSSippiis??ii??sii?i?sisS?issiissisipppc          surf/int
|←- helix>|             |←-----helix ---→|              predict
    |←-helix>|        |←-----helix 4 --------→|         expt
```

TABLE 4

Sequences of the leptin genes used in the analysis

HUMAN SEQ.ID.NO:32
VPIQKVQDDTKTLIKTIVTRINDISHTQSVSSKQKVTGLDFIPGLHPILTLSKMDQTLAVYQQILTSMPSRNVIQISNDLENLRDL
LHVLAFSKSCHLPWASGLETLDSLGGVLEASGYSTEVVALSRLQGSLQDMLWQLDLSPGC
GORILLA SEQ.ID.NO:33
VPIQKVQDDTKTLIKTIVTRISDISHTQSVSSKQKVTGLDFIPGLHPILTLSKMDQTLAVYQQILTSMPSRNMIQISNDLENLRDL
LHVLAFSKSCHLPWASGLETLDSLGGVLEASGYSTEVVALSRLQGSLQDMLWQLDLSPGC
CHIMP SEQ.ID.NO:34
VPIQKVQDDTKTLIKTIVTRINDISHTQSVSSKQKVTGLDFIPGLHPILTLSKMDQTLAVYQQILTSMPSRNMIQISNDLENLRDL
LHVLAFSKSCHLPWASGLETLDSLGGVLEASGYSTEVVALSRLQGSLQDMLWQLDLSPGC
ORANGUTAN SEQ.ID.NO:35
VPIQKVQDDTKTLIKTVITRINDISHTQSVSSKQKVTGLDFIPGLHPILTLSKMDQTLAVYQQILTSMPSRNVIQISNDLENLRDL
LHVLAFSKSCHLPWASGLETLDRLGGVLEASGYSTEVVALSRLQRSLQDMLWQLDLSPGC
RHESUS SEQ.ID.NO:36
VPIQKVQSDTKTLIKTIVTRINDISHTQSVSSKQRVTGLDFIPGLHPVLTLSQMDQTLAIYQQILINLPSRNVIQISNDLENLRDL
LHLLAFSKSCHLPLASGLETLESLGDVLEASLYSTEVVALSRLQGSLQDMLWQLDLSPGC
DOG SEQ.ID.NO:37
VPIRKVQDDTKTLIKTIVARINDISHTQSVSSKQRVAGLDFIPGLQPVLSLSRMDQTLAIYQQILNSLHSRNVVQISNDLENLRDL
LHLLASSKSCPLPRARGLETFESLGGVLEASLYSTEVVALSRLQAALQDMLRRLDLSPGC
PIG SEQ.ID.NO:38
VPIWRVQDDTKTLIKTIVTRISDISHMQSVSSKQRVTGLDFIPGLHPVLSLSKMDQTLAIYQQILTSLPSRNVIQISNDLENLRDL
LHLLASSKSCPLPQARALETLESLGGVLEASLYSTEVVALSRLQGALQDMLRQLDLSPGC
OX SEQ.ID.NO:39
VPIRKVQDDTKTLIKTIVTRINDISHTQSVSSKQRVTGLDFIPGLHPLLSLSKMDQTLAIYQQILTSLPSRNVVQISNDLENLRDL
LHLLAASKSCPLPQVRALESLESLGVVLEASLYSTEVVALSRLQGSLQDMLRQLDLSPGC
SHEEP SEQ.ID.NO:40
VPIRKVQDDTKTLIKTIVTRINDISHTQSVSSKQRVTGLDFIPGLHPLLSLSKMDQTLAIYQQILASLPSRNVIQISNDLENLRDL
LHLLAASKSCPLPQVRALESLESLGVVLEASLYSTEVVALSRLQGSLQDMLRQLDLSPGC
RAT1 SEQ.ID.NO:41
VPIHKVQDDTKTLIKTIVTRINDISHTQSVSARQRVTGLDFIPGLHPILSLSKMDQTLAVYQQILTSLPSQNVLQIAHDLENLRDL
LHLLAFSKSCSLPQTRGLQKPESLDGVLEASLYSTEVVALSRLQGSLQDILQQLDLSPEC
MOUSE SEQ.ID.NO:42
VPIQKVQDDTKTLIKTIVTRINDISHTQSVSAKQRVTGLDFIPGLHPILSLSKMGQTLAVYQQVLTSLPSQNVLQIANDLENLRDL

TABLE 4-continued

Sequences of the leptin genes used in the analysis

LHLLAFSKSCSKPQTSGLQKPESLDGVLEASLYSTEVVALSRLQGSLQDILQQ————
RATNOR SEQ.ID.NO:43
VPIHKVQDDTKTLIKTIVTRINDIDHTQSVSAKQRVTGLDFIPGLHPOLSLSKMDQTLAVYQQVLTSLPSQNVLQIANDLENLRDL
LHLLAFSKSCSLPQTRGLQKPESLDGVLEASLYSTEVVALSRLQGSLQDILQQLDVSPEC

TABLE 5

Sequences of the leptin genes used in the analysis

HUMAN SEQ.ID.NO:45
GTGCCCATCCAAAAAGTCCAAGATGACACCAAAACCCTCATCAAGACAATTGTCACCAGGATCAATGACATTTCACACACAGTC
AGTCTCCTCCAAACAGAAAGTCACCGGTTTGGACTTCATTCCTGGGCTCCACCCCATCCTGACCTTATCCAAGATGGACCAGACAC
TGGCAGTCTACCAACAGATCCTCACCAGTATGCCTTCCAGAAACGTGATCCAAATATCCAACGACCTGGAGAACCTCCGGGATCTT
CTTCACGTGCTGGCCTTCTCTAAGAGCTGCCACTTGCCCTGGGCCAGTGGCCTGGAGACCTTGGACAGCCTGGGGGGTGTCCTGGA
AGCTTCAGGCTACTCCACAGAGGTGGTGGCCCTGAGCAGGCTGCAGGGGTCTCTGCAGGACATGCTGTGGCAGCTGGACCTCAGCC
CTGGGTGCTGA
GORILLA SEQ.ID.NO:46
GTGCCCATCCAAAAAGTCCAAGATGACACCAAAACCCTCATCAAGACAATTGTCACCAGGATCAGTGACATTTCACACACGCAGTC
AGTCTCCTCCAAACAGAAGGTCACCGGTTTGGACTTCATTCCTGGGCTCCACCCCATCCTGACCTTATCCAAGATGGACCAGACAC
TGGCAGTCTACCAACAGATCCTCACCAGTATGCCTTCCAGAAACATGATCCAAATATCCAACGACCTGGAGAACCTCCGGGACCTT
CTTCACGTGCTGGCCTTCTCTAAGAGCTGCCACTTGCCCTGGGCCAGTGGCCTGGAGACCTTGGACAGCCTGGGGGGTGTCCTGGA
AGCTTCAGGCTACTCCACAGAGGTGGTGGCCCTGAGCAGGCTGCAGGGGTCTCTGCAGGACATGCTGTGGCAGCTGGACCTCAGCC
CTGGGTGCTGA
CHIMP SEQ.ID.NO:47
GTGCCCATCCAAAAAGTCCAGGATGACACCAAAACCCTCATCAAGACAATTGTCACCAGGATCAATGACATTTCACACACGCAGTC
AGTCTCCTCCAAACAGAAGGTCACCGGTTTGGACTTCATTCCTGGGCTCCACCCTATCCTGACCTTATCCAAGATGGACCAGACAC
TGGCAGTCTACCAACAGATCCTCACCAGTATGCCTTCCAGAAACATGATCCAAATATCCAACGACCTGGAGAACCTCCGGGACCTT
CTTCACGTGCTGGCCTTCTCTAAGAGCTGCCACTTGCCCTGGGCCAGTGGCCTGGAGACCTTGGACAGCCTGGGGGGTGTCCTGGA
AGCTTCAGGCTACTCCACAGAGGTGGTGGCCCTGAGCAGGCTGCAGGGGTCTCTGCAGGACATGCTGTGGCAGCTGGACCTCAGCC
CTGGGTGCTGA
ORANGUTAN SEQ.ID.NO:48
GTGCCCATCCAAAAAGTCCAAGATGACACCAAAACCCTCATCAAGACAGTTATCACCAGGATCAATGACATTTCACACACGCAGTC
AGTCTCCTCCAAACAGAAGGTCACCGGTTTGGACTTCATTCCTGGGCTCCACCCCATCCTGACCTTATCCAAGATGGACCAGACAC
TGGCAGTCTACCAACAGATCCTCACCAGTATGCCTTCCAGAAACGTGATCCAAATATCCAACGACCTGGAGAACCTCCGGGACCTT
CTTCACGTGCTGGCCTTCTCTAAGAGCTGCCACTTGCCCTGGGCCAGTGGCCTGGAGACCTTGGACAGGCTGGGGGGTGTCCTGGA
AGCTTCAGGCTACTCCACAGAGGTGGTGGCCCTTAGCAGGCTGCAGCGGTCTCTGCAGGACATGCTGTGGCAGCTGGACCTCAGCC
CTGGGTGCTGA
RHESUS SEQ.ID.NO:49
GTGCCCATCCAAAAAGTCCAAAGTGACACCAAAACCCTCATCAAGACAATTGTCACCAGGATCAATGACATTTCACACACGCAGTC
GGTCTCCTCCAAACAGAGGGTCACTGGTTTGGACTTCATTCCTGGGCTCCACCCCGTCCTGACCTTATCCCAGATGGACCAGACAC
TGGCAATCTACCAACAGATCCTCATCAATCTGCCTTCCAGAAACGTGATCCAAATATCCAACGACTTGGAGAATCTCCGGGACCTT
CTTCACCTGCTGGCCTTCTCTAAGAGCTGCCATTTGCCCTTGGCCAGTGGCCTGGAGACCTTGGAGAGCCTGGGGGATGTCCTGGA
AGCTTCACTCTACTCCACGGAGGTGGTGGCCCTGAGCAGGCTGCAGGGGTCTCTGCAGGACATGCTGTGGCAGCTGGACCTCAGCC
CTGGGTGCTGA
DOG SEQ.ID.NO:50
GTGCCAATCCGAAAAGTCCAGGATGACACCAAAACCCTCATCAAGACGATTGTCGCCAGGATCAATGACATTTCACACACGCAGTC
TGTCTCCTCCAAACAGAGGGTCGCTGGTCTGGACTTCATTCCTGGGCTCCAACCAGTCCTGAGTTTGTCCAGGATGGACCAGACGT
TGGCCATCTACCAACAGATCCTCAACAGTCTGCATTCCAGAAATGTGGTCCAAATATCTAATGACCTGGAGAACCTCCGGGACCTT
CTCCACCTGCTGGCCTCCTCCAAGAGCTGAAAATTGCCCCGGGCCAGGGGCCTGGAGACCCTTTGAGAGCCTGGGCGGCGTCCTGGA
AGCCTCACTCTACTCCACAGAGGTGGTGGCTCTGAGCAGACTGCAGGCGGCCCTCCAGGACATGCTTCGGCGGCTGGACCTCAGCC
CTGGGTGCTGA
PIG SEQ.ID.NO:51
GTGCCCATCTGGAGAGTCCAGGATGACACCAAAACCCTCATCAAGACGATTGTCACCAGGATCAGTGACATTTCACACATGCAGTC
TGTCTCCTCCAAACAGAGGGTCACCGGTTTGGACTTCATCCCTGGGCTCCATCCTGTCCTGAGTTTGTCCAAGATGGACCAGACCC
TGGCGATCTACCAACAGATCCTCACCAGTCTGCCTTCCAGAAATGTGATCCAAATATCGAATGACCTGGAGAACCTCCGGGACCTT
CTCCACCTGCTGGCCTCCTCCAAGAGCTGCCCCTTGCCCAGGCCAGGGCCCTGGAGACCTTGGAGAGCCTGGGCGGCGTCCTGGA
AGCCTCCCTCTACTCCACGGAGGTGGTGGCCCTGAGCAGGCTGCAGGGGGCTCTGCAGGACATGCTGCGGCAGCTGGACCTCAGCC
CTGGCTGCTGA
OX SEQ.ID.NO:52
GTGCCCATCCGCAAGGTCCAGGATGACACCAAAACCCTCATCAAGACAATTGTCACCAGGATCAATGACATCTCACACACGCAGTC
CGTCTCCTCCAAACAGAGGGTCACTGGTTTGGACTTCATCCCTGGGCTCCACCCTCTCCTGAGTTTGTCCAAGATGGACCAGACAT
TGGCGATCTACCAACAGATCCTCACCAGTCTGCCTTCCAGAAATGTGGTCCAAATATCCAATGACCTGGAGAACCTCCGGGACCTT
CTCCACCTGCTGGCCGCCTCCAAGAGCTGCCCCTTGCCGCAGGTCAGGGCCCTGGAGAGCTTGGAGAGCTTGGGCGTTGTCCTGGA
AGCTTCCCTCTACTCCACCGAGGTGGTGGCCCTGAGCCGGCTGCAGGGGTCACTACAGGACATGTTGCGGCAGCTGGACCTCAGTC
CCGGGTGCTGA
SHEEP SEQ.ID.NO:53
GTGCCCATCCGCAAGGTCCAGGATGACACCAAAACCCTCATCAAGACGATTGTCACCAGGATCAATGACATCTCACACACGCAGTC
CGTCTCCTCCAAACAGAGGGTCACTGGTTTGGACTTCATCCCTGGGCTCCACCCTCTCCTGAGTTTGTCCAAGATGGACCAGACAT
TGGCAATCTACCAACAGATCCTCGCCAGTCTGCCTTCCAAAAATGTGATCCAAATATTAATGACCTGGAGAACCTCCGGGACCTT
CTCCACCTGCTGGCCGCCTCCAAGAGCTGCCCCTTGCCGCAGGTCAGGGCCCTGGAGAGCTTGGAGAGCTTGGGCGTCGTCCTGGA
AGCCTCCCTCTACTCCACCGAGGTGGTGGCCCTGAGCCGGCTACAGGGGTCTCTACAGGACATGTTGCGGCAGCTGGACCTCAGTC
CCGGGTGCTGA
RAT1 SEQ.ID.NO:54
GTGCCTATCCACAAAGTCCAGGATGACACCAAAACCCTCATCAAGACCATTGTCACCAGGATCAATGACATTTCACACACGCAGTC

TABLE 5-continued

Sequences of the leptin genes used in the analysis

GGTATCCGCCAGGCAGAGGGTCACCGGTTTGGACTTCATTCCCGGGCTTCACCCCATTCTGAGTTTGTCCAAGATGGACCAGACCC
TGGCAGTCTATCAACAGATCCTCACCAGCTTGCCTTCCCAAAACGTGCTGCAGATAGCTCATGACCTGGAGAACCTGCGAGACCTC
CTCCATCTGCTGGCCTTCTCCAAGAGCTGCTCCCTGCCGCAGACCCGTGGCCTGCAGAAGCCAGAGAGCCTGGATGGCGTCCTGGA
AGCCTCGCTCTACTCCACAGAGGTGGTGGCTCTGAGCAGGCTGCAGGGCTCTCTGCAGGACATTCTTCAACAGTTGGACCTTAGCC
CTGAATGCTGA
MOUSE SEQ.ID.NO:55
GTGCCTATCCAGAAAGTCCAGGATGACACCAAAACCCTCATCAAGACCATTGTCACCAGGATCAATGACATTTCACACACGCAGTC
GGTATCCGCCAAGCAGAGGGTCACTGGCTTGGACTTCATTCCTGGGCTTCACCCCATTCTGAGTTTGTCCAAGATGGACCAGACTC
TGGCAGTCTATCAACAGGTCCTCACCAGCTGCCTTCCCAAAATGTGCTGCAGATAGCCAATGACCTGGAGAATCTCCGAGACCTC
CTCCATCTGCTGGCCTTCTCCAAGAGCTGCTCCCTGCCTCAGACCAGTGGCCTGCAGAAGCCAGAGAGCCTGGATGGCGTCCTGGA
AGCCTCACTCTACTCCACAGAGGTGGTGGCTTTGAGCAGGCTGCAGGGCTCTCTGCAGGACATTCTTCAACAGTTGGATGTT---

RATNOR SEQ.ID.NO:56
GTGCCTATCCACAAAGTCCAGGATGACACCAAAACCCTCATCAAGACCATTGTCACCAGGATCAATGACATTTCACACACGCAGTC
GGTATCCGCCAGGCAGAGGGTCACCGGTTTGGACTTCATTCCCGGGCTTCACCCCATTCTGAGTTTGTCCAAGATGGACCAGACCC
TGGCAGTCTATCAACAGATCCTCACCAGCTTGCCTTCCCAAAACGTGCTGCAGATAGCTCATGACCTGGAGAACCTGCGAGACCTC
CTCCATCTGCTGGCCTTCTCCAAGAGCTGCTCCCTGCCGCAGACCCGTGGCCTGCAGAAGCCAGAGAGCCTGGATGGCGTCCTGGA
AGCCTCGCTCTACTCCACAGAGGTGGTGGCTCTGAGCAGGCTGCAGGGCTCTCTGCAGGACATTCTTCAACAGTTGGATGTTAGCC
CTGAATGCTGA

TABLE 6

Consensus secondary structure prediction for the 6-phospho-β-D-galactosidase superfamily

| | | | | |
|---|---|---|---|---|
| strand A | 009–011 | strand A | 049–051 | |
| strand B* | 014–020 | strand B* | 053–060 | internal |
| helix 1* | 072–084 | helix 1* | 095–107 | amphiphilic |
| strand C? | 089–093 | strand C | 111–115 | amphiphilic |
| act site a | 095–102 | act site a | 117–125 | |
| helix 2* | 116–130 | helix 2* | 138–153 | amphiphilic |
| strand D* | 136–140 | strand D* | 159–163 | internal |
| act sit b* | 141 | act sit b* | 164–166 | |
| helix 3* | 158–177 | helix 3* | 181–198 | amphiphilic |
| strand E | 182–185 | strand E | 205–208 | |
| act sit c | 184–187 | act sit c | 207–209 | |
| helix 4* | 212–226 | helix 4* | 248–268 | largely internal |
| strand x | 242–245 | | | |
| helix x | 259–273 | | | ambiguous alignment |
| strand y | 275–280 | | 318–320 | shifted alignment |
| helix 5* | 286–293 | helix 5* | 332–342 | amphiphilic |
| strand F | 323–327 | strand F | 381–388 | interior |
| helix y | 329–339 | gap | | ambiguous alignment |
| strand z | 375–382 | strand z | 446–452† | amphiphilic |
| helix 6* | 385–398 | helix 6* | 456–469 | amphiphilic |
| strand G | 404–407 | strand G* | 476–479 | internal |
| act site d* | 408–410 | act site d* | 480–482 | |
| helix 7* | 431–448 | helix 7* | 497–517 | amphiphilic |
| strand H* | 450–454 | strand H* | 521–525 | amphiphilic |
| strand I* | 456–459 | strand I* | 527–530 | interior |
| strand J* | 464–467 | strand J* | 535–539 | interior |
| strand K* | 478–482 | strand K* | 548–554 | interior |
| helix 8* | 496–509 | helix 8* | 563–576 | amphiphilic |

Assignments in the consensus model (which applies to the entire superfamily) are designated with upper case letters A–K (for beta strands) and Arabic numerals 1–8 (for alpha helices). Strands and helices designated by "x", "y", and "z" are not part of the consensus model, and may be present in only some members of the superfamily. Assignments marked with "?" are weak within one subfamily, but confirm a stronger assignment in the other subfamily.

*Reliable assignments.

†The multiple alignment is ambiguous; see text.

TABLE 7

Multiple alignment of the two subfamilies of the 6-phospho-beta-D-galactosidase superfamily. Underlined residues correspond to parses. In regions where the alignment has been readjusted by hand, surface and interior assignments may not correspond to those produced by the automated computer output. The key follows:

Subfamily a (a b c j k o):

a -- (p11546) lacg_lacla 6-phospho-strand-galactosidase (E.C. 3.2.1.85) (beta-d-phosphogalactoside galactohydrolase). *Lactococcus lactis* (subsp. lactis) (*Streptococcus lactis*). SEQ. NO. 57 b -- (p11175) lacg_staau 6-phospho-strand-galactosidase (E.C. 3.2.1.85) (beta-d-phosphogalactoside galactohydrolase). *Staphylococcus aureus*. SEQ. NO. 58 c -- (p14696) lacg_lacca 6-phospho-strand-galactosidase (E.C. 3.2.1.85) (beta-d-phosphogalactoside galactohydrolase) (p-strand-gal) (pbg). *Lactobacillus casei*. SEQ. NO. 59 d -- (p24240) ascb_ecoli 6-phospho-strand-glucosidase (E.C. 3.2.1.86). *Escherichia coli*. SEQ. NO. 60 e -- (p26206) arbb_erwch 6-phospho-strand-glucosidase (E.C. 3.2.1.86). *Erwinia chrysanthemi*. SEQ. NO. 61 f -- (p11988) bglb_ecoli 6-phospho-strand-glucosidase (E.C. 3.2.1.86). *Escherichia coli*. SEQ. NO. 62

TABLE 7-continued

Subfamily b (d e f g h i l m n p q r):

| | |
|---|---|
| a -- | (p2608) bgla_clotm strand-glucosidase a (E.C. 3.2.1.21) (gentiobiase) (cellobiase) (beta-d- glucoside glucohydrolase). *Clostridium thermocellum*. SEQ. NO. 63 |
| b -- | (p10482) bgls_calsa strand-glucosidase a (E.C. 3.2.1.21) (gentiobiase) (cellobiase) (beta-d- glucoside glucohydrolase) (amygdalase). *Caldocellum saccharolyticum*. SEQ. NO. 64 |
| c -- | (p22073) bgla_bacpo strand-glucosidase a (E.C. 3.2.1.21) (gentiobiase) (cellobiase) (beta-d- glucoside glucohydrolase) (amygdalase). *Bacillus polymyxa*. SEQ. NO. 65 |
| d -- | (q03506) bgla_bacci strand-glucosidase (E.C. 3.2.1.21) (gentiobiase) (cellobiase) (beta-d- glucoside glucohydrolase) (amygdalase). *Bacillus circulans*. SEQ. NO. 66 |
| e -- | (p22505) bglb_bacpo strand-glucosidase b (E.C. 3.2.1.21) (gentiobiase) (cellobiase) (beta-d- glucoside glucohydrolase) (amygdalase). *Bacillus polymyxa*. SEQ. NO. 67 |
| f -- | (p12614) bgls_agrsp strand-glucosidase (E.C. 3.2.1.21) (gentiobiase) (cellobiase) (beta-d- glucoside glucohydrolase) (amygdalase). *Agrobacterium sp.* (strain atcc 21400). SEQ. NO. 68 |
| g -- | (q00326) myro_brana myrosinase precursor (E.C. 3.2.3.1) (sinigrinase) (thioglucosidase). *Brassica napus* (rape). SEQ. NO. 69 |
| h -- | (p09849) lph_rabit pos 1361 to 1926 of lactase-phlorizin hydrolase precursor (E.C. 3.2.1.108) (E.C. 3.2.1.62) (lactase-glycosylceramidase) (lph). *Oryctolagus cuniculus* (rabbit). SEQ. NO. 70 |
| i -- | (p29092) myr3_sinal myrosinase mb3 precursor (E.C. 3.2.3.1) (sinigrinase) (thioglucosidase). *Sinapis alba* (white mustard). SEQ. NO. 71 |
| j -- | (p26204) bgls_trirp non-cyanogenic strand-glucosidase precursor (E.C. 3.2.1.21). *Trifolium repens* (creeping white clover). SEQ. NO. 72 |
| k -- | (p09848) lph_human pos 1361 to 1927 of lactase-phlorizin hydrolase precursor (E.C. 3.2.1.108) (E.C. 3.2.1.62) (lactase-glycosylceramidase). *Homo sapiens* (human). SEQ. NO. 73 |
| l -- | (p26205) bglt_trirp cyanogenic strand-glucosidase precursor (E.C. 3.2.1.21) (linamarase) (fragment). *Trifolium repens* (creeping white clover). SEQ. NO. 74 |

| Subfamily a | | | | Subfamily b | | | | | | | | | |
|---|---|---|---|---|---|---|---|---|---|---|---|---|---|
| Pos | cba | def | SIAPred | Pos | e | ba | dc | f | lj | ig | kh | SIAPred | |
| | | | | 040 | - | -- | -- | - | L | LL | -- | i | |
| 001 | M M | M | . | 041 | - | -- | -- | - | S | SS | -- | a | |
| 002 | S T | S | s | 042 | - | -- | -- | - | R | SS | -- | s | |
| 003 | KKK | N- | s | 043 | - | -- | -- | - | S | KK | -- | s | |
| 004 | QTT | P- | . | 044 | - | -- | -- | - | S | NN | -- | s | |
| 005 | LLL | FFF | I | -045 | F | FF | FF | F | FF | FF | FF | I | |
| 006 | PPP | PPP | . | =046 | P | PP | PP | P | AP | GG | PP | . | parse |
| 007 | QEK | EAE | S | -047 | A | KK | SQ | G | PR | KK | EE | s | parse |
| 008 | DDD | SHT | s | -048 | T | GD | DD | D | GG | DD | GG | s | parse |
| 009 | FFF | FFF | I | strand | =049 | F | FF | FF | F | FF | FF | FF | I | strand core |
| 010 | VII | LLL | I | strand | -050 | M | LI | KM | L | VI | II | IV | I | strand |
| 011 | MFF | WWW | I | strand | -051 | W | WW | WW | F | FF | FF | WW | I | strand |
| 012 | GGG | GGG | . | parse | =052 | G | GG | GG | G | GG | GG | SS | . | |
| 013 | GGG | GGG | . | parse | 053 | T | AS | VT | V | TA | VV | AT | | strand core |
| 014 | AAA | AAA | I | strand | -054 | S | AA | AA | A | AG | AA | AS | i | strand |
| 015 | TTT | LIT | i | strand | 055 | T | TT | TT | T | SS | SS | ST | | strand |
| 016 | AAA | AAA | I | strand | -056 | S | AA | AA | A | SS | SS | AA | i | strand |
| 017 | AAA | AAA | I | strand | -057 | S | SA | AA | S | AA | AA | AA | i | strand |
| 018 | YYY | NNN | i | strand | 058 | Y | YY | YY | F | FY | YY | YF | I | strand |
| 019 | QQQ | QQQ | A | strand | =059 | Q | QQ | QQ | Q | QQ | QQ | QQ | A | strand |
| 020 | VAA | SVV | i | strand | 060 | I | II | II | I | YF | II | II | I | strand |
| 021 | EEE | EEE | A | act site | =061 | E | EE | EE | E | EE | EE | EE | A | act site? |
| 022 | GGG | GGG | . | =062 | G | GG | GG | G | GG | GG | GG | . | parse |
| 023 | AAA | AAA | I | -063 | A | AA | AA | S | AA | GG | AA | i | parse |
| 024 | TTT | FYW | i | -064 | T | WY | YY | T | AV | _ | WW | i | parse |
| 025 | KNH | RLQ | S | 065 | D | NN | NQ | K | FN | _ | RR | S | parse |
| 026 | ETT | ETE | s | 066 | E | EE | EE | A | EE | _ | AA | s | parse |
| 027 | DDD | GDD | s | parse | =067 | G | DD | DD | D | DG | RR | DD | s | parse |
| 028 | GGG | DGG | s | parse | =068 | G | GG | GG | G | GG | GG | GG | . | parse |
| 029 | KKK | KKK | A | -069 | R | KK | RR | R | KR | RR | KK | s | parse |
| 030 | GGG | GGG | . | -070 | T | GG | GG | K | GG | GG | GG | . | parse |
| 031 | _ | LLI | i | | | | | | | | | | |
| 032 | _ | TSS | s | | | | | | | | | | |
| 033 | _ | TTT | a | | | | | | | | | | |
| 034 | _ | VSS | . | | | | | | | | | | |
| 035 | _ | DDD | a | | | | | | | | | | |
| 036 | _ | MLL | i | | | | | | | | | | |
| 037 | _ | IQQ | s | | | | | | | | | | |
| 038 | _ | PPP | . | | | | | | | | | | |
| 039 | _ | HQH | s | | | | | | | | | | |

TABLE 7-continued

| | | | | | | | | | | | | | |
|---|---|---|---|---|---|---|---|---|---|---|---|---|---|
| 040 | _ | GGG | . | | | | | | | | | | |
| 041 | _ | IV | i | | | | | | | | | | |
| 042 | _ | FM | i | | | | | | | | | | |
| 043 | _ | GG | . | | | | | | | | | | |
| 044 | _ | EK | S | | | | | | | | | | |
| 045 | _ | IM | i | | | | | | | | | | |
| 046 | _ | EVE | S | | | | | | | | | | |
| 047 | _ | HTP | s | | | | | | | | | | |
| 048 | RRP | RRR | S | parse | 071 P | EE | ML | P | PP | VV | LL | . | parse |
| 049 | VVV | MQI | i | | 072 S | SS | SS | S | SS | NN | SG | s | parse |
| 050 | LAA | APL | i | parse | 073 I | II | II | I | II | VV | II | I | |
| 051 | WWW | VGG | i | parse | =074 W | WW | WW | W | WW | WW | WW | I | |
| 052 | DDD | KDK | S | parse | =075 D | DD | DD | D | DD | DD | DD | A | |
| 053 | DTK | LSE | S | parse | 076 T | RR | TT | A | TT | GG | TT | s | |
| 054 | FYY | GGN | s | parse | -077 F | FF | FF | F | FF | FF | FF | I | |
| 055 | LLL | LII | I | | 078 C | TS | AA | C | TT | SS | ST | | |
| 056 | DEE | EKK | S | | 079 Q | HH | HH | N | HH | HH | HH | s | |
| 057 | KED | K_ | S | | 080 I | QT | TT | M | KK | RR | TT | S | |
| 058 | QNN | R_ | s | | 081 _ | _ | _ | _ | YY | YY | _ | i | |
| 059 | GYY | F_ | i | | 082 P | KP | PP | P | PP | PP | PR | S | parse |
| 060 | _ | Q_ | a | | 083 G | RG | GG | G | EE | EE | LL | s | parse |
| 061 | _ | L_ | . | | 084 K | NN | KK | H | KK | KK | RK | S | |
| 062 | _ | R_ | a | | 085 V | II | VV | V | II | SA | VI | i | |
| 063 | _ | D_ | a | | 086 I | LA | KF | F | _ | GG | EE | s | parse |
| 064 | _ | D_ | a | | 087 G | YD | NN | G | KR | SS | NN | s | parse |
| 065 | _ | E_ | a | | 088 _ | _ | _ | _ | DD | DD | DD | a | parse |
| 066 | RWW | F_ | s | | 089 G | GG | GG | R | RG | LL | AD | S | parse |
| 067 | FYY | Y_ | i | | 090 D | HH | DD | H | TS | KK | II | s | parse |
| 068 | KTT | P_ | s | | 091 C | NT | NN | N | NN | NN | _ | s | parse |
| 069 | PAA | S_ | i | parse | 092 G | GG | GG | G | GA | GG | GA | . | parse |
| 070 | DEE | HDD | S | parse | 093 D | DD | NN | D | DD | DD | DD | s | parse |
| 071 | PPP | EVV | s | parse | 094 V | VV | VV | I | VI | TT | VV | I | |
| 072 | AAA | AAA | I | helix | -095 A | AA | AA | A | AT | ST | AA | S | helix |
| 073 | ASS | TII | i | helix | 096 C | CC | CC | C | IV | CC | CC | I | helix |
| 074 | DDD | DDD | A | helix | -097 D | DD | DD | D | DD | EE | DD | s | helix |
| 075 | FFF | FFF | I | helix | 098 H | HH | SS | H | EQ | SS | SS | s | helix |
| 076 | YYY | YYY | I | helix | -099 F | YY | YY | Y | YY | YY | YY | I | helix |
| 077 | HNH | HHH | S | helix | -100 H | HH | HH | N | HH | TT | HH | | helix |
| 078 | RRK | RRR | S | helix | -101 H | RR | RR | R | RR | RR | KK | s | helix |
| 079 | YYY | YYY | I | helix | -102 F | FY | WY | W | YY | WW | II | I | helix |
| 080 | DPP | KPP | S | helix? | 103 K | EE | EE | E | KK | KQ | AS | S | helix |
| 081 | EVV | EQE | s | helix | 104 E | EE | EE | E | EE | KK | EE | s | helix |
| 082 | DDD | DDD | A | act site | =105 D | DD | DD | D | DD | DD | DD | A | helix act site |
| 083 | LLL | II | I | helix | -106 V | VI | VI | L | IV | LV | LV | I | helix |
| 084 | AEE | AAA | . | helix | 107 Q | SK | QR | D | GG | ED | VV | S | helix |
| 085 | LLL | LLL | I | break | -108 L | LI | LL | L | II | IV | TA | I | break |
| 086 | ASA | MFF | i | | 109 M | MM | LM | I | MM | MM | LL | I | |
| 087 | EEE | AAA | . | | 110 K | KK | KK | K | KK | GG | QQ | s | |
| 088 | KKE | EEE | S | | 111 Q | EE | DE | E | DD | EE | NN | s | strand |
| 089 | YFY | MMM | I | strand? | 112 L | LI | LL | M | MQ | LL | LL | I | strand |
| 090 | GGG | GGG | . | strand? | -113 G | GG | GG | G | NN | NN | GA | s | strand |
| 091 | HVV | FFF | i | strand? | 114 F | LI | VI | V | LM | AA | VV | I | strand |
| 092 | QNN | KTT | s | strand? | 115 L | KK | KR | E | DD | TT | ST | s | strand |
| 093 | VGG | VCC | i | strand? | 116 H | AS | VT | A | AS | GG | HH | s | |
| 094 | III | FLL | I | | 117 Y | YY | YY | Y | YY | YY | YY | I | act site |
| 095 | RRR | RRR | A | act site | =118 R | RR | RR | R | RR | RR | RR | A | act site |
| 096 | VII | TII | i | | 119 F | FF | FF | F | FF | FF | FF | I | act site |
| 097 | SSS | SSS | A | act site | =120 S | SS | SS | S | SS | SS | SS | A | act site |
| 098 | III | III | I | | -121 V | II | IV | L | II | FF | II | I | |
| 099 | AAA | AAA | I | | -122 A | AS | SS | A | SS | AA | SS | i | |
| 100 | WWW | WWW | I | act site | =123 W | WW | WW | W | WW | WW | WW | I | act site |
| 101 | SSS | STA | | | -124 P | TP | PP | P | PP | SS | SS | s | |
| 102 | RRR | RRR | A | act site | =125 R | RR | RR | R | RR | RR | RR | A | act site |
| 103 | III | LII | I | | 126 I | II | VI | I | VI | II | II | I | |
| 104 | FFF | FFF | I | | -127 M | FF | LF | I | LL | VI | LL | I | |
| 105 | PPP | PPP | . | parse | -128 P | PP | PP | P | PP | PP | PP | . | parse |
| 106 | DNT | QQQ | S | parse | -129 A | DE | QN | D | KK | KK | DD | s | parse |
| 107 | GGG | GGG | . | parse | =130 _ | GG | GG | G | GG | GG | GG | . | parse |
| 108 | AYY | _ | i | | 131 _ | _ | _ | _ | KK | KK | TT | s | parse |
| 109 | GGG | DDD | s | | 132 _ | _ | _ | _ | LL | VV | _ | i | parse |
| 110 | EEE | EEE | A | | 133 A | FT | TD | F | SS | SS | TT | s | parse |
| 111 | VVV | IAV | I | | 134 G | GG | GG | G | GG | RR | RN | S | |
| 112 | ENN | TEE | S | parse | -135 I | TK | EE | P | GG | GG | YY | s | |
| 113 | PPE | PPP | S | parse | 136 I | VL | VV | I | VI | VV | II | I | |
| 114 | _ | NNN | a | parse | 137 N | NN | NN | N | NN | DN | NN | S | break |
| 115 | _ | QEE | s | | 138 E | QQ | RQ | E | RH | QQ | EE | S | helix |
| 116 | RKK | QAA | s | helix | 139 E | KK | AE | K | EE | AG | AA | s | helix |
| 117 | GGG | GGG | . | helix | =140 G | GG | GG | G | GG | GG | GG | . | helix |
| 118 | VVV | ILL | I | helix | -141 L | LL | LL | L | II | LL | LL | I | helix |

TABLE 7-continued

| | | | | | | | | | | | | | |
|---|---|---|---|---|---|---|---|---|---|---|---|---|---|
| 119 | AEE | AAA | . | helix | 142 L | ED | DD | D | NK | DD | NN | s | helix |
| 120 | FYF | FFF | I | helix | -143 F | FF | YY | F | YY | YY | YY | I | helix |
| 121 | YYY | YYY | I | helix | =144 Y | YY | YY | Y | YY | YY | YY | I | helix |
| 122 | HHH | RDD | s | helix | -145 E | DK | HH | D | NN | HH | VV | s | helix |
| 123 | KKK | SRR | s | helix | -146 H | RR | RR | R | NN | NK | RR | S | helix |
| 124 | LLL | VLL | I | helix | -147 L | LL | LV | L | LL | LL | LL | I | helix |
| 125 | FFF | FFF | I | helix | 148 L | IT | VV | V | II | II | II | I | helix |
| 126 | AAA | EDD | s | helix | 149 D | NN | DD | D | NN | DD | DD | s | helix |
| 127 | DEE | EEE | s | helix | 150 E | KL | EL | G | EE | AA | TA | s | helix |
| 128 | CCC | CLM | I | helix | -151 I | LL | LL | C | VL | LL | LL | I | helix |
| 129 | AHH | KAA | s | helix | 152 E | VL | L<u>N</u> | K | LL | LL | LL | i | helix |
| 130 | AKK | KKQ | S | helix | 153 L | EE | A<u>D</u> | A | AA | EE | AA | s | helix |
| 131 | HRR | YYA | . | break | 154 A | <u>NN</u> | <u>NN</u> | R | <u>NN</u> | KK | AA | s | break |
| 132 | HHH | GGG | . | | 155 G | <u>GG</u> | <u>GG</u> | G | <u>GG</u> | NN | SN | S | parse |
| 133 | IVV | III | I | | 156 L | II | II | I | MI | II | II | I | |
| 134 | EEE | EQK | S | | -157 I | EM | EE | K | QQ | TT | QK | S | |
| 135 | PPP | PPP | . | parse? | =158 P | PP | PP | T | PP | PP | PP | s | parse? |
| 136 | FFF | LLL | I | strand | 159 M | VA | FF | Y | YF | FF | QQ | I | strand |
| 137 | VVV | VVV | I | strand | -160 L | VI | CC | A | VV | VV | VV | I | strand |
| 138 | TTT | TTT | A | strand | =161 T | TT | TT | T | TT | TT | TT | A | strand |
| 139 | LLL | LLL | I | strand | =162 L | LL | LL | L | LL | LL | IM | I | strand |
| 140 | HHH | CSS | . | strand | 163 Y | YY | YY | Y | FF | FF | YY | I | strand |
| 141 | HHH | HHH | A | act site | =164 H | HH | HH | H | HH | HH | HH | A | active site |
| 142 | FFF | FYY | I | | 165 W | WW | WW | W | WW | WW | WF | s | |
| 143 | DDD | DEE | s | | =166 D | DD | DD | D | DD | DD | DD | A | active site |
| 144 | TTT | VMM | i | | 167 L | LL | LL | L | VL | LL | LL | I | |
| 145 | PPP | PPP | . | | =168 P | PP | PP | P | PP | PP | PP | . | parse |
| 146 | EEE | MYY | . | | 169 Q | QQ | QQ | L | QQ | QQ | QQ | I | |
| 147 | RVA | HGG | s | | 170 W | KK | AA | T | AV | TT | TA | s | |
| 148 | LLL | LLL | I | | -171 I | LL | LL | L | LL | LL | LL | I | |
| 149 | HHH | VVV | i | | 172 E | QQ | QQ | M | EE | QQ | QQ | . | |
| 150 | EKS | TEK | S | parse | 173 D | DD | DD | <u>G</u> | DD | DD | DD | s | parse |
| 151 | A<u>D</u>N | EKN | S | parse | -174 E | IK | QA | <u>D</u> | EE | EE | _ | s | parse |
| 152 | _ | YHY | s | parse | 175 _ | _ | _ | _ | YY | YY | VV | i | parse |
| 153 | <u>GGG</u> | GGG | . | parse | -176 <u>G</u> | <u>GG</u> | <u>GG</u> | <u>G</u> | RG | EE | <u>GG</u> | s | parse |
| 154 | <u>DDD</u> | SGG | s | parse | -177 <u>G</u> | <u>GG</u> | <u>GG</u> | <u>G</u> | <u>GG</u> | GG | <u>GG</u> | . | parse |
| 155 | WFF | WWW | I | | -178 W | WW | WW | W | FF | FF | WW | I | |
| 156 | LLL | RGA | s | | -179 T | AK | <u>GG</u> | A | LL | LL | EE | s | |
| 157 | SNN | NNN | s | | -180 Q | <u>NN</u> | S<u>N</u> | S | G<u>N</u> | DD | NN | S | break |
| 158 | QRR | RRR | s | helix | 181 R | P<u>R</u> | RR | R | R<u>S</u> | RR | EE | s | helix amph |
| 159 | EKE | KLA | S | helix | 182 E | ED | IR | S | N<u>G</u> | QQ | TT | S | helix |
| 160 | MTN | LTV | | helix | 183 T | IT | TT | T | IV | II | II | I | helix |
| 161 | LII | VII | I | helix | -184 I | VT | II | A | VI | II | VV | I | helix |
| 162 | DDE | EDD | S | helix | 185 Q | ND | DQ | D | DN | QQ | QQ | S | helix |
| 163 | DYH | FCH | S | helix | 186 H | YY | AA | A | DD | DD | RR | i | helix |
| 164 | FFF | FFF | I | helix | =187 F | YF | FF | F | FF | FF | FF | I | helix |
| 165 | VVI | SEE | s | helix | 188 K | FT | AV | Q | RR | KK | KK | s | helix |
| 166 | ADD | RRH | S | helix | 189 T | DE | EQ | R | DD | DD | EE | s | helix |
| 167 | YYY | YYY | I | helix | =190 Y | YY | YF | Y | YY | YY | YY | I | helix |
| 168 | AAA | AAA | I | helix | =191 A | AS | AA | A | AT | AA | AA | i | helix |
| 169 | KEA | RRR | S | helix | 192 S | ME | EE | K | ED | DD | DD | S | helix |
| 170 | FYF | TTT | i | helix | 193 V | LV | LT | T | LL | LL | VV | I | helix |
| 171 | CCC | CVV | I | helix | -194 I | VI | MM | V | CC | CC | LL | I | helix |
| 172 | FFF | FFF | I | helix | -195 M | IF | FF | M | FF | FF | FF | I | helix |
| 173 | EKE | EAT | S | helix | 196 D | NK | KR | A | KK | KK | QQ | s | helix |
| 174 | EEE | ARR | s | helix | -197 R | RN | EE | R | EE | EE | RR | s | helix |
| 175 | FFF | FYY | I | helix | -198 F | YL | LF | L | FF | FF | LL | I | helix |
| 176 | SPP | DRQ | S | helix | 199 G | K<u>G</u> | <u>G</u>H | G | <u>GG</u> | <u>GG</u> | <u>GG</u> | s | parse |
| 177 | EEE | GHH | s | helix | 200 E | <u>DD</u> | <u>GG</u> | D | <u>DD</u> | <u>G</u>G | <u>DD</u> | s | parse |
| 178 | _ | LKK | s | | 201 R | KI | KK | R | RR | KK | KK | S | |
| 179 | VVV | VVV | I | | -202 I | VV | II | L | VV | VV | VV | I | |
| 180 | KKN | KKA | S | | -203 N | KP | KQ | D | KR | KK | KK | S | |
| 181 | YYY | YRL | s | | 204 W | KI | QH | A | HY | NH | FF | S | |
| 182 | WWW | WWW | I | strand | -205 W | WW | WW | V | WW | WW | WW | I | strand |
| 183 | ITT | LLL | I | strand | 206 N | IF | IL | A | IS | II | II | I | strand |
| 184 | TTT | TTT | A | strand | -207 T | TT | TT | T | TT | TT | TT | A | strand |
| 185 | IFF | FFF | I | strand | =208 I | FH | FF | F | LL | II | LL | I | strand |
| 186 | NNN | NNN | A | act site | =209 N | NN | NN | N | NN | NN | NN | A | act site |
| 187 | EEE | EEE | A | | -210 E | EE | EE | E | EE | QQ | EE | s | |
| 188 | P<u>II</u> | III | i | parse | 211 P | P<u>P</u> | PP | P | PP | LL | PP | i | parse |
| 189 | T<u>GG</u> | NNN | s | parse | 212 Y | Y<u>G</u> | WW | W | WW | YY | FF | i | strand, int |
| 190 | S<u>PP</u> | INM | i | parse | 213 C | CV | CC | C | GV | TT | VV | i | strand |
| 191 | MII | MSS | i | | 214 A | IV | MI | A | VF | VV | IV | I | strand |
| 192 | A<u>GG</u> | LLL | i | | 215 S | AS | AA | V | S<u>S</u> | PP | AA | i | strand |
| 193 | V<u>DD</u> | HHH | . | | 216 I | FL | FF | W | M<u>N</u> | TT | YY | i | |
| 194 | Q<u>GG</u> | <u>S</u>AA | . | | 217 L | LL | LL | L | <u>N</u>S | RR | QH | s | |
| 195 | QQQ | PPP | . | | 218 G | GG | SS | S | A<u>G</u> | GG | GG | . | parse |
| 196 | YYY | FFF | I | | 219 Y | YH | NN | H | YY | YY | YY | i | |
| 197 | TLL | STT | s | | 220 G | FF | YM | L | AA | AA | GG | i | |

TABLE 7-continued

| | | | | | | | | | | | | | |
|---|---|---|---|---|---|---|---|---|---|---|---|---|---|
| 198 | _ | GGG | . | | 221 | T | HL | LL | Y | YL | LI | YT | I | |
| 199 | TVV | AVV | i | | 222 | G | GG | GG | G | GG | GG | GG | . | |
| 200 | GGG | GGG | . | | 223 | E | II | VV | V | TT | TT | TL | . | |
| 201 | TKK | LLL | . | | 224 | H | HH | HH | H | FN | DD | AY | s | |
| 202 | FFF | VPA | i | parse | -225 | A | AA | AA | A | AA | AA | AA | I | |
| 203 | PPP | FPE | S | parse | -226 | P | PP | PP | P | PP | PP | PP | . | parse |
| 204 | PPP | EDE | S | parse | 227 | G | GG | GG | G | GG | GG | GG | . | parse |
| 205 | AGG | ESS | s | parse | 228 | _ | _ | _ | _ | RR | RR | VI | s | |
| 206 | EII | GDG | s | parse | 229 | _ | _ | _ | _ | CC | CC | SY | s | |
| 207 | SKK | EKE | S | | 230 | _ | _ | _ | _ | SS | SS | NF | s | parse |
| 208 | GYY | NAA | s | | 231 | _ | _ | _ | _ | DA | PP | RR | i | parse |
| | | | | | 232 | _ | _ | _ | _ | WS | KM | _ | s | parse |
| | | | | | 233 | _ | _ | _ | _ | LN | VV | _ | . | parse |
| | | | | | 234 | _ | _ | _ | _ | KV | DD | _ | S | |
| | | | | | 235 | _ | _ | _ | _ | LA | TT | _ | i | |
| | | | | | 236 | _ | _ | _ | _ | NK | KK | _ | S | |
| | | | | | 237 | | | | | | | | | |
| | | | | | 238 | | | | | | | | | |
| | | | | | 239 | _ | _ | _ | _ | _ | QH | _ | S | |
| | | | | | 240 | _ | _ | _ | _ | _ | RR | _ | s | |
| | | | | | 241 | _ | _ | _ | _ | C_ | CC | _ | i | |
| | | | | | 242 | _ | _ | _ | _ | T_ | YY | _ | s | |
| | | | | | 243 | _ | _ | _ | _ | GP | GG | _ | . | parse |
| | | | | | 244 | H | II | NL | E | GG | GG | _ | . | parse |
| | | | | | 245 | E | KK | KT | R | DD | NN | _ | s | parse |
| 209 | RDD | Q_ | S | | 246 | N | DD | DN | N | SS | SS | PP | . | parse |
| 210 | FFL | D_ | . | | -247 | W | FL | LL | M | GG | SS | GG | . | parse |
| 211 | DEA | Q | S | | 248 | R | KR | QQ | Q | RT | TT | TT | s | helix internal |
| 212 | KKK | VAE | s | helix | 249 | E | VT | LT | A | EG | EE | AA_ | s | helix (bl) |
| 213 | TVV | KIV | s | helix | 250 | A | AS | AA | A | PP | PP | PP | i | helix (bl) |
| 214 | FFF | YYY | I | helix | -251 | F | ML | II | L | YY | YY | YY | i | helix |
| 215 | QQQ | QQQ | A | helix | 252 | T | DE | DD | A | LI | II | II | si | helix |
| 216 | ASS | AAA | i | helix | 253 | A | VV | VV | A | AV | VV | VV | I | helix |
| 217 | EHH | AII | s | helix | 254 | A | VS | SG | M | AT | AA | GG | . | helix |
| 218 | HHH | HHH | A | helix | =255 | H | HH | HH | H | HH | HH | HH | A | helix act site |
| 219 | NNN | HHH | . | helix | -256 | H | SN | HH | H | YN | NN | NN | s | helix |
| 220 | QMM | QQQ | . | helix | 257 | I | LL | LL | I | QQ | QQ | LL | I | helix |
| 221 | MMM | LLL | I | helix | -258 | L | ML | LL | N | LI | LL | II | i | helix |
| 222 | VVV | VVV | I | helix | 259 | M | LL | VV | L | LL | LL | KK | i | helix |
| 223 | AAS | AAA | i | helix | -260 | C | SS | AA | A | AA | AA | AA | i | helix |
| 224 | HHH | SSS | . | helix | -261 | H | HH | HH | H | HH | HH | HH | . | helix |
| 225 | AAA | AAA | I | helix | -262 | G | FG | GG | G | AA | AA | AA | i | helix |
| 226 | RRR | LRR | s | helix | -263 | I | KK | RL | F | AE | AT | EE | S | helix |
| 227 | IAA | AAA | I | break | -264 | A | VA | AS | G | AA | IV | AA | i | helix |
| 228 | VVV | TVV | i | | 265 | S | VV | VV | V | AV | VV | WW | i | helix |
| 229 | NKK | KKK | s | | -266 | N | KK | TR | E | RH | DD | HH | S | helix |
| 230 | LLL | IAA | I | | -267 | L | AL | LR | A | LV | LL | LL | . | helix |
| 231 | YFY | ACC | I | | 268 | H | VF | FF | S | YY | YY | YY | i | helix |
| 232 | KKK | HHH | s | | 269 | K | KR | RR | R | KK | RR | NN | s | helix |
| 233 | SDD | EDS | S | parse | -270 | E | EE | EE | H | TT | TT | DD | s | |
| 234 | MGK | VML | S | parse | 271 | K | NM | LL | V | KK | NK | VV | S | |
| | | | | | 272 | _ | _ | _ | _ | YY | YY | YY | . | |
| | | | | | 273 | _ | _ | _ | _ | QQ | _ | RR | s | |
| | | | | | 274 | _ | _ | _ | _ | AA | AK | AA | S | |
| 235 | QGG | NIL | s | parse | -275 | G | NN | GG | A | SY | FF | SS | . | |
| 236 | LYY | PPP | i | parse | -276 | L | II | IT | P | QQ | QQ | QQ | i | parse |
| 237 | GKK | QDE | S | parse | -277 | T | DD | SS | K | NK | NK | GG | S | parse |
| 238 | GGG | NAA | s | parse | -278 | G | VA | GG | V | GG | GG | GG | i | parse |
| 239 | QEE | QQK | S | | -279 | K | EQ | EQ | P | IK | KK | VV | S | |
| 240 | III | VII | I | | -280 | I | VI | II | V | II | II | II | I | |
| 241 | GGG | GGG | . | | -281 | G | GG | GG | G | GG | GG | SS | . | parse |
| 242 | IVV | CNN | . | strand | 282 | I | II | II | L | II | PP | II | i | parse |
| 243 | VVV | MMM | I | strand | 283 | T | TA | AA | V | TT | VV | TT | I | |
| 244 | HHH | LLL | i | strand | 284 | L | LL | PP | L | LL | MM | II | i | parse |
| 245 | AAA | ALL | I | strand | 285 | N | NN | NN | N | VV | VV | SS | i | parse |
| 246 | LLL | GGG | i | parse | 286 | M | LL | TV | A | SS | TT | SS | i | |
| 247 | QPP | GAG | s | parse | 287 | E | TS | SS | H | HN | RR | DD | s | |
| 248 | TTT | NML | s | parse | 288 | H | PY | WW | S | WW | WW | WW | i | |
| 249 | VKK | FLV | . | s | -289 | V | VH | AA | A | FL | FF | AA | I | |
| 250 | YYY | YYY | I | | -290 | D | YY | VV | I | EM | LL | EE | s | |
| 251 | PPP | PPP | . | parse? | -291 | A | LP | PP | P | PP | PP | PP | . | parse? |
| 252 | YFY | YLL | I | | -292 | A | QA | YY | A | AL | YF | RR | i | |
| 253 | SDD | STT | . | parse | -293 | S | TS | RS | S | SD | DD | DD | S | parse |
| 254 | DPP | CSC | s | parse | 294 | E | EE | RT | D | KD | EE | PP | S | parse |
| 255 | SSE | KKQ | S | parse | 295 | R | R_ | TS | G | EN | SS | SS | s | parse |
| 256 | ANN | PPP | S | parse | 296 | _ | L_ | _ | _ | _ | _ | _ | . | |
| 257 | VPP | _ | . | | 297 | _ | G_ | _ | _ | _ | _ | _ | . | |
| 258 | _EA | | S | | 298 | _ | Y_ | _ | _ | _ | _ | _ | | |
| | | | | | 299 | _ | KK | _ | _ | KS | DD | NN | s | parse |

TABLE 7-continued

|     |     |     |   |       |      |   |    |    |    |    |    |    |    |   |        |
|-----|-----|-----|---|-------|------|---|----|----|----|----|----|----|----|---|--------|
|     |     |     |   |       | 300  | P | VA | KE | E  | I  | PP | QQ | s  |   |        |
|     |     |     |   |       | 301  | E | SE | EE | A  | AP | AA | EE | s  |   |        |
| 259 | DDD | EEQ | S | helix | -302 | D | ED | DD | D  | DD | CS | DD | s  |   |        |
| 260 | HVV | DDD | s | helix | 303  | V | II | MK | L  | VI | II | VV | .  |   |        |
| 261 | HRR | VVM | . | si    | 304  | A | EE | EA | K  | DK | EE | EE | S  |   |        |
| 262 | AAA | WML | I | helix | -305 | A | RA | AA | A  | AA | AA | AA | i  |   |        |
| 263 | AAA | AEQ | s | helix | -306 | A | EA | CC | A  | AA | AA | AA | i  |   |        |
| 264 | EEE | ASA | S | helix | -307 | I | ME | LA | E  | KE | EE | RK | S  |   |        |
| 265 | LLL | LLM | I | helix | 308  | R | VL | RR | R  | RR | RR | RR | s  |   |        |
| 266 | QEE | EHE | S | helix | 309  | R | SS | VT | A  | GS | MM | YY | s  |   |        |
| 267 | DDD | KQE | S | helix | 310  | D | LF | NI | F  | LL | NN | VV | s  |   |        |
| 268 | AII | DNN | s | helix | 311  | _ | S_ | _  | _  | _  | _  | _  | s  |   |        |
| 269 | LII | RRR | . | helix | 312  | _ | S_ | _  | _  | _  | _  | _  | s  |   |        |
| 270 | EHH | EER | S | helix | 313  | G | QS | GS | Q  | DD | QQ | QQ | s  |   |        |
| 271 | NNN | NWW | s | helix | 314  | F | LL | WL | F  | FF | FF | FF | I  |   |        |
| 272 | RKK | LLM | s | helix | 315  | I | DA | SH | H  | MQ | FF | MM | s  |   |        |
| 273 | LFF | FFF | I | helix | 316  | N | NG | GS | N  | LF | HH | GG | s  |   |        |
| 274 | YII | FFF | I | break | 317  | R | QR | DD | G  | GG | GG | GG | s  |   |        |
|     |     |     |   |       | 318  | W | LW | WW | A  | WL | WW | WW | I  |   | strand |
|     |     |     |   |       | -319 | F | FY | YF | F  | FF | YY | FF | I  |   | strand |
| 275 | LLL | IGG | i | strand| 320  | A | LL | LL | F  | MM | MM | AA | I  |   | strand |
| 276 | DDD | DDD |   | strand| -321 | E | DD | DQ | D  | HE | EE | HH | S  |   |        |
| 277 | GAA | VVV | i | strand| 322  | P | PP | PP | P  | PQ | PP | PP | I  |   |        |
| 278 | TTT | QQQ | i | strand| 323  | L | VV | II | V  | LL | LL | II | I  |   |        |
| 279 | LYY | AVA | I | strand| 324  | F | LL | YY | F  | TT | TT | FF | I  |   |        |
| 280 | ALL | RRR | . | strand| 325  | N | KK | FQ | K  | KT | KK | KK | s  |   |        |
|     |     |     |   |       | 326  | _ | _  | _  | _  | _  | _  | NN | a  |   | parse  |
| 281 | GGG | GGG | . |       | =327 | G | GG | GG | G  | GG | GG | GG | .  |   | parse  |
| 282 | EKH | TAQ | S |       | 328  | K | SR | ES | E  | RD | RR | DD | S  |   | parse  |
| 283 | YYY | YYY | I |       | =329 | Y | YY | YY | Yi | YY | YY | YY | I  |   |        |
| 284 | HSS | PPP | s | parse | -330 | P | PP | PP | P  | PS | PP | NN | s  |   | parse  |
| 285 | QRD | AGG | S | parse | -331 | E | QE | KQ | As | EK | DD | EE | S  |   | parse  |
| 286 | EEK | YYY | S | helix | -332 | D | KN | FF | Es | SS | II | VV | s  |   | helix  |
| 287 | TTT | SMM | i | helix | 333  | M | LA | ML | Mi | MN | MM | MM | I  |   | helix  |
| 288 | LMM | AHQ | i | helix | 334  | V | LL | LV | Mi | RR | RR | KK | s  |   | helix  |
| 289 | AEE | RRR | s | heiix | -335 | E | DK | DD | Es | YR | QQ | TT | s  |   | helix  |
| 290 | LGG | VYF | i | helix | 336  | W | YL | WW | Ai | LI | II | RQ |    |   | helix  |
| 291 | VVV | FFF | I | helix | -337 | Y | LY | YF | Li | VV | VV | II | i  |   | helix  |
| 292 | KQN | RRR | S | helix | 338  | G | VK | EA | Gs | RK | GG | RR | s  |   | helix  |
| 293 | EHH | EED | s | helix | -339 | T | QK | NE | Ds | KN | SS | DE | S  |   | helix  |
| 294 | III | —   | i |       | 340  | Y | KK | LQ | Rs | RR | RR | RR |    |   | helix  |
| 295 | LLL | —   | i |       | 341  | L | DG | GG | Ms | LL | LL | SS |    |   | helix  |
| 296 | DSA | —   | s |       | 342  | N | LI | YA | P  | PP | PP | LL | i  |   | helix  |
| 297 | AVE | —   | S |       | 343  | _ | _  | _  | _  | _  | _  | _  |    |   |        |
| 298 | NNN | —   | a | parse | 344  | _ | _  | _  | _  | _  | _  | _  |    |   |        |
| 299 | HGG | KQH | s | parse | 345  | _ | _  | _  | _  | _  | _  | _  |    |   |        |
| 300 | QGG | GGN | S | parse | 346  | _ | _  | _  | _  | _  | _  | _  |    |   |        |
| 301 | PKE | VII | S | parse | 347  | _ | _  | _  | _  | _  | _  | _  |    |   |        |
| 302 | MLL | TTT | i |       | 348  | _ | _  | _  | _  | _  | _  | AA |    |   |        |
| 303 | F_  | ILI | i |       | 349  | _ | _  | _  | _  | _  | _  | AA |    |   |        |
| 304 | QND | NNE | S |       | 350  | _ | _  | _  | _  | _  | _  | GG |    |   |        |
| 305 | SIL | KIM | s |       | 351  | _ | _  | _  | _  | _  | _  | LL |    |   |        |
| 306 | TTR | ATT | S |       | 352  | _ | _  | _  | _  | _  | _  | NN |    |   |        |
| 307 | PDD | PAE | S | parse | 353  | _ | _  | _  | _  | _  | _  | KE |    |   |        |
| 308 | QEE | GQS | s | parse | 354  | _ | _  | _  | _  | _  | _  | SS |    |   |        |
| 309 | EDD | DDD | s | parse | 355  | G | LE | KT | _  | _  | _  | RR |    |   |        |
| 310 | MYF | DKA |   | parse | 356  | L | DL | PV | _  | _  | _  | LL |    |   |        |
| 311 | KAQ | —   | S |       | 357  | D | SS | PP | _  | _  | _  | PP |    |   |        |
| 312 | AIA | —   | s |       | 358  | F | QF | II | V  | _  | _  | _  |    |   |        |
| 313 | ILL | —   | I |       | 359  | V | KP | VQ | V  | _  | _  | _  |    |   |        |
|     |     |     |   |       | 360  | _ | _  | _  | E  | _  | _  | _  |    |   |        |
|     |     |     |   |       | 361  | _ | _  | _  | _  | _  | _  | _  |    |   |        |
|     |     |     |   |       | 362  | _ | _  | _  | _  | _  | _  | _  |    |   |        |
|     |     |     |   |       | 363  | _ | _  | _  | _  | _  | _  | _  |    |   |        |
|     |     |     |   |       | 364  | _ | A_ | _  | _  | _  | _  | _  |    |   |        |
|     |     |     |   |       | 365  | _ | L_ | _  | _  | _  | _  | _  |    |   |        |
|     |     |     |   |       | 366  | _ | S_ | _  | _  | KK | NN | EE | s  |   |        |
|     |     |     |   |       | 367  | _ | M_ | _  | _  | FF | FF | FF | i  |   |        |
|     |     |     |   |       | 368  | Q | Q_ | _  | _  | SS | TT | TT | s  |   |        |
|     |     |     |   |       | 369  | P | QE | DD | A  | TK | EE | EE | s  |   | parse  |
| 314 | DDD | EQE | S | helix | 370  | G | ED | GG | E  | EF | AE | SS | S  |   | parse  |
| 315 | EAA | IDD | s | helix | 371  | D | VD | DD | D  | EE | EE | EE | s  |   | parse  |
| 316 | AAA | LLL | i | helix | 372  | M | KL | MM | L  | SS | AA | KK | s  |   |        |
| 317 | AKK | KKK | s | helix | 373  | E | EK | ED | G  | KS | EE | RR | S  |   | coil   |
| 318 | HDD | NAH | s | helix | 374  | L | NL | LI | I  | EL | LL | RR | s  |   |        |
| 319 | QLL | TTT | i | helix | 375  | I | FI | II | I  | LV | VV | II | I  |   |        |
| 320 | LNN | VVV | is|       | 376  | Q | IS | HG | S  | TN | AA | NN | s  |   |        |
|     |     |     |   |       | 377  | Q | FQ | QE | Q  | GG | GG | GG | s  |   |        |
|     |     |     |   |       | 378  | P | PP | PP | K  | SS | SS | TT | s  |   | parse  |

TABLE 7-continued

| | | | | | | | | | | | | | | |
|---|---|---|---|---|---|---|---|---|---|---|---|---|---|---|
| 321 | DDD | DDD | A | | 379 | G | I | II | L | FF | YY | YY | i | parse |
| 322 | FFF | FFF | | strand? | =380 | D | DD | DD | D | DD | DD | DD | A | parse |
| 323 | VLL | VII | I | strand? | -381 | F | FF | FM | W | FF | FF | FF | I | strand |
| 324 | GGG | SSS | . | strand? | -382 | L | LI | II | W | LI | LL | FF | I | strand |
| 325 | VII | FFF | I | strand? | -383 | G | GA | GG | G | GG | GG | GG | . | strand |
| 326 | NNN | SSS | | strand? | -384 | I | IF | II | L | LI | LL | FF | I | strand |
| 327 | NYY | YYY | . | strand? | -385 | N | NN | NN | N | NN | NN | NN | | strand |
| 328 | YYY | YYY | I | break | -386 | Y | YN | YY | Y | YY | YY | HH | i | strand |
| 329 | FMM | AMM | I | helix | =387 | Y | YY | YY | Y | YY | YY | YY | I | strand |
| 330 | SSS | STT | s | helix | 388 | T | TS | TS | T | SS | VV | TT | i | strand |
| 331 | KDD | RGG | S | helix | -389 | R | RS | SM | P | SS | TT | TT | s | |
| 332 | WWW | CCC | i | helix | 390 | S | AE | SS | M | YS | QQ | VV | s | |
| 333 | LMM | AVV | I | helix | 391 | I | VF | MV | R | YY | YY | LL | i | |
| 334 | RRQ | STS | S | helix | 392 | I | RI | NN | V | AI | AA | AA | | |
| 335 | AGA | ATH | s | helix | -393 | R | LK | RR | A | AS | KQ | YY | | |
| 336 | YYF | EDD | s | helix | 394 | S | YY | YF | D | KN | PP | NN | S | |
| 337 | HDD | MEE | S | helix | 395 | T | DD | NN | D | AA | KK | LF | i | |
| 338 | GGG | NAS | s | helix | 396 | N | EP | PP | A | PP | PP | NN | S | parse |
| 339 | KEE | AQI | s | helix | 397 | _ | _ | _ | _ | RS | NN | _ | s | parse |
| 340 | SST | NLN | S | break | 398 | _ | _ | _ | _ | IH | _ | _ | s | |
| 341 | EEE | NEK | S | | 399 | _ | _ | _ | _ | PG | _ | _ | . | |
| 342 | TII | _ | . | | 400 | _ | _ | _ | _ | NN | _ | _ | a | |
| 343 | ITI | _ | S | | 401 | _ | _ | _ | _ | AA | PP | _ | i | parse |
| 344 | HHH | _ | a | | 402 | _ | _ | _ | _ | RK | YY | YY | s | |
| 345 | NNN | _ | a | parse | 403 | _ | _ | _ | _ | PP | PP | AP | . | parse |
| 346 | GAG | _ | . | parse | 404 | _ | _ | _ | _ | AS | SS | TS | S | parse |
| 347 | DTK | _ | S | parse | 405 | _ | _ | _ | _ | IY | EE | AI | s | |
| 348 | GGG | _ | . | parse | 406 | _ | _ | _ | _ | QS | TT | IM | s | |
| 349 | TDE | _ | S | | 407 | _ | _ | _ | _ | TT | HH | SS | . | |
| 350 | KKK | _ | a | | 408 | _ | _ | _ | _ | DN | TT | ST | s | |
| 351 | GGG | _ | . | | 409 | _ | _ | _ | _ | SP | AA | FV | i | |
| 352 | SGS | SKN | S | parse | 410 | _ | _ | _ | _ | LM | LM | DD | s | |
| 353 | SSS | STA | s | parse | 411 | _ | _ | _ | _ | IT | MM | AA | i | |
| 354 | VKK | ARQ | S | | 412 | D | _ | _ | T | NN | DD | DD | s | parse |
| 355 | AYY | AGG | i | | 413 | _ | _ | _ | P | AI | AA | RR | s | parse |
| 356 | RQQ | NNN | s | | 414 | _ | NS | G_ | G | _ | GG | GG | s | parse |
| 357 | LLI | VII | I | | 415 | _ | SS | _ | V | _ | VV | VV | i | |
| 358 | QKK | _ | s | | 416 | _ | SE | EE | E | _ | DK | AA | S | |
| 359 | GGG | _ | . | | 417 | _ | WS | _ | _ | _ | LL | SS | i | |
| 360 | VVV | _ | i | | 418 | _ | IG | _ | _ | TS | TT | II | s | |
| 361 | GGG | _ | . | | 419 | _ | FF | _ | _ | FF | FY | AV | i | |
| 362 | EQR | _ | S | | 420 | _ | PS | _ | _ | EE | ND | DD | S | |
| 363 | ERR | _ | s | | 421 | _ | _ | _ | _ | HK | NN | RR | s | |
| 364 | KE_ | _ | s | | 422 | _ | _ | _ | _ | NH | SS | SS | s | |
| 365 | LF_ | VLL | i | | 423 | _ | _ | _ | _ | _ | RR | WW | . | |
| 366 | _D_ | KNN | s | | 424 | _ | _ | _ | _ | GG | GG | PP | s | parse |
| 367 | _VV | SMM | i | | 425 | _ | _ | _ | _ | KI | EE | DG | s | parse |
| 368 | _DA | LVI | S | | 426 | _ | P_ | _ | _ | PP | YF | SS | i | parse |
| 369 | PP_ | RPP | s | parse | 427 | _ | _A | AA | F | LL | PL | GG | i | parse |
| 370 | DD_ | NNN | s | parse | 428 | A | _N | G_ | P | GG | GG | SS | s | parse |
| 371 | _ | PPP | . | parse | 429 | S | _S | GG | A | PP | PP | FY | . | |
| 372 | GY_ | YYH | s | parse | 430 | L | _I | MF | T | MR | VL | WW | | |
| 373 | IVV | LLL | I | | 431 | L | _L | LL | M | FF | LL | LL | i | |
| 374 | EPP | QEK | S | | 432 | Q | _E | SQ | P | AA | AV | KK | s | |
| | | | | | 433 | V | _K | SS | A | SS | EE | MM | s | |
| | | | | | 434 | E | _F | EE | P | _ | _ | _ | s | |
| | | | | | 435 | Q | _ | AE | A | _ | _ | _ | s | |
| | | | | | 436 | V | I_ | II | V | _ | _ | _ | i | |
| | | | | | 437 | H | R_ | SN | S | _ | _ | _ | s | |
| | | | | | 438 | M | W_ | MM | _ | _ | _ | _ | i | |
| | | | | | 439 | E | E_ | GG | _ | _ | _ | _ | s | |
| | | | | | 440 | E | H_ | AL | D | _ | _ | _ | s | |
| | | | | | 441 | P | P_ | PP | V | SI | _D | _ | | |
| | | | | | 442 | _ | A_ | _ | _ | WW | _K | _ | | |
| | | | | | 443 | _ | G_ | _ | _ | LI | _V | _ | | |
| | | | | | 444 | _ | _ | _ | _ | CY | DN | _ | | |
| | | | | | 445 | _ | EE | _ | _ | IV | AG | _ | | |
| 375 | TRR | VSS | s | strand | 446 | V | YK | KV | K | _ | _ | _ | . | strand (b1) |
| 376 | TTT | SSS | i | strand | -447 | T | TT | TT | T | _ | _ | _ | | strand (b1) |
| 377 | DDD | DEE | s | strand | -448 | D | ED | DD | D | _ | _ | _ | | strand (b1) |
| 378 | WWW | WWW | I | strand | 449 | M | MM | II | I | _ | _ | _ | | strand (b1) |
| 379 | DDD | GGG | s | strand | -450 | G | GG | GG | G | YY | NN | TT | | strand (b1) |
| 380 | WWW | WWW | I | strand | -451 | W | WW | WW | W | PP | SS | PP | | strand (b1) |
| 381 | SMI | GQQ | s | strand | 452 | E | EI | EP | E | -Y | YY | FF | s/i | strand (b1) |
| 382 | III | III | I | strand | -453 | I | VI | IV | V | -M | YY | GG | i | |
| 383 | YYY | DDD | . | parse | 454 | H | FY | YE | Y | -F | YY | FF | i | |
| 384 | PPP | PPP | . | parse | -455 | P | PP | AS | A | -I | PP | RR | s | |
| 385 | RQE | LLV | S | helix | -456 | E | QE | ER | P | -Q | KK | RR | s | helix |
| 386 | GGG | GGG | . | helix | -457 | S | GG | GG | A | -E | GG | II | i | helix |

TABLE 7-continued

| | | | | | | | | | | | | | | |
|---|---|---|---|---|---|---|---|---|---|---|---|---|---|---|
| 387 | MLL | LLL | I | helix | 458 F | LL | LL | L | -D | II | LL | i | | helix |
| 388 | YYY | RRR | . | helix | 459 Y | FY | YY | H | -F | YY | NN | i | | helix |
| 389 | DDD | IYV | . | helix | -460 K | DD | DE | T | -E | YY | WW | s/i | | helix |
| 390 | IQQ | TLL | i | helix | -461 L | LL | LV | L | -I | VV | LI | i | | helix |
| 391 | LII | MLL | I | helix | -462 L | LL | LL | V | -F | MM | KK | i | | helix |
| 392 | MMM | NNN | is | helix | 463 T | IM | RH | E | -C | DD | EE | s | | helix |
| 393 | RRR | MFT | s | helix | -464 R | WL | YY | T | -Y | YY | EE | s | | helix |
| 394 | IVV | MLL | I | helix | 465 I | IL | TL | L | -I | FF | YY | i | | helix |
| 395 | HVK | YYW | S | helix | 466 E | KD | AQ | Y | -L | KK | _ | s | | helix |
| 396 | NKN | DDD | S | helix | -467 K | ER | D_ | E | -K | TT | _ | s | | helix |
| 397 | DDD | RRR | s | helix | -468 D | SD | KK | R | -I | KK | _ | s | | helix |
| 398 | YYY | YYY | I | helix | -469 F | YY | YY | Y | -N | YY | _ | S | | helix |
| 399 | PPP | QQQ | . | parse | 470 _ | _ | _ | _ | -I | _ | _ | i | | |
| | | | | | 471 S | _ | _ | _ | -. | _ | _ | s | | |
| 400 | LNN | _ | s | parse | 472 K | PG | GG | D | -T | NG | NN | S | | parse |
| 401 | VYY | _ | i | | 473 G | QK | NN | L | -I | ND | DN | S | | parse |
| 402 | PHK | KKK | S | parse | 474 L | IP | PI | P | -L | PP | PP | . | | parse |
| 403 | VKK | PPP | s | parse | 475 P | PN | TD | E | -Q | LL | PP | s | | parse |
| 404 | TII | LLL | i | | -476 I | II | LI | C | -F | II | II | i | | strand |
| 405 | YYY | FFF | I | strand | 477 L | YV | YY | Y | -S | YY | YY | i | | strand |
| 406 | VII | LII | I | strand | -478 I | II | II | I | -I | IV | VV | i | | strand |
| 407 | TTT | VVV | i | strand | -479 T | TS | TT | T | -T | TT | TT | . | | strand |
| 408 | EEE | EEE | A | act site | =480 E | EE | EE | E | -E | EE | EE | a | | act site |
| 409 | NNN | NNN | A | act site | =481 N | NN | NN | N | -N | NN | NN | a | | act site |
| 410 | GGG | GGG | . | act site | =482 G | GG | GG | G | -G | GG | GG | . | | act site |
| 411 | ILL | LLL | I | | 483 A | AA | AA | A | -M | IF | VV | i | | |
| 412 | GGG | GGG | . | | 484 A | AA | CC | C | -N | SS | SS | i | | |
| 413 | LYY | AAA | I | | 485 M | YF | YI | Y | -E | TT | QH | s | | |
| 414 | KKK | KKK | A | | -486 R | NK | NN | N | -F | PP | RR | s | | parse |
| 415 | EDD | DDD | s | | -487 D | DD | DD | M | -N | GS | EG | S | | parse |
| 416 | SEE | EKS | S | | -488 E | IE | GE | G | -D | SS | ED | S | | parse |
| 417 | LFF | FIV | I | | -489 L | VI | LV | V | -A | EE | TS | s | | |
| 418 | PIV | AEE | s | | 490 V | TG | SV | E | -T | SN | DY | S | | parse |
| 419 | EED | AEA | S | | 491 N | ES | LN | N | -L | RR | LL | s | | parse |
| 420 | NSN | NND | S | parse | 492 G | DN | DG | G | -p | CE | NN | S | | parse |
| 421 | A_ | GGG | . | parse | 493 Q | GG | GK | Q | -V | _ | _ | s | | parse |
| 422 | T_ | EDS | S | parse | 494 _ | KK | R_ | _ | -E | _ | _ | S | | |
| 423 | P_ | _ | . | parse | 495 _ | _ | _ | _ | -E | EQ | _ | S | | |
| 424 | DE_ | _ | s | parse | 496 _ | _ | _ | _ | -A | AA | _ | i | | |
| 425 | TK_ | _ | s | | | | | | | | | | | |
| 426 | VTT | _ | . | | | | | | | | | | | |
| 427 | IVV | III | I | | -497 I | VI | IV | V | -L | II | _ | i | | helix |
| 428 | EHY | NYQ | S | | -498 E | HE | HQ | N | -L | AA | _ | s | | helix |
| 429 | DDD | DDD | A | parse | -499 D | DD | DD | D | -N | DD | DD | s | | helix |
| 430 | PDD | DDD | s | parse | 500 T | ST | QD | Q | -T | YY | TT | s | | helix |
| 431 | KAG | YYY | . | helix | -501 G | KK | RR | P | -Y | KK | AT | s | | helix |
| 432 | RRR | RRR | A | helix | =502 R | RR | RR | R | -R | RR | RR | a | | helix |
| 433 | III | III | I | helix | -503 H | II | II | L | -I | II | II | i | | helix |
| 434 | DDD | SRA | S | helix | -504 G | EQ | DS | D | -D | ND | YY | S | | helix |
| 435 | YYY | YYY | I | helix | =505 Y | YY | YY | Y | -Y | YY | YY | i | | helix |
| 436 | VVV | LLL | I | helix | 506 I | LL | LM | Y | -Y | LL | LL | i | | helix |
| 437 | KRK | RNN | S | helix | -507 E | KK | AQ | A | -Y | CC | RR | s | | helix |
| 438 | KQQ | EDD | s | helix | -508 E | QD | MQ | E | -R | SS | TS | s | | helix |
| 439 | YHH | HHH | i | helix | -509 H | HY | HH | H | -H | HH | YY | i | | helix |
| 440 | LLL | ILL | I | helix | -510 L | FL | LL | L | -L | LL | II | i | | helix |
| 441 | SNE | RVV | S | helix | -511 K | ET | IV | G | -Y | CC | NN | s | | helix |
| 442 | AVV | AQQ | i | helix | -512 A | AQ | QQ | I | -Y | FF | EE | i | | helix |
| 443 | MIL | MVV | I | helix | -513 C | AA | AV | V | -I | LL | AA | i | | helix |
| 444 | AAS | GGN | S | parse | 514 H | RH | SH | A | -R | RR | LL | s | | helix |
| 445 | DDD | GEE | s | parse | 515 R | KR | RR | D | -S | KK | KK | S | | helix |
| 446 | AAA | TAA | i | helix | -516 F | AA | AT | L | -A | VV | AA | i | | helix |
| 447 | III | III | I | helix | -517 I | II | II | I | -I | II | VV | i | | helix |
| 448 | HIA | ADA | s | helix | 518 _ | _ | _ | _ | -R | RK | _Q | S | | |
| | | | | | 519 E | EQ | EH | R | -A | EE | QQ | S | | |
| 449 | DDD | DDD | A | | -520 E | ND | DD | D | -_ | KK | DD | s | | |
| 450 | GGG | GGG | . | strand | -521 G | GG | GG | G | -G | GG | KK | s | | strand |
| 451 | AAA | IVV | I | strand | 522 G | VV | IL | Y | -S | VV | VV | i | | strand |
| 452 | NNN | PED | S | strand | -523 Q | DN | NH | P | -N | NN | DD | s | | strand |
| 453 | VVV | LVI | I | strand | -524 L | LL | LV | M | -V | IV | LL | i | | strand |
| 454 | KKK | MLM | s | strand | 525 K | RK | KK | R | -K | RR | RR | S | | strand |
| 455 | GGG | GGG | i | | -526 G | GA | GG | Gi | -G | GG | GG | . | | |
| 456 | YYY | YYY | I | strand | -527 Y | YY | YY | Yi | -F | YY | YYi | i | | strand |
| 457 | FFF | TTT | i | strand | -528 F | FY | MM | Fi | -Y | FF | TTi | i | | strand |
| 458 | III | TCS | i | strand | 529 V | VL | EA | As | -A | AA | VVi | s | | strand |
| 459 | WWW | WWW | I | strand | =530 W | WW | WW | Wi | -W | WW | WWi | i | | strand |
| 460 | SSS | GGG | . | parse | 531 S | SS | SS | S | -S | AA | STi | s | | strand |
| 461 | LLL | CPP | i | parse | 532 F | LL | LL | Li | -F | LL | ALi | i | | strand |
| 462 | QMM | III | i | | -533 L | ML | ML | Mi | -L | GG | MMi | i | | strand |
| 463 | DDD | DDD | A | act site | =534 D | DD | DD | D | -D | DD | DD | a | | act site |

TABLE 7-continued

| | | | | | | | | | | | | | | |
|---|---|---|---|---|---|---|---|---|---|---|---|---|---|---|
| 464 | QVV | LLL | i | | 535 | N | NN | NN | N | -C | NN | NN | s | |
| 465 | FFF | VVV | I | | 536 | F | FF | FF | F | -N | YY | FF | i | |
| 466 | SSS | SSS | A | | 537 | E | EE | EE | E | -E | EE | EE | a | |
| 467 | WWW | AAA | I | | 538 | W | WW | WW | W | -W | FF | WW | i | |
| 468 | TSS | CSS | s | | 539 | A | AA | AA | A | -F | CC | AY | i | |
| 469 | NNN | TKH | S | | 540 | W | MY | EE | E | -A | KK | TT | s | |
| 470 | GGG | GAS | . | | -541 | G | GG | GG | G | -G | GG | GG | . | |
| 471 | _ | EEQ | S | | | | | | | | | | | |
| 472 | YYY | MMM | I | | 542 | Y | YY | YY | Y | -F | FF | FF | i | |
| 473 | SEE | SSS | s | | 543 | S | TN | GN | R | -T | TT | SS | s | |
| 474 | KKK | KKK | A | | -544 | K | KK | KK | M | -V | VV | ED | S | |
| 475 | RRR | RRR | A | | =545 | R | RR | RR | R | -R | RR | RK | S | |
| 476 | YYY | YYY | I | | 546 | F | FF | FF | F | -F | FF | FF | i | |
| 477 | GGG | GGG | . | | =547 | G | GG | GG | G | -G | GG | GG | . | |
| 478 | LLL | FFF | I | strand | 548 | I | II | LM | L | -L | LL | LL | i | strand |
| 479 | FFF | VII | I | strand | -549 | v | IV | VI | V | -N | SS | HH | i | strand |
| 480 | FYY | FYY | I | strand | -550 | H | YH | HH | H | -F | YY | FF | i | strand |
| 481 | VVV | VVV | I | strand | -551 | I | VV | VV | V | -V | VV | VV | i | strand |
| 482 | DDD | DDD | A | strand | -552 | N | DN | DD | D | -D | NN | NN | s | strand |
| 483 | FFF | RRR | . | | 553 | Y | YF | YF | Y | -- | WW | YY | i | strand |
| 484 | PED | DDD | S | parse | -554 | E | ED | DR | Q | -- | DE | SS | S | strand |
| 485 | _ | DDD | a | parse | 555 | _ | _ | _ | _ | -- | DD | DD | a | |
| 486 | _ | AAN | S | parse | 556 | _ | _ | _ | _ | -- | LL | PP | i | |
| 487 | _ | GGG | . | parse | | | | | | | | | | |
| 488 | _ | NHE | S | parse | | | | | | | | | | |
| 489 | _ | GGG | . | parse | | | | | | | | | | |
| 490 | TTT | TSS | . | | -557 | T | TT | TT | T | -- | DD | SS | i | |
| 491 | QQQ | LLL | i | | -558 | Q | QL | LQ | Q | -- | _ | LL | . | |
| 492 | NEE | TET | S | | 559 | E | KE | VV | V | -- | DD | PP | s | |
| 493 | RRR | RRR | A | | =560 | R | RR | RR | R | -- | RR | RR | a | |
| 494 | YYY | TRT | s | | 561 | T | IK | TT | T | -- | NN | II | s | |
| 495 | IPP | HRR | . | break | -562 | P | KI | PP | V | -- | LL | PP | s | |
| 496 | KKK | RKK | s | helix | -563 | K | KK | KK | K | -- | KK | KR | S | helix |
| 497 | QKK | KKK | s | helix | 564 | Q | DD | DE | N | -- | EE | AE | S | helix |
| 498 | SSS | SSS | A | helix | =565 | S | SS | SS | S | -- | SS | SS | a | helix |
| 499 | AAA | FFF | I | helix | -566 | A | FG | FY | G | -- | GG | AA | i | helix |
| 500 | EYH | WYG | S | helix | 567 | L | YY | YY | K | -- | KK | KK | s | helix |
| 501 | WWW | WWW | I | helix | -568 | W | FW | WW | W | -- | WW | FF | i | helix |
| 502 | FYY | YYY | I | helix | -569 | F | YY | YY | Y | -- | YY | YY | i | helix |
| 503 | KKK | KQA | s | helix | -570 | K | QK | KR | S | -- | -- | AA | s | helix |
| 504 | SEK | KSE | S | helix | 571 | Q | QE | GN | A | -- | -- | SS | s | helix |
| 505 | VLL | VVV | I | helix | -572 | M | YV | VV | L | -- | -- | VI | i | helix |
| 506 | SAA | III | i | helix | -573 | M | II | IV | A | -- | -- | VV | i | helix |
| 507 | EEE | A-K | s | helix | -574 | A | KK | SS | S | -- | -- | RR | s | helix |
| 508 | TTT | S-T | . | helix | 575 | K | EN | RN | R | -- | -- | CC | s | helix |
| 509 | H-Q | N-R | S | helix | 576 | N | NN | GN | - | -- | -- | NN | s | helix |
| 510 | I-V | --- | . | | 577 | - | -- | -- | - | -- | -- | GG | . | |
| 511 | I-I | --- | . | | 578 | - | -- | -- | - | -- | -- | FF | i | |
| | | | | | 579 | - | -- | -- | - | -- | -- | PP | . | |
| | | | | | 580 | | | | | -- | -- | DD | a | |
| | | | | | 581 | | | | | -- | -- | PP | . | |
| | | | | | 582 | | | | | -- | -- | AA | i | |
| | | | | | 583 | | | | | -- | -- | TE | S | |
| | | | | | 584 | | | | | -- | -- | GG | . | |

What is claimed is:

1. A method for excluding homology between two protein families that is comprised of:
   (a) constructing models for secondary structural elements for each family,
   (b) aligning said secondary structural elements of one family with said secondary structural elements from the other family around sequence motifs, and
   (c) determining whether secondary structural elements flanking those motifs from one family are congruent to secondary structural elements in the other, to generate as a useful and practical result the statement of condition that the two families might be related by common ancestry or are not, wherein said secondary structure model for at least one protein family is built by prediction.

2. The method claim 1, wherein said predicted secondary structure model is produced by a method that comprises constructing an alignment of the sequences of the proteins within said family, using patterns of conservation and variation of said sequences between proteins with clearly defined evolutionary relationships to make assignments of positions in the alignment to the surface of the folded structure, the inside of the folded structure, active site, or parsing segments.

3. The method of claim 2, wherein the method to make said assignments of positions to the surface of the folded structure is comprised of dividing the proteins in the family into subgroups based on evolutionary relationships, identifying positions where n subgroups have variation, where n is two or greater, when at least one of the variable subgroups contains at that position at least one amino acid selected from the group consisting of aspartic acid, glutamic acid, lysine, arginine, and asparagine.

4. The method of claim 2, wherein the method to make said assignments of positions to the surface of the folded structure of said protein is comprised of dividing the proteins in the family into subgroups based on evolutionary relationships, identifying positions where n subgroups have variation, where n is two or greater, when at least one of the nonvariable subgroups contains an amino acid selected from the group consisting of aspartic acid, glutamic acid, lysine, arginine, and asparagine.

5. The method of claim 2, wherein the method to make said assignments of positions to the surface of the folded structure of said protein is comprised of dividing the proteins in the family into subgroups based on evolutionary relationships, identifying positions where variation is present in one subgroup, where said variable subgroup contains at least one a hydrophilic amino acid side selected from the group consisting of aspartic acid, glutamic acid, lysine, arginine, and asparagine, and the non-variable subgroups contain no amino acids other than those selected from the group consisting of alanine, cysteine, aspartic acid, glutamic acid, lysine, arginine, asparagine, glycine, histidine, proline, glutamine, serine, and threonine.

6. The method of claim 2, wherein the method to make said assignments of positions to the surface of the folded structure of said protein is comprised of dividing the proteins in the family into subgroups based on evolutionary relationships, identifying positions where all subgroups are non-variable, all subgroups contain no amino acids other than selected from the group consisting of alanine, cysteine, aspartic acid, glutamic acid, lysine, arginine, asparagine, glycine, histidine, proline, glutamine, serine, and threonine, and at least one subgroup containing one of the amino acids selected from the group consisting of aspartic acid, glutamic acid, lysine, arginine, and asparagine.

7. The method of claim 2, wherein the method to make said assignments of positions to the interior of the folded structure of said protein is comprised of identifying positions where an amino acid selected from the group consisting of phenylalanine, alanine, methionine, isoleucine, leucine, tyrosine, valine, and tryptophan is conserved in all proteins in an alignment.

8. The method of claim 2, wherein the method to make said assignments of positions to the interior of the folded structure of said protein is comprised of dividing the proteins in the family into subgroups based on evolutionary relationships, identifying positions where variation at a position in n subgroups, where n is two or greater, when no subgroup contains a amino acid selected from the group consisting of cysteine, aspartic acid, glutamic acid, lysine, arginine, asparagine, glycine, histidine, glutamine, serine, and threonine.

9. The method of claim 2, wherein the method to make said assignments of positions to the interior of the folded structure of said protein is comprised of dividing the proteins in the family into subgroups based on evolutionary relationships, identifying positions where no subgroup displays variability, and where all subgroups contain amino acids selected from the group consisting of cysteine, histidine, glutamine, serine, threonine, phenylalanine, alanine, methionine, isoleucine, leucine, tyrosine, valine, and tryptophan.

10. The method of claim 2, wherein the method to make said assignments of positions to the interior of the folded structure of said protein is comprised of dividing said proteins in the family into subgroups based on evolutionary relationships, identifying positions where variation in one subgroup, where all subgroups contain only amino acids selected from the group consisting of phenylalanine, alanine, methionine, isoleucine, leucine, tyrosine, valine, and tryptophan.

11. The method of claim 2, wherein the method to make said assignments of positions to the interior of the folded structure of said protein is comprised of dividing said proteins in the family into subgroups based on evolutionary relationships, identifying positions where variation in one subgroup, where over 85% of the amino acids at that position are selected from the group consisting of phenylalanine, alanine, methionine, isoleucine, leucine, tyrosine, valine, and tryptophan.

12. A method for detecting homology between two protein families that is comprised of:
   (a) constructing models for secondary structures for each of said families,
   (b) aligning the secondary structural elements of one family with the secondary structural elements from the other around sequence motifs, and
   (c) determining whether the core secondary structural elements flanking those motifs from one family are congruent to core secondary structural elements in the other, to generate as a useful and practical result the statement of condition that the two families might be related by common ancestry or are not, wherein said secondary structure model for at least one protein family is built by prediction.

13. The method claim 12, wherein said core secondary structural elements correspond to polypeptide segments in each of the proteins in the multiple sequence alignment, where the protein contains some sequences that are between 100 and 150 PAM units divergent.

14. The method claim 12, wherein said core elements are regions of the multiple alignment where said pairwise alignment constructed for any pair of sequences in said multiple alignment by dynamic programming is consistent with the pairwise alignment of every other pair of sequences.

15. The method claim 12, wherein said core elements are regions of the multiple alignment where the overall sequence divergence is greater than the average within said proteins in the alignment.

16. A process for constructing a database of protein sequences comprised of (a) identifying families of homologous protein sequences within said database, (b) constructing for each family a multiple sequence alignment, an evolutionary tree, and ancestral sequences at nodes in the tree, (c) constructing a corresponding multiple alignment for the DNA sequences that encode the proteins in the protein family, (d) assigning silent and expressed mutations in the DNA sequences to each branch of the DNA evolutionary tree (e) predicting a consensus secondary structure for the family, and (f) aligning this predicted secondary structure with the ancestral sequence at the root of the tree in said database.

17. A process for the identification of in vitro behaviors of proteins that contribute to their physiological function, comprised of (a) identifying branches in an evolutionary tree describing the evolution of the family of related protein that have high expressed to silent ratios, (b) reconstructing the sequences of ancestral proteins at nodes in the tree before and after the episode of rapid sequence evolution, (c) preparing proteins that have the reconstructed sequences corresponding to the ancestral proteins before, during, and after episodes of high expressed to silent ratio of substitution in a protein, (d) measuring in the laboratory the behaviors of the ancestral proteins before, during, and after the evolution of new biological function, and (e) determining which behaviors change rapidly during this episode to generate as a useful and practical result a list of behaviors in the protein family that might contribute to fitness by different members of the family in different organism.

18. A process for constructing a surrogate database comprised of (a) identifying all of the families of proteins, (b) constructing ancestral sequences for the evolutionary family to generate as a useful and practical result a database within which each protein family is represented by a single ancestral sequence.

19. The process of claim 18 wherein said ancestral sequences are reconstructed by maximum parsimony methods.

20. The process of claim 18 wherein said ancestral sequences are reconstructed by maximum likelihood methods.

21. The process of claim 18 wherein said ancestral sequences are reconstructed for a point in the evolutionary tree of the family near the root of the tree.

22. The process of claim 18 wherein said ancestral sequences are reconstructed for a point in the evolutionary tree of the family near the center of gravity of the tree.

23. A process for searching for homologs of a probe sequence comprised of (a) providing a database of reconstructed ancestral sequences where one ancestral sequence represents each family of proteins within the database, (b) aligning the probe sequence against said database of reconstructed ancestral sequences, (c) identifying significant matches, to generate as a useful and practical result a list of families that are possible homologs of the probe sequence.

* * * * *

SEQUENCE LISTING (1) GENERAL INFORMATION:

(iii) NUMBER OF SEQUENCES: 74

(2) INFORMATION FOR SEQ ID NO: 1:

(i) SEQUENCE CHARACTERISTICS:
    (A) LENGTH: 219
    (B) TYPE: amino acid
    (D) TOPOLOGY: linear (ii) MOLECULE TYPE: amino acid (vi) ORIGINAL SOURCE:
    (A) ORGANISM: Saccharomyc es cerevisiae (ix) FEATURE:
    (D) OTHER INFORMATION:HS8_2_YEAST HEAT SHOCK PROTEIN HSP90

(xi) SEQUENCE DESCRIPTION: SEQ ID NO: 1:

Met Ala Ser Glu Thr Phe Glu Phe Gln Ala Glu Ile Thr Gln Leu
                 5                  10                  15

Met Ser Leu Ile Ile Asn Thr Val Tyr Ser Asn Lys Glu Ile Phe
                20                  25                  30

Leu Arg Glu Leu Ile Ser Asn Ala Ser Asp Ala Leu Asp Lys Ile
                35                  40                  45

Arg Tyr Lys Ser Leu Ser Asp Pro Lys Gln Leu Glu Thr Glu Pro
                50                  55                  60

Asp Leu Phe Ile Arg Ile Thr Pro Lys Pro Glu Gln Lys Val Leu
                65                  70                  75

Glu Ile Arg Asp Ser Gly Ile Gly Met Thr Lys Ala Glu Leu Ile
                80                  85                  90

Asn Asn Leu Gly Thr Ile Ala Lys Ser Gly Thr Lys Ala Phe Met
                95                 100                 105

Glu Ala Leu Ser Ala Gly Ala Asp Val Ser Met Ile Gly Gln Phe
               110                 115                 120

Gly Val Gly Phe Tyr Ser Leu Phe Leu Val Ala Asp Arg Val Gln
               125                 130                 135

Val Ile Ser Lys Ser Asn Asp Asp Glu Gln Tyr Ile Trp Glu Ser
               140                 145                 150

Asn Ala Gly Gly Ser Phe Thr Val Thr Leu Asp Glu Val Asn Glu
               155                 160                 165

Arg Ile Gly Arg Gly Thr Ile Leu Arg Leu Phe Leu Lys Asp Asp
               170                 175                 180

Gln Leu Glu Tyr Leu Glu Glu Lys Arg Ile Lys Glu Val Ile Lys
               185                 190                 195

Arg His Ser Glu Phe Val Ala Tyr Pro Ile Gln Leu Val Val Thr
               200                 205                 210

Lys Glu Val Glu Lys Glu Val Pro Ile
               215

(2) INFORMATION FOR SEQ ID NO: 2:

(i) SEQUENCE CHARACTERISTICS:
        (A) LENGTH: 216
        (B) TYPE: amino acid
        (D) TOPOLOGY: linear (ii) MOLECULE TYPE: amino acid (vi) ORIGINAL SOURCE:
        (A) ORGANISM: Saccharomyces cerevisiae (ix) FEATURE:
        (D) OTHER INFORMATION:HS8_3_YEAST HEAT SHOCK COGNATE PROTEIN
            HSC82

(xi) SEQUENCE DESCRIPTION: SEQ ID NO: 2:

Glu Thr Phe Glu Phe Gln Ala Glu Ile Thr Gln Leu Met Ser Leu
                 5                  10                  15

Ile Ile Asn Thr Val Tyr Ser Asn Lys Glu Ile Phe Leu Arg Glu
                20                  25                  30

Leu Ile Ser Asn Ala Ser Asp Ala Leu Asp Lys Ile Arg Tyr Gln
                35                  40                  45

```
Ala Leu Ser Asp Pro Lys Gln Leu Glu Thr Glu Pro Asp Leu Phe
                50                  55                  60

Ile Arg Ile Thr Pro Lys Pro Glu Glu Lys Val Leu Glu Ile Arg
                65                  70                  75

Asp Ser Gly Ile Gly Met Thr Lys Ala Glu Leu Ile Asn Asn Leu
                80                  85                  90

Gly Thr Ile Ala Lys Ser Gly Thr Lys Ala Phe Met Glu Ala Leu
                95                 100                 105

Ser Ala Gly Ala Asp Val Ser Met Ile Gly Gln Phe Gly Val Gly
               110                 115                 120

Phe Tyr Ser Leu Phe Leu Val Ala Asp Arg Val Gln Val Ile Ser
               125                 130                 135

Lys Asn Asn Glu Asp Glu Gln Tyr Ile Trp Glu Ser Asn Ala Gly
               140                 145                 150

Gly Ser Phe Thr Val Thr Leu Asp Glu Val Asn Glu Arg Ile Gly
               155                 160                 165

Arg Gly Thr Val Leu Arg Leu Phe Leu Lys Asp Asp Gln Leu Glu
               170                 175                 180

Tyr Leu Glu Glu Lys Arg Ile Lys Glu Val Ile Lys Arg His Ser
               185                 190                 195

Glu Phe Val Ala Tyr Pro Ile Gln Leu Leu Val Thr Lys Glu Val
               200                 205                 210

Glu Lys Glu Val Pro Ile
               215
```

(2) INFORMATION FOR SEQ ID NO: 3:

(i) SEQUENCE CHARACTERISTICS:
        (A) LENGTH: 219
        (B) TYPE: amino acid
        (D) TOPOLOGY: linear (ii) MOLECULE TYPE: amino acid (vi) ORIGINAL SOURCE:
        (A) ORGANISM: Candida albicans (ix) FEATURE:
        (D) OTHER INFORMATION:HS9 0_CANAL HEAT SHOCK PROTEIN 90 HOMOLOG (xi) SEQUENCE DESCRIPTION: SEQ ID NO: 3:

```
Ala Lys Val Glu Thr His Glu Phe Thr Ala Glu Ile Ser Gln Leu
                 5                  10                  15

Met Ser Leu Ile Ile Asn Thr Val Tyr Ser Asn Lys Glu Ile Phe
                20                  25                  30

Leu Arg Glu Leu Ile Ser Asn Ala Ser Asp Ala Leu Asp Lys Ile
                35                  40                  45

Arg Tyr Gln Ala Leu Ser Asp Pro Ser Gln Leu Glu Ser Glu Pro
                50                  55                  60

Glu Leu Phe Ile Arg Ile Ile Pro Gln Lys Asp Gln Lys Val Leu
                65                  70                  75

Glu Ile Arg Asp Ser Gly Ile Gly Met Thr Lys Ala Asp Leu Val
                80                  85                  90

Asn Asn Leu Gly Thr Ile Ala Lys Ser Gly Thr Lys Ser Phe Met
                95                 100                 105

Glu Ala Leu Ser Ala Gly Ala Asp Val Ser Met Ile Gly Gln Phe
               110                 115                 120

Gly Val Gly Phe Tyr Ser Leu Phe Leu Val Ala Asp His Val Gln
```

```
                    125                 130                 135
Val Ile Ser Lys His Asn Asp Asp Glu Gln Tyr Val Trp Glu Ser
                140                 145                 150

Asn Ala Gly Gly Lys Phe Thr Val Thr Leu Asp Glu Thr Asn Glu
                155                 160                 165

Arg Leu Gly Arg Gly Thr Met Leu Arg Leu Phe Leu Lys Glu Asp
                170                 175                 180

Gln Leu Glu Tyr Leu Glu Lys Arg Ile Lys Glu Val Val Lys
                185                 190                 195

Lys His Ser Glu Phe Val Ala Tyr Pro Ile Gln Leu Val Val Thr
                200                 205                 210

Lys Glu Val Glu Lys Glu Val Pro Glu
                215
```

(2) INFORMATION FOR SEQ ID NO: 4:

(i) SEQUENCE CHARACTERISTICS:
        (A) LENGTH: 216
        (B) TYPE: amino acid
        (D) TOPOLOGY: linear (ii) MOLECULE TYPE: amino acid (vi) ORIGINAL SOURCE:
        (A) ORGANISM: Schizosacch aromyces pombe (ix) FEATURE:
        (D) OTHER INFORMATION:HS9 0_SCHPO HEAT SHOCK PROTEIN 90 HOMOLOG (xi) SEQUENCE DESCRIPTION: SEQ ID NO: 4:

```
Glu Thr Phe Lys Phe Asp Trp Glu Ile Ser Gln Leu Met Ser Leu
                 5                  10                  15

Ile Ile Asn Thr Val Tyr Ser Asn Lys Glu Ile Phe Leu Arg Glu
                20                  25                  30

Leu Ile Ser Asn Ala Ser Asp Ala Leu Asp Lys Ile Arg Tyr Gln
                35                  40                  45

Ser Leu Ser Asp Pro His Ala Leu Asp Ala Glu Lys Asp Leu Phe
                50                  55                  60

Ile Arg Ile Thr Pro Asp Lys Glu Asn Lys Ile Leu Thr Ile Arg
                65                  70                  75

Asp Thr Gly Ile Gly Met Thr Lys Asn Asp Leu Ile Asn Asn Leu
                80                  85                  90

Gly Val Ile Ala Lys Ser Gly Thr Lys Gln Phe Met Glu Ala Ala
                95                 100                 105

Ala Ser Gly Ala Asp Ile Ser Met Ile Gly Gln Phe Gly Val Gly
               110                 115                 120

Phe Tyr Ser Ala Tyr Leu Val Ala Asp Lys Val Gln Val Val Ser
               125                 130                 135

Lys His Asn Asp Asp Glu Gln Tyr Ile Trp Glu Ser Ser Ala Gly
               140                 145                 150

Gly Ser Phe Thr Val Thr Leu Asp Thr Asp Gly Pro Arg Leu Leu
               155                 160                 165

Arg Gly Thr Glu Ile Arg Leu Phe Met Lys Glu Asp Gln Leu Gln
               170                 175                 180

Tyr Leu Glu Glu Lys Thr Ile Lys Asp Thr Val Lys Lys His Ser
               185                 190                 195

Glu Phe Ile Ser Tyr Pro Ile Gln Leu Val Val Thr Arg Glu Val
               200                 205                 210
```

```
Glu Lys Glu Val Pro Glu
            215
```

(2) INFORMATION FOR SEQ ID NO: 5:

(i) SEQUENCE CHARACTERISTICS:
        (A) LENGTH: 216
        (B) TYPE: amino acid
        (D) TOPOLOGY: linear (ii) MOLECULE TYPE: amino acid (vi) ORIGINAL SOURCE:
        (A) ORGANISM: Ajellomyces capsulata (ix) FEATURE:
        (D) OTHER INFORMATION:HS8 2_AJECA HEAT SHOCK PROTEIN 82

(xi) SEQUENCE DESCRIPTION: SEQ ID NO: 5:

```
Glu Thr Phe Glu Phe Gln Ala Glu Ile Ser G ln Leu Leu Ser Leu
                 5                  10                  15

Ile Ile Asn Thr Val Tyr Ser Asn Lys Glu I le Phe Leu Arg Glu
                20                  25                  30

Leu Ile Ser Asn Phe Ser Asp Ala Leu Asp L ys Ile Arg Tyr Lys
                35                  40                  45

Ala Leu Ser Asp Pro Ser Lys Leu Glu Ser A sp Lys Asp Leu Arg
                50                  55                  60

Ile Asp Ile Thr Pro Asp Lys Gly Asn Lys T hr Leu Thr Ile Arg
                65                  70                  75

Asp Thr Gly Ile Gly Met Thr Lys Ala Asp L eu Val Asn Asn Leu
                80                  85                  90

Gly Thr Ile Ala Arg Ser Gly Thr Lys Gln P he Met Glu Ala Leu
                95                 100                 105

Thr Ala Gly Ala Asp Ile Ser Met Ile Gly G ln Phe Gly Val Gly
               110                 115                 120

Phe Tyr Ser Ala Tyr Leu Val Ala Asp Lys V al Thr Val Ile Ser
               125                 130                 135

Lys Ser Asn Asp Asp Glu Gln Tyr Ile Trp G lu Ser Asn Ala Gly
               140                 145                 150

Gly Thr Phe Lys Val Thr Gln Asp Asp Asp G ly Arg Ala Ile Gly
               155                 160                 165

Arg Gly Thr Lys Met Ile Leu His Leu Lys A sp Glu Gln Thr Glu
               170                 175                 180

Tyr Leu Asn Glu Ser Lys Ile Lys Glu Val V al Lys Lys Gln Ser
               185                 190                 195

Glu Phe Ile Phe Tyr Pro Ile Tyr Leu His V al Leu Lys Glu Asn
               200                 205                 210

Glu Lys Glu Val Pro Asp
            215
```

(2) INFORMATION FOR SEQ ID NO: 6:

(i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
        (A) ORGANISM: Gallus g allus (ix) FEATURE:
        (D) OTHER INFORMATION:HS9_B_CHICK HEAT SHOCK COGNATE PROTEIN
            HSP 90-B ETA (xi) SEQUENCE DESCRIPTION: SEQ ID NO: 6:

Asp Glu Val Glu Thr Phe Ala Phe Gln Ala Glu Ile Ala Gln Leu
                 5                  10                  15

Met Ser Leu Ile Ile Asn Thr Phe Tyr Ser Asn Lys Glu Ile Phe
                20                  25                  30

Leu Arg Glu Leu Ile Ser Asn Ala Ser Asp Ala Leu Asp Lys Ile
                35                  40                  45

Arg Tyr Glu Ser Leu Thr Asp Pro Ser Lys Leu Asp Thr Gly Lys
                50                  55                  60

Asp Leu Lys Ile Asp Ile Val Pro Asn Pro Arg Asp Pro Thr Leu
                65                  70                  75

Thr Leu Leu Asp Thr Gly Ile Gly Met Thr Lys Ala Asp Leu Val
                80                  85                  90

Asn Asn Leu Gly Thr Ile Ala Lys Ser Gly Thr Lys Ala Phe Met
                95                 100                 105

Glu Ala Leu Gln Ala Gly Ala Asp Ile Ser Met Ile Gly Gln Phe
               110                 115                 120

Gly Val Gly Phe Tyr Ser Ala Tyr Leu Val Ala Glu Lys Val Val
               125                 130                 135

Val Ile Thr Lys His Asn Asp Asp Glu Gln Tyr Ala Trp Glu Ser
               140                 145                 150

Ser Ala Gly Gly Ser Phe Thr Val Arg Thr Asp His Gly Glu Pro
               155                 160                 165

Ile Gly Arg Gly Thr Lys Val Ile Leu Tyr Leu Lys Glu Asp Gln
               170                 175                 180

Thr Glu Tyr Leu Glu Glu Arg Arg Val Lys Glu Val Val Lys Lys
               185                 190                 195

His Ser Gln Phe Ile Gly Tyr Pro Ile Thr Leu Tyr Val Glu Lys
               200                 205                 210

Glu Arg Glu Lys Glu Val Ser Asp
               215

(2) INFORMATION FOR SEQ ID NO: 7:

(i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
        (A) ORGANISM: Oryza sativa (ix) FEATURE:
        (D) OTHER INFORMATION:HS8_2_ORYSA HEAT SHOCK PROTEIN 82

(xi) SEQUENCE DESCRIPTION: SEQ ID NO: 7:

Glu Thr Glu Thr Phe Ala Phe Gln Ala Glu Ile Asn Gln Leu Leu
                 5                  10                  15

Ser Leu Ile Ile Asn Thr Phe Tyr Ser Asn Lys Glu Ile Phe Leu
                20                  25                  30

Arg Glu Leu Ile Ser Asn Ser Ser Asp Ala Leu Asp Lys Ile Arg
                35                  40                  45

```
Phe Glu Ser Leu Thr Asp Lys Ser Lys Leu Asp Ala Gln Pro Glu
                 50                  55                  60

Leu Phe Ile His Ile Val Pro Asp Lys Ala Ser Asn Thr Leu Ser
                 65                  70                  75

Ile Ile Asp Ser Gly Ile Gly Met Thr Lys Ser Asp Leu Val Asn
                 80                  85                  90

Asn Leu Gly Thr Ile Ala Arg Ser Gly Thr Lys Glu Phe Met Glu
                 95                 100                 105

Ala Leu Ala Ala Gly Ala Asp Val Ser Met Ile Gly Gln Phe Gly
                110                 115                 120

Val Gly Phe Tyr Ser Ala Tyr Leu Val Ala Glu Arg Val Val Val
                125                 130                 135

Thr Thr Lys His Asn Asp Asp Glu Gln Tyr Val Trp Glu Ser Gln
                140                 145                 150

Ala Gly Gly Ser Phe Thr Val Thr Arg Asp Thr Ser Gly Glu Gln
                155                 160                 165

Leu Gly Arg Gly Thr Lys Ile Thr Leu Tyr Leu Lys Asp Asp Gln
                170                 175                 180

Leu Glu Tyr Leu Glu Glu Arg Arg Leu Lys Asp Leu Ile Lys Lys
                185                 190                 195

His Ser Glu Phe Ile Ser Tyr Pro Ile Ser Leu Trp Thr Glu Lys
                200                 205                 210

Thr Thr Glu Lys Glu Ile Ser Asp
                215
```

(2) INFORMATION FOR SEQ ID NO: 8:

(i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
        (A) ORGANISM: Arabidopsis thaliana (ix) FEATURE:
        (D) OTHER INFORMATION:HS8 1_ARATH HEAT SHOCK PROTEIN 81
           (HSP81-1)

(xi) SEQUENCE DESCRIPTION: SEQ ID NO: 8:

```
Asp Ala Glu Thr Phe Ala Phe Gln Ala Glu Ile Asn Gln Leu Leu
                  5                  10                  15

Ser Leu Ile Ile Asn Thr Phe Tyr Ser Asn Lys Glu Ile Phe Leu
                 20                  25                  30

Arg Glu Leu Ile Ser Asn Ser Ser Asp Ala Leu Asp Lys Ile Arg
                 35                  40                  45

Phe Glu Ser Leu Thr Asp Lys Ser Lys Leu Asp Gly Gln Pro Glu
                 50                  55                  60

Leu Phe Ile Arg Leu Val Pro Asp Lys Ser Asn Lys Thr Leu Ser
                 65                  70                  75

Ile Ile Asp Ser Gly Ile Gly Met Thr Lys Ala Asp Leu Val Asn
                 80                  85                  90

Asn Leu Gly Thr Ile Ala Arg Ser Gly Thr Lys Glu Phe Met Glu
                 95                 100                 105

Ala Leu Gln Ala Gly Ala Asp Val Ser Met Ile Gly Gln Phe Gly
                110                 115                 120
```

-continued

```
Val Gly Phe Tyr Ser Ala Tyr Leu Val Ala Glu Lys Val Val Val
                125                 130                 135

Thr Thr Lys His Asn Asp Asp Glu Gln Tyr Val Trp Glu Ser Gln
                140                 145                 150

Ala Gly Gly Ser Phe Thr Val Thr Arg Asp Val Asp Gly Glu Pro
                155                 160                 165

Leu Gly Arg Gly Thr Lys Ile Thr Leu Phe Leu Lys Asp Asp Gln
                170                 175                 180

Leu Glu Tyr Leu Glu Glu Arg Arg Leu Lys Asp Leu Val Lys Lys
                185                 190                 195

His Ser Glu Phe Ile Ser Tyr Pro Ile Tyr Leu Trp Ile Glu Lys
                200                 205                 210

Thr Thr Glu Lys Glu Ile Ser Asp
                215
```

(2) INFORMATION FOR SEQ ID NO: 9:

(i) SEQUENCE CHARACTERISTICS:
        (A) LENGTH: 216
        (B) TYPE: amino acid
        (D) TOPOLOGY: linear (ii) MOLECULE TYPE: amino acid (vi) ORIGINAL SOURCE:
        (A) ORGANISM: Lycopersicon esculentum (ix) FEATURE:
        (D) OTHER INFORMATION:HS80_LYCES HEAT SHOCK COGNATE PROTEIN 80

(xi) SEQUENCE DESCRIPTION: SEQ ID NO: 9:

```
Glu Thr Phe Ala Phe Gln Ala Glu Ile Asn Gln Leu Leu Ser Leu
                 5                  10                  15

Ile Ile Asn Thr Phe Tyr Ser Asn Lys Glu Ile Phe Leu Arg Glu
                20                  25                  30

Leu Ile Ser Asn Ser Ser Asp Ala Leu Asp Lys Ile Arg Phe Glu
                35                  40                  45

Ser Leu Thr Asp Lys Ser Lys Leu Asp Gly Gln Pro Glu Leu Phe
                50                  55                  60

Ile His Ile Ile Pro Asp Lys Ala Asn Asn Thr Leu Thr Ile Ile
                65                  70                  75

Asp Ser Gly Ile Gly Met Thr Lys Ala Asp Leu Val Asn Asn Leu
                80                  85                  90

Gly Thr Ile Ala Arg Ser Gly Thr Lys Glu Phe Met Glu Ala Leu
                95                  100                 105

Ala Ala Gly Ala Asp Val Ser Met Ile Gly Gln Phe Gly Val Gly
                110                 115                 120

Phe Tyr Ser Ala Tyr Leu Val Ala Glu Lys Val Val Val Thr Thr
                125                 130                 135

Lys His Asn Asp Asp Glu Gln Tyr Val Trp Glu Ser Gln Ala Gly
                140                 145                 150

Gly Ser Phe Thr Val Thr Arg Asp Thr Ser Gly Glu Asn Leu Gly
                155                 160                 165

Arg Gly Thr Lys Met Val Leu Tyr Leu Lys Glu Asp Gln Leu Glu
                170                 175                 180

Tyr Leu Glu Glu Arg Arg Leu Lys Asp Leu Ile Lys Lys His Ser
                185                 190                 195

Glu Phe Ile Ser Tyr Pro Ile Ser Leu Trp Val Glu Lys Thr Ile
```

```
                    200                 205                 210
Glu Lys Glu Ile Ser Asp
                215

(2) INFORMATION FOR SEQ ID NO: 10:

(i) SEQUENCE CHARACTERISTICS:
        (A) LENGTH: 219
        (B) TYPE: amino acid
        (D) TOPOLOGY: linear (ii) MOLECULE TYPE: amino acid (vi) ORIGINAL SOURCE:
        (A) ORGANISM: Zea mays (ix) FEATURE:
        (D) OTHER INFORMATION:HS8_2_MAIZE HEAT SHOCK PROTEIN 82

(xi) SEQUENCE DESCRIPTION: SEQ ID NO: 10:

Glu Thr Glu Thr Phe Ala Phe Gln Ala Glu I le Asn Gln Leu Leu
                 5                  10                  15

Ser Leu Ile Ile Asn Thr Phe Tyr Ser Asn L ys Glu Ile Phe Leu
                20                  25                  30

Arg Glu Leu Ile Ser Asn Ala Ser Asp Ala L eu Asp Lys Ile Arg
                35                  40                  45

Phe Glu Ser Leu Thr Asp Lys Ser Asn Val A sn Ala Gln Pro Glu
                50                  55                  60

Leu Phe Ile Arg Leu Val Pro Asp Lys Ala S er Lys Thr Leu Ser
                65                  70                  75

Ile Ile Asp Ser Gly Val Gly Met Thr Lys S er Asp Leu Val Asn
                80                  85                  90

Asn Leu Gly Thr Ile Ala Arg Ser Gly Thr L ys Glu Phe Met Glu
                95                 100                 105

Ala Leu Ala Ala Gly Ala Thr Asp Val Ser M et Ile Gly Gln Phe
               110                 115                 120

Gly Val Gly Phe Tyr Ser Ala Tyr Leu Val A la Asp Arg Val Met
               125                 130                 135

Val Thr Thr Lys His Asn Asp Asp Glu Gln T yr Val Trp Glu Ser
               140                 145                 150

Gln Ala Gly Gly Ser Phe Thr Val Thr His A sp Thr Thr Gly Glu
               155                 160                 165

Gln Leu Gly Arg Gly Thr Lys Ile Thr Leu P he Leu Lys Asp Asp
               170                 175                 180

Gln Leu Glu Tyr Leu Glu Glu Arg Arg Leu L ys Asp Leu Val Lys
               185                 190                 195

Lys His Ser Glu Phe Ile Ser Tyr Pro Ile T yr Leu Trp Thr Glu
               200                 205                 210

Lys Thr Thr Glu Lys Glu Ile Ser Asp
               215

(2) INFORMATION FOR SEQ ID NO: 11:

(i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
```

(A) ORGANISM: Drosophila pseudoobscura (ix) FEATURE:
            (D) OTHER INFORMATION:HS8 3_DROPS HEAT SHOCK PROTEIN 83
                (HSP 82) (FRAGMENT)

(xi) SEQUENCE DESCRIPTION: SEQ ID NO: 11:

Glu Glu Ala Glu Thr Phe Ala Phe Gln Ala Glu Ile Ala Gln Leu
                 5                  10                  15

Met Ser Leu Ile Ile Asn Thr Phe Tyr Ser Asn Lys Glu Ile Phe
                20                  25                  30

Leu Arg Glu Leu Ile Ser Asn Ala Ser Asp Ala Leu Asp Lys Ile
                35                  40                  45

Arg Tyr Glu Ser Leu Thr Asp Pro Ser Lys Leu Asp Ser Gly Lys
                50                  55                  60

Glu Leu Tyr Ile Lys Leu Ile Pro Asn Lys Thr Ala Gly Thr Leu
                65                  70                  75

Thr Ile Ile Asp Thr Gly Ile Gly Met Thr Lys Ser Asp Leu Val
                80                  85                  90

Asn Asn Leu Gly Thr Ile Ala Lys Ser Gly Thr Lys Ala Phe Met
                95                 100                 105

Glu Ala Leu Gln Ala Gly Ala Asp Ile Ser Met Ile Gly Gln Phe
               110                 115                 120

Gly Val Gly Phe Tyr Ser Ala Tyr Leu Ile Ala Asp Arg Val Thr
               125                 130                 135

Val Thr Ser Lys Asn Asn Asp Asp Glu Gln Tyr Val Trp Glu Ser
               140                 145                 150

Ser Ala Gly Gly Ser Phe Thr Val Lys Ala Asp Asn Ser Glu Pro
               155                 160                 165

Leu Gly Arg Gly Thr Lys Ile Val Leu Tyr Ile Lys Glu Asp Gln
               170                 175                 180

Thr Asp Tyr Leu Glu Glu Ser Lys Ile Lys Glu Ile Val Asn Lys
               185                 190                 195

His Ser Gln Phe Ile Gly Tyr Pro Ile Lys Leu Leu Val Glu Lys
               200                 205                 210

Glu Arg Glu Lys Glu Val Ser Asp
               215

(2) INFORMATION FOR SEQ ID NO: 12:

(i) SEQUENCE CHARACTERISTICS:
            (A) LENGTH: 218
            (B) TYPE: amino acid
            (D) TOPOLOGY: linear (ii) MOLECULE TYPE: amino acid (vi) ORIGINAL SOURCE:
            (A) ORGANISM: Cricetulus griseus (ix) FEATURE:
            (D) OTHER INFORMATION:HS9 A_CRIGR HEAT SHOCK PROTEIN HSP
                90-ALPHA (HSP 86)

(xi) SEQUENCE DESCRIPTION: SEQ ID NO: 12:

Glu Glu Val Glu Thr Phe Ala Phe Gln Ala Glu Ile Ala Gln Leu
                 5                  10                  15

Met Ser Leu Ile Ile Asn Thr Phe Tyr Ser Asn Lys Glu Ile Phe
                20                  25                  30

Leu Arg Glu Leu Ile Ser Asn Ser Ser Asp Ala Leu Asp Lys Ile

```
                    35                  40                  45
Arg Tyr Glu Ser Leu Thr Asp Pro Ser Lys L eu Asp Ser Gly Lys
                50                  55                  60
Glu Leu His Ile Asn Ile Ile Pro Asn Lys G ln Asp Arg Thr Leu
                65                  70                  75
Thr Ile Val Asp Thr Gly Ile Gly Met Thr L ys Ala Asp Leu Ile
                80                  85                  90
Asn Asn Leu Gly Thr Ile Ala Lys Ser Gly T hr Lys Ala Phe Met
                95                 100                 105
Glu Ala Leu Gln Ala Gly Ala Asp Ile Ser M et Ile Gly Gln Phe
               110                 115                 120
Gly Val Gly Phe Tyr Thr Ala Tyr Leu Val A la Glu Lys Val Thr
               125                 130                 135
Val Ile Thr Lys His Asn Asp Asp Glu Gln T yr Ala Trp Glu Ser
               140                 145                 150
Ser Ala Gly Gly Ser Phe Thr Val Arg Thr A sp Thr Gly Glu Pro
               155                 160                 165
Met Gly Arg Gly Thr Lys Val Ile Leu His L eu Lys Glu Asp Gln
               170                 175                 180
Thr Glu Tyr Met Glu Glu Arg Arg Ile Lys G lu Ile Val Lys Lys
               185                 190                 195
His Ser Gln Phe Ile Gly Tyr Pro Ile Thr L eu Phe Val Glu Lys
               200                 205                 210
Glu Arg Asp Lys Glu Val Ser Asp
               215

(2) INFORMATION FOR SEQ ID NO: 13:

(i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
        (A) ORGANISM: Homo sap iens (ix) FEATURE:
        (D) OTHER INFORMATION:HS9 A_HUMAN HEAT SHOCK PROTEIN HSP
            90-ALPHA (HSP 86)

(xi) SEQUENCE DESCRIPTION: SEQ ID NO: 13:

Glu Glu Val Glu Thr Phe Ala Phe Gln Ala G lu Ile Ala Gln Leu
                 5                  10                  15
Met Ser Leu Ile Ile Asn Thr Phe Tyr Ser A sn Lys Glu Ile Phe
                20                  25                  30
Leu Arg Glu Leu Ile Ser Asn Ser Ser Asp A la Leu Asp Lys Ile
                35                  40                  45
Arg Tyr Glu Thr Leu Thr Asp Pro Ser Lys L eu Asp Ser Gly Lys
                50                  55                  60
Glu Leu His Ile Asn Leu Ile Pro Asn Lys G ln Asp Arg Thr Leu
                65                  70                  75
Thr Ile Val Asp Thr Gly Ile Gly Met Thr L ys Ala Asp Leu Ile
                80                  85                  90
Asn Asn Leu Gly Thr Ile Ala Lys Ser Gly T hr Lys Ala Phe Met
                95                 100                 105
Glu Ala Leu Gln Ala Gly Ala Asp Ile Ser M et Ile Gly Gln Phe
```

```
                         110                 115                 120
Gly Val Gly Phe Tyr Ser Ala Tyr Leu Val A la Glu Lys Val Thr
                125                 130                 135
Val Ile Thr Lys His Asn Asp Asp Glu Gln T yr Ala Trp Glu Ser
                140                 145                 150
Ser Ala Gly Gly Ser Phe Thr Val Arg Thr A sp Thr Gly Glu Pro
                155                 160                 165
Met Gly Arg Gly Thr Lys Val Ile Leu His L eu Lys Glu Asp Gln
                170                 175                 180
Thr Glu Tyr Leu Glu Glu Arg Arg Ile Lys G lu Ile Val Lys Lys
                185                 190                 195
His Ser Gln Phe Ile Gly Tyr Pro Ile Thr L eu Phe Val Glu Lys
                200                 205                 210
Glu Arg Asp Lys Glu Val Ser Asp
                215

(2) INFORMATION FOR SEQ ID NO: 14:

(i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
        (A) ORGANISM: Drosophila melanogaster (ix) FEATURE:
        (D) OTHER INFORMATION:HS8 3_DROME HEAT SHOCK PROTEIN 83
            (HSP 82)

(xi) SEQUENCE DESCRIPTION: SEQ ID NO: 14:

Glu Glu Ala Glu Thr Phe Ala Phe Gln Ala G lu Ile Ala Gln Leu
                 5                   10                  15
Met Ser Leu Ile Ile Asn Thr Phe Tyr Ser A sn Lys Glu Ile Phe
                20                  25                  30
Leu Arg Glu Leu Ile Ser Asn Ala Ser Asp A la Leu Asp Lys Ile
                35                  40                  45
Arg Tyr Glu Ser Leu Thr Asp Pro Ser Lys L eu Asp Ser Gly Lys
                50                  55                  60
Glu Leu Tyr Ile Lys Leu Ile Pro Asn Lys T hr Ala Gly Thr Leu
                65                  70                  75
Thr Ile Ile Asp Thr Gly Ile Gly Met Thr L ys Ser Asp Leu Val
                80                  85                  90
Asn Asn Leu Gly Thr Ile Ala Lys Ser Gly T hr Lys Ala Phe Met
                95                  100                 105
Glu Ala Leu Gln Ala Gly Ala Asp Ile Ser M et Ile Gly Gln Phe
                110                 115                 120
Gly Val Gly Phe Tyr Ser Ala Tyr Leu Val A la Asp Lys Val Thr
                125                 130                 135
Val Thr Ser Lys Asn Asn Asp Asp Glu Gln T yr Val Trp Glu Ser
                140                 145                 150
Ser Ala Gly Gly Ser Phe Thr Val Arg Ala A sp Asn Ser Glu Pro
                155                 160                 165
Leu Gly Arg Gly Thr Lys Ile Val Leu Tyr I le Lys Glu Asp Gln
                170                 175                 180
Thr Asp Tyr Leu Glu Glu Ser Lys Ile Lys G lu Ile Val Asn Lys
```

```
                         185                 190                 195
His Ser Gln Phe Ile Gly Tyr Pro Ile Lys L eu Leu Val Glu Lys
                 200                 205                 210

Glu Arg Glu Lys Glu Val Ser Asp
                215

(2) INFORMATION FOR SEQ ID NO: 15:

(i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
        (A) ORGANISM: Homo sap iens (ix) FEATURE:
        (D) OTHER INFORMATION:HS9 B_HUMAN HEAT SHOCK PROTEIN HSP
            90-BETA (HSP 84) (HSP 90)

(xi) SEQUENCE DESCRIPTION: SEQ ID NO: 15:

Glu Glu Val Glu Thr Phe Ala Phe Gln Ala G lu Ile Ala Gln Leu
                 5                  10                  15

Met Ser Leu Ile Ile Asn Thr Phe Tyr Ser A sn Lys Glu Ile Phe
                20                  25                  30

Leu Arg Glu Leu Ile Ser Asn Ala Ser Asp A la Leu Asp Lys Ile
                35                  40                  45

Arg Tyr Glu Ser Leu Thr Asp Pro Ser Lys L eu Asp Ser Gly Lys
                50                  55                  60

Glu Leu Lys Ile Asp Ile Ile Pro Asn Pro G ln Glu Arg Thr Leu
                65                  70                  75

Thr Leu Val Asp Thr Gly Ile Gly Met Thr L ys Ala Asp Leu Ile
                80                  85                  90

Asn Asn Leu Gly Thr Ile Ala Lys Ser Gly T hr Lys Ala Phe Met
                95                 100                 105

Glu Ala Leu Gln Ala Gly Ala Asp Ile Ser M et Ile Gly Gln Phe
                110                 115                 120

Gly Val Gly Phe Tyr Ser Ala Tyr Leu Val A la Glu Lys Val Val
                125                 130                 135

Val Ile Arg Lys His Asn Asp Asp Glu Gln T yr Ala Trp Glu Ser
                140                 145                 150

Ser Ala Gly Gly Ser Phe Thr Val Arg Ala A sp His Gly Glu Pro
                155                 160                 165

Ile Gly Met Gly Thr Lys Val Ile Leu His L eu Lys Glu Asp Gln
                170                 175                 180

Thr Glu Tyr Leu Glu Glu Arg Arg Val Lys G lu Val Val Lys Lys
                185                 190                 195

His Ser Gln Phe Ile Gly Tyr Pro Ile Thr L eu Tyr Leu Glu Lys
                200                 205                 210

Glu Arg Glu Lys Glu Ile Ser Asp
                215

(2) INFORMATION FOR SEQ ID NO: 16:

(i) SEQUENCE CHARACTERISTICS:
        (A) LENGTH: 218
        (B) TYPE: amino acid
        (D) TOPOLOGY: linear
```

(ii) MOLECULE TYPE: amino acid (vi) ORIGINAL SOURCE:
    (A) ORGANISM: Gallus g allus (ix) FEATURE:
    (D) OTHER INFORMATION:HS9 A_CHICK HEAT SHOCK PROTEIN HSP
        90-ALPHA (xi) SEQUENCE DESCRIPTION: SEQ ID NO: 16:

```
Glu Glu Val Glu Thr Phe Ala Phe Gln Ala G lu Ile Ala Gln Leu
                 5                  10                  15
Met Ser Leu Ile Ile Asn Thr Phe Tyr Ser A sn Lys Glu Ile Phe
                20                  25                  30
Leu Arg Glu Leu Ile Ser Asn Ser Ser Asp A la Leu Asp Lys Ile
                35                  40                  45
Arg Tyr Glu Ser Leu Thr Asp Pro Ser Lys L eu Asp Ser Gly Lys
                50                  55                  60
Asp Leu Lys Ile Asn Leu Ile Pro Asn Lys H is Asp Arg Thr Leu
                65                  70                  75
Thr Ile Val Asp Thr Gly Ile Gly Met Thr L ys Ala Asp Leu Val
                80                  85                  90
Asn Asn Leu Gly Thr Ile Ala Lys Ser Gly T hr Lys Ala Phe Met
                95                  100                 105
Glu Ala Leu Gln Ala Gly Ala Asp Ile Ser M et Ile Gly Gln Phe
                110                 115                 120
Gly Val Gly Ser Tyr Ser Ala Tyr Leu Val A la Glu Lys Val Thr
                125                 130                 135
Val Ile Thr Lys His Asn Asp Asp Glu Gln T yr Ala Trp Glu Ser
                140                 145                 150
Ser Ala Gly Gly Ser Phe Thr Val Arg Leu A sp Asn Gly Glu Pro
                155                 160                 165
Leu Gly Arg Gly Thr Lys Val Ile Leu His L eu Lys Glu Asp Gln
                170                 175                 180
Thr Glu Tyr Leu Glu Glu Arg Arg Ile Lys G lu Ile Val Lys Lys
                185                 190                 195
His Ser Gln Phe Ile Gly Tyr Pro Ile Arg L eu Phe Val Glu Lys
                200                 205                 210
Glu Arg Asp Lys Glu Val Ser Asp
                215
```

(2) INFORMATION FOR SEQ ID NO: 17:

(i) SEQUENCE CHARACTERISTICS:
        (A) LENGTH: 216
        (B) TYPE: amino acid
        (D) TOPOLOGY: linear (ii) MOLECULE TYPE: amino acid (vi) ORIGINAL SOURCE:
        (A) ORGANISM: Trypanosoma  cruzi (ix) FEATURE:
        (D) OTHER INFORMATION:HS8 5_TRYCR HEAT SHOCK LIKE 85 KD PROTEIN (xi) SEQUENCE DESCRIPTION: SEQ ID NO: 17:

```
Thr Glu Thr Phe Ala Phe Gln Ala Glu Ile A sn Gln Leu Met Ser
                 5                  10                  15
Leu Ile Ile Asn Thr Phe Tyr Ser Asn Lys G lu Ile Phe Leu Arg
```

```
                        20                  25                  30
Glu Leu Ile Ser Asn Ser Ser Asp Ala Cys Asp Lys Ile Arg Tyr
                    35                  40                  45
Gln Ser Leu Thr Asn Gln Ala Val Leu Gly Asp Glu Ser His Leu
                    50                  55                  60
Arg Ile Arg Val Val Pro Asp Lys Ala Asn Lys Thr Leu Thr Val
                65                  70                  75
Glu Asp Thr Gly Ile Gly Met Thr Lys Ala Glu Leu Val Asn Asn
                80                  85                  90
Leu Gly Thr Ile Ala Arg Ser Gly Thr Lys Ala Phe Met Glu Ala
                    95                 100                 105
Leu Glu Ala Gly Gly Asp Met Ser Met Ile Gly Gln Phe Gly Val
                   110                 115                 120
Gly Phe Tyr Ser Ala Tyr Leu Val Ala Asp Arg Val Thr Val Val
                   125                 130                 135
Ser Lys Asn Asn Asp Asp Glu Ala Tyr Thr Trp Glu Ser Ser Ala
                   140                 145                 150
Gly Gly Thr Phe Thr Val Thr Pro Thr Pro Asp Cys Asp Leu Lys
                   155                 160                 165
Arg Gly Thr Arg Ile Val Leu His Leu Lys Glu Asp Gln Gln Glu
                   170                 175                 180
Tyr Leu Glu Glu Arg Arg Leu Lys Asp Leu Ile Lys Lys His Ser
                   185                 190                 195
Glu Phe Ile Gly Tyr Asp Ile Glu Leu Met Val Glu Lys Ala Thr
                   200                 205                 210
Glu Lys Glu Val Thr Asp
                   215

(2) INFORMATION FOR SEQ ID NO: 18:

(i) SEQUENCE CHARACTERISTICS:
        (A) LENGTH: 216
        (B) TYPE: amino acid
        (D) TOPOLOGY: linear (ii) MOLECULE TYPE: amino acid (vi) ORIGINAL SOURCE:
        (A) ORGANISM: Theileria parva (ix) FEATURE:
        (D) OTHER INFORMATION:HS9 0_THEPA HEAT SHOCK PROTEIN 90 (HSP90)

(xi) SEQUENCE DESCRIPTION: SEQ ID NO: 18:

Glu Val Tyr Ala Phe Asn Ala Asp Ile Ser Gln Leu Leu Ser Leu
                 5                  10                  15
Ile Ile Asn Ala Phe Tyr Ser Asn Lys Glu Ile Phe Leu Arg Glu
                    20                  25                  30
Leu Ile Ser Asn Ala Ser Asp Ala Leu Glu Lys Ile Arg Tyr Glu
                    35                  40                  45
Ala Ile Lys Asp Pro Lys Gln Ile Glu Asp Gln Pro Asp Tyr Tyr
                    50                  55                  60
Ile Arg Leu Tyr Ala Asp Lys Asn Asn Asn Thr Leu Thr Ile Glu
                65                  70                  75
Asp Ser Gly Ile Gly Met Thr Lys Ala Asp Leu Val Asn Asn Leu
                80                  85                  90
Gly Thr Ile Ala Lys Ser Gly Thr Arg Ala Phe Met Glu Ala Leu
                    95                 100                 105
```

```
Gln Ala Gly Ser Asp Met Ser Met Ile Gly Gln Phe Gly Val Gly
                110                 115                 120

Phe Tyr Ser Ala Tyr Leu Val Ala Asp Lys Val Thr Val Val Ser
                125                 130                 135

Lys Asn Ala Asp Asp Gln Tyr Val Trp Glu Ser Thr Ala Ser
                140                 145                 150

Gly His Phe Thr Val Lys Lys Asp Asp Ser His Glu Pro Leu Lys
                155                 160                 165

Arg Gly Thr Arg Leu Ile Leu His Leu Lys Glu Asp Gln Thr Glu
                170                 175                 180

Tyr Leu Glu Glu Arg Arg Leu Lys Glu Leu Val Lys Lys His Ser
                185                 190                 195

Glu Phe Ile Ser Phe Pro Ile Ser Leu Ser Val Glu Lys Thr Gln
                200                 205                 210

Glu Thr Glu Val Thr Asp
                215
```

(2) INFORMATION FOR SEQ ID NO: 19:

(i) SEQUENCE CHARACTERISTICS:
        (A) LENGTH: 216
        (B) TYPE: amino acid
        (D) TOPOLOGY: linear (ii) MOLECULE TYPE: amino acid (vi) ORIGINAL SOURCE:
        (A) ORGANISM: Leishmania amazonensis (ix) FEATURE:
        (D) OTHER INFORMATION:HS8 3_LEIAM HEAT SHOCK PROTEIN 83
        (HSP 83)

(xi) SEQUENCE DESCRIPTION: SEQ ID NO: 19:

```
Thr Glu Thr Phe Ala Phe Gln Ala Glu Ile Asn Gln Leu Met Ser
                 5                  10                  15

Leu Ile Ile Asn Thr Phe Tyr Ser Asn Lys Glu Ile Phe Leu Arg
                20                  25                  30

Asp Val Ile Ser Asn Ala Ser Asp Ala Cys Asp Lys Ile Arg Tyr
                35                  40                  45

Gln Ser Leu Thr Asp Pro Ser Val Leu Gly Asp Ala Thr Arg Leu
                50                  55                  60

Cys Val Arg Val Pro Asp Lys Glu Asn Lys Thr Leu Thr Val
                65                  70                  75

Glu Asp Asn Gly Ile Gly Met Thr Lys Ala Asp Leu Val Asn Asn
                80                  85                  90

Leu Gly Thr Ile Ala Arg Ser Gly Thr Lys Ala Phe Met Glu Ala
                95                  100                 105

Leu Glu Ala Gly Ala Asp Met Ser Met Ile Gly Gln Phe Gly Val
                110                 115                 120

Gly Phe Tyr Ser Ala Tyr Leu Val Ala Asp Arg Val Thr Val Thr
                125                 130                 135

Ser Lys Asn Asn Ser Asp Glu Val Tyr Val Trp Glu Ser Ser Ala
                140                 145                 150

Gly Gly Thr Phe Thr Ile Thr Ser Ala Pro Glu Ser Asp Met Lys
                155                 160                 165

Leu Pro Ala Arg Ile Thr Leu His Leu Lys Glu Asp Gln Leu Glu
                170                 175                 180
```

Tyr Leu Glu Ala Arg Arg Leu Lys Glu Leu Ile Lys Lys His Ser
                185                 190                 195

Glu Phe Ile Gly Tyr Asp Ile Glu Leu Met Val Glu Lys Thr Thr
                200                 205                 210

Glu Lys Glu Val Thr Asp
                215

(2) INFORMATION FOR SEQ ID NO: 20:

(i) SEQUENCE CHARACTERISTICS:
        (A) LENGTH: 216
        (B) TYPE: amino acid
        (D) TOPOLOGY: linear (ii) MOLECULE TYPE: amino acid (vi) ORIGINAL SOURCE:
        (A) ORGANISM: Trypanosoma brucei brucei (ix) FEATURE:
        (D) OTHER INFORMATION:HS8_3_TRYBB HEAT SHOCK PROTEIN 83

(xi) SEQUENCE DESCRIPTION: SEQ ID NO: 20:

Thr Glu Thr Phe Ala Phe Gln Ala Glu Ile Asn Gln Leu Met Ser
                5                   10                  15

Leu Ile Ile Asn Thr Phe Tyr Ser Asn Lys Glu Ile Phe Leu Arg
                20                  25                  30

Glu Leu Ile Ser Asn Ser Ser Asp Ala Cys Asp Lys Ile Arg Tyr
                35                  40                  45

Gln Ser Leu Thr Asn Gln Ser Val Leu Gly Asp Glu Pro His Leu
                50                  55                  60

Arg Ile Arg Val Ile Pro Asp Arg Val Asn Lys Thr Leu Thr Val
                65                  70                  75

Glu Asp Ser Gly Ile Gly Met Thr Lys Ala Asp Leu Val Asn Asn
                80                  85                  90

Leu Gly Thr Ile Ala Arg Ser Gly Thr Lys Ser Phe Met Glu Ala
                95                  100                 105

Leu Glu Ala Gly Gly Asp Met Ser Met Ile Gly Gln Phe Gly Val
                110                 115                 120

Gly Phe Tyr Ser Ala Tyr Leu Val Ala Asp Arg Val Thr Val Val
                125                 130                 135

Ser Lys Asn Asn Glu Asp Asp Ala Tyr Thr Trp Glu Ser Ser Ala
                140                 145                 150

Gly Gly Thr Phe Thr Val Thr Ser Thr Pro Asp Cys Asp Leu Lys
                155                 160                 165

Arg Gly Thr Arg Ile Val Leu His Leu Lys Glu Asp Gln Gln Glu
                170                 175                 180

Tyr Leu Glu Glu Arg Arg Leu Lys Asp Leu Ile Lys Lys His Ser
                185                 190                 195

Glu Phe Ile Gly Tyr Asp Ile Glu Leu Met Val Glu Asn Thr Thr
                200                 205                 210

Glu Lys Glu Val Thr Asp
                215

(2) INFORMATION FOR SEQ ID NO: 21:

(i) SEQUENCE CHARACTERISTICS:
        (A) LENGTH: 221
        (B) TYPE: amino acid (D) TOPOLOGY: linear (ii) MOLECULE TYPE: amino acid (vi) ORIGINAL SOURCE:
    (A) ORGANISM: Hordeum vulgare (ix) FEATURE:
    (D) OTHER INFORMATION:ENP L_HORVU ENDOPLASMIN HOMOLOG PRECURSOR (GRP94 H OMOLOG)

(xi) SEQUENCE DESCRIPTION: SEQ ID NO: 21:

```
Asn Ser Ala Glu Lys Phe Glu Phe Gln Ala G lu Val Ser Arg Leu
                 5                  10                  15
Met Asp Ile Ile Ile Asn Ser Leu Tyr Ser A sn Lys Asp Ile Phe
                20                  25                  30
Leu Arg Glu Leu Ile Ser Asn Ala Ser Asp A la Leu Asp Lys Ile
                35                  40                  45
Arg Phe Leu Ala Leu Thr Asp Lys Glu Val M et Gly Glu Gly Asp
                50                  55                  60
Thr Ala Lys Leu Glu Ile Gln Ile Lys Leu A sp Lys Glu Asn Lys
                65                  70                  75
Ile Leu Ser Ile Arg Asp Arg Gly Val Gly M et Thr Lys Glu Asp
                80                  85                  90
Leu Ile Lys Asn Leu Gly Thr Ile Ala Lys S er Gly Thr Ser Ala
                95                 100                 105
Phe Val Glu Lys Met Gln Thr Gly Gly Asp L eu Asn Leu Ile Gly
               110                 115                 120
Gln Phe Gly Val Gly Phe Tyr Ser Val Tyr L eu Val Ala Asp Tyr
               125                 130                 135
Val Glu Val Val Ser Lys His Asn Asp Asp L ys Gln Tyr Val Trp
               140                 145                 150
Glu Ser Lys Ala Asp Gly Ser Phe Ala Ile S er Glu Asp Thr Trp
               155                 160                 165
Asn Glu Pro Leu Gly Arg Gly Thr Glu Ile L ys Leu His Leu Arg
               170                 175                 180
Asp Glu Ala Lys Glu Tyr Leu Glu Glu Gly L ys Leu Lys Asp Leu
               185                 190                 195
Val Lys Lys Tyr Ser Glu Phe Ile Asn Phe P ro Ile Tyr Leu Trp
               200                 205                 210
Ala Thr Lys Glu Val Asp Val Glu Val Pro A la
               215                 220
```

(2) INFORMATION FOR SEQ ID NO: 22:

(i) SEQUENCE CHARACTERISTICS:
        (A) LENGTH: 221
        (B) TYPE: amino acid
        (D) TOPOLOGY: linear (ii) MOLECULE TYPE: amino acid (vi) ORIGINAL SOURCE:
        (A) ORGANISM: Catharanthu s roseus (ix) FEATURE:
        (D) OTHER INFORMATION:ENP L_CATRO ENDOPLASMIN HOMOLOG PRECURSOR (GRP94 H OMOLOG)

(xi) SEQUENCE DESCRIPTION: SEQ ID NO: 22:

```
Ser Asp Ala Glu Lys Phe Glu Phe Gln Ala G lu Val Ser Arg Leu
                 5                  10                  15
```

```
Met Asp Ile Ile Ile Asn Ser Leu Tyr Ser A sn Lys Asp Ile Phe
            20                  25                  30

Leu Arg Glu Leu Ile Ser Asn Ala Ser Asp A la Leu Asp Lys Ile
            35                  40                  45

Arg Phe Leu Ala Leu Thr Asp Lys Glu Ile L eu Gly Glu Gly Asp
            50                  55                  60

Thr Ala Lys Leu Glu Ile Gln Ile Lys Leu A sp Lys Glu Lys Lys
            65                  70                  75

Ile Leu Ser Ile Arg Asp Arg Gly Ile Gly M et Thr Lys Glu Asp
            80                  85                  90

Leu Ile Lys Asn Leu Gly Thr Ile Ala Lys S er Gly Thr Ser Ala
            95                  100                 105

Phe Val Glu Lys Met Gln Thr Ser Gly Asp L eu Asn Leu Ile Gly
            110                 115                 120

Gln Phe Gly Val Gly Phe Tyr Ser Val Tyr L eu Val Pro Asp Tyr
            125                 130                 135

Val Glu Val Ile Ser Lys His Asn Asp Asp L ys Gln Tyr Ile Trp
            140                 145                 150

Glu Ser Lys Ala Asp Gly Ala Phe Ala Ile S er Glu Asp Val Trp
            155                 160                 165

Asn Glu Pro Leu Gly Arg Gly Thr Glu Ile A rg Leu His Leu Arg
            170                 175                 180

Asp Glu Ala Gln Glu Tyr Leu Asp Glu Phe L ys Leu Lys Glu Leu
            185                 190                 195

Val Lys Arg Tyr Ser Glu Phe Ile Asn Phe P ro Ile Tyr Leu Trp
            200                 205                 210

Ala Ser Lys Glu Val Glu Val Glu Val Pro A la
            215                 220

(2) INFORMATION FOR SEQ ID NO: 23:

(i) SEQUENCE CHARACTERISTICS:
        (A) LENGTH: 223
        (B) TYPE: amino acid
        (D) TOPOLOGY: linear (ii) MOLECULE TYPE: amino acid (vi) ORIGINAL SOURCE:
        (A) ORGANISM: Gallus g allus (ix) FEATURE:
        (D) OTHER INFORMATION:ENP L_CHICK ENDOPLASMIN PRECURSOR
            (TRANSFEROR IN- BINDING PROTEIN)

(xi) SEQUENCE DESCRIPTION: SEQ ID NO: 23:

Glu Lys Ser Glu Lys Phe Ala Phe Gln Ala G lu Val Asn Arg Met
            5                   10                  15

Met Lys Leu Ile Ile Asn Ser Leu Tyr Lys A sn Lys Glu Ile Phe
            20                  25                  30

Leu Arg Glu Leu Ile Ser Asn Ala Ser Asp A la Leu Asp Lys Ile
            35                  40                  45

Arg Leu Ile Ser Leu Thr Asp Glu Asn Ala L eu Ala Gly Asn Glu
            50                  55                  60

Glu Leu Thr Val Lys Ile Lys Cys Asp Lys G lu Lys Asn Met Leu
            65                  70                  75

His Val Thr Asp Thr Gly Ile Gly Met Thr L ys Glu Glu Leu Ile
            80                  85                  90
```

```
Lys Asn Leu Gly Thr Ile Ala Lys Ser Gly T hr Ser Glu Phe Leu
                95                  100                 105

Asn Lys Met Thr Glu Met Gln Asp Asp Ser G ln Ser Thr Ser Glu
                110                 115                 120

Leu Ile Gly Gln Phe Gly Val Gly Phe Tyr S er Ala Phe Leu Val
                125                 130                 135

Ala Asp Arg Val Ile Val Thr Ser Lys His A sn Asn Asp Thr Gln
                140                 145                 150

His Ile Trp Glu Ser Asp Ser Asn Glu Phe S er Val Ile Asp Asp
                155                 160                 165

Pro Arg Gly Asn Thr Leu Gly Arg Gly Thr T hr Ile Thr Leu Val
                170                 175                 180

Leu Lys Glu Glu Ala Ser Asp Tyr Leu Glu L eu Asp Thr Val Lys
                185                 190                 195

Asn Leu Val Lys Lys Tyr Ser Gln Phe Ile A sn Phe Pro Ile Tyr
                200                 205                 210

Val Trp Ser Ser Lys Thr Glu Thr Val Glu G lu Pro Val
                215                 220
```

(2) INFORMATION FOR SEQ ID NO: 24:

(i) SEQUENCE CHARACTERISTICS:
        (A) LENGTH: 223
        (B) TYPE: amino acid
        (D) TOPOLOGY: linear (ii) MOLECULE TYPE: amino acid (vi) ORIGINAL SOURCE:
        (A) ORGANISM: Canis fa miliaris (ix) FEATURE:
        (D) OTHER INFORMATION:ENP L_CANFA ENDOPLASMIN PRECURSOR
            (94 KD GLUCOSE- REGULATED PROTEIN) (GRP94)

(xi) SEQUENCE DESCRIPTION: SEQ ID NO: 24:

```
Glu Lys Ser Glu Lys Phe Ala Phe Gln Ala G lu Val Asn Arg Met
                5                   10                  15

Met Lys Leu Ile Ile Asn Ser Leu Tyr Lys A sn Lys Glu Ile Phe
                20                  25                  30

Leu Arg Glu Leu Ile Ser Asn Ala Ser Asp A la Leu Asp Lys Ile
                35                  40                  45

Arg Leu Ile Ser Leu Thr Asp Glu Asn Ala L eu Ala Gly Asn Glu
                50                  55                  60

Glu Leu Thr Val Lys Ile Lys Cys Asp Lys G lu Lys Asn Leu Leu
                65                  70                  75

His Val Thr Asp Thr Gly Val Gly Met Thr A rg Glu Glu Leu Val
                80                  85                  90

Lys Asn Leu Gly Thr Ile Ala Lys Ser Gly T hr Ser Glu Phe Leu
                95                  100                 105

Asn Lys Met Thr Glu Ala Gln Glu Asp Gly G ln Ser Thr Ser Glu
                110                 115                 120

Leu Ile Gly Gln Phe Gly Val Gly Phe Tyr S er Ala Phe Leu Val
                125                 130                 135

Ala Asp Lys Val Ile Val Thr Ser Lys His A sn Asn Asp Thr Gln
                140                 145                 150

His Ile Trp Glu Ser Asp Ser Asn Glu Phe S er Val Ile Ala Asp
                155                 160                 165
```

```
Pro Arg Gly Asn Thr Leu Gly Arg Gly Thr Thr Ile Thr Leu Val
                170                 175                 180

Leu Lys Glu Glu Ala Ser Asp Tyr Leu Glu Leu Asp Thr Ile Lys
                185                 190                 195

Asn Leu Val Lys Lys Tyr Ser Gln Phe Ile Asn Phe Pro Ile Tyr
                200                 205                 210

Val Trp Ser Ser Lys Thr Glu Thr Val Glu Glu Pro Met
                215                 220
```

(2) INFORMATION FOR SEQ ID NO: 25:

(i) SEQUENCE CHARACTERISTICS:
        (A) LENGTH: 223
        (B) TYPE: amino acid
        (D) TOPOLOGY: linear (ii) MOLECULE TYPE: amino acid (vi) ORIGINAL SOURCE:
        (A) ORGANISM: Homo sap iens (ix) FEATURE:
        (D) OTHER INFORMATION:ENP L_HUMAN ENDOPLASMIN PRECURSOR
            (94 KD GLUCOSE- REGULATED PROTEIN) (GRP94)

(xi) SEQUENCE DESCRIPTION: SEQ ID NO: 25:

```
Glu Lys Ser Glu Lys Phe Ala Phe Gln Ala Glu Val Asn Arg Met
                5                   10                  15

Met Lys Leu Ile Ile Asn Ser Leu Tyr Lys Asn Lys Glu Ile Phe
                20                  25                  30

Leu Arg Glu Leu Ile Ser Asn Ala Ser Asp Ala Leu Asp Lys Ile
                35                  40                  45

Arg Leu Ile Ser Leu Thr Asp Glu Asn Ala Leu Ser Gly Asn Glu
                50                  55                  60

Glu Leu Thr Val Lys Ile Lys Cys Asp Lys Glu Lys Asn Leu Leu
                65                  70                  75

His Val Thr Asp Thr Gly Val Gly Met Thr Arg Glu Glu Leu Val
                80                  85                  90

Lys Asn Leu Gly Thr Ile Ala Lys Ser Gly Thr Ser Glu Phe Leu
                95                  100                 105

Asn Lys Met Thr Glu Ala Gln Glu Asp Gly Gln Ser Thr Ser Glu
                110                 115                 120

Leu Ile Gly Gln Phe Gly Val Gly Phe Tyr Ser Ala Phe Leu Val
                125                 130                 135

Ala Asp Lys Val Ile Val Thr Ser Lys His Asn Asn Asp Thr Gln
                140                 145                 150

His Ile Trp Glu Ser Asp Ser Asn Glu Phe Ser Val Ile Ala Asp
                155                 160                 165

Pro Arg Gly Asn Thr Leu Gly Arg Gly Thr Thr Ile Thr Leu Val
                170                 175                 180

Leu Lys Glu Glu Ala Ser Asp Tyr Leu Glu Leu Asp Thr Ile Lys
                185                 190                 195

Asn Leu Val Lys Lys Tyr Ser Gln Phe Ile Asn Phe Pro Ile Tyr
                200                 205                 210

Val Trp Ser Ser Lys Thr Glu Thr Val Glu Glu Pro Met
                215                 220
```

(2) INFORMATION FOR SEQ ID NO: 26:

(i) SEQUENCE CHARACTERISTICS:
    (A) LENGTH: 223
    (B) TYPE: amino acid
    (D) TOPOLOGY: linear (ii) MOLECULE TYPE: amino acid (vi) ORIGINAL SOURCE:
    (A) ORGANISM: Mus musc ulus (ix) FEATURE:
    (D) OTHER INFORMATION:ENP L_MOUSE ENDOPLASMIN PRECURSOR
        (94 KD GLUCOSE- P11427) REGULATED PROTEIN) (GRP94)

(xi) SEQUENCE DESCRIPTION: SEQ ID NO: 26:

```
Glu Lys Ser Glu Lys Phe Ala Phe Gln Ala G lu Val Asn Arg Met
                  5                  10                  15

Met Lys Leu Ile Ile Asn Ser Leu Tyr Lys A sn Lys Glu Ile Phe
                 20                  25                  30

Leu Arg Glu Leu Ile Ser Asn Ala Ser Asp A la Leu Asp Lys Ile
                 35                  40                  45

Arg Leu Ile Ser Leu Thr Asp Glu Asn Ala L eu Ala Gly Asn Glu
                 50                  55                  60

Glu Leu Thr Val Lys Ile Lys Cys Asp Lys G lu Lys Asn Leu Leu
                 65                  70                  75

His Val Thr Asp Thr Gly Val Gly Met Thr A rg Glu Glu Leu Val
                 80                  85                  90

Lys Asn Leu Gly Thr Ile Ala Lys Ser Gly T hr Ser Glu Phe Leu
                 95                 100                 105

Asn Lys Met Thr Glu Ala Gln Glu Asp Gly G ln Ser Thr Ser Glu
                110                 115                 120

Leu Ile Gly Gln Phe Gly Val Gly Phe Tyr S er Ala Phe Leu Val
                125                 130                 135

Ala Asp Lys Val Ile Val Thr Ser Lys His A sn Asn Asp Thr Gln
                140                 145                 150

His Ile Trp Glu Ser Asp Ser Asn Glu Phe S er Val Ile Ala Asp
                155                 160                 165

Pro Arg Gly Asn Thr Leu Gly Arg Gly Thr T hr Ile Thr Leu Val
                170                 175                 180

Leu Lys Glu Glu Ala Ser Asp Tyr Leu Glu L eu Asp Thr Ile Lys
                185                 190                 195

Asn Leu Val Arg Lys Tyr Ser Gln Phe Ile A sn Phe Pro Ile Tyr
                200                 205                 210

Val Trp Ser Ser Lys Thr Glu Thr Val Glu G lu Pro Leu
                215                 220
```

(2) INFORMATION FOR SEQ ID NO: 27:

(i) SEQUENCE CHARACTERISTICS:
        (A) LENGTH: 214
        (B) TYPE: amino acid
        (D) TOPOLOGY: linear (ii) MOLECULE TYPE: amino acid (vi) ORIGINAL SOURCE:
        (A) ORGANISM: Haemophilus  influenzae (ix) FEATURE:
        (D) OTHER INFORMATION:HTP G_HAEIN HEAT SHOCK PROTEIN HTPG (xi) SEQUENCE DESCRIPTION: SEQ ID NO: 27:

Glu Thr Arg Gly Phe Gln Ser Glu Val Lys G ln Leu Leu Gln Leu
                    5                   10                  15

Met Ile His Ser Leu Tyr Ser Asn Lys Glu I le Phe Leu Arg Glu
                20                  25                  30

Leu Ile Ser Asn Ala Ser Asp Ala Ala Asp L ys Leu Arg Phe Lys
                35                  40                  45

Ala Leu Ser Asn Pro Ala Leu Tyr Glu Gly A sp Gly Asp Leu Arg
                50                  55                  60

Val Arg Val Ser Phe Asp Ala Asp Lys Gly T hr Ile Thr Ile Ser
                65                  70                  75

Asp Asn Gly Ile Gly Met Thr Arg Glu Gln V al Ile Asp His Leu
                80                  85                  90

Gly Thr Ile Ala Lys Ser Gly Thr Lys Glu P he Leu Thr Ala Leu
                95                  100                 105

Gly Gln Asp Gln Ala Lys Asn Ser Gln Leu I le Gly Gln Phe Gly
                110                 115                 120

Val Gly Phe Tyr Ser Ala Phe Ile Val Ala A sp Lys Val Thr Val
                125                 130                 135

Lys Thr Arg Ala Ala Gly Glu Glu Ala Asp L ys Ala Val Leu Trp
                140                 145                 150

Glu Ser Ala Gly Glu Gly Glu Tyr Ser Val A la Asp Ile Glu Lys
                155                 160                 165

Lys Ser Arg Gly Thr Asp Val Ile Leu His L eu Arg Glu Asp Glu
                170                 175                 180

Lys Glu Phe Leu Asn Glu Trp Arg Leu Arg G lu Ile Ile Gly Lys
                185                 190                 195

Tyr Ser Asp His Ile Gly Leu Pro Val Glu M et Leu Thr Lys Glu
                200                 205                 210

Tyr Asp Asp Glu (2) INFORMATION FOR SEQ ID NO: 28:

(i) SEQUENCE CHARACTERISTICS:
        (A) LENGTH: 212
        (B) TYPE: amino acid
        (D) TOPOLOGY: linear (ii) MOLECULE TYPE: amino acid (vi) ORIGINAL SOURCE:
        (A) ORGANISM: Escherichia coli (ix) FEATURE:
        (D) OTHER INFORMATION:HTP G_ECOLI HEAT SHOCK PROTEIN HTPG (xi) SEQUENCE DESCRIPTION: SEQ ID NO: 28:

Glu Thr Arg Gly Phe Gln Ser Glu Val Lys G ln Leu Leu His Leu
                5                   10                  15

Met Ile His Ser Leu Tyr Ser Asn Lys Glu I le Phe Leu Arg Glu
                20                  25                  30

Leu Ile Ser Asn Ala Ser Asp Ala Ala Asp L ys Leu Arg Phe Arg
                35                  40                  45

Ala Leu Ser Asn Pro Asp Leu Tyr Glu Gly A sp Gly Glu Leu Arg
                50                  55                  60

Val Arg Val Ser Phe Asp Lys Asp Lys Arg T hr Leu Thr Ile Ser
                65                  70                  75

Asp Asn Gly Val Gly Met Thr Arg Asp Glu V al Ile Asp His Leu

```
                    80                  85                  90
Gly Thr Ile Ala Lys Ser Gly Thr Lys Ser Phe Leu Glu Ser Leu
                    95                 100                 105

Gly Ser Asp Gln Ala Lys Asp Ser Gln Leu Ile Gly Gln Phe Gly
                   110                 115                 120

Val Gly Phe Tyr Ser Ala Phe Ile Val Ala Asp Lys Val Thr Val
                   125                 130                 135

Arg Thr Arg Ala Ala Gly Glu Lys Pro Glu Asn Gly Val Phe Trp
                   140                 145                 150

Glu Ser Ala Gly Glu Gly Tyr Thr Val Ala Asp Ile Thr Lys
                   155                 160                 165

Glu Asp Arg Gly Thr Glu Ile Thr Leu His Leu Arg Glu Gly Glu
                   170                 175                 180

Asp Glu Phe Leu Asp Asp Trp Arg Val Arg Ser Ile Ile Ser Lys
                   185                 190                 195

Tyr Ser Asp His Ile Ala Leu Pro Val Glu Ile Glu Lys Arg Glu
                   200                 205                 210

Glu Lys (2) INFORMATION FOR SEQ ID NO: 29:

(i) SEQUENCE CHARACTERISTICS:
        (A) LENGTH: 215
        (B) TYPE: amino acid
        (D) TOPOLOGY: linear (ii) MOLECULE TYPE: amino acid (vi) ORIGINAL SOURCE:
        (A) ORGANISM: Bacillus subtilis (ix) FEATURE:
        (D) OTHER INFORMATION:HTPG_BACSU HEAT SHOCK PROTEIN HTPG
            HOMOLOG (xi) SEQUENCE DESCRIPTION: SEQ ID NO: 29:

Phe Lys Ala Glu Ser Lys Arg Leu Leu Asp Met Met Ile Asn Ser
                     5                  10                  15

Ile Tyr Thr Gln Lys Glu Ile Phe Leu Arg Glu Leu Ile Ser Asn
                    20                  25                  30

Ser Ser Asp Ala Ile Asp Lys Ile Tyr Tyr Lys Ala Leu Thr Asp
                    35                  40                  45

Asp Ala Leu Thr Phe Asp Lys Asp Ser Tyr Tyr Ile Lys Val Ala
                    50                  55                  60

Ala Asp Lys Asp Ala Arg Thr Leu Thr Ile Ser Asp Thr Gly Ile
                    65                  70                  75

Gly Met Thr Lys Asp Glu Leu Glu Gln His Leu Gly Thr Ile Ala
                    80                  85                  90

Lys Ser Gly Ser Leu Ala Phe Lys Glu Asn Glu Leu Lys Asp
                    95                 100                 105

Gly His Asp Ile Ile Gly Gln Phe Gly Val Gly Phe Tyr Ala Ala
                   110                 115                 120

Phe Met Val Ala Asp Val Val Thr Val Ile Ser Lys Ala Leu Gly
                   125                 130                 135

Ser Glu Glu Ala Tyr Lys Trp Glu Ser Ala Gly Ala Asp Gly Tyr
                   140                 145                 150

Thr Ile Glu Pro Cys Glu Lys Asp Ser Val Gly Thr Asp Ile Ile
                   155                 160                 165
```

Leu Lys Ile Lys Glu Asn Thr Glu Asp Asp S er Tyr Asp Glu Phe
                170                 175                 180

Leu Glu Glu Tyr Arg Leu Lys Ala Ile Ile L ys Lys Tyr Ser Asp
                185                 190                 195

Phe Ile Arg Tyr Pro Ile Lys Met Asp Thr T hr Ile Asn Lys Pro
                200                 205                 210

Lys Glu Gly Ser Glu
                215

(2) INFORMATION FOR SEQ ID NO: 30:

(i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
        (A) ORGANISM: Rattus s p. brain (ix) FEATURE:
        (D) OTHER INFORMATION:HEA T SHOCK PROTEIN 90

(xi) SEQUENCE DESCRIPTION: SEQ ID NO: 30:

Glu Glu Val Glu Thr Phe Ala Phe Gln Ala G lu Ile Ala Gln Leu
                5                   10                  15

Met Ser Leu Ile Ile Asn Thr Phe Tyr Ser A sn Lys Glu Ile Phe
                20                  25                  30

Leu Arg Glu Leu Ile Ser Asn Ala Ser Asp A la Leu Asp Lys Ile
                35                  40                  45

Arg Tyr Glu Ser Leu Thr Asp Pro Ser Lys L eu Asp Ser Gly Lys
                50                  55                  60

Glu Leu Lys Ile Asp Ile Ile Pro Asn Pro G ln Glu Ala Thr Leu
                65                  70                  75

Thr Leu Val Asp Thr Gly Ile Gly Met Thr L ys Ala Asp Leu Ile
                80                  85                  90

Asn Asn Leu Gly Thr Ile Ala Lys Ser Gly T hr Lys Ala Phe Met
                95                  100                 105

Glu Ala Leu Gln Ala Gly Ala Asp Ile Ser M et Ile Gly Gln Phe
                110                 115                 120

Gly Val Gly Phe Tyr Ser Ala Tyr Leu Val A la Glu Lys Val Val
                125                 130                 135

Val Ile Thr Lys His Asn Asp Asp Glu Gln T yr Ala Trp Glu Ser
                140                 145                 150

Ser Ala Gly Gly Ser Phe Thr Val Arg Ala A sp His Gly Glu Pro
                155                 160                 165

Ile Gly Arg Gly Thr Lys Val Ile Leu His L eu Lys Glu Asp Gln
                170                 175                 180

Thr Glu Tyr Leu Glu Glu Arg Arg Val Lys G lu Val Val Lys Lys
                185                 190                 195

His Ser Gln Phe Ile Gly Tyr Pro Ile Thr L eu Tyr Leu Glu Lys
                200                 205                 210

Glu Arg Glu Lys Glu Ile Ser Asp
                215

(2) INFORMATION FOR SEQ ID NO: 31:

```
    (i) SEQUENCE CHARACTERISTICS:
        (A) LENGTH: 218
        (B) TYPE: amino acid
        (D) TOPOLOGY: linear (ii) MOLECULE TYPE: amino acid (vi) ORIGINAL SOURCE:
        (A) ORGANISM: Pharbitis nil (ix) FEATURE:
        (D) OTHER INFORMATION:HEA T SHOCK PROTEIN 83 (HSP83) GENE (xi) SEQUENCE DESCRIPTION: SEQ ID NO: 31:

Glu Ala Glu Thr Phe Ala Phe Gln Ala Glu I le Asn Gln Leu Leu
                5                   10                  15

Ser Leu Ile Ile Asn Thr Phe Tyr Ser Asn L ys Glu Ile Phe Leu
            20                  25                  30

Arg Glu Leu Ile Ser Asn Ala Ser Asp Ala L eu Asp Lys Ile Arg
            35                  40                  45

Phe Glu Ser Leu Thr Asp Lys Ser Lys Leu A sp Ala Gln Pro Glu
            50                  55                  60

Leu Phe Ile Arg Leu Val Pro Asp Lys Thr A sn Lys Thr Leu Ser
            65                  70                  75

Ile Ile Asp Ser Gly Val Gly Met Ala Lys A la Asp Leu Val Asn
            80                  85                  90

Asn Leu Gly Thr Ile Ala Arg Ser Gly Thr L ys Glu Phe Met Glu
            95                  100                 105

Ala Leu Gln Ala Gly Ala Asp Val Ser Met I le Gly Gln Phe Gly
            110                 115                 120

Val Gly Phe Tyr Ser Ala Tyr Leu Val Ala G lu Lys Val Ile Val
            125                 130                 135

Thr Thr Lys His Asn Asp Asp Glu Gln Tyr I le Trp Glu Ser Gln
            140                 145                 150

Ala Gly Gly Ser Phe Thr Val Thr Arg Asp V al Asp Gly Glu Gln
            155                 160                 165

Leu Gly Arg Gly Thr Lys Ile Thr Leu Phe L eu Lys Glu Asp Gln
            170                 175                 180

Leu Glu Tyr Leu Glu Glu Arg Arg Ile Lys A sp Leu Val Lys Lys
            185                 190                 195

His Ser Glu Phe Ile Ser Tyr Pro Ile Tyr L eu Trp Thr Glu Lys
            200                 205                 210

Thr Thr Glu Lys Glu Ile Ser Asp
            215

(2) INFORMATION FOR SEQ ID NO: 32:

(i) SEQUENCE CHARACTERISTICS:
        (A) LENGTH: 146
        (B) TYPE: amino acid
        (D) TOPOLOGY: linear (ii) MOLECULE TYPE: amino acid (vi) ORIGINAL SOURCE:
        (A) ORGANISM: human (ix) FEATURE:
        (D) OTHER INFORMATION:lep tin (xi) SEQUENCE DESCRIPTION: SEQ ID NO: 32:

Val Pro Ile Gln Lys Val Gln Asp Asp Thr L ys Thr Leu Ile Lys
```

```
                5                  10                 15
Thr Ile Val Thr Arg Ile Asn Asp Ile Ser His Thr Gln Ser Val
                20                 25                 30
Ser Ser Lys Gln Lys Val Thr Gly Leu Asp Phe Ile Pro Gly Leu
                35                 40                 45
His Pro Ile Leu Thr Leu Ser Lys Met Asp Gln Thr Leu Ala Val
                50                 55                 60
Tyr Gln Gln Ile Leu Thr Ser Met Pro Ser Arg Asn Val Ile Gln
                65                 70                 75
Ile Ser Asn Asp Leu Glu Asn Leu Arg Asp Leu Leu His Val Leu
                80                 85                 90
Ala Phe Ser Lys Ser Cys His Leu Pro Trp Ala Ser Gly Leu Glu
                95                 100                105
Thr Leu Asp Ser Leu Gly Gly Val Leu Glu Ala Ser Gly Tyr Ser
                110                115                120
Thr Glu Val Val Ala Leu Ser Arg Leu Gln Gly Ser Leu Gln Asp
                125                130                135
Met Leu Trp Gln Leu Asp Leu Ser Pro Gly Cys
                140                145
```

(2) INFORMATION FOR SEQ ID NO: 33:

(i) SEQUENCE CHARACTERISTICS:
        (A) LENGTH: 146
        (B) TYPE: amino acid
        (D) TOPOLOGY: linear (ii) MOLECULE TYPE: amino acid (vi) ORIGINAL SOURCE:
        (A) ORGANISM: gorilla (ix) FEATURE:
        (D) OTHER INFORMATION: leptin (xi) SEQUENCE DESCRIPTION: SEQ ID NO: 33:

```
Val Pro Ile Gln Lys Val Gln Asp Asp Thr Lys Thr Leu Ile Lys
                5                  10                 15
Thr Ile Val Thr Arg Ile Ser Asp Ile Ser His Thr Gln Ser Val
                20                 25                 30
Ser Ser Lys Gln Lys Val Thr Gly Leu Asp Phe Ile Pro Gly Leu
                35                 40                 45
His Pro Ile Leu Thr Leu Ser Lys Met Asp Gln Thr Leu Ala Val
                50                 55                 60
Tyr Gln Gln Ile Leu Thr Ser Met Pro Ser Arg Asn Met Ile Gln
                65                 70                 75
Ile Ser Asn Asp Leu Glu Asn Leu Arg Asp Leu Leu His Val Leu
                80                 85                 90
Ala Phe Ser Lys Ser Cys His Leu Pro Trp Ala Ser Gly Leu Glu
                95                 100                105
Thr Leu Asp Ser Leu Gly Gly Val Leu Glu Ala Ser Gly Tyr Ser
                110                115                120
Thr Glu Val Val Ala Leu Ser Arg Leu Gln Gly Ser Leu Gln Asp
                125                130                135
Met Leu Trp Gln Leu Asp Leu Ser Pro Gly Cys
                140                145
```

(2) INFORMATION FOR SEQ ID NO: 34:

(i) SEQUENCE CHARACTERISTICS:
    (A) LENGTH: 146
    (B) TYPE: amino acid
    (D) TOPOLOGY: linear (ii) MOLECULE TYPE: amino acid (vi) ORIGINAL SOURCE:
    (A) ORGANISM: chimp (ix) FEATURE:
    (D) OTHER INFORMATION:lep tin (xi) SEQUENCE DESCRIPTION: SEQ ID NO: 34:

Val Pro Ile Gln Lys Val Gln Asp Asp Thr L ys Thr Leu Ile Lys
                 5                  10                  15

Thr Ile Val Thr Arg Ile Asn Asp Ile Ser H is Thr Gln Ser Val
                20                  25                  30

Ser Ser Lys Gln Lys Val Thr Gly Leu Asp P he Ile Pro Gly Leu
                35                  40                  45

His Pro Ile Leu Thr Leu Ser Lys Met Asp G ln Thr Leu Ala Val
                50                  55                  60

Tyr Gln Gln Ile Leu Thr Ser Met Pro Ser A rg Asn Met Ile Gln
                65                  70                  75

Ile Ser Asn Asp Leu Glu Asn Leu Arg Asp L eu Leu His Val Leu
                80                  85                  90

Ala Phe Ser Lys Ser Cys His Leu Pro Trp A la Ser Gly Leu Glu
                95                 100                 105

Thr Leu Asp Ser Leu Gly Gly Val Leu Glu A la Ser Gly Tyr Ser
               110                 115                 120

Thr Glu Val Val Ala Leu Ser Arg Leu Gln G ly Ser Leu Gln Asp
               125                 130                 135

Met Leu Trp Gln Leu Asp Leu Ser Pro Gly C ys
               140                 145

(2) INFORMATION FOR SEQ ID NO: 35:

(i) SEQUENCE CHARACTERISTICS:
        (A) LENGTH: 146
        (B) TYPE: amino acid
        (D) TOPOLOGY: linear (ii) MOLECULE TYPE: amino acid (vi) ORIGINAL SOURCE:
        (A) ORGANISM: orangutan (ix) FEATURE:
        (D) OTHER INFORMATION:lep tin (xi) SEQUENCE DESCRIPTION: SEQ ID NO: 35:

Val Pro Ile Gln Lys Val Gln Asp Asp Thr L ys Thr Leu Ile Lys
                 5                  10                  15

Thr Val Ile Thr Arg Ile Asn Asp Ile Ser H is Thr Gln Ser Val
                20                  25                  30

Ser Ser Lys Gln Lys Val Thr Gly Leu Asp P he Ile Pro Gly Leu
                35                  40                  45

His Pro Ile Leu Thr Leu Ser Lys Met Asp G ln Thr Leu Ala Val
                50                  55                  60

Tyr Gln Gln Ile Leu Thr Ser Met Pro Ser A rg Asn Val Ile Gln
                65                  70                  75

```
Ile Ser Asn Asp Leu Glu Asn Leu Arg Asp Leu Leu His Val Leu
            80                  85                  90

Ala Phe Ser Lys Ser Cys His Leu Pro Trp Ala Ser Gly Leu Glu
            95                 100                 105

Thr Leu Asp Arg Leu Gly Gly Val Leu Glu Ala Ser Gly Tyr Ser
           110                 115                 120

Thr Glu Val Val Ala Leu Ser Arg Leu Gln Arg Ser Leu Gln Asp
           125                 130                 135

Met Leu Trp Gln Leu Asp Leu Ser Pro Gly Cys
           140                 145
```

(2) INFORMATION FOR SEQ ID NO: 36:

(i) SEQUENCE CHARACTERISTICS:
        (A) LENGTH: 146
        (B) TYPE: amino acid
        (D) TOPOLOGY: linear (ii) MOLECULE TYPE: amino acid (vi) ORIGINAL SOURCE:
        (A) ORGANISM: rhesus (ix) FEATURE:
        (D) OTHER INFORMATION: leptin (xi) SEQUENCE DESCRIPTION: SEQ ID NO: 36:

```
Val Pro Ile Gln Lys Val Gln Ser Asp Thr Lys Thr Leu Ile Lys
             5                  10                  15

Thr Ile Val Thr Arg Ile Asn Asp Ile Ser His Thr Gln Ser Val
            20                  25                  30

Ser Ser Lys Gln Arg Val Thr Gly Leu Asp Phe Ile Pro Gly Leu
            35                  40                  45

His Pro Val Leu Thr Leu Ser Gln Met Asp Gln Thr Leu Ala Ile
            50                  55                  60

Tyr Gln Gln Ile Leu Ile Asn Leu Pro Ser Arg Asn Val Ile Gln
            65                  70                  75

Ile Ser Asn Asp Leu Glu Asn Leu Arg Asp Leu Leu His Leu Leu
            80                  85                  90

Ala Phe Ser Lys Ser Cys His Leu Pro Leu Ala Ser Gly Leu Glu
            95                 100                 105

Thr Leu Glu Ser Leu Gly Asp Val Leu Glu Ala Ser Leu Tyr Ser
           110                 115                 120

Thr Glu Val Val Ala Leu Ser Arg Leu Gln Gly Ser Leu Gln Asp
           125                 130                 135

Met Leu Trp Gln Leu Asp Leu Ser Pro Gly Cys
           140                 145
```

(2) INFORMATION FOR SEQ ID NO: 37:

(i) SEQUENCE CHARACTERISTICS:
        (A) LENGTH: 146
        (B) TYPE: amino acid
        (D) TOPOLOGY: linear (ii) MOLECULE TYPE: amino acid (vi) ORIGINAL SOURCE:
        (A) ORGANISM: dog (ix) FEATURE:
        (D) OTHER INFORMATION: leptin (xi) SEQUENCE DESCRIPTION: SEQ ID NO: 37:

Val Pro Ile Arg Lys Val Gln Asp Asp Thr Lys Thr Leu Ile Lys
                 5                  10                  15

Thr Ile Val Ala Arg Ile Asn Asp Ile Ser His Thr Gln Ser Val
                20                  25                  30

Ser Ser Lys Gln Arg Val Ala Gly Leu Asp Phe Ile Pro Gly Leu
                35                  40                  45

Gln Pro Val Leu Ser Leu Ser Arg Met Asp Gln Thr Leu Ala Ile
                50                  55                  60

Tyr Gln Gln Ile Leu Asn Ser Leu His Ser Arg Asn Val Val Gln
                65                  70                  75

Ile Ser Asn Asp Leu Glu Asn Leu Arg Asp Leu Leu His Leu Leu
                80                  85                  90

Ala Ser Ser Lys Ser Cys Pro Leu Pro Arg Ala Arg Gly Leu Glu
                95                  100                 105

Thr Phe Glu Ser Leu Gly Gly Val Leu Glu Ala Ser Leu Tyr Ser
                110                 115                 120

Thr Glu Val Val Ala Leu Ser Arg Leu Gln Ala Ala Leu Gln Asp
                125                 130                 135

Met Leu Arg Arg Leu Asp Leu Ser Pro Gly Cys
                140                 145

(2) INFORMATION FOR SEQ ID NO: 38:

(i) SEQUENCE CHARACTERISTICS:
       (A) LENGTH: 146
       (B) TYPE: amino acid
       (D) TOPOLOGY: linear (ii) MOLECULE TYPE: amino acid (vi) ORIGINAL SOURCE:
       (A) ORGANISM: pig (ix) FEATURE:
       (D) OTHER INFORMATION: leptin (xi) SEQUENCE DESCRIPTION: SEQ ID NO: 38:

Val Pro Ile Trp Arg Val Gln Asp Asp Thr Lys Thr Leu Ile Lys
                 5                  10                  15

Thr Ile Val Thr Arg Ile Ser Asp Ile Ser His Met Gln Ser Val
                20                  25                  30

Ser Ser Lys Gln Arg Val Thr Gly Leu Asp Phe Ile Pro Gly Leu
                35                  40                  45

His Pro Val Leu Ser Leu Ser Lys Met Asp Gln Thr Leu Ala Ile
                50                  55                  60

Tyr Gln Gln Ile Leu Thr Ser Leu Pro Ser Arg Asn Val Ile Gln
                65                  70                  75

Ile Ser Asn Asp Leu Glu Asn Leu Arg Asp Leu Leu His Leu Leu
                80                  85                  90

Ala Ser Ser Lys Ser Cys Pro Leu Pro Gln Ala Arg Ala Leu Glu
                95                  100                 105

Thr Leu Glu Ser Leu Gly Gly Val Leu Glu Ala Ser Leu Tyr Ser
                110                 115                 120

Thr Glu Val Val Ala Leu Ser Arg Leu Gln Gly Ala Leu Gln Asp
                125                 130                 135

Met Leu Arg Gln Leu Asp Leu Ser Pro Gly Cys
                140                 145

(2) INFORMATION FOR SEQ ID NO: 39:

(i) SEQUENCE CHARACTERISTICS:
        (A) LENGTH: 146
        (B) TYPE: amino acid
        (D) TOPOLOGY: linear (ii) MOLECULE TYPE: amino acid (vi) ORIGINAL SOURCE:
        (A) ORGANISM: Bos taur us (ix) FEATURE:
        (D) OTHER INFORMATION:lep tin (xi) SEQUENCE DESCRIPTION: SEQ ID NO: 39:

```
Val Pro Ile Arg Lys Val Gln Asp Asp Thr L ys Thr Leu Ile Lys
                 5                  10                      15

Thr Ile Val Thr Arg Ile Asn Asp Ile Ser H is Thr Gln Ser Val
                20                  25                      30

Ser Ser Lys Gln Arg Val Thr Gly Leu Asp P he Ile Pro Gly Leu
                35                  40                      45

His Pro Leu Leu Ser Leu Ser Lys Met Asp G ln Thr Leu Ala Ile
                50                  55                      60

Tyr Gln Gln Ile Leu Thr Ser Leu Pro Ser A rg Asn Val Val Gln
                65                  70                      75

Ile Ser Asn Asp Leu Glu Asn Leu Arg Asp L eu Leu His Leu Leu
                80                  85                      90

Ala Ala Ser Lys Ser Cys Pro Leu Pro Gln V al Arg Ala Leu Glu
                95                 100                     105

Ser Leu Glu Ser Leu Gly Val Val Leu Glu A la Ser Leu Tyr Ser
               110                 115                     120

Thr Glu Val Val Ala Leu Ser Arg Leu Gln G ly Ser Leu Gln Asp
               125                 130                     135

Met Leu Arg Gln Leu Asp Leu Ser Pro Gly C ys
               140                 145
```

(2) INFORMATION FOR SEQ ID NO: 40:

(i) SEQUENCE CHARACTERISTICS:
        (A) LENGTH: 146
        (B) TYPE: amino acid
        (D) TOPOLOGY: linear (ii) MOLECULE TYPE: amino acid (vi) ORIGINAL SOURCE:
        (A) ORGANISM: sheep (ix) FEATURE:
        (D) OTHER INFORMATION:lep tin (xi) SEQUENCE DESCRIPTION: SEQ ID NO: 40:

```
Val Pro Ile Arg Lys Val Gln Asp Asp Thr L ys Thr Leu Ile Lys
                 5                  10                      15

Thr Ile Val Thr Arg Ile Asn Asp Ile Ser H is Thr Gln Ser Val
                20                  25                      30

Ser Ser Lys Gln Arg Val Thr Gly Leu Asp P he Ile Pro Gly Leu
                35                  40                      45

His Pro Leu Leu Ser Leu Ser Lys Met Asp G ln Thr Leu Ala Ile
                50                  55                      60
```

Tyr Gln Gln Ile Leu Ala Ser Leu Pro Ser Arg Asn Val Ile Gln
                65                  70                  75

Ile Ser Asn Asp Leu Glu Asn Leu Arg Asp Leu Leu His Leu Leu
                80                  85                  90

Ala Ala Ser Lys Ser Cys Pro Leu Pro Gln Val Arg Ala Leu Glu
                95                 100                 105

Ser Leu Glu Ser Leu Gly Val Val Leu Glu Ala Ser Leu Tyr Ser
               110                 115                 120

Thr Glu Val Val Ala Leu Ser Arg Leu Gln Gly Ser Leu Gln Asp
               125                 130                 135

Met Leu Arg Gln Leu Asp Leu Ser Pro Gly Cys
               140                 145

(2) INFORMATION FOR SEQ ID NO: 41:

(i) SEQUENCE CHARACTERISTICS:
       (A) LENGTH: 146
       (B) TYPE: amino acid
       (D) TOPOLOGY: linear (ii) MOLECULE TYPE: amino acid (vi) ORIGINAL SOURCE:
       (A) ORGANISM: rat (ix) FEATURE:
       (D) OTHER INFORMATION:leptin (xi) SEQUENCE DESCRIPTION: SEQ ID NO: 41:

Val Pro Ile His Lys Val Gln Asp Asp Thr Lys Thr Leu Ile Lys
                 5                  10                  15

Thr Ile Val Thr Arg Ile Asn Asp Ile Ser His Thr Gln Ser Val
                20                  25                  30

Ser Ala Arg Gln Arg Val Thr Gly Leu Asp Phe Ile Pro Gly Leu
                35                  40                  45

His Pro Ile Leu Ser Leu Ser Lys Met Asp Gln Thr Leu Ala Val
                50                  55                  60

Tyr Gln Gln Ile Leu Thr Ser Leu Pro Ser Gln Asn Val Leu Gln
                65                  70                  75

Ile Ala His Asp Leu Glu Asn Leu Arg Asp Leu Leu His Leu Leu
                80                  85                  90

Ala Phe Ser Lys Ser Cys Ser Leu Pro Gln Thr Arg Gly Leu Gln
                95                 100                 105

Lys Pro Glu Ser Leu Asp Gly Val Leu Glu Ala Ser Leu Tyr Ser
               110                 115                 120

Thr Glu Val Val Ala Leu Ser Arg Leu Gln Gly Ser Leu Gln Asp
               125                 130                 135

Ile Leu Gln Gln Leu Asp Leu Ser Pro Glu Cys
               140                 145

(2) INFORMATION FOR SEQ ID NO: 42:

(i) SEQUENCE CHARACTERISTICS:
       (A) LENGTH: 146
       (B) TYPE: amino acid
       (D) TOPOLOGY: linear (ii) MOLECULE TYPE: amino acid (vi) ORIGINAL SOURCE:
       (A) ORGANISM: mouse (ix) FEATURE:
    (D) OTHER INFORMATION:lep tin (xi) SEQUENCE DESCRIPTION: SEQ ID NO: 42:

Val Pro Ile Gln Lys Val Gln Asp Asp Thr L ys Thr Leu Ile Lys
              5                   10                        15

Thr Ile Val Thr Arg Ile Asn Asp Ile Ser H is Thr Gln Ser Val
             20                   25                        30

Ser Ala Lys Gln Arg Val Thr Gly Leu Asp P he Ile Pro Gly Leu
             35                   40                        45

His Pro Ile Leu Ser Leu Ser Lys Met Asp G ln Thr Leu Ala Val
             50                   55                        60

Tyr Gln Gln Val Leu Thr Ser Leu Pro Ser G ln Asn Val Leu Gln
             65                   70                        75

Ile Ala Asn Asp Leu Glu Asn Leu Arg Asp L eu Leu His Leu Leu
             80                   85                        90

Ala Phe Ser Lys Ser Cys Ser Leu Pro Gln T hr Ser Gly Leu Gln
             95                  100                       105

Lys Pro Glu Ser Leu Asp Gly Val Leu Glu A la Ser Leu Tyr Ser
            110                  115                       120

Thr Glu Val Val Ala Leu Ser Arg Leu Gln G ly Ser Leu Gln Asp
            125                  130                       135

Ile Leu Gln Gln Leu Asp Val Ser Pro Glu C ys
            140                  145

(2) INFORMATION FOR SEQ ID NO: 43:

(i) SEQUENCE CHARACTERISTICS:
        (A) LENGTH: 146
        (B) TYPE: amino acid
        (D) TOPOLOGY: linear (ii) MOLECULE TYPE: amino acid (vi) ORIGINAL SOURCE:
        (A) ORGANISM: rat (ix) FEATURE:
        (D) OTHER INFORMATION:lep tin (xi) SEQUENCE DESCRIPTION: SEQ ID NO: 43:

Val Pro Ile His Lys Val Gln Asp Asp Thr L ys Thr Leu Ile Lys
              5                   10                        15

Thr Ile Val Thr Arg Ile Asn Asp Ile Ser H is Thr Gln Ser Val
             20                   25                        30

Ser Ala Arg Gln Arg Val Thr Gly Leu Asp P he Ile Pro Gly Leu
             35                   40                        45

His Pro Ile Leu Ser Leu Ser Lys Met Asp G ln Thr Leu Ala Val
             50                   55                        60

Tyr Gln Gln Ile Leu Thr Ser Leu Pro Ser G ln Asn Val Leu Gln
             65                   70                        75

Ile Ala His Asp Leu Glu Asn Leu Arg Asp L eu Leu His Leu Leu
             80                   85                        90

Ala Phe Ser Lys Ser Cys Ser Leu Pro Gln T hr Arg Gly Leu Gln
             95                  100                       105

Lys Pro Glu Ser Leu Asp Gly Val Leu Glu A la Ser Leu Tyr Ser
            110                  115                       120

Thr Glu Val Val Ala Leu Ser Arg Leu Gln G ly Ser Leu Gln Asp
            125                  130                       135

Ile Leu Gln Gln Leu Asp Val Ser Pro Glu C ys
            140                 145

(2) INFORMATION FOR SEQ ID NO: 44:

(i) SEQUENCE CHARACTERISTICS:
        (A) LENGTH: 51
        (B) TYPE: amino acid
        (D) TOPOLOGY: linear (ii) MOLECULE TYPE: amino acid (vi) ORIGINAL SOURCE:
        (A) ORGANISM: bacterium (ix) FEATURE:
        (D) OTHER INFORMATION:lep tin potential bacterial homolog (xi) SEQUENCE DESCRIPTION: SEQ ID NO: 44:

Met Arg Leu Phe Glu Val Gln Leu Gly Ser P he Val Leu Leu Ala
                5                  10                  15

Leu Met Ile Ser Leu Phe Leu Leu Asp Gly S er Ser Met Lys Asp
            20                  25                  30

Ile Met Met Asn Trp Asp Asp Ala Gly Cys A la Phe Val Pro Pro
            35                  40                  45

Ala Phe Thr Phe Leu Cys
            50

(2) INFORMATION FOR SEQ ID NO: 45:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: human (ix) FEATURE:
        (D) OTHER INFORMATION:lep tin (xi) SEQUENCE DESCRIPTION: SEQ ID NO: 45:

GTGCCCATCC AAAAAGTCCA AGATGACACC AAAACCCTCA TCAAGACAAT T GTCACCAGG        60

ATCAATGACA TTTCACACAC ACAGTCAGTC TCCTCCAAAC AGAAAGTCAC C GGTTTGGAC       120

TTCATTCCTG GGCTCCACCC CATCCTGACC TTATCCAAGA TGGACCAGAC A CTGGCAGTC      180

TACCAACAGA TCCTCACCAG TATGCCTTCC AGAAACGTGA TCCAAATATC C AACGACCTG      240

GAGAACCTCC GGGATCTTCT TCACGTGCTG GCCTTCTCTA AGAGCTGCCA C TTGCCCTGG      300

GCCAGTGGCC TGGAGACCTT GGACAGCCTG GGGGGTGTCC TGGAAGCTTC A GGCTACTCC      360

ACAGAGGTGG TGGCCCTGAG CAGGCTGCAG GGGTCTCTGC AGGACATGCT G TGGCAGCTG      420

GACCTCAGCC CTGGGTGCTG A                                                 441

(2) INFORMATION FOR SEQ ID NO: 46:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
     (A) ORGANISM: gorilla (ix) FEATURE:
     (D) OTHER INFORMATION:lep tin (xi) SEQUENCE DESCRIPTION: SEQ ID NO: 46:

| | | | | | |
|---|---|---|---|---|---|
| GTGCCCATCC | AAAAAGTCCA | AGATGACACC | AAAACCCTCA | TCAAGACAAT T | GTCACCAGG      60 |
| ATCAGTGACA | TTTCACACAC | GCAGTCAGTC | TCCTCCAAAC | AGAAGGTCAC C | GGTTTGGAC     120 |
| TTCATTCCTG | GGCTCCACCC | CATCCTGACC | TTATCCAAGA | TGGACCAGAC A | CTGGCAGTC     180 |
| TACCAACAGA | TCCTCACCAG | TATGCCTTCC | AGAAACATGA | TCCAAATATC C | AACGACCTG     240 |
| GAGAACCTCC | GGGACCTTCT | TCACGTGCTG | GCCTTCTCTA | AGAGCTGCCA C | TTGCCCTGG     300 |
| GCCAGTGGCC | TGGAGACCTT | GGACAGCCTG | GGGGTGTCC  | TGGAAGCTTC A | GGCTACTCC     360 |
| ACAGAGGTGG | TGGCCCTGAG | CAGGCTGCAG | GGGTCTCTGC | AGGACATGCT G | TGGCAGCTG     420 |
| GACCTCAGCC | CTGGGTGCTG | A          |            |              |               441 |

(2) INFORMATION FOR SEQ ID NO: 47:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
         (A) ORGANISM: chimp (ix) FEATURE:
         (D) OTHER INFORMATION:lep tin (xi) SEQUENCE DESCRIPTION: SEQ ID NO: 47:

| | | | | | |
|---|---|---|---|---|---|
| GTGCCCATCC | AAAAAGTCCA | GGATGACACC | AAAACCCTCA | TCAAGACAAT T | GTCACCAGG      60 |
| ATCAATGACA | TTTCACACAC | GCAGTCAGTC | TCCTCCAAAC | AGAAGGTCAC C | GGTTTGGAC     120 |
| TTCATTCCTG | GGCTCCACCC | TATCCTGACC | TTATCCAAGA | TGGACCAGAC A | CTGGCAGTC     180 |
| TACCAACAGA | TCCTCACCAG | TATGCCTTCC | AGAAACATGA | TCCAAATATC C | AACGACCTG     240 |
| GAGAACCTCC | GGGACCTTCT | TCACGTGCTG | GCCTTCTCTA | AGAGCTGCCA C | TTGCCCTGG     300 |
| GCCAGTGGCC | TGGAGACCTT | GGACAGCCTG | GGGGTGTCC  | TGGAAGCTTC A | GGCTACTCC     360 |
| ACAGAGGTGG | TGGCCCTGAG | CAGGCTGCAG | GGGTCTCTGC | AGGACATGCT G | TGGCAGCTG     420 |
| GACCTCAGCC | CTGGGTGCTG | A          |            |              |               441 |

(2) INFORMATION FOR SEQ ID NO: 48:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
         (A) ORGANISM: orangutan (ix) FEATURE:
         (D) OTHER INFORMATION:lep tin (xi) SEQUENCE DESCRIPTION: SEQ ID NO: 48:

```
GTGCCCATCC AAAAAGTCCA AGATGACACC AAAACCCTCA TCAAGACAGT T ATCACCAGG    60

ATCAATGACA TTTCACACAC GCAGTCAGTC TCCTCCAAAC AGAAGGTCAC C GGTTTGGAC   120

TTCATTCCTG GGCTCCACCC CATCCTGACC TTATCCAAGA TGGACCAGAC A CTGGCAGTC   180

TACCAACAGA TCCTCACCAG TATGCCTTCC AGAAACGTGA TCCAAATATC C AACGACCTG   240

GAGAACCTCC GGGACCTTCT TCACGTGCTG GCCTTCTCTA AGAGCTGCCA C TTGCCCTGG   300

GCCAGTGGCC TGGAGACCTT GGACAGGCTG GGGGGTGTCC TGGAAGCTTC A GGCTACTCC   360

ACAGAGGTGG TGGCCCTTAG CAGGCTGCAG CGGTCTCTGC AGGACATGCT G TGGCAGCTG   420

GACCTCAGCC CTGGGTGCTG A                                              441

(2) INFORMATION FOR SEQ ID NO: 49:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: rhesus (ix) FEATURE:
        (D) OTHER INFORMATION:lep tin (xi) SEQUENCE DESCRIPTION: SEQ ID NO: 49:

GTGCCCATCC AAAAAGTCCA AAGTGACACC AAAACCCTCA TCAAGACAAT T GTCACCAGG    60

ATCAATGACA TTTCACACAC GCAGTCGGTC TCCTCCAAAC AGAGGGTCAC T GGTTTGGAC   120

TTCATTCCTG GGCTCCACCC CGTCCTGACC TTATCCCAGA TGGACCAGAC A CTGGCAATC   180

TACCAACAGA TCCTCATCAA TCTGCCTTCC AGAAACGTGA TCCAAATATC C AACGACTTG   240

GAGAATCTCC GGGACCTTCT TCACCTGCTG GCCTTCTCTA AGAGCTGCCA T TTGCCCTTG   300

GCCAGTGGCC TGGAGACCTT GGAGAGCCTG GGGGATGTCC TGGAAGCTTC A CTCTACTCC   360

ACGGAGGTGG TGGCCCTGAG CAGGCTGCAG GGGTCTCTGC AGGACATGCT G TGGCAGCTG   420

GACCTCAGCC CTGGGTGCTG A                                              441

(2) INFORMATION FOR SEQ ID NO: 50:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: dog (ix) FEATURE:
        (D) OTHER INFORMATION:lep tin (xi) SEQUENCE DESCRIPTION: SEQ ID NO: 50:

GTGCCAATCC GAAAAGTCCA GGATGACACC AAAACCCTCA TCAAGACGAT T GTCGCCAGG    60

ATCAATGACA TTTCACACAC GCAGTCTGTC TCCTCCAAAC AGAGGGTCGC T GGTCTGGAC   120

TTCATTCCTG GGCTCCAACC AGTCCTGAGT TTGTCCAGGA TGGACCAGAC G TTGGCCATC   180

TACCAACAGA TCCTCAACAG TCTGCATTCC AGAAATGTGG TCCAAATATC T AATGACCTG   240

GAGAACCTCC GGGACCTTCT CCACCTGCTG GCCTCCTCCA AGAGCTGCCC C TTGCCCCGG   300
```

```
GCCAGGGGCC TGGAGACCTT TGAGAGCCTG GGCGGCGTCC TGGAAGCCTC A CTCTACTCC       360

ACAGAGGTGG TGGCTCTGAG CAGACTGCAG GCGGCCCTCC AGGACATGCT T CGGCGGCTG       420

GACCTCAGCC CTGGGTGCTG A                                                  441
```

(2) INFORMATION FOR SEQ ID NO: 51:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: pig (ix) FEATURE:
        (D) OTHER INFORMATION:lep tin (xi) SEQUENCE DESCRIPTION: SEQ ID NO: 51:

```
GTGCCCATCT GGAGAGTCCA GGATGACACC AAAACCCTCA TCAAGACGAT T GTCACCAGG       60

ATCAGTGACA TTTCACACAT GCAGTCTGTC TCCTCCAAAC AGAGGGTCAC C GGTTTGGAC       120

TTCATCCCTG GCTCCATCC TGTCCTGAGT TTGTCCAAGA TGGACCAGAC C CTGGCGATC       180

TACCAACAGA TCCTCACCAG TCTGCCTTCC AGAAATGTGA TCCAAATATC G AATGACCTG       240

GAGAACCTCC GGGACCTTCT CCACCTGCTG GCCTCCTCCA AGAGCTGCCC C TTGCCCCAG       300

GCCAGGGCCC TGGAGACCTT GGAGAGCCTG GGCGGCGTCC TGGAAGCCTC C CTCTACTCC       360

ACGGAGGTGG TGGCCCTGAG CAGGCTGCAG GGGGCTCTGC AGGACATGCT G CGGCAGCTG       420

GACCTCAGCC CTGGCTGCTG A                                                  441
```

(2) INFORMATION FOR SEQ ID NO: 52:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: Bos taur us (ix) FEATURE:
        (D) OTHER INFORMATION:lep tin (xi) SEQUENCE DESCRIPTION: SEQ ID NO: 52:

```
GTGCCCATCC GCAAGGTCCA GGATGACACC AAAACCCTCA TCAAGACAAT T GTCACCAGG       60

ATCAATGACA TCTCACACAC GCAGTCCGTC TCCTCCAAAC AGAGGGTCAC T GGTTTGGAC       120

TTCATCCCTG GCTCCACCC TCTCCTGAGT TTGTCCAAGA TGGACCAGAC A TTGGCGATC       180

TACCAACAGA TCCTCACCAG TCTGCCTTCC AGAAATGTGG TCCAAATATC C AATGACCTG       240

GAGAACCTCC GGGACCTTCT CCACCTGCTG GCCGCCTCCA AGAGCTGCCC C TTGCCGCAG       300

GTCAGGGCCC TGGAGAGCTT GGAGAGCTTG GCGTTGTCC TGGAAGCTTC C CTCTACTCC       360

ACCGAGGTGG TGGCCCTGAG CCGGCTGCAG GGGTCACTAC AGGACATGTT G CGGCAGCTG       420

GACCTCAGTC CCGGGTGCTG A                                                  441
```

(2) INFORMATION FOR SEQ ID NO: 53:

```
    (i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: sheep (ix) FEATURE:
        (D) OTHER INFORMATION:lep tin (xi) SEQUENCE DESCRIPTION: SEQ ID NO: 53:

GTGCCCATCC GCAAGGTCCA GGATGACACC AAAACCCTCA TCAAGACGAT T GTCACCAGG      60

ATCAATGACA TCTCACACAC GCAGTCCGTC TCCTCCAAAC AGAGGGTCAC T GGTTTGGAC     120

TTCATCCCTG GCTCCACCC TCTCCTGAGT TTGTCCAAGA TGGACCAGAC A TTGGCAATC     180

TACCAACAGA TCCTCGCCAG TCTGCCTTCC AGAAATGTGA TCCAAATATC T AATGACCTG     240

GAGAACCTCC GGGACCTTCT CCACCTGCTG GCCGCCTCCA AGAGCTGCCC C TTGCCGCAG     300

GTCAGGGCCC TGGAGAGCTT GGAGAGCCTG GGCGTCGTCC TGGAAGCCTC C CTCTACTCC     360

ACCGAGGTGG TGGCCCTGAG CCGGCTACAG GGGTCTCTAC AGGACATGTT G CGGCAGCTG     420

GACCTCAGTC CCGGGTGCTG A                                                441

(2) INFORMATION FOR SEQ ID NO: 54:

(i) SEQUENCE CHARACTERISTICS:
        (A) LENGTH: 441
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: rat (ix) FEATURE:
        (D) OTHER INFORMATION:lep tin (xi) SEQUENCE DESCRIPTION: SEQ ID NO: 54:

GTGCCTATCC ACAAAGTCCA GGATGACACC AAAACCCTCA TCAAGACCAT T GTCACCAGG      60

ATCAATGACA TTTCACACAC GCAGTCGGTA TCCGCCAGGC AGAGGGTCAC C GGTTTGGAC     120

TTCATTCCCG GCTTCACCC CATTCTGAGT TTGTCCAAGA TGGACCAGAC C CTGGCAGTC     180

TATCAACAGA TCCTCACCAG CTTGCCTTCC CAAAACGTGC TGCAGATAGC T CATGACCTG     240

GAGAACCTGC GAGACCTCCT CCATCTGCTG GCCTTCTCCA AGAGCTGCTC C CTGCCGCAG     300

ACCCGTGGCC TGCAGAAGCC AGAGAGCCTG GATGGCGTCC TGGAAGCCTC G CTCTACTCC     360

ACAGAGGTGG TGGCTCTGAG CAGGCTGCAG GGCTCTCTGC AGGACATTCT T CAACAGTTG     420

GACCTTAGCC CTGAATGCTG A                                                441

(2) INFORMATION FOR SEQ ID NO: 55:

(i) SEQUENCE CHARACTERISTICS:
        (A) LENGTH: 426
        (B) TYPE: nucleic acid
        (C) STRANDEDNESS: single
        (D) TOPOLOGY: linear (ii) MOLECULE TYPE: DNA
```

(vi) ORIGINAL SOURCE:
         (A) ORGANISM: mouse (ix) FEATURE:
         (D) OTHER INFORMATION:lep tin (xi) SEQUENCE DESCRIPTION: SEQ ID NO: 55:

GTGCCTATCC AGAAAGTCCA GGATGACACC AAAACCCTCA TCAAGACCAT T GTCACCAGG     60

ATCAATGACA TTTCACACAC GCAGTCGGTA TCCGCCAAGC AGAGGGTCAC T GGCTTGGAC    120

TTCATTCCTG GGCTTCACCC CATTCTGAGT TTGTCCAAGA TGGACCAGAC T CTGGCAGTC    180

TATCAACAGG TCCTCACCAG CCTGCCTTCC CAAAATGTGC TGCAGATAGC C AATGACCTG    240

GAGAATCTCC GAGACCTCCT CCATCTGCTG GCCTTCTCCA AGAGCTGCTC C CTGCCTCAG    300

ACCAGTGGCC TGCAGAAGCC AGAGAGCCTG GATGGCGTCC TGGAAGCCTC A CTCTACTCC    360

ACAGAGGTGG TGGCTTTGAG CAGGCTGCAG GGCTCTCTGC AGGACATTCT T CAACAGTTG    420

GATGTT                                                                426

(2) INFORMATION FOR SEQ ID NO: 56:

(i) SEQUENCE CHARACTERISTICS:
         (A) LENGTH: 441
         (B) TYPE: nucleic acid
         (C) STRANDEDNESS: single
         (D) TOPOLOGY: linear (ii) MOLECULE TYPE: DNA (vi) ORIGINAL SOURCE:
         (A) ORGANISM: rat (ix) FEATURE:
         (D) OTHER INFORMATION:lep tin (xi) SEQUENCE DESCRIPTION: SEQ ID NO: 56:

GTGCCTATCC ACAAAGTCCA GGATGACACC AAAACCCTCA TCAAGACCAT T GTCACCAGG     60

ATCAATGACA TTTCACACAC GCAGTCGGTA TCCGCCAGGC AGAGGGTCAC C GGTTTGGAC    120

TTCATTCCCG GGCTTCACCC CATTCTGAGT TTGTCCAAGA TGGACCAGAC C CTGGCAGTC    180

TATCAACAGA TCCTCACCAG CTTGCCTTCC CAAAACGTGC TGCAGATAGC T CATGACCTG    240

GAGAACCTGC GAGACCTCCT CCATCTGCTG GCCTTCTCCA AGAGCTGCTC C CTGCCGCAG    300

ACCCGTGGCC TGCAGAAGCC AGAGAGCCTG GATGGCGTCC TGGAAGCCTC G CTCTACTCC    360

ACAGAGGTGG TGGCTCTGAG CAGGCTGCAG GGCTCTCTGC AGGACATTCT T CAACAGTTG    420

GATGTTAGCC CTGAATGCTG A                                                441

(2) INFORMATION FOR SEQ ID NO: 57:

(i) SEQUENCE CHARACTERISTICS:
         (A) LENGTH: 467
         (B) TYPE: amino acid
         (D) TOPOLOGY: linear (ii) MOLECULE TYPE: amino acid (vi) ORIGINAL SOURCE:
         (A) ORGANISM: Lactococcus  lactis (ix) FEATURE:
         (D) OTHER INFORMATION:lac g_lacla  6-phospho-strand-
              galactosida se (E.C. 3.2.1.85)

(xi) SEQUENCE DESCRIPTION: SEQ ID NO: 57:

Met Thr Lys Thr Leu Pro Lys Asp Phe Ile P he Gly Gly Ala Thr

```
                    5                    10                   15
Ala Ala Tyr Gln Ala Glu Gly Ala Thr His T  hr Asp Gly Lys Gly
                20                   25                   30
Pro Val Ala Trp Asp Lys Tyr Leu Glu Asp A  sn Tyr Trp Tyr Thr
                35                   40                   45
Ala Glu Pro Ala Ser Asp Phe Tyr His Lys T  yr Pro Val Asp Leu
                50                   55                   60
Glu Leu Ala Glu Glu Tyr Gly Val Asn Gly I  le Arg Ile Ser Ile
                65                   70                   75
Ala Trp Ser Arg Ile Phe Pro Thr Gly Tyr G  ly Glu Val Asn Glu
                80                   85                   90
Lys Gly Val Glu Phe Tyr His Lys Leu Phe A  la Glu Cys His Lys
                95                  100                  105
Arg His Val Glu Pro Phe Val Thr Leu His H  is Phe Asp Thr Pro
               110                  115                  120
Glu Ala Leu His Ser Asn Gly Asp Phe Leu A  sn Arg Glu Asn Ile
               125                  130                  135
Glu His Phe Ile Asp Tyr Ala Ala Phe Cys P  he Glu Glu Phe Pro
               140                  145                  150
Glu Val Asn Tyr Trp Thr Thr Phe Asn Glu I  le Gly Pro Ile Gly
               155                  160                  165
Asp Gly Gln Tyr Leu Val Gly Lys Phe Pro P  ro Gly Ile Lys Tyr
               170                  175                  180
Asp Leu Ala Lys Val Phe Gln Ser His His A  sn Met Met Val Ser
               185                  190                  195
His Ala Arg Ala Val Lys Leu Tyr Lys Asp L  ys Gly Tyr Lys Gly
               200                  205                  210
Glu Ile Gly Val Val His Ala Leu Pro Thr L  ys Tyr Pro Tyr Asp
               215                  220                  225
Pro Glu Asn Pro Ala Asp Val Arg Ala Ala G  lu Leu Glu Asp Ile
               230                  235                  240
Ile His Asn Lys Phe Ile Leu Asp Ala Thr T  yr Leu Gly His Tyr
               245                  250                  255
Ser Asp Lys Thr Met Glu Gly Val Asn His I  le Leu Ala Glu Asn
               260                  265                  270
Gly Gly Glu Leu Asp Leu Arg Asp Glu Asp P  he Gln Ala Leu Asp
               275                  280                  285
Ala Ala Lys Asp Leu Asn Asp Phe Leu Gly I  le Asn Tyr Tyr Met
               290                  295                  300
Ser Asp Trp Met Gln Ala Phe Asp Gly Glu T  hr Glu Ile Ile His
               305                  310                  315
Asn Gly Lys Gly Glu Lys Gly Ser Ser Lys T  yr Gln Ile Lys Gly
               320                  325                  330
Val Gly Arg Arg Val Ala Pro Asp Tyr Val P  ro Arg Thr Asp Trp
               335                  340                  345
Asp Trp Ile Ile Tyr Pro Glu Gly Leu Tyr A  sp Gln Ile Met Arg
               350                  355                  360
Val Lys Asn Asp Tyr Pro Asn Tyr Lys Lys I  le Tyr Ile Thr Glu
               365                  370                  375
Asn Gly Leu Gly Tyr Lys Asp Glu Phe Val A  sp Asn Thr Val Tyr
               380                  385                  390
Asp Asp Gly Arg Ile Asp Tyr Val Lys Gln H  is Leu Glu Val Leu
               395                  400                  405
```

```
Ser Asp Ala Ile Ala Asp Gly Ala Asn Val Lys Gly Tyr Phe Ile
                410                 415                 420

Trp Ser Leu Met Asp Val Phe Ser Trp Ser Asn Gly Tyr Glu Lys
                425                 430                 435

Arg Tyr Gly Leu Phe Tyr Val Asp Phe Asp Thr Gln Glu Arg Tyr
                440                 445                 450

Pro Lys Lys Ser Ala His Trp Tyr Lys Lys Leu Ala Glu Thr Gln
                455                 460                 465

Val Ile (2) INFORMATION FOR SEQ ID NO: 58:

(i) SEQUENCE CHARACTERISTICS:
        (A) LENGTH: 464
        (B) TYPE: amino acid
        (D) TOPOLOGY: linear (ii) MOLECULE TYPE: amino acid (vi) ORIGINAL SOURCE:
        (A) ORGANISM: Staphylococcus aureus (ix) FEATURE:
        (D) OTHER INFORMATION:lac g_staau 6-phospho-strand-
            galactosidase (E.C. 3.2.1.85)

(xi) SEQUENCE DESCRIPTION: SEQ ID NO: 58:

Lys Thr Leu Pro Glu Asp Phe Ile Phe Gly Gly Ala Thr Ala Ala
                 5                  10                  15

Tyr Gln Ala Glu Gly Ala Thr Asn Thr Asp Gly Lys Gly Arg Val
                20                  25                  30

Ala Trp Asp Thr Tyr Leu Glu Glu Asn Tyr Trp Tyr Thr Ala Glu
                35                  40                  45

Pro Ala Ser Asp Phe Tyr Asn Arg Tyr Pro Val Asp Leu Glu Leu
                50                  55                  60

Ser Glu Lys Phe Gly Val Asn Gly Ile Arg Ile Ser Ile Ala Trp
                65                  70                  75

Ser Arg Ile Phe Pro Asn Gly Tyr Gly Glu Val Asn Pro Lys Gly
                80                  85                  90

Val Glu Tyr Tyr His Lys Leu Phe Ala Glu Cys His Lys Arg His
                95                 100                 105

Val Glu Pro Phe Val Thr Leu His His Phe Asp Thr Pro Glu Val
               110                 115                 120

Leu His Lys Asp Gly Asp Phe Leu Asn Arg Lys Thr Ile Asp Tyr
               125                 130                 135

Phe Val Asp Tyr Ala Glu Tyr Cys Phe Lys Glu Phe Pro Glu Val
               140                 145                 150

Lys Tyr Trp Thr Thr Phe Asn Glu Ile Gly Pro Ile Gly Asp Gly
               155                 160                 165

Gln Tyr Leu Val Gly Lys Phe Pro Pro Gly Ile Lys Tyr Asp Phe
               170                 175                 180

Glu Lys Val Phe Gln Ser His His Asn Met Met Val Ala His Ala
               185                 190                 195

Arg Ala Val Lys Leu Phe Lys Asp Gly Gly Tyr Lys Gly Glu Ile
               200                 205                 210

Gly Val Val His Ala Leu Pro Thr Lys Tyr Pro Phe Asp Pro Ser
               215                 220                 225
```

-continued

```
Asn Pro Glu Asp Val Arg Ala Ala Glu Leu Glu Asp Ile Ile His
                230                 235                 240

Asn Lys Phe Ile Leu Asp Ala Thr Tyr Leu Gly Lys Tyr Ser Arg
                245                 250                 255

Glu Thr Met Glu Gly Val Gln His Ile Leu Ser Val Asn Gly Gly
                260                 265                 270

Lys Leu Asn Ile Thr Asp Glu Asp Tyr Ala Ile Leu Asp Ala Ala
                275                 280                 285

Lys Asp Leu Asn Asp Phe Leu Gly Ile Asn Tyr Tyr Met Ser Asp
                290                 295                 300

Trp Met Arg Gly Tyr Asp Gly Glu Ser Glu Ile Thr His Asn Ala
                305                 310                 315

Thr Gly Asp Lys Gly Gly Ser Lys Tyr Gln Leu Lys Gly Val Gly
                320                 325                 330

Gln Arg Glu Phe Asp Val Asp Val Pro Arg Thr Asp Trp Asp Trp
                335                 340                 345

Met Ile Tyr Pro Gln Gly Leu Tyr Asp Gln Ile Met Arg Val Val
                350                 355                 360

Lys Asp Tyr Pro Asn Tyr His Lys Ile Tyr Ile Thr Glu Asn Gly
                365                 370                 375

Leu Gly Tyr Lys Asp Glu Phe Ile Glu Ser Glu Lys Thr Val His
                380                 385                 390

Asp Asp Ala Arg Ile Asp Tyr Val Arg Gln His Leu Asn Val Ile
                395                 400                 405

Ala Asp Ala Ile Ile Asp Gly Ala Asn Val Lys Gly Tyr Phe Ile
                410                 415                 420

Trp Ser Leu Met Asp Val Phe Ser Trp Ser Asn Gly Tyr Glu Lys
                425                 430                 435

Arg Tyr Gly Leu Phe Tyr Val Asp Phe Glu Thr Gln Glu Arg Tyr
                440                 445                 450

Pro Lys Lys Ser Ala Tyr Trp Tyr Lys Glu Leu Ala Glu Thr
                455                 460
```

(2) INFORMATION FOR SEQ ID NO: 59:

(i) SEQUENCE CHARACTERISTICS:
        (A) LENGTH: 472
        (B) TYPE: amino acid
        (D) TOPOLOGY: linear (ii) MOLECULE TYPE: amino acid (vi) ORIGINAL SOURCE:
        (A) ORGANISM: Lactobacillus casei (ix) FEATURE:
        (D) OTHER INFORMATION:lac g_lacca 6-phospho-strand-
        galactosida se (E.C. 3.2.1.85)

(xi) SEQUENCE DESCRIPTION: SEQ ID NO: 59:

```
Met Ser Lys Gln Leu Pro Gln Asp Phe Val Met Gly Gly Ala Thr
                  5                  10                  15

Ala Ala Tyr Gln Val Glu Gly Ala Thr Lys Glu Asp Gly Lys Gly
                 20                  25                  30

Arg Val Leu Trp Asp Asp Phe Leu Asp Lys Gln Gly Arg Phe Lys
                 35                  40                  45

Pro Asp Pro Ala Ala Asp Phe Tyr His Arg Tyr Asp Glu Asp Leu
                 50                  55                  60
```

-continued

```
Ala Leu Ala Glu Lys Tyr Gly His Gln Val Ile Arg Val Ser Ile
                 65                  70                  75

Ala Trp Ser Arg Ile Phe Pro Asp Gly Ala Gly Glu Val Glu Pro
                 80                  85                  90

Arg Gly Val Ala Phe Tyr His Lys Leu Phe Ala Asp Cys Ala Ala
                 95                 100                 105

His His Ile Glu Pro Phe Val Thr Leu His His Phe Asp Thr Pro
                110                 115                 120

Glu Arg Leu His Glu Ala Gly Asp Trp Leu Ser Gln Glu Met Leu
                125                 130                 135

Asp Asp Phe Val Ala Tyr Ala Lys Phe Cys Phe Glu Glu Phe Ser
                140                 145                 150

Glu Val Lys Tyr Trp Ile Thr Ile Asn Glu Pro Thr Ser Met Ala
                155                 160                 165

Val Gln Gln Tyr Thr Thr Gly Thr Phe Pro Pro Ala Glu Ser Gly
                170                 175                 180

Arg Phe Asp Lys Thr Phe Gln Ala Glu His Asn Gln Met Val Ala
                185                 190                 195

His Ala Arg Ile Val Asn Leu Tyr Lys Ser Met Gln Leu Gly Gly
                200                 205                 210

Gln Ile Gly Ile Val His Ala Leu Gln Thr Val Tyr Pro Tyr Ser
                215                 220                 225

Asp Ser Ala Val Asp His His Ala Ala Glu Leu Gln Asp Ala Leu
                230                 235                 240

Glu Asn Arg Leu Tyr Leu Asp Gly Thr Leu Ala Gly Glu Tyr His
                245                 250                 255

Gln Glu Thr Leu Ala Leu Val Lys Glu Ile Leu Asp Ala Asn His
                260                 265                 270

Gln Pro Met Phe Gln Ser Thr Pro Gln Glu Met Lys Ala Ile Asp
                275                 280                 285

Glu Ala Ala His Gln Leu Asp Phe Val Gly Val Asn Asn Tyr Phe
                290                 295                 300

Ser Lys Trp Leu Arg Ala Tyr His Gly Lys Ser Glu Thr Ile His
                305                 310                 315

Asn Gly Asp Gly Thr Lys Gly Ser Ser Val Ala Arg Leu Gln Gly
                320                 325                 330

Val Gly Glu Glu Lys Leu Pro Asp Gly Ile Glu Thr Thr Asp Trp
                335                 340                 345

Asp Trp Ser Ile Tyr Pro Arg Gly Met Tyr Asp Ile Leu Met Arg
                350                 355                 360

Ile His Asn Asp Tyr Pro Leu Val Pro Val Thr Tyr Val Thr Glu
                365                 370                 375

Asn Gly Ile Gly Leu Lys Glu Ser Leu Pro Glu Asn Ala Thr Pro
                380                 385                 390

Asp Thr Val Ile Glu Asp Pro Lys Arg Ile Asp Tyr Val Lys Lys
                395                 400                 405

Tyr Leu Ser Ala Met Ala Asp Ala Ile His Asp Gly Ala Asn Val
                410                 415                 420

Lys Gly Tyr Phe Ile Trp Ser Leu Gln Asp Gln Phe Ser Trp Thr
                425                 430                 435

Asn Gly Tyr Ser Lys Arg Tyr Gly Leu Phe Phe Val Asp Phe Pro
                440                 445                 450

Thr Gln Asn Arg Tyr Ile Lys Gln Ser Ala Glu Trp Phe Lys Ser
```

```
                    455                 460                 465
Val Ser Glu Thr His Ile Ile
                    470

(2) INFORMATION FOR SEQ ID NO: 60:

(i) SEQUENCE CHARACTERISTICS:
        (A) LENGTH: 466
        (B) TYPE: amino acid
        (D) TOPOLOGY: linear (ii) MOLECULE TYPE: amino acid (vi) ORIGINAL SOURCE:
        (A) ORGANISM: Escherichia  coli (ix) FEATURE:
        (D) OTHER INFORMATION:asc b_ecoli  6-phospho-strand-
            glucosidase  (E.C. 3.2.1.86)

(xi) SEQUENCE DESCRIPTION: SEQ ID NO: 60:

Phe Pro Glu Ser Phe Leu Trp Gly Gly Ala L eu Ala Ala Asn Gln
                 5                  10                  15

Ser Glu Gly Ala Phe Arg Glu Gly Asp Lys G ly Leu Thr Thr Val
                20                  25                  30

Asp Met Ile Pro His Gly Glu His Arg Met A la Val Lys Leu Gly
                35                  40                  45

Leu Glu Lys Arg Phe Gln Leu Arg Asp Asp G lu Phe Tyr Pro Ser
                50                  55                  60

His Glu Ala Thr Asp Phe Tyr His Arg Tyr L ys Glu Asp Ile Ala
                65                  70                  75

Leu Met Ala Glu Met Gly Phe Lys Val Phe A rg Thr Ser Ile Ala
                80                  85                  90

Trp Ser Arg Leu Phe Pro Gln Gly Asp Glu I le Thr Pro Asn Gln
                95                 100                 105

Gln Gly Ile Ala Phe Tyr Arg Ser Val Phe G lu Glu Cys Lys Lys
               110                 115                 120

Tyr Gly Ile Glu Pro Leu Val Thr Leu Cys H is Phe Asp Val Pro
               125                 130                 135

Met His Leu Val Thr Glu Tyr Gly Ser Trp A rg Asn Arg Lys Leu
               140                 145                 150

Val Glu Phe Phe Ser Arg Tyr Ala Arg Thr C ys Phe Glu Ala Phe
               155                 160                 165

Asp Gly Leu Val Lys Tyr Trp Leu Thr Phe A sn Glu Ile Asn Ile
               170                 175                 180

Met Leu His Ser Pro Phe Ser Gly Ala Gly L eu Val Phe Glu Glu
               185                 190                 195

Gly Glu Asn Gln Asp Gln Val Lys Tyr Gln A la Ala His His Gln
               200                 205                 210

Leu Val Ala Ser Ala Leu Ala Thr Lys Ile A la His Glu Val Asn
               215                 220                 225

Pro Gln Asn Gln Val Gly Cys Met Leu Ala G ly Gly Asn Phe Tyr
               230                 235                 240

Pro Tyr Ser Cys Lys Pro Glu Asp Val Trp A la Ala Leu Glu Lys
               245                 250                 255

Asp Arg Glu Asn Leu Phe Phe Ile Asp Val G ln Ala Arg Gly Thr
               260                 265                 270

Tyr Pro Ala Tyr Ser Ala Arg Val Phe Arg G lu Lys Gly Val Thr
```

-continued

```
                    275                 280                 285
Ile Asn Lys Ala Pro Gly Asp Asp Glu Ile Leu Lys Asn Thr Val
                290                 295                 300
Asp Phe Val Ser Phe Ser Tyr Tyr Ala Ser Arg Cys Ala Ser Ala
                305                 310                 315
Glu Met Asn Ala Asn Asn Ser Ser Ala Ala Asn Val Val Lys Ser
                320                 325                 330
Leu Arg Asn Pro Tyr Leu Gln Val Ser Asp Trp Gly Trp Gly Ile
                335                 340                 345
Asp Pro Leu Gly Leu Arg Ile Thr Met Asn Met Met Tyr Asp Arg
                350                 355                 360
Tyr Gln Lys Pro Leu Phe Leu Val Glu Asn Gly Leu Gly Ala Lys
                365                 370                 375
Asp Glu Phe Ala Ala Asn Gly Glu Ile Asn Asp Asp Tyr Arg Ile
                380                 385                 390
Ser Tyr Leu Arg Glu His Ile Arg Ala Met Gly Gly Thr Ile Ala
                395                 400                 405
Asp Gly Ile Pro Leu Met Gly Tyr Thr Thr Trp Gly Cys Ile Asp
                410                 415                 420
Leu Val Ser Ala Cys Thr Gly Glu Met Ser Lys Arg Tyr Gly Phe
                425                 430                 435
Val Phe Val Asp Arg Asp Asp Ala Gly Asn Gly Thr Leu Thr Arg
                440                 445                 450
Thr His Arg Lys Ser Phe Trp Trp Tyr Lys Lys Val Ile Ala Ser
                455                 460                 465
Asn
```

(2) INFORMATION FOR SEQ ID NO: 61:

(i) SEQUENCE CHARACTERISTICS:
        (A) LENGTH: 456
        (B) TYPE: amino acid
        (D) TOPOLOGY: linear (ii) MOLECULE TYPE: amino acid (vi) ORIGINAL SOURCE:
        (A) ORGANISM: Erwinia chrysanthemi (ix) FEATURE:
        (D) OTHER INFORMATION:arb_b_erwch  6-phospho-strand-
            glucosidase (E.C. 3.2.1.86)

(xi) SEQUENCE DESCRIPTION: SEQ ID NO: 61:

```
Met Ser Asn Pro Phe Pro Ala His Phe Leu Trp Gly Gly Ala Ile
                  5                  10                  15
Ala Ala Asn Gln Val Glu Gly Ala Tyr Leu Thr Asp Gly Lys Gly
                 20                  25                  30
Leu Ser Thr Ser Asp Leu Gln Pro Gln Gly Ile Phe Gly Glu Ile
                 35                  40                  45
Val Thr Arg Gln Pro Gly Asp Ser Gly Ile Lys Asp Val Ala Ile
                 50                  55                  60
Asp Phe Tyr His Arg Tyr Pro Gln Asp Ile Ala Leu Phe Ala Glu
                 65                  70                  75
Met Gly Phe Thr Cys Leu Arg Ile Ser Ile Ala Trp Thr Arg Ile
                 80                  85                  90
Phe Pro Gln Gly Asp Glu Ala Glu Pro Asn Glu Ala Gly Leu Ala
                 95                 100                 105
```

```
Phe Tyr Asp Arg Leu Phe Asp Glu Leu Ala Lys Tyr Gly Ile Gln
                110                 115                 120

Pro Leu Val Thr Leu Ser His Tyr Glu Met Pro Tyr Gly Leu Val
            125                 130                 135

Glu Lys His Gly Gly Trp Gly Asn Arg Leu Thr Ile Asp Cys Phe
            140                 145                 150

Glu Arg Tyr Ala Arg Thr Val Phe Ala Arg Tyr Arg His Lys Val
            155                 160                 165

Lys Arg Trp Leu Thr Phe Asn Glu Ile Asn Met Ser Leu His Ala
            170                 175                 180

Pro Phe Thr Gly Val Gly Leu Pro Pro Asp Ser Asp Lys Ala Ala
            185                 190                 195

Ile Tyr Gln Ala Ile His His Gln Leu Val Ala Ser Ala Arg Ala
            200                 205                 210

Val Lys Ala Cys His Asp Met Ile Pro Asp Ala Gln Ile Gly Asn
            215                 220                 225

Met Leu Leu Gly Ala Met Leu Tyr Pro Leu Thr Ser Lys Pro Glu
            230                 235                 240

Asp Val Met Glu Ser Leu His Gln Asn Arg Glu Trp Leu Phe Phe
            245                 250                 255

Gly Asp Val Gln Val Arg Gly Ala Tyr Pro Gly Tyr Met His Arg
            260                 265                 270

Tyr Phe Arg Glu Gln Gly Ile Thr Leu Asn Ile Thr Ala Gln Asp
            275                 280                 285

Lys Gln Asp Leu Lys Ala Thr Val Asp Phe Ile Ser Phe Ser Tyr
            290                 295                 300

Tyr Met Thr Gly Cys Val Thr Thr Asp Glu Ala Gln Leu Glu Lys
            305                 310                 315

Thr Arg Gly Asn Ile Leu Asn Met Val Pro Asn Pro Tyr Leu Glu
            320                 325                 330

Ser Ser Glu Trp Gly Trp Gln Ile Asp Pro Leu Gly Leu Arg Tyr
            335                 340                 345

Leu Leu Asn Phe Leu Tyr Asp Arg Tyr Gln Lys Pro Leu Phe Ile
            350                 355                 360

Val Glu Asn Gly Leu Gly Ala Lys Asp Lys Ile Glu Glu Asn Gly
            365                 370                 375

Asp Ile Tyr Asp Asp Tyr Arg Ile Arg Tyr Leu Asn Asp His Leu
            380                 385                 390

Val Gln Val Gly Glu Ala Ile Asp Asp Gly Val Glu Val Leu Gly
            395                 400                 405

Tyr Thr Cys Trp Gly Pro Ile Asp Leu Val Ser Ala Ser Lys Ala
            410                 415                 420

Glu Met Ser Lys Arg Tyr Gly Phe Ile Tyr Val Asp Arg Asp Asp
            425                 430                 435

Ala Gly His Gly Ser Leu Glu Arg Arg Lys Lys Ser Phe Tyr
            440                 445                 450

Trp Tyr Gln Ser Val Ile
            455

(2) INFORMATION FOR SEQ ID NO: 62:

(i) SEQUENCE CHARACTERISTICS:
       (A) LENGTH: 455
       (B) TYPE: amino acid
```

(D) TOPOLOGY: linear (ii) MOLECULE TYPE: amino acid (vi) ORIGINAL SOURCE:
         (A) ORGANISM: Escherichia coli (ix) FEATURE:
         (D) OTHER INFORMATION:bgl b_ecoli  6-phospho-strand-
             glucosidase (E.C. 3.2.1.86)

(xi) SEQUENCE DESCRIPTION: SEQ ID NO: 62:

Phe Pro Glu Thr Phe Leu Trp Gly Gly Ala T hr Ala Ala Asn Gln
                 5                  10                  15

Val Glu Gly Ala Trp Gln Glu Asp Gly Lys G ly Ile Ser Thr Ser
                20                  25                  30

Asp Leu Gln Pro His Gly Val Met Gly Lys M et Glu Pro Arg Ile
                35                  40                  45

Leu Gly Lys Glu Asn Ile Lys Asp Val Ala I le Asp Phe Tyr His
                50                  55                  60

Arg Tyr Pro Glu Asp Ile Ala Leu Phe Ala G lu Met Gly Phe Thr
                65                  70                  75

Cys Leu Arg Ile Ser Ile Ala Trp Ala Arg I le Phe Pro Gln Gly
                80                  85                  90

Asp Glu Val Glu Pro Asn Glu Ala Gly Leu A la Phe Tyr Asp Arg
                95                 100                 105

Leu Phe Asp Glu Met Ala Gln Ala Gly Ile L ys Pro Leu Val Thr
               110                 115                 120

Leu Ser His Tyr Glu Met Pro Tyr Gly Leu V al Lys Asn Tyr Gly
               125                 130                 135

Gly Trp Ala Asn Arg Ala Val Ile Asp His P he Glu His Tyr Ala
               140                 145                 150

Arg Thr Val Phe Thr Arg Tyr Gln His Lys V al Ala Leu Trp Leu
               155                 160                 165

Thr Phe Asn Glu Ile Asn Met Ser Leu His A la Pro Phe Thr Gly
               170                 175                 180

Val Gly Leu Ala Glu Glu Ser Gly Glu Ala G lu Val Tyr Gln Ala
               185                 190                 195

Ile His His Gln Leu Val Ala Ser Ala Arg A la Val Lys Ala Cys
               200                 205                 210

His Ser Leu Leu Pro Glu Ala Lys Ile Gly A sn Met Leu Leu Gly
               215                 220                 225

Gly Leu Val Tyr Pro Leu Thr Cys Gln Pro G ln Asp Met Leu Gln
               230                 235                 240

Ala Met Glu Glu Asn Arg Arg Trp Met Phe P he Gly Asp Val Gln
               245                 250                 255

Ala Arg Gly Gln Tyr Pro Gly Tyr Met Gln A rg Phe Phe Arg Asp
               260                 265                 270

His Asn Ile Thr Ile Glu Met Thr Glu Ser A sp Ala Glu Asp Leu
               275                 280                 285

Lys His Thr Val Asp Phe Ile Ser Phe Ser T yr Tyr Met Thr Gly
               290                 295                 300

Cys Val Ser His Asp Glu Ser Ile Asn Lys A sn Ala Gln Gly Asn
               305                 310                 315

Ile Leu Asn Met Ile Pro Asn Pro His Leu L ys Ser Ser Glu Trp
               320                 325                 330

-continued

```
Gly Trp Gln Ile Asp Pro Val Gly Leu Arg V al Leu Leu Asn Thr
                335                 340                 345

Leu Trp Asp Arg Tyr Gln Lys Pro Leu Phe I le Val Glu Asn Gly
                350                 355                 360

Leu Gly Ala Lys Asp Ser Val Glu Ala Asp G ly Ser Ile Gln Asp
                365                 370                 375

Asp Tyr Arg Ile Ala Tyr Leu Asn Asp His L eu Val Gln Val Asn
                380                 385                 390

Glu Ala Ile Ala Asp Gly Val Asp Ile Met G ly Tyr Thr Ser Trp
                395                 400                 405

Gly Pro Ile Asp Leu Val Ser Ala Ser His S er Gln Met Ser Lys
                410                 415                 420

Arg Tyr Gly Phe Ile Tyr Val Asp Arg Asp A sp Asn Gly Glu Gly
                425                 430                 435

Ser Leu Thr Arg Thr Arg Lys Lys Ser Phe G ly Trp Tyr Ala Glu
                440                 445                 450

Val Ile Lys Thr Arg
                455
```

(2) INFORMATION FOR SEQ ID NO: 63:

(i) SEQUENCE CHARACTERISTICS:
        (A) LENGTH: 441
        (B) TYPE: amino acid
        (D) TOPOLOGY: linear (ii) MOLECULE TYPE: amino acid (vi) ORIGINAL SOURCE:
        (A) ORGANISM: Clostridium thermocellum (ix) FEATURE:
        (D) OTHER INFORMATION:bgl a_clotm strand-
            glucosidase a (E.C. 3.2.1.21)

(xi) SEQUENCE DESCRIPTION: SEQ ID NO: 63:

```
Phe Pro Lys Asp Phe Ile Trp Gly Ser Ala T hr Ala Ala Tyr Gln
                  5                  10                  15

Ile Glu Gly Ala Tyr Asn Glu Asp Gly Lys G ly Glu Ser Ile Trp
                 20                  25                  30

Asp Arg Phe Ser His Thr Pro Gly Asn Ile A la Asp Gly His Thr
                 35                  40                  45

Gly Asp Val Ala Cys Asp His Tyr His Arg T yr Glu Glu Asp Ile
                 50                  55                  60

Lys Ile Met Lys Glu Ile Gly Ile Lys Ser T yr Arg Phe Ser Ile
                 65                  70                  75

Ser Trp Pro Arg Ile Phe Pro Glu Gly Thr G ly Lys Leu Asn Gln
                 80                  85                  90

Lys Gly Leu Asp Phe Tyr Lys Arg Leu Thr A sn Leu Leu Leu Glu
                 95                 100                 105

Asn Gly Ile Met Pro Ala Ile Thr Leu Tyr H is Trp Asp Leu Pro
                110                 115                 120

Gln Lys Leu Gln Asp Lys Gly Gly Trp Lys A sn Arg Asp Thr Thr
                125                 130                 135

Asp Tyr Phe Thr Glu Tyr Ser Glu Val Ile P he Lys Asn Leu Gly
                140                 145                 150

Asp Ile Val Pro Ile Trp Phe Thr His Asn G lu Pro Gly Val Val
                155                 160                 165
```

```
Ser Leu Leu Gly His Phe Leu Gly Ile His Ala Pro Gly Ile Lys
                170                 175                 180

Asp Leu Arg Thr Ser Leu Glu Val Ser His Asn Leu Leu Leu Ser
                185                 190                 195

His Gly Lys Ala Val Lys Leu Phe Arg Glu Met Asn Ile Asp Ala
                200                 205                 210

Gln Ile Gly Ile Ala Leu Asn Leu Ser Tyr His Tyr Pro Ala Ser
                215                 220                 225

Glu Lys Ala Glu Asp Ile Glu Ala Ala Glu Leu Ser Phe Ser Leu
                230                 235                 240

Ala Gly Arg Trp Tyr Leu Asp Pro Val Leu Lys Gly Arg Tyr Pro
                245                 250                 255

Glu Asn Ala Leu Lys Leu Tyr Lys Lys Lys Gly Ile Glu Leu Ser
                260                 265                 270

Phe Pro Glu Asp Asp Leu Lys Leu Ile Ser Gln Pro Ile Asp Phe
                275                 280                 285

Ile Ala Phe Asn Asn Tyr Ser Ser Glu Phe Ile Lys Tyr Asp Pro
                290                 295                 300

Ser Ser Glu Ser Gly Phe Ser Pro Ala Asn Ser Ile Leu Glu Lys
                305                 310                 315

Phe Glu Lys Thr Asp Met Gly Trp Ile Ile Tyr Pro Glu Gly Leu
                320                 325                 330

Tyr Asp Leu Leu Met Leu Leu Asp Arg Asp Tyr Gly Lys Pro Asn
                335                 340                 345

Ile Val Ile Ser Glu Asn Gly Ala Ala Phe Lys Asp Glu Ile Gly
                350                 355                 360

Ser Asn Gly Lys Ile Glu Asp Thr Lys Arg Ile Gln Tyr Leu Lys
                365                 370                 375

Asp Tyr Leu Thr Gln Ala His Arg Ala Ile Gln Asp Gly Val Asn
                380                 385                 390

Leu Lys Ala Tyr Tyr Leu Trp Ser Leu Leu Asp Asn Phe Glu Trp
                395                 400                 405

Ala Tyr Gly Tyr Asn Lys Arg Phe Gly Ile Val His Val Asn Phe
                410                 415                 420

Asp Thr Leu Glu Arg Lys Ile Lys Asp Ser Gly Tyr Trp Tyr Lys
                425                 430                 435

Glu Val Ile Lys Asn Asn
                440
```

(2) INFORMATION FOR SEQ ID NO: 64:

(i) SEQUENCE CHARACTERISTICS:
        (A) LENGTH: 450
        (B) TYPE: amino acid
        (D) TOPOLOGY: linear (ii) MOLECULE TYPE: amino acid (vi) ORIGINAL SOURCE:

(ix) FEATURE:
        (D) OTHER INFORMATION:bgl s_calsa strand-glucosidase a
        (E.C. 3. 2.1.21)

(xi) SEQUENCE DESCRIPTION: SEQ ID NO: 64:

```
Phe Pro Lys Gly Phe Leu Trp Gly Ala Ala Thr Ala Ser Tyr Gln
                 5                  10                  15

Ile Glu Gly Ala Trp Asn Glu Asp Gly Lys Gly Glu Ser Ile Trp
```

-continued

```
                   20                  25                  30
Asp Arg Phe Thr His Gln Lys Arg Asn Ile L eu Tyr Gly His Asn
                   35                  40                  45
Gly Asp Val Ala Cys Asp His Tyr His Arg P he Glu Glu Asp Val
                   50                  55                  60
Ser Leu Met Lys Glu Leu Gly Leu Lys Ala T yr Arg Phe Ser Ile
                   65                  70                  75
Ala Trp Thr Arg Ile Phe Pro Asp Gly Phe G ly Thr Val Asn Gln
                   80                  85                  90
Lys Gly Leu Glu Phe Tyr Asp Arg Leu Ile A sn Lys Leu Val Glu
                   95                 100                 105
Asn Gly Ile Glu Pro Val Val Thr Leu Tyr H is Trp Asp Leu Pro
                  110                 115                 120
Gln Lys Leu Gln Asp Ile Gly Gly Trp Ala A sn Pro Glu Ile Val
                  125                 130                 135
Asn Tyr Tyr Phe Asp Tyr Ala Met Leu Val I le Asn Arg Tyr Lys
                  140                 145                 150
Asp Lys Val Lys Lys Trp Ile Thr Phe Asn G lu Pro Tyr Cys Ile
                  155                 160                 165
Ala Phe Leu Gly Tyr Phe His Gly Ile His A la Pro Gly Ile Lys
                  170                 175                 180
Asp Phe Lys Val Ala Met Asp Val Val His S er Leu Met Leu Ser
                  185                 190                 195
His Phe Lys Val Val Lys Ala Val Lys Glu A sn Asn Ile Asp Val
                  200                 205                 210
Glu Val Gly Ile Thr Leu Asn Leu Thr Pro V al Tyr Leu Gln Thr
                  215                 220                 225
Glu Arg Leu Gly Tyr Lys Val Ser Glu Ile G lu Arg Glu Met Val
                  230                 235                 240
Ser Leu Ser Ser Gln Leu Asp Asn Gln Leu P he Leu Asp Pro Val
                  245                 250                 255
Leu Lys Gly Ser Tyr Pro Gln Lys Leu Leu A sp Tyr Leu Val Gln
                  260                 265                 270
Lys Asp Leu Leu Asp Ser Gln Lys Ala Leu S er Met Gln Gln Glu
                  275                 280                 285
Val Lys Glu Asn Phe Ile Phe Pro Asp Phe L eu Gly Ile Asn Tyr
                  290                 295                 300
Tyr Thr Arg Ala Val Arg Leu Tyr Asp Glu A sn Ser Ser Trp Ile
                  305                 310                 315
Phe Pro Ile Arg Trp Glu His Pro Ala Gly G lu Tyr Thr Glu Met
                  320                 325                 330
Gly Trp Glu Val Phe Pro Gln Gly Leu Phe A sp Leu Leu Ile Trp
                  335                 340                 345
Ile Lys Glu Ser Tyr Pro Gln Ile Pro Ile T yr Ile Thr Glu Asn
                  350                 355                 360
Gly Ala Ala Tyr Asn Asp Ile Val Thr Glu A sp Gly Lys Val His
                  365                 370                 375
Asp Ser Lys Arg Ile Glu Tyr Leu Lys Gln H is Phe Glu Ala Ala
                  380                 385                 390
Arg Lys Ala Ile Glu Asn Gly Val Asp Leu A rg Gly Tyr Phe Val
                  395                 400                 405
Trp Ser Leu Met Asp Asn Phe Glu Trp Ala M et Gly Tyr Thr Lys
                  410                 415                 420
```

```
Arg Phe Gly Ile Ile Tyr Val Asp Tyr Glu Thr Gln Lys Arg Ile
                425                 430                 435

Lys Lys Asp Ser Phe Tyr Phe Tyr Gln Gln Tyr Ile Lys Glu Asn
                440                 445                 450

(2) INFORMATION FOR SEQ ID NO: 65:

(i) SEQUENCE CHARACTERISTICS:
        (A) LENGTH: 437
        (B) TYPE: amino acid
        (D) TOPOLOGY: linear (ii) MOLECULE TYPE: amino acid (vi) ORIGINAL SOURCE:
        (A) ORGANISM: Bacillus polymyxa (ix) FEATURE:
        (D) OTHER INFORMATION:bgl a_bacpo  strand-glucosidase a
            (E.C. 3. 2.1.21)

(xi) SEQUENCE DESCRIPTION: SEQ ID NO: 65:

Phe Pro Gln Asp Phe Met Trp Gly Thr Ala Thr Ala Ala Tyr Gln
                 5                  10                  15

Ile Glu Gly Ala Tyr Gln Glu Asp Gly Arg Gly Leu Ser Ile Trp
                20                  25                  30

Asp Thr Phe Ala His Thr Pro Gly Lys Val Phe Asn Gly Asp Asn
                35                  40                  45

Gly Asn Val Ala Cys Asp Ser Tyr His Arg Tyr Glu Glu Asp Ile
                50                  55                  60

Arg Leu Met Lys Glu Leu Gly Ile Arg Thr Tyr Arg Phe Ser Val
                65                  70                  75

Ser Trp Pro Arg Ile Phe Pro Asn Gly Asp Gly Glu Val Asn Gln
                80                  85                  90

Glu Gly Leu Asp Tyr Tyr His Arg Val Val Asp Leu Leu Asn Asp
                95                  100                 105

Asn Gly Ile Glu Pro Phe Cys Thr Leu Tyr His Trp Asp Leu Pro
                110                 115                 120

Gln Ala Leu Gln Asp Ala Gly Gly Trp Gly Asn Arg Arg Thr Ile
                125                 130                 135

Gln Ala Phe Val Gln Phe Ala Glu Thr Met Phe Arg Glu Phe His
                140                 145                 150

Gly Lys Ile Gln His Trp Leu Thr Phe Asn Glu Pro Trp Cys Ile
                155                 160                 165

Ala Phe Leu Ser Asn Met Leu Gly Val His Ala Pro Gly Leu Thr
                170                 175                 180

Asn Leu Gln Thr Ala Ile Asp Val Gly His His Leu Leu Val Ala
                185                 190                 195

His Gly Leu Ser Val Arg Arg Phe Arg Glu Leu Gly Thr Ser Gly
                200                 205                 210

Gln Ile Gly Ile Ala Pro Asn Val Ser Trp Ala Val Pro Tyr Ser
                215                 220                 225

Thr Ser Glu Glu Asp Lys Ala Ala Cys Ala Arg Thr Ile Ser Leu
                230                 235                 240

His Ser Asp Trp Phe Leu Gln Pro Ile Tyr Gln Gly Ser Tyr Pro
                245                 250                 255

Gln Phe Leu Val Asp Trp Phe Ala Glu Gln Gly Ala Thr Val Pro
                260                 265                 270
```

-continued

```
Ile Gln Asp Gly Asp Met Asp Ile Ile Gly G lu Pro Ile Asp Met
                275                 280                 285

Ile Gly Ile Asn Tyr Tyr Ser Met Ser Val A sn Arg Phe Asn Pro
                290                 295                 300

Glu Ala Gly Phe Leu Gln Ser Glu Glu Ile A sn Met Gly Leu Pro
                305                 310                 315

Val Thr Asp Ile Gly Trp Pro Val Glu Ser A rg Gly Leu Tyr Glu
                320                 325                 330

Val Leu His Tyr Leu Gln Lys Tyr Gly Asn I le Asp Ile Tyr Ile
                335                 340                 345

Thr Glu Asn Gly Ala Cys Ile Asn Asp Glu V al Val Asn Gly Lys
                350                 355                 360

Val Gln Asp Asp Arg Arg Ile Ser Tyr Met G ln Gln His Leu Val
                365                 370                 375

Gln Val His Arg Thr Ile His Asp Gly Leu H is Val Lys Gly Tyr
                380                 385                 390

Met Ala Trp Ser Leu Leu Asp Asn Phe Glu T rp Ala Glu Gly Tyr
                395                 400                 405

Asn Met Arg Phe Gly Met Ile His Val Asp P he Arg Thr Gln Val
                410                 415                 420

Arg Thr Pro Lys Glu Ser Tyr Tyr Trp Tyr A rg Asn Val Val Ser
                425                 430                 435

Asn Asn (2) INFORMATION FOR SEQ ID NO: 66:

(i) SEQUENCE CHARACTERISTICS:
        (A) LENGTH: 441
        (B) TYPE: amino acid
        (D) TOPOLOGY: linear (ii) MOLECULE TYPE: amino acid (vi) ORIGINAL SOURCE:
        (A) ORGANISM: Bacillus circulans (ix) FEATURE:
        (D) OTHER INFORMATION:bgl a_bacci  strand-glucosidase
            (E.C. 3. 2.1.21)

(xi) SEQUENCE DESCRIPTION: SEQ ID NO: 66:

Phe Pro Ser Asp Phe Lys Trp Gly Val Ala T hr Ala Ala Tyr Gln
                 5                  10                  15

Ile Glu Gly Ala Tyr Asn Glu Asp Gly Arg G ly Met Ser Ile Trp
                20                  25                  30

Asp Thr Phe Ala His Thr Pro Gly Lys Val L ys Asn Gly Asp Asn
                35                  40                  45

Gly Asn Val Ala Cys Asp Ser Tyr His Arg V al Glu Glu Asp Val
                50                  55                  60

Gln Leu Leu Lys Asp Leu Gly Val Lys Val T yr Arg Phe Ser Ile
                65                  70                  75

Ser Trp Pro Arg Val Leu Pro Gln Gly Thr G ly Glu Val Asn Arg
                80                  85                  90

Ala Gly Leu Asp Tyr Tyr His Arg Leu Val A sp Glu Leu Leu Ala
                95                  100                 105

Asn Gly Ile Glu Pro Phe Cys Thr Leu Tyr H is Trp Asp Leu Pro
                110                 115                 120
```

-continued

```
Gln Ala Leu Gln Asp Gln Gly Gly Trp Gly Ser Arg Ile Thr Ile
                125                 130                 135

Asp Ala Phe Ala Glu Tyr Ala Glu Leu Met Phe Lys Glu Leu Gly
                140                 145                 150

Gly Lys Ile Lys Gln Trp Ile Thr Phe Asn Glu Pro Trp Cys Met
                155                 160                 165

Ala Phe Leu Ser Asn Tyr Leu Gly Val His Ala Pro Gly Asn Lys
                170                 175                 180

Asp Leu Gln Leu Ala Ile Asp Val Ser His His Leu Leu Val Ala
                185                 190                 195

His Gly Arg Ala Val Thr Leu Phe Arg Glu Leu Gly Ile Ser Gly
                200                 205                 210

Glu Ile Gly Ile Ala Pro Asn Thr Ser Trp Ala Val Pro Tyr Arg
                215                 220                 225

Arg Thr Lys Glu Asp Met Glu Ala Cys Leu Arg Val Asn Gly Trp
                230                 235                 240

Ser Gly Asp Trp Tyr Leu Asp Pro Ile Tyr Phe Gly Glu Tyr Pro
                245                 250                 255

Lys Phe Met Leu Asp Trp Tyr Glu Asn Leu Gly Tyr Lys Pro Pro
                260                 265                 270

Ile Val Asp Gly Asp Met Glu Leu Ile His Gln Pro Ile Asp Phe
                275                 280                 285

Ile Gly Ile Asn Tyr Tyr Thr Ser Ser Met Asn Arg Tyr Asn Pro
                290                 295                 300

Gly Glu Ala Gly Gly Met Leu Ser Ser Glu Ala Ile Ser Met Gly
                305                 310                 315

Ala Pro Lys Thr Asp Ile Gly Trp Glu Ile Tyr Ala Glu Gly Leu
                320                 325                 330

Tyr Asp Leu Leu Arg Tyr Thr Ala Asp Lys Tyr Gly Asn Pro Thr
                335                 340                 345

Leu Tyr Ile Thr Glu Asn Gly Ala Cys Tyr Asn Asp Gly Leu Ser
                350                 355                 360

Leu Asp Gly Arg Ile His Asp Gln Arg Arg Ile Asp Tyr Leu Ala
                365                 370                 375

Met His Leu Ile Gln Ala Ser Arg Ala Ile Glu Asp Gly Ile Asn
                380                 385                 390

Leu Lys Gly Tyr Met Glu Trp Ser Leu Met Asp Asn Phe Glu Trp
                395                 400                 405

Ala Glu Gly Tyr Gly Met Arg Phe Gly Leu Val His Val Asp Tyr
                410                 415                 420

Asp Thr Leu Val Arg Thr Pro Lys Asp Ser Phe Tyr Trp Tyr Lys
                425                 430                 435

Gly Val Ile Ser Arg Gly
                440
```

(2) INFORMATION FOR SEQ ID NO: 67:

(i) SEQUENCE CHARACTERISTICS:
        (A) LENGTH: 439
        (B) TYPE: amino acid
        (D) TOPOLOGY: linear (ii) MOLECULE TYPE: amino acid (vi) ORIGINAL SOURCE:
        (A) ORGANISM: Bacillus polymyxa -continued (ix) FEATURE:
    (D) OTHER INFORMATION:bgl_b_bacpo strand-glucosidase b
        (E.C. 3. 2.1.21)

(xi) SEQUENCE DESCRIPTION: SEQ ID NO: 67:

```
Phe Pro Ala Thr Phe Met Trp Gly Thr Ser Thr Ser Ser Tyr Gln
              5                  10                  15

Ile Glu Gly Gly Thr Asp Glu Gly Gly Arg Thr Pro Ser Ile Trp
             20                  25                  30

Asp Thr Phe Cys Gln Ile Pro Gly Lys Val Ile Gly Gly Asp Cys
             35                  40                  45

Gly Asp Val Ala Cys Asp His Phe His His Phe Lys Glu Asp Val
             50                  55                  60

Gln Leu Met Lys Gln Leu Gly Phe Leu His Tyr Arg Phe Ser Val
             65                  70                  75

Ala Trp Pro Arg Ile Met Pro Ala Ala Gly Ile Ile Asn Glu Glu
             80                  85                  90

Gly Leu Leu Phe Tyr Glu His Leu Leu Asp Glu Ile Glu Leu Ala
             95                 100                 105

Gly Leu Ile Pro Met Leu Thr Leu Tyr His Trp Asp Leu Pro Gln
            110                 115                 120

Trp Ile Glu Asp Glu Gly Gly Trp Thr Gln Arg Glu Thr Ile Gln
            125                 130                 135

His Phe Lys Thr Tyr Ala Ser Val Ile Met Asp Arg Phe Gly Glu
            140                 145                 150

Arg Ile Asn Trp Trp Asn Thr Ile Asn Glu Pro Tyr Cys Ala Ser
            155                 160                 165

Ile Leu Gly Tyr Gly Thr Gly Glu His Ala Pro Gly His Glu Asn
            170                 175                 180

Trp Arg Glu Ala Phe Thr Ala Ala His His Ile Leu Met Cys His
            185                 190                 195

Gly Ile Ala Ser Asn Leu His Lys Glu Lys Gly Leu Thr Gly Lys
            200                 205                 210

Ile Gly Ile Thr Leu Asn Met Glu His Val Asp Ala Ala Ser Glu
            215                 220                 225

Arg Pro Glu Asp Val Ala Ala Ile Arg Arg Asp Gly Phe Ile
            230                 235                 240

Asn Arg Trp Phe Ala Glu Pro Leu Phe Asn Gly Lys Tyr Pro Glu
            245                 250                 255

Asp Met Val Glu Trp Tyr Gly Thr Tyr Leu Asn Gly Leu Asp Phe
            260                 265                 270

Val Gln Pro Gly Asp Met Glu Leu Ile Gln Gln Pro Gly Asp Phe
            275                 280                 285

Leu Gly Ile Asn Tyr Tyr Thr Arg Ser Ile Ile Arg Ser Thr Asn
            290                 295                 300

Asp Ala Ser Leu Leu Gln Val Glu Gln Val His Met Glu Glu Pro
            305                 310                 315

Val Thr Asp Met Gly Trp Glu Ile His Pro Glu Ser Phe Tyr Lys
            320                 325                 330

Leu Leu Thr Arg Ile Glu Lys Asp Phe Ser Lys Gly Leu Pro Ile
            335                 340                 345

Leu Ile Thr Glu Asn Gly Ala Ala Met Arg Asp Glu Leu Val Asn
            350                 355                 360

Gly Gln Ile Glu Asp Thr Gly Arg His Gly Tyr Ile Glu Glu His
```

```
                      365                 370                 375
Leu Lys Ala Cys His Arg Phe Ile Glu Glu G ly Gly Gln Leu Lys
                  380                 385                 390
Gly Tyr Phe Val Trp Ser Phe Leu Asp Asn P he Glu Trp Ala Trp
                  395                 400                 405
Gly Tyr Ser Lys Arg Phe Gly Ile Val His I le Asn Tyr Glu Thr
                  410                 415                 420
Gln Glu Arg Thr Pro Lys Gln Ser Ala Leu T rp Phe Lys Gln Met
                  425                 430                 435
Met Ala Lys Asn
```

(2) INFORMATION FOR SEQ ID NO: 68:

(i) SEQUENCE CHARACTERISTICS:
        (A) LENGTH: 449
        (B) TYPE: amino acid
        (D) TOPOLOGY: linear (ii) MOLECULE TYPE: amino acid (vi) ORIGINAL SOURCE:
        (A) ORGANISM: Agrobacteri um sp. (strain atcc 21400)

(ix) FEATURE:
        (D) OTHER INFORMATION:bgl s_agrsp  strand-glucosidase
           (E.C. 3. 2.1.21)

(xi) SEQUENCE DESCRIPTION: SEQ ID NO: 68:

```
Phe Pro Gly Asp Phe Leu Phe Gly Val Ala T hr Ala Ser Phe Gln
                  5                   10                  15
Ile Glu Gly Ser Thr Lys Ala Asp Gly Arg L ys Pro Ser Ile Trp
                  20                  25                  30
Asp Ala Phe Cys Asn Met Pro Gly His Val P he Gly Arg His Asn
                  35                  40                  45
Gly Asp Ile Ala Cys Asp His Tyr Asn Arg T rp Glu Glu Asp Leu
                  50                  55                  60
Asp Leu Ile Lys Glu Met Gly Val Glu Ala T yr Arg Phe Ser Leu
                  65                  70                  75
Ala Trp Pro Arg Ile Ile Pro Asp Gly Phe G ly Pro Ile Asn Glu
                  80                  85                  90
Lys Gly Leu Asp Phe Tyr Asp Arg Leu Val A sp Gly Cys Lys Ala
                  95                  100                 105
Arg Gly Ile Lys Thr Tyr Ala Thr Leu Tyr H is Trp Asp Leu Pro
                  110                 115                 120
Leu Thr Leu Met Gly Asp Gly Gly Trp Ala S er Arg Ser Thr Ala
                  125                 130                 135
His Ala Phe Gln Arg Tyr Ala Lys Thr Val M et Ala Arg Leu Gly
                  140                 145                 150
Asp Arg Leu Asp Ala Val Ala Thr Phe Asn G lu Pro Trp Cys Ala
                  155                 160                 165
Val Trp Leu Ser His Leu Tyr Gly Val His A la Pro Gly Glu Arg
                  170                 175                 180
Asn Met Glu Ala Ala Leu Ala Ala Met His H is Ile Asn Leu Ala
                  185                 190                 195
His Gly Phe Gly Val Glu Ala Ser Arg His V al Ala Pro Lys Val
                  200                 205                 210
Pro Val Gly Leu Val Leu Asn Ala His Ser A la Ile Pro Ala Ser
                  215                 220                 225
```

```
Asp Gly Glu Ala Asp Leu Lys Ala Ala Glu A rg Ala Phe Gln Phe
                230                 235                 240

His Asn Gly Ala Phe Phe Asp Pro Val Phe L ys Gly Glu Tyr Pro
                245                 250                 255

Ala Glu Met Met Glu Ala Leu Gly Asp Arg M et Pro Val Val Glu
                260                 265                 270

Ala Glu Asp Leu Gly Ile Ile Ser Gln Lys L eu Asp Trp Trp Gly
                275                 280                 285

Leu Asn Tyr Tyr Thr Pro Met Arg Val Ala A sp Asp Ala Thr Pro
                290                 295                 300

Gly Val Glu Phe Pro Ala Thr Met Pro Ala P ro Ala Val Ser Asp
                305                 310                 315

Val Lys Thr Asp Ile Gly Trp Glu Val Tyr A la Pro Ala Leu His
                320                 325                 330

Thr Leu Val Glu Thr Leu Tyr Glu Arg Tyr A sp Leu Pro Glu Cys
                335                 340                 345

Tyr Ile Thr Glu Asn Gly Ala Cys Tyr Asn M et Gly Val Glu Asn
                350                 355                 360

Gly Gln Val Asn Asp Gln Pro Arg Leu Asp T yr Tyr Ala Glu His
                365                 370                 375

Leu Gly Ile Val Ala Asp Leu Ile Arg Asp G ly Tyr Pro Met Arg
                380                 385                 390

Gly Tyr Phe Ala Trp Ser Leu Met Asp Asn P he Glu Trp Ala Glu
                395                 400                 405

Gly Tyr Arg Met Arg Phe Gly Leu Val His V al Asp Tyr Gln Thr
                410                 415                 420

Gln Val Arg Thr Val Lys Asn Ser Gly Lys T rp Tyr Ser Ala Leu
                425                 430                 435

Ala Ser Gly Phe Pro Lys Gly Asn His Gly V al Ala Lys Gly
                440                 445
```

(2) INFORMATION FOR SEQ ID NO: 69:

(i) SEQUENCE CHARACTERISTICS:
        (A) LENGTH: 476
        (B) TYPE: amino acid
        (D) TOPOLOGY: linear (ii) MOLECULE TYPE: amino acid (vi) ORIGINAL SOURCE:
        (A) ORGANISM: Brassica napus (ix) FEATURE:
        (D) OTHER INFORMATION:myr o_brana  myrosinase precursor
           (E.C. 3. 2.3.1)

(xi) SEQUENCE DESCRIPTION: SEQ ID NO: 69:

```
Leu Ser Ser Lys Asn Phe Gly Lys Asp Phe I le Phe Gly Val Ala
                5                   10                  15

Ser Ser Ala Tyr Gln Ile Glu Gly Gly Arg G ly Arg Gly Val Asn
                20                  25                  30

Val Trp Asp Gly Phe Ser His Arg Tyr Pro G lu Lys Ala Gly Ser
                35                  40                  45

Asp Leu Lys Asn Gly Asp Thr Thr Cys Glu S er Tyr Thr Arg Trp
                50                  55                  60

Gln Lys Asp Val Asp Val Met Gly Glu Leu A sn Ala Thr Gly Tyr
                65                  70                  75
```

-continued

```
Arg Phe Ser Phe Ala Trp Ser Arg Ile Ile P ro Lys Gly Lys Val
                80                  85                  90

Ser Arg Gly Val Asn Gln Gly Gly Leu Asp T yr Tyr His Lys Leu
                95                 100                 105

Ile Asp Ala Leu Leu Glu Lys Asn Ile Thr P ro Phe Val Thr Leu
               110                 115                 120

Phe His Trp Asp Leu Pro Gln Thr Leu Gln A sp Glu Tyr Glu Gly
               125                 130                 135

Phe Leu Asp Arg Gln Ile Ile Gln Asp Phe L ys Asp Tyr Ala Asp
               140                 145                 150

Leu Cys Phe Lys Glu Phe Gly Gly Lys Val L ys His Trp Ile Thr
               155                 160                 165

Ile Asn Gln Leu Tyr Thr Val Pro Thr Arg G ly Tyr Ala Ile Gly
               170                 175                 180

Thr Asp Ala Pro Gly Arg Cys Ser Pro Met V al Asp Thr Lys His
               185                 190                 195

Arg Cys Tyr Gly Gly Asn Ser Ser Thr Glu P ro Tyr Ile Val Ala
               200                 205                 210

His Asn Gln Leu Leu Ala His Ala Thr Val V al Asp Leu Tyr Arg
               215                 220                 225

Thr Lys Tyr Lys Phe Gln Lys Gly Lys Ile G ly Pro Val Met Ile
               230                 235                 240

Thr Arg Trp Phe Leu Pro Phe Asp Glu Ser A sp Pro Ala Ser Ile
               245                 250                 255

Glu Ala Ala Glu Arg Met Asn Gln Phe Phe H is Gly Trp Tyr Met
               260                 265                 270

Glu Pro Leu Thr Lys Gly Arg Tyr Pro Asp I le Met Arg Gln Ile
               275                 280                 285

Val Gly Ser Arg Leu Pro Asn Phe Thr Glu G lu Glu Ala Glu Leu
               290                 295                 300

Val Ala Gly Ser Tyr Asp Phe Leu Gly Leu A sn Tyr Tyr Val Thr
               305                 310                 315

Gln Tyr Ala Gln Pro Lys Pro Asn Pro Tyr P ro Ser Glu Thr His
               320                 325                 330

Thr Ala Met Met Asp Ala Gly Val Lys Leu T hr Tyr Asp Asn Ser
               335                 340                 345

Arg Gly Glu Phe Leu Gly Pro Leu Phe Val G lu Asp Lys Val Asn
               350                 355                 360

Gly Asn Ser Tyr Tyr Tyr Pro Lys Gly Ile T yr Tyr Val Met Asp
               365                 370                 375

Tyr Phe Lys Thr Lys Tyr Gly Asp Pro Leu I le Tyr Val Thr Glu
               380                 385                 390

Asn Gly Phe Ser Thr Pro Ser Ser Glu Asn A rg Glu Gln Ala Ile
               395                 400                 405

Ala Asp Tyr Lys Arg Ile Asp Tyr Leu Cys S er His Leu Cys Phe
               410                 415                 420

Leu Arg Lys Val Ile Lys Glu Lys Gly Val A sn Val Arg Gly Tyr
               425                 430                 435

Phe Ala Trp Ala Leu Gly Asp Asn Tyr Glu P he Cys Lys Gly Phe
               440                 445                 450

Thr Val Arg Phe Gly Leu Ser Tyr Val Asn T rp Glu Asp Leu Asp
               455                 460                 465
```

-continued

```
Asp Arg Asn Leu Lys Glu Ser Gly Lys Trp Tyr
                470                 475
```

(2) INFORMATION FOR SEQ ID NO: 70:

(i) SEQUENCE CHARACTERISTICS:
        (A) LENGTH: 471
        (B) TYPE: amino acid
        (D) TOPOLOGY: linear (ii) MOLECULE TYPE: amino acid (vi) ORIGINAL SOURCE:
       (A) ORGANISM: Oryctolagus cuniculus (ix) FEATURE:
       (D) OTHER INFORMATION:lac tase-phlorizin hydrolase (xi) SEQUENCE DESCRIPTION: SEQ ID NO: 70:

```
Phe Pro Glu Gly Phe Val Trp Ser Thr Ser Thr Ala Ala Phe Gln
                 5                  10                  15

Ile Glu Gly Ala Trp Arg Ala Asp Gly Lys Gly Leu Gly Ile Trp
                20                  25                  30

Asp Thr Phe Thr His Thr Arg Leu Lys Ile Glu Asn Asp Asp Ile
                35                  40                  45

Ala Asp Val Ala Cys Asp Ser Tyr His Lys Ile Ser Glu Asp Val
                50                  55                  60

Val Ala Leu Gln Asn Leu Ala Val Thr His Tyr Arg Phe Ser Ile
                65                  70                  75

Ser Trp Ser Arg Ile Leu Pro Asp Gly Thr Thr Asn Tyr Ile Asn
                80                  85                  90

Glu Ala Gly Leu Asn Tyr Tyr Val Arg Leu Ile Asp Ala Leu Leu
                95                 100                 105

Ala Ala Asn Ile Lys Pro Gln Val Thr Met Tyr His Phe Asp Leu
               110                 115                 120

Pro Gln Ala Leu Gln Asp Val Gly Gly Trp Glu Asn Glu Thr Ile
               125                 130                 135

Val Gln Arg Phe Lys Glu Tyr Ala Asp Val Leu Phe Gln Arg Leu
               140                 145                 150

Gly Asp Lys Val Lys Phe Trp Ile Thr Leu Asn Glu Pro Phe Val
               155                 160                 165

Val Ala Tyr His Gly Tyr Gly Thr Gly Leu Tyr Ala Pro Gly Ile
               170                 175                 180

Tyr Phe Arg Pro Gly Thr Ala Pro Tyr Ile Val Gly His Asn Leu
               185                 190                 195

Ile Lys Ala His Ala Glu Ala Trp His Leu Tyr Asn Asp Val Tyr
               200                 205                 210

Arg Ala Ser Gln Gly Gly Val Ile Ser Ile Thr Ile Ser Ser Asp
               215                 220                 225

Trp Ala Glu Pro Arg Asp Pro Ser Asn Gln Glu Asp Val Glu Ala
               230                 235                 240

Ala Lys Arg Tyr Val Gln Phe Met Gly Gly Trp Phe Ala His Pro
               245                 250                 255

Ile Phe Lys Asn Gly Asp Tyr Asn Glu Val Met Lys Thr Gln Ile
               260                 265                 270

Arg Glu Arg Ser Leu Ala Ala Gly Leu Asn Glu Ser Arg Leu Pro
               275                 280                 285

Glu Phe Thr Glu Ser Glu Lys Arg Arg Ile Asn Gly Thr Tyr Asp
```

```
                    290                 295                 300
Phe Phe Gly Phe Asn His Tyr Thr Thr Val L eu Ala Tyr Asn Phe
                305                 310                 315
Asn Tyr Pro Ser Ile Met Ser Thr Val Asp A la Asp Arg Gly Val
                320                 325                 330
Ala Ser Ile Val Asp Arg Ser Trp Pro Gly S er Gly Ser Tyr Trp
                335                 340                 345
Leu Lys Met Thr Pro Phe Gly Phe Arg Arg I le Leu Asn Trp Ile
                350                 355                 360
Lys Glu Glu Tyr Asn Asn Pro Pro Ile Tyr V al Thr Glu Asn Gly
                365                 370                 375
Val Ser His Arg Gly Asp Ser Tyr Leu Asn A sp Thr Thr Arg Ile
                380                 385                 390
Tyr Tyr Leu Arg Ser Tyr Ile Asn Glu Ala L eu Lys Ala Val Gln
                395                 400                 405
Gln Asp Lys Val Asp Leu Arg Gly Tyr Thr V al Trp Thr Leu Met
                410                 415                 420
Asp Asn Phe Glu Trp Tyr Thr Gly Phe Ser A sp Lys Phe Gly Leu
                425                 430                 435
His Phe Val Asn Tyr Ser Asp Pro Ser Leu P ro Arg Ile Pro Arg
                440                 445                 450
Glu Ser Ala Lys Phe Tyr Ala Ser Ile Val A rg Cys Asn Gly Phe
                455                 460                 465
Pro Asp Pro Ala Glu Gly
                470

(2) INFORMATION FOR SEQ ID NO: 71:

(i) SEQUENCE CHARACTERISTICS:
        (A) LENGTH: 473
        (B) TYPE: amino acid
        (D) TOPOLOGY: linear (ii) MOLECULE TYPE: amino acid (vi) ORIGINAL SOURCE:
        (A) ORGANISM: Sinapis alba (ix) FEATURE:
        (D) OTHER INFORMATION:myr 3_sinal  myrosinase mb3 precursor
            (E.C. 3. 2.3.1)

(xi) SEQUENCE DESCRIPTION: SEQ ID NO: 71:

Leu Ser Ser Lys Asn Phe Gly Lys Asp Phe I le Phe Gly Val Ala
                5                   10                  15
Ser Ser Ala Tyr Gln Ile Glu Gly Gly Arg G ly Arg Gly Val Asn
                20                  25                  30
Val Trp Asp Gly Phe Ser His Arg Tyr Pro G lu Lys Ser Gly Ser
                35                  40                  45
Asp Leu Lys Asn Gly Asp Thr Ser Cys Glu S er Tyr Thr Arg Trp
                50                  55                  60
Lys Lys Asp Val Glu Ile Met Gly Glu Leu A sn Ala Thr Gly Tyr
                65                  70                  75
Arg Phe Ser Phe Ala Trp Ser Arg Ile Val P ro Lys Gly Lys Val
                80                  85                  90
Ser Arg Gly Val Asp Gln Ala Gly Leu Asp T yr Tyr His Asn Leu
                95                  100                 105
Ile Asp Ala Leu Leu Glu Lys Asn Ile Thr P ro Phe Val Thr Leu
```

```
                110              115              120
Phe His Trp Asp Leu Pro Gln Thr Leu Gln Asp Glu Tyr Glu Gly
                125              130              135
Phe Leu Asp Arg Gln Ile Ile Gln Asp Phe Lys Asp Tyr Ala Asp
                140              145              150
Leu Cys Phe Lys Glu Phe Gly Gly Lys Val Lys Asn Trp Ile Thr
                155              160              165
Ile Asn Gln Leu Tyr Thr Val Pro Thr Arg Gly Tyr Ala Leu Gly
                170              175              180
Thr Asp Ala Pro Gly Arg Cys Ser Pro Lys Val Asp Thr Lys Gln
                185              190              195
Arg Cys Tyr Gly Gly Asn Ser Ser Thr Glu Pro Tyr Ile Val Ala
                200              205              210
His Asn Gln Leu Leu Ala His Ala Ala Ile Val Asp Leu Tyr Arg
                215              220              225
Thr Asn Tyr Ala Phe Gln Asn Gly Lys Ile Gly Pro Val Met Ile
                230              235              240
Thr Arg Trp Phe Leu Pro Tyr Asp Glu Ser Asp Pro Ala Cys Ile
                245              250              255
Glu Ala Ala Glu Arg Met Asn Gln Phe Phe His Gly Trp Tyr Met
                260              265              270
Glu Pro Leu Thr Lys Gly Arg Tyr Pro Asp Ile Met Arg Gln Ile
                275              280              285
Val Gly Ser Arg Leu Pro Asn Phe Thr Glu Ala Glu Ala Glu Leu
                290              295              300
Val Ala Gly Ser Tyr Asp Phe Leu Gly Leu Asn Tyr Tyr Val Thr
                305              310              315
Gln Tyr Ala Lys Pro Lys Pro Asn Pro Tyr Pro Ser Glu Thr His
                320              325              330
Thr Ala Leu Met Asp Ala Gly Val Asp Leu Thr Phe Asn Asn Ser
                335              340              345
Arg Gly Glu Tyr Pro Gly Pro Val Phe Ala Glu Asp Ala Asn Ser
                350              355              360
Tyr Tyr Tyr Pro Lys Gly Ile Tyr Tyr Val Met Asp Tyr Phe Lys
                365              370              375
Thr Lys Tyr Asn Asn Pro Leu Ile Tyr Ile Thr Glu Asn Gly Ile
                380              385              390
Ser Thr Pro Gly Ser Glu Ser Arg Cys Glu Ala Ile Ala Asp Tyr
                395              400              405
Lys Arg Ile Asn Tyr Leu Cys Ser His Leu Cys Phe Leu Arg Lys
                410              415              420
Val Ile Arg Glu Lys Gly Val Asn Ile Arg Gly Tyr Phe Ala Trp
                425              430              435
Ala Leu Gly Asp Asn Tyr Glu Phe Cys Lys Gly Phe Thr Val Arg
                440              445              450
Phe Gly Leu Ser Tyr Val Asn Trp Asp Asp Leu Asp Asp Arg Asn
                455              460              465
Leu Lys Glu Ser Gly Lys Trp Tyr
                470
```

(2) INFORMATION FOR SEQ ID NO: 72:

(i) SEQUENCE CHARACTERISTICS:
        (A) LENGTH: 459

```
        (B) TYPE: amino acid
        (D) TOPOLOGY: linear (ii) MOLECULE TYPE: amino acid (vi) ORIGINAL SOURCE:
         (A) ORGANISM: Trifolium repens (ix) FEATURE:
         (D) OTHER INFORMATION: bgls_trirp  non-cyanogenic strand-
             glucosidase  precursor (xi) SEQUENCE DESCRIPTION: SEQ ID NO: 72:

Leu Ser Arg Ser Ser Phe Pro Arg Gly Phe Ile Phe Gly Ala Gly
                 5                  10                  15

Ser Ser Ala Tyr Gln Phe Glu Gly Ala Val Asn Glu Gly Gly Arg
             20                  25                  30

Gly Pro Ser Ile Trp Asp Thr Phe Thr His Lys Tyr Pro Glu Lys
             35                  40                  45

Ile Arg Asp Gly Ser Asn Ala Asp Ile Thr Val Asp Gln Tyr His
             50                  55                  60

Arg Tyr Lys Glu Asp Val Gly Ile Met Lys Asp Gln Asn Met Asp
             65                  70                  75

Ser Tyr Arg Phe Ser Ile Ser Trp Pro Arg Ile Leu Pro Lys Gly
             80                  85                  90

Lys Leu Ser Gly Gly Ile Asn His Glu Gly Ile Lys Tyr Tyr Asn
             95                 100                 105

Asn Leu Ile Asn Glu Leu Leu Ala Asn Gly Ile Gln Pro Phe Val
            110                 115                 120

Thr Leu Phe His Trp Asp Leu Pro Gln Val Leu Glu Asp Glu Tyr
            125                 130                 135

Gly Gly Phe Leu Asn Ser Gly Val Ile Asn Asp Phe Arg Asp Tyr
            140                 145                 150

Thr Asp Leu Cys Phe Lys Glu Phe Gly Asp Arg Val Arg Tyr Trp
            155                 160                 165

Ser Thr Leu Asn Glu Pro Trp Val Phe Ser Asn Ser Gly Tyr Ala
            170                 175                 180

Leu Gly Thr Asn Ala Pro Gly Arg Cys Ser Ala Ser Asn Val Ala
            185                 190                 195

Lys Pro Gly Asp Ser Gly Thr Gly Pro Tyr Ile Val Thr His Asn
            200                 205                 210

Gln Ile Leu Ala His Ala Glu Ala Val His Val Tyr Lys Thr Lys
            215                 220                 225

Tyr Gln Ala Tyr Gln Lys Gly Lys Ile Gly Ile Thr Leu Val Ser
            230                 235                 240

Asn Trp Leu Met Pro Leu Asp Asp Asn Ser Ile Pro Asp Ile Lys
            245                 250                 255

Ala Ala Glu Arg Ser Leu Asp Phe Gln Phe Gly Leu Phe Met Glu
            260                 265                 270

Gln Leu Thr Thr Gly Asp Tyr Ser Lys Ser Met Arg Arg Ile Val
            275                 280                 285

Lys Asn Arg Leu Pro Lys Phe Ser Lys Phe Glu Ser Ser Leu Val
            290                 295                 300

Asn Gly Ser Phe Asp Phe Ile Gly Ile Asn Tyr Tyr Ser Ser Ser
            305                 310                 315

Tyr Ile Ser Asn Ala Pro Ser His Gly Asn Ala Lys Pro Ser Tyr
            320                 325                 330
```

-continued

```
Ser Thr Asn Pro Met Thr Asn Ile Ser Phe G lu Lys His Gly Ile
            335                 340                 345

Pro Leu Gly Pro Arg Ala Ala Ser Ile Trp I le Tyr Val Tyr Pro
            350                 355                 360

Tyr Met Phe Ile Gln Glu Asp Phe Glu Ile P he Cys Tyr Ile Leu
            365                 370                 375

Lys Ile Asn Ile Thr Ile Leu Gln Phe Ser I le Thr Glu Asn Gly
            380                 385                 390

Met Asn Glu Phe Asn Asp Ala Thr Leu Pro V al Glu Glu Ala Leu
            395                 400                 405

Leu Asn Thr Tyr Arg Ile Asp Tyr Tyr Tyr A rg His Leu Tyr Tyr
            410                 415                 420

Ile Arg Ser Ala Ile Arg Ala Gly Ser Asn V al Lys Gly Phe Tyr
            425                 430                 435

Ala Trp Ser Phe Leu Asp Cys Asn Glu Trp P he Ala Gly Phe Thr
            440                 445                 450

Val Arg Phe Gly Leu Asn Phe Val Asp
            455
```

(2) INFORMATION FOR SEQ ID NO: 73:

(i) SEQUENCE CHARACTERISTICS:
  (A) LENGTH: 470
  (B) TYPE: amino acid
  (D) TOPOLOGY: linear (ii) MOLECULE TYPE: amino acid (vi) ORIGINAL SOURCE:
  (A) ORGANISM: Homo sap iens (ix) FEATURE:
  (D) OTHER INFORMATION:lph _human  pos 1361 to 1927 of
   lactase-phl orizin hydrolase (xi) SEQUENCE DESCRIPTION: SEQ ID NO: 73:

```
Phe Pro Glu Gly Phe Ile Trp Ser Ala Ala S er Ala Ala Tyr Gln
            5                   10                  15

Ile Glu Gly Ala Trp Arg Ala Asp Gly Lys G ly Leu Ser Ile Trp
            20                  25                  30

Asp Thr Phe Ser His Thr Pro Leu Arg Val G lu Asn Asp Ala Ile
            35                  40                  45

Gly Asp Val Ala Cys Asp Ser Tyr His Lys I le Ala Glu Asp Leu
            50                  55                  60

Val Thr Leu Gln Asn Leu Gly Val Ser His T yr Arg Phe Ser Ile
            65                  70                  75

Ser Trp Ser Arg Ile Leu Pro Asp Gly Thr T hr Arg Tyr Ile Asn
            80                  85                  90

Glu Ala Gly Leu Asn Tyr Tyr Val Arg Leu I le Asp Thr Leu Leu
            95                  100                 105

Ala Ala Ser Ile Gln Pro Gln Val Thr Ile T yr His Trp Asp Leu
            110                 115                 120

Pro Gln Thr Leu Gln Asp Val Gly Gly Trp G lu Asn Glu Thr Ile
            125                 130                 135

Val Gln Arg Phe Lys Glu Tyr Ala Asp Val L eu Phe Gln Arg Leu
            140                 145                 150

Gly Asp Lys Val Lys Phe Trp Ile Thr Leu A sn Glu Pro Phe Val
            155                 160                 165
```

```
Ile Ala Tyr Gln Gly Tyr Gly Tyr Gly Thr A la Ala Pro Gly Val
            170                 175                 180

Ser Asn Arg Pro Gly Thr Ala Pro Tyr Ile V al Gly His Asn Leu
            185                 190                 195

Ile Lys Ala His Ala Glu Ala Trp His Leu T yr Asn Asp Val Tyr
            200                 205                 210

Arg Ala Ser Gln Gly Gly Val Ile Ser Ile T hr Ile Ser Ser Asp
            215                 220                 225

Trp Ala Glu Pro Arg Asp Pro Ser Asn Gln G lu Asp Val Glu Ala
            230                 235                 240

Ala Arg Arg Tyr Val Gln Phe Met Gly Gly T rp Phe Ala His Pro
            245                 250                 255

Ile Phe Lys Asn Gly Asp Tyr Asn Glu Val M et Lys Thr Arg Ile
            260                 265                 270

Arg Asp Arg Ser Leu Ala Ala Gly Leu Asn L ys Ser Arg Leu Pro
            275                 280                 285

Glu Phe Thr Glu Ser Glu Lys Arg Arg Ile A sn Gly Thr Tyr Asp
            290                 295                 300

Phe Phe Gly Phe Asn His Tyr Thr Thr Val L eu Ala Tyr Asn Leu
            305                 310                 315

Asn Tyr Ala Thr Ala Ile Ser Ser Phe Asp A la Asp Arg Gly Val
            320                 325                 330

Ala Ser Ile Ala Asp Arg Ser Trp Pro Asp S er Gly Ser Phe Trp
            335                 340                 345

Leu Lys Met Thr Pro Phe Gly Phe Arg Arg I le Leu Asn Trp Leu
            350                 355                 360

Lys Glu Glu Tyr Asn Asp Pro Pro Ile Tyr V al Thr Glu Asn Gly
            365                 370                 375

Val Ser Gln Arg Glu Glu Thr Asp Leu Asn A sp Thr Ala Arg Ile
            380                 385                 390

Tyr Tyr Leu Arg Thr Tyr Ile Asn Glu Ala L eu Lys Ala Val Gln
            395                 400                 405

Asp Lys Val Asp Leu Arg Gly Tyr Thr Val T rp Ser Ala Met Asp
            410                 415                 420

Asn Phe Glu Trp Ala Thr Gly Phe Ser Glu A rg Phe Gly Leu His
            425                 430                 435

Phe Val Asn Tyr Ser Asp Pro Ser Leu Pro A rg Ile Pro Lys Ala
            440                 445                 450

Ser Ala Lys Phe Tyr Ala Ser Val Val Arg C ys Asn Gly Phe Pro
            455                 460                 465

Asp Pro Ala Thr Gly
            470

(2) INFORMATION FOR SEQ ID NO: 74:

(i) SEQUENCE CHARACTERISTICS:
        (A) LENGTH: 356
        (B) TYPE: amino acid
        (D) TOPOLOGY: linear (ii) MOLECULE TYPE: amino acid (vi) ORIGINAL SOURCE:
        (A) ORGANISM: Trifolium repens (ix) FEATURE:
        (D) OTHER INFORMATION:bgl t_trirp  cyanogenic strand-
``` glucosidase (xi) SEQUENCE DESCRIPTION: SEQ ID NO: 74:

```
Phe Ala Pro Gly Phe Val Phe Gly Thr Ala Ser Ser Ala Phe Gln
                 5                  10                  15
Tyr Glu Gly Ala Ala Phe Glu Asp Gly Lys Gly Pro Ser Ile Trp
                20                  25                  30
Asp Thr Phe Thr His Lys Tyr Pro Glu Lys Ile Lys Asp Arg Thr
                35                  40                  45
Asn Gly Asp Val Ala Ile Asp Glu Tyr His Arg Tyr Lys Glu Asp
                50                  55                  60
Ile Gly Ile Met Lys Asp Met Asn Leu Asp Ala Tyr Arg Phe Ser
                65                  70                  75
Ile Ser Trp Pro Arg Val Leu Pro Lys Gly Lys Leu Ser Gly Gly
                80                  85                  90
Val Asn Arg Glu Gly Ile Asn Tyr Tyr Asn Asn Leu Ile Asn Glu
                95                 100                 105
Val Leu Ala Asn Gly Met Gln Pro Tyr Val Thr Leu Phe His Trp
               110                 115                 120
Asp Val Pro Gln Ala Leu Glu Asp Glu Tyr Arg Gly Phe Leu Gly
               125                 130                 135
Arg Asn Ile Val Asp Asp Phe Arg Asp Tyr Ala Glu Leu Cys Phe
               140                 145                 150
Lys Glu Phe Gly Asp Arg Val Lys His Trp Ile Thr Leu Asn Glu
               155                 160                 165
Pro Trp Gly Val Ser Met Asn Ala Tyr Ala Tyr Gly Thr Phe Ala
               170                 175                 180
Pro Gly Arg Cys Ser Asp Trp Leu Lys Leu Asn Cys Thr Gly Gly
               185                 190                 195
Asp Ser Gly Arg Glu Pro Tyr Leu Ala Ala His Tyr Gln Leu Leu
               200                 205                 210
Ala His Ala Ala Ala Arg Leu Tyr Lys Thr Lys Tyr Gln Ala
               215                 220                 225
Ser Gln Asn Gly Ile Ile Gly Ile Thr Leu Val Ser His Trp Phe
               230                 235                 240
Glu Pro Ala Ser Lys Glu Lys Ala Asp Val Asp Ala Ala Lys Arg
               245                 250                 255
Gly Leu Asp Phe Met Leu Gly Trp Phe Met His Pro Leu Thr Lys
               260                 265                 270
Gly Arg Tyr Pro Glu Ser Met Arg Tyr Leu Val Arg Lys Arg Leu
               275                 280                 285
Pro Lys Phe Ser Thr Glu Glu Ser Lys Glu Leu Thr Gly Ser Phe
               290                 295                 300
Asp Phe Leu Gly Leu Asn Tyr Tyr Ser Ser Tyr Tyr Ala Ala Lys
               305                 310                 315
Ala Pro Arg Ile Pro Asn Ala Arg Pro Ala Ile Gln Thr Asp Ser
               320                 325                 330
Leu Ile Asn Ala Thr Phe Glu His Asn Gly Lys Pro Leu Gly Pro
               335                 340                 345
Met Ala Ala Ser Ser Trp Leu Cys Ile Tyr Pro
               350                 355
```